(12) United States Patent
Zink

(10) Patent No.: US 10,971,688 B2
(45) Date of Patent: *Apr. 6, 2021

(54) ORGANIC MOLECULES FOR USE IN ORGANIC OPTOELECTRONIC DEVICES

(71) Applicant: CYNORA GMBH, Bruchsal (DE)

(72) Inventor: Daniel Zink, Bruchsal (DE)

(73) Assignee: CYNORA GMBH, Bruchsal (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/343,954

(22) PCT Filed: Jul. 10, 2017

(86) PCT No.: PCT/EP2017/067267
§ 371 (c)(1),
(2) Date: Apr. 22, 2019

(87) PCT Pub. No.: WO2018/077492
PCT Pub. Date: May 3, 2018

(65) Prior Publication Data
US 2019/0248741 A1    Aug. 15, 2019

(30) Foreign Application Priority Data

Oct. 25, 2016 (DE) ..................... 10 2016 120 373.4
Apr. 13, 2017 (DE) ..................... 10 2017 107 997.1

(51) Int. Cl.
| | |
|---|---|
| *H01L 51/54* | (2006.01) |
| *H01L 51/00* | (2006.01) |
| *C07D 403/14* | (2006.01) |
| *C09K 11/06* | (2006.01) |
| *C07D 403/10* | (2006.01) |
| *H05B 33/14* | (2006.01) |
| *C07D 209/86* | (2006.01) |

(Continued)

(52) U.S. Cl.
CPC ........ *H01L 51/0072* (2013.01); *C07D 209/86* (2013.01); *C07D 209/94* (2013.01); *C07D 403/10* (2013.01); *C07D 403/14* (2013.01); *C07D 519/00* (2013.01); *C09K 11/06* (2013.01); *H01L 51/0067* (2013.01); *H05B 33/14* (2013.01); *H01L 51/001* (2013.01); *H01L 51/5012* (2013.01)

(58) Field of Classification Search
CPC .. C07D 209/86; C07D 209/88; C07D 209/94; C07D 401/00; C07D 401/10; C07D 401/14; C07D 403/00; C07D 403/10; C07D 403/14; C07D 405/00; C07D 405/10; C07D 405/14; C07D 487/00; C07D 487/02; C07D 487/04; C07D 493/00; C07D 493/02; C07D 493/04; C07D 519/00; C09K 11/06; C09K 2211/00; C09K 2211/10; C09K 2211/1007; C09K 2211/1014; C09K 2211/1029; C09K 2211/1018; C09K 2211/1044; H01L 51/0032; H01L 51/005; H01L 51/0003; H01L 51/001; H01L 51/006; H01L 51/0067; H01L 51/0071; H01L 51/0072; H01L 51/0073; H01L 51/0074; H01L 51/0096; H01L 51/50; H01L 51/5012; H01L 51/5016; H01L 51/5071; H01L 51/5088; H01L 51/5096; H01L 51/5206; H01L 51/5221; H01L 2251/5376; H05B 33/14
See application file for complete search history.

(56) References Cited

U.S. PATENT DOCUMENTS 10,439,151 B2 * 10/2019 Fabio ................... C07D 493/04

FOREIGN PATENT DOCUMENTS

| | | |
|---|---|---|
| EP | 2709183 A | 3/2014 |
| JP | 2007227656 A * | 9/2007 |

(Continued)

*Primary Examiner* — Andrew K Bohaty
(74) *Attorney, Agent, or Firm* — Ryan, Mason & Lewis, LLP

(57) ABSTRACT

An organic molecule is disclosed having
a first chemical unit consisting of a structure according to Formula I

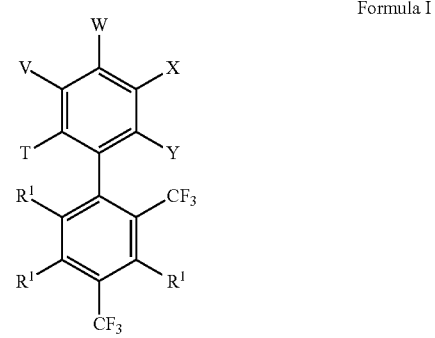

Formula I and
two second chemical units, which in each case are the same or different in each occurrence, having a structure according to Formula II.

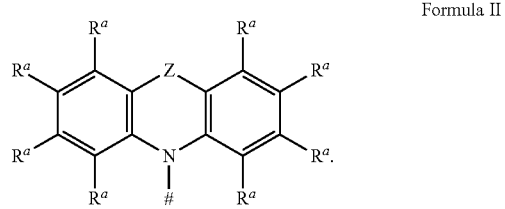

Formula II

20 Claims, 7 Drawing Sheets

(51) Int. Cl.
  *C07D 209/94*  (2006.01)
  *C07D 519/00*  (2006.01)
  *H01L 51/50*  (2006.01)

(56) References Cited

FOREIGN PATENT DOCUMENTS

| WO | 2015175678 A1 | 11/2015 | | |
|---|---|---|---|---|
| WO | WO-2015175678 A1 | * | 11/2015 | ........... C07D 471/04 |
| WO | 2016116497 A1 | | 7/2016 | |
| WO | PCT/EP2017/067267 | | 9/2017 | |

* cited by examiner

ORGANIC MOLECULES FOR USE IN ORGANIC OPTOELECTRONIC DEVICES

CROSS-REFERENCE TO RELATED APPLICATIONS

This application claims priority to International patent application PCT/EP2017/067267, filed Jul. 10, 2017, German Patent Application No. 10 2017 107 997.1, filed Apr. 13, 2017, and German Patent Application No. 10 2016 120 373.4, filed Oct. 25, 2016, the disclosures of which are incorporated by reference herein in their entireties.

Field of Invention

The invention relates to purely organic molecules and the use thereof in organic light-emitting diodes (OLEDs) and in other organic optoelectronic devices.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
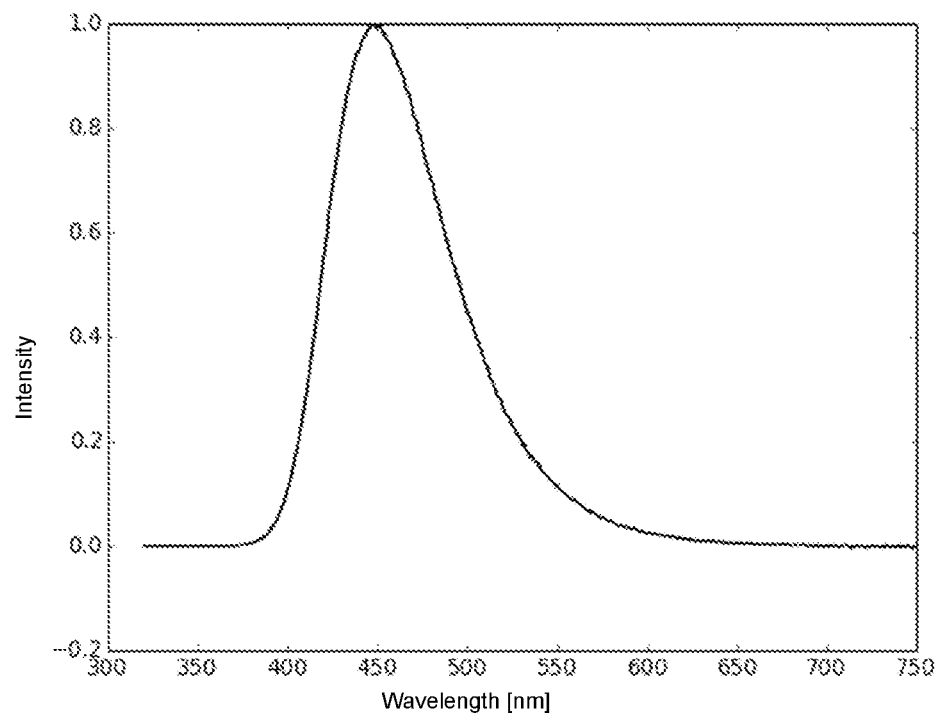
FIG. 1 is an emission spectrum of Example 1 (10% in PMMA).

Exemplary embodiments of the invention will now be discussed in further detail. This invention may, however, be embodied in many different forms and should not be construed as limited to the embodiments set forth herein.

The underlying object of the present invention was to provide molecules which are suitable for use in optoelectronic devices.

This object is achieved through the invention to provide a new class of organic molecules.

The organic molecules according to the invention are purely organic molecules; i.e. they do not have any metal ions, and thus differ from the metal complex compounds known for use in organic optoelectronic devices.

The organic molecules according to the invention are characterized by emissions in the blue, sky blue, or green spectral range. The photoluminescence quantum yields of the organic molecules according to the invention are, in particular, 20% and more. The molecules according to the invention exhibit, in particular, thermally activated delayed fluorescence (TADF). The use of the molecules according to the invention in an optoelectronic device, for example an organic light-emitting diode (OLED), results in higher efficiencies of the device. Corresponding OLEDs have a higher stability than OLEDs having known emitter materials and comparable color.

The blue spectral range is understood here to be the visible range below 470 nm. The sky blue spectral range is understood here to be the range between 470 nm and 499 nm. The green spectral range is understood here to be the range between 500 nm and 599 nm. The emission maximum is in the respective range.

The organic molecules contain a first chemical unit comprising a or consisting of a structure according to Formula I:

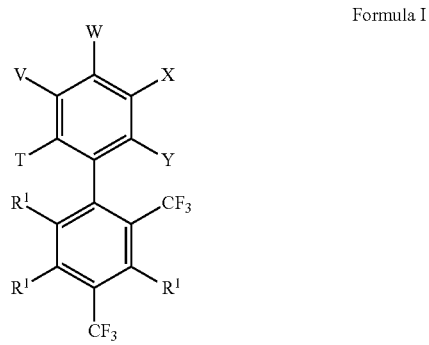

Formula I and
two second chemical units D, which are respectively the same or different in each occurrence, comprising or consisting of a structure according to Formula II,

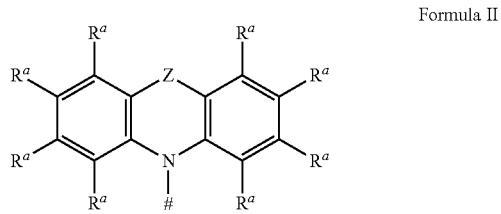

Formula II

The first chemical unit is thereby respectively connected to the two second chemical units D via a single bond.
T is the point of attachment of the single bond between the chemical unit as per Formula I and a second chemical unit D or H.
V is the point of attachment of the single bond between the chemical unit as per Formula I and a chemical unit D or H;
W is the point of attachment of the single bond between the first chemical unit as per Formula I and a second chemical unit D or is selected from the group consisting of H, CN and $CF_3$.
X is the point of attachment of the single bond between the chemical unit as per Formula I and a chemical unit D or is selected from the group consisting of H, CN and $CF_3$.

Y is the point of attachment of the single bond between the chemical unit as per Formula I and a chemical unit D or is selected from the group consisting of H, CN and $CF_3$;

# is the point of attachment of the single bond between the respective second chemical unit D and the chemical unit as per Formula I.

Z is the same or different in each occurrence as a direct bond or is selected from the group consisting of $CR^3R^4$, $C=CR^3R^4$, $C=O$, $C=NR^3$, $NR^3$, O, $SiR^3R^4$, S, $S(O)$ and $S(O)_2$.

$R^1$ is the same or different in each occurrence as H, deuterium, a linear alkyl group having 1 to 5 C atoms, a linear alkenyl or alkynyl group having 2 to 8 C atoms, a branched or cyclic alkyl, alkenyl or alkynyl group having 3 to 10 C atoms, wherein one or more H atoms can be replaced by deuterium or an aromatic or heteroaromatic ring system having 5 to 15 aromatic ring atoms, which can in each case be substituted with one or more radicals $R^6$.

$R^a$, $R^3$ and $R^4$ is the same or different in each occurrence as H, deuterium, $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms or a linear alkenyl or alkynyl group having 2 to 40 C atoms or a branched or cyclic alkyl, alkenyl, alkynyl, alkoxy or thioalkoxy group having 3 to 40 C atoms, which can be respectively substituted with one or more radicals $R^5$, wherein one or more non-adjacent $CH_2$ groups can be replaced by $R^5C=CR^5$, C≡C, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be substituted with deuterium, CN, $CF_3$ or $NO_2$; or an aromatic or heteroaromatic ring system having 5 to 60 aromatic ring atoms, which can be respectively substituted with one or more radicals $R^5$, or an aryloxy or heteroaryloxy group having 5 to 60 aromatic ring atoms, which can be substituted with one or more radicals $R^5$, or a diarylamino group, diheteroarylamino group or arylheteroarylamino group having 10 to 40 aromatic ring atoms, which can be substituted with one or more radicals $R^5$.

$R^5$ is the same or different in each occurrence, as H, deuterium, $N(R^6)_2$, OH, $Si(R^6)_3$, $B(OR^6)_2$, $OSO_2R^6$, $CF_3$, CN, F, Br, I, a linear alkyl, alkoxy or thioalkoxy group having 1 to 40 C atoms or a linear alkenyl or alkinyl group having 2 to 40 C atoms or a branched or cyclic alkyl, alkenyl, alkinyl, alkoxy or thioalkoxy group having 3 to 40 C atoms, which can in each case be substituted with one or more radicals $R^6$, wherein one or more non-adjacent $CH_2$ groups can be replaced by $R^6C=CR^6$, C≡C, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more H atoms can be substituted with deuterium, CN, $CF_3$ or $NO_2$; or an aromatic or heteroaromatic ring system having 5 to 60 aromatic ring atoms, which can in each case be substituted with one or more radicals $R^6$, or an aryloxy or heteroaryloxy group having 5 to 60 aromatic ring atoms, which can be substituted with one or more radicals $R^6$, or a diarylamino group, diheteroarylamino group or arylheteroarylamino group having 10 to 40 aromatic ring atoms, which can be substituted with one or more radicals $R^6$.

$R^6$ is the same or different in each occurrence, as H, deuterium, OH, $CF_3$, CN, F, a linear alkyl, alkoxy or thioalkoxy group having 1 to 5 C atoms or a linear alkenyl or alkinyl group having 2 to 5 C atoms or a branched or cyclic alkyl, alkenyl, alkinyl, alkoxy or thioalkoxy group having 3 to 5 C atoms, wherein one or more H atoms can be replaced by deuterium, CN, $CF_3$ or $NO_2$; or an aromatic or heteroaromatic ring system having 5 to 60 aromatic ring atoms or an aryloxy or heteroaryloxy group having 5 to 60 aromatic ring atoms or a diarylamino group, diheteroarylamino group or arylheteroarylamino group having 10 to 40 aromatic ring atoms.

According to the invention, each of the radicals $R^a$, $R^3$, $R^4$ or $R^5$ can also form a mono- or polycyclic, aliphatic, aromatic and/or benzoannelated ring system with one or more further radicals $R^a$, $R^3$, $R^4$ or $R^5$.

According to the invention, exactly one radical selected from W, X and Y is CN or $CF_3$ and exactly two radicals selected from the group consisting of T, V, W, X and Y are a point of attachment of a single bond between the chemical unit as per Formula I and a chemical unit D.

In one embodiment $R^1$ is the same or different H, methyl or phenyl in each occurrence.

In one embodiment, W is CN.

In a further embodiment of the organic molecules, in each occurrence the second chemical group D is the same or different comprising a structure of Formula IIa or consisting of a structure of Formula IIa:

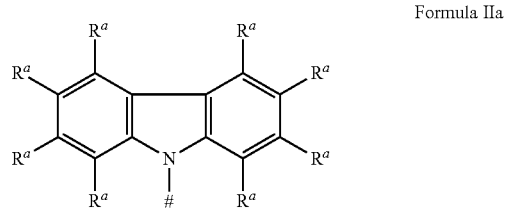

Formula IIa wherein the definitions stated for Formula I and II apply for # and $R^a$.

In a further embodiment of the organic molecules according to the invention, in each occurrence the second chemical unit D is the same or different comprising a structure of Formula IIb, Formula IIb-2, Formula IIb-3 or Formula IIb-4 or consisting thereof:

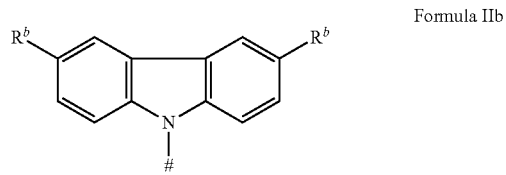

Formula IIb

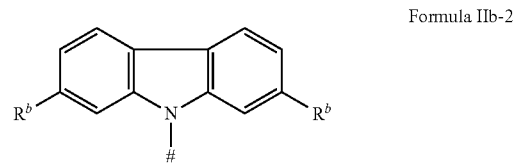

Formula IIb-2

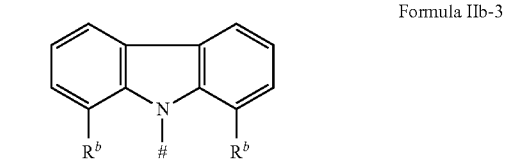

Formula IIb-3

Formula IIb-4

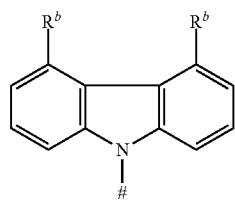

Formula IIc-4

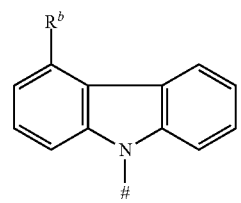

wherein the following applies $R^b$ is the same or different in each occurrence, as $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms or a linear alkenyl or alkinyl group having 2 to 40 C atoms or a branched or cyclic alkyl, alkenyl, alkinyl, alkoxy or thioalkoxy group having 3 to 40 C atoms, which can be respectively substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be substituted with deuterium, CN, $CF_3$ or $NO_2$; or an aromatic or heteroaromatic ring system having 5 to 60 aromatic ring atoms, which can be respectively substituted with one or more radicals $R^5$, or an aryloxy or heteroaryloxy group having 5 to 60 aromatic ring atoms, which can be substituted with one or more radicals $R^5$, or a diarylamino group, diheteroarylamino group or arylheteroarylamino group having 10 to 40 aromatic ring atoms, which can be substituted with one or more radicals $R^5$. Otherwise, the above-mentioned definitions apply.

In a further embodiment of the organic molecules according to the invention, in each occurrence the second chemical unit D is the same or different comprising a structure of Formula IIc, Formula IIc-2, Formula IIc-3 or Formula IIc-4 or consisting thereof:

Formula IIc

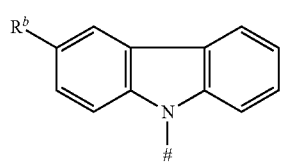

Formula IIc-2

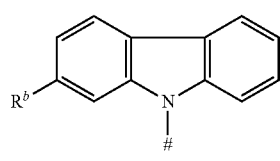

Formula IIc-3

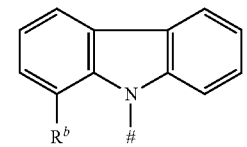

wherein the abovementioned definitions apply.

In a further embodiment of the organic molecules according to the invention, in each occurrence $R^b$ is independently selected from the group consisting of Me, $^iPr$, $^tBu$, CN, $CF_3$, Ph, which can be respectively substituted with one or more radicals selected from Me, $^iPr$, $^tBu$, CN, $CF_3$ and Ph, pyridinyl, which can be respectively substituted with one or more radicals selected from Me, $^iPr$, $^tBu$, CN, $CF_3$ and Ph, pyrimidinyl, which can be respectively substituted with one or more radicals selected from Me, $^iPr$, $^tBu$, CN, $CF_3$ and Ph, carbazolyl, which can be respectively substituted with one or more radicals selected from Me, $^iPr$, $^tBu$, CN, $CF_3$ and Ph, triazinyl, which can be respectively substituted with one or more radicals selected from Me, $^iPr$, $^tBu$, CN, $CF_3$ and Ph, and $N(Ph)_2$.

Embodiments of chemical Group D are shown in the following as examples:

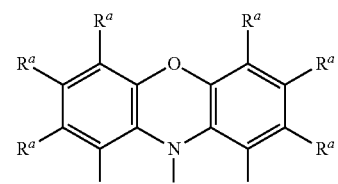

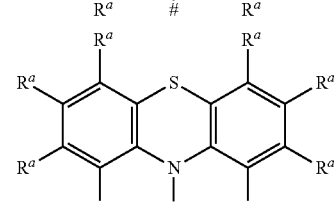

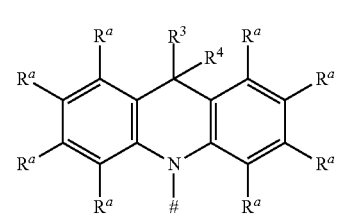

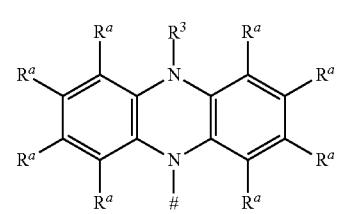

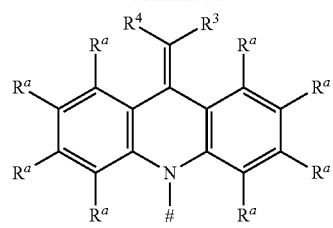
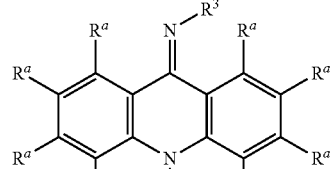
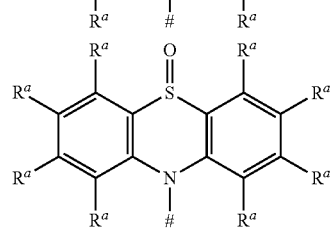
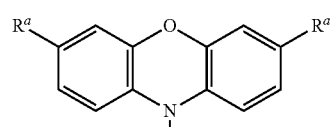
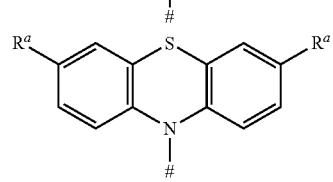
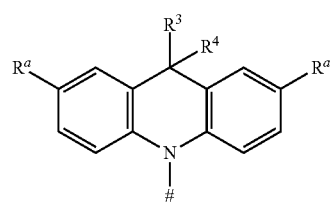
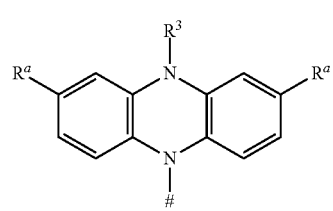
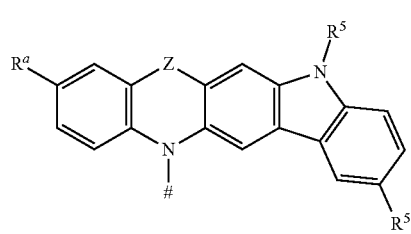
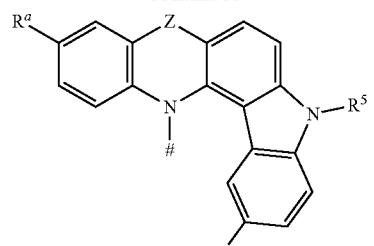
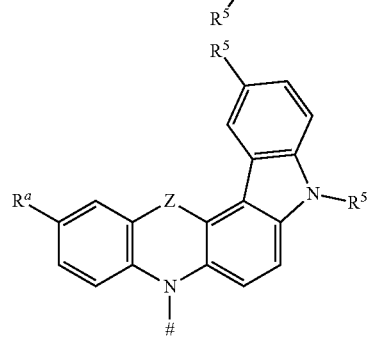
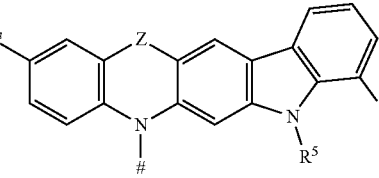
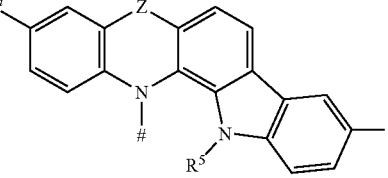
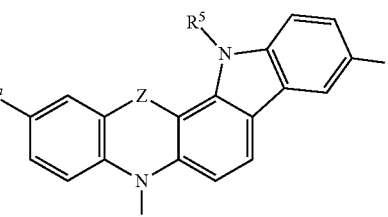
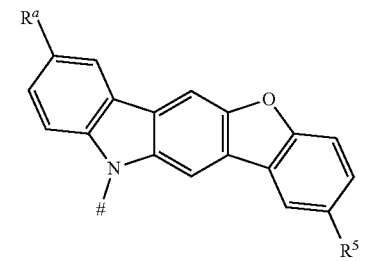
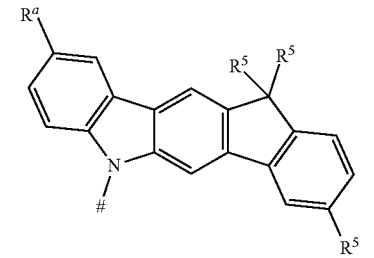

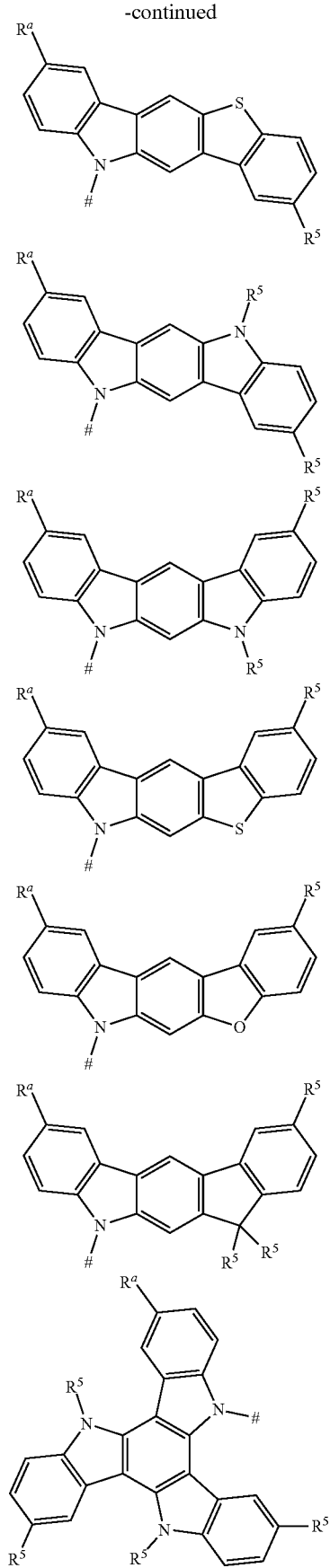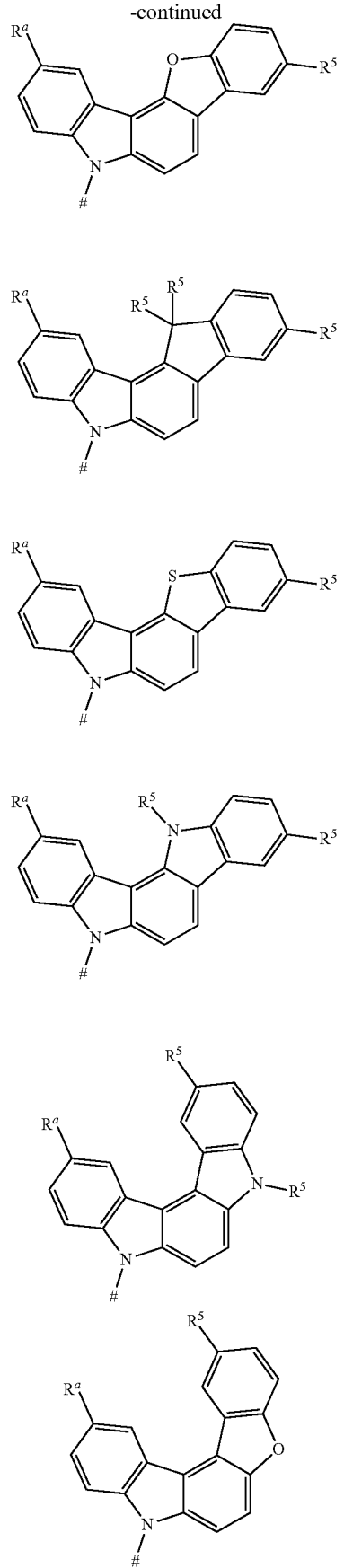

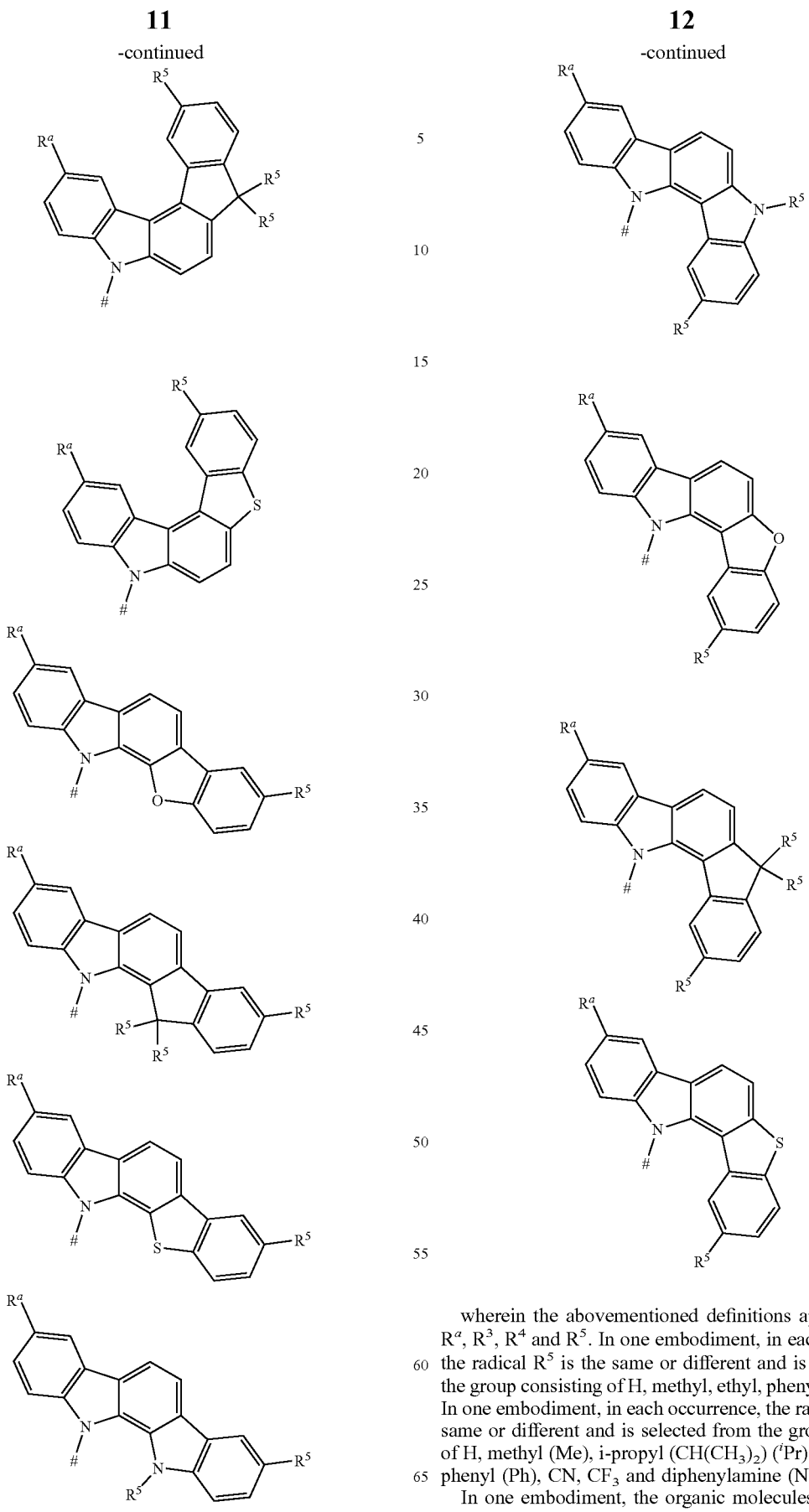

wherein the abovementioned definitions apply for #, Z, R$^a$, R$^3$, R$^4$ and R$^5$. In one embodiment, in each occurrence, the radical R$^5$ is the same or different and is selected from the group consisting of H, methyl, ethyl, phenyl and mesityl. In one embodiment, in each occurrence, the radical R$^a$ is the same or different and is selected from the group consisting of H, methyl (Me), i-propyl (CH(CH$_3$)$_2$) ($^i$Pr), t-butyl ($^t$Bu), phenyl (Ph), CN, CF$_3$ and diphenylamine (NPh$_2$).

In one embodiment, the organic molecules according to the invention have a structure of Formula III:

Formula III wherein the abovementioned definitions apply.

In a further embodiment, the organic molecules according to the invention have a structure of Formula IIIa:

Formula IIIa wherein

In each occurrence $R^c$ is independently selected from the group consisting of Me, $^i$Pr, $^t$Bu, CN, CF$_3$, Ph, which can be respectively substituted with one or more radicals selected from Me, $^i$Pr, $^t$Bu, CN, CF$_3$ or Ph, pyridinyl, which can be respectively substituted with one or more radicals selected from Me, $^i$Pr, $^t$Bu, CN, CF$_3$ or Ph, pyrimidinyl, which can be respectively substituted with one or more radicals selected from Me, $^i$Pr, $^t$Bu, CN, CF$_3$ or Ph, carbazolyl, which can be respectively substituted with one or more radicals selected from Me, $^i$Pr, $^t$Bu, CN, CF$_3$ and Ph, triazinyl, which can be respectively substituted with one or more radicals selected from Me, $^i$Pr, $^t$Bu, CN, CF$_3$ or Ph, and is N(Ph)$_2$.

In a further embodiment, the organic molecules according to the invention have a structure of Formula IIIb:

Formula IIIb wherein the abovementioned definitions apply.

In a further embodiment, the organic molecules according to the invention have a structure of Formula IIIc:

Formula IIIc wherein the abovementioned definitions apply.

In a further embodiment, the organic molecules according to the invention have a structure of Formula IIId:

Formula IIId wherein the abovementioned definitions apply.

In a further embodiment, the organic molecules according to the invention have a structure of Formula IIIe:

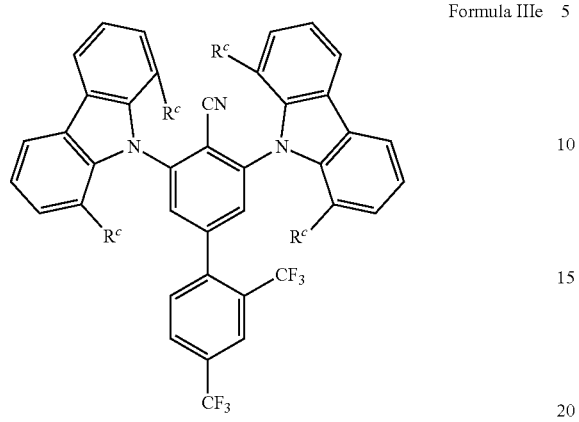

Formula IIIe wherein the abovementioned definitions apply.

In a further embodiment, the organic molecules according to the invention have a structure of Formula IIIf:

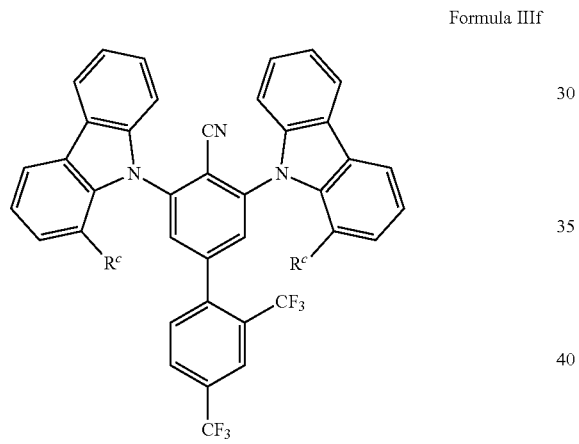

Formula IIIf wherein the abovementioned definitions apply.

In a further embodiment, the organic molecules according to the invention have a structure of Formula IIIg:

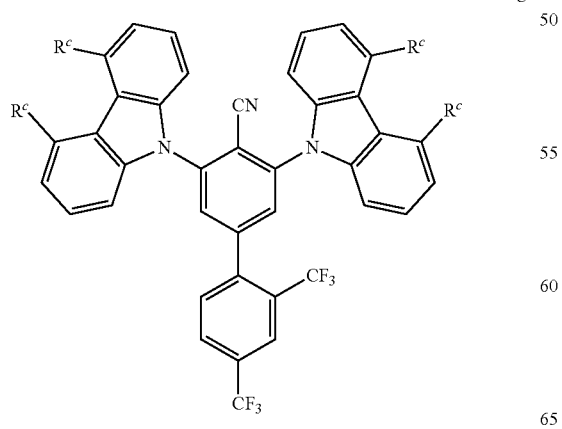

Formula IIIg wherein the abovementioned definitions apply.

In a further embodiment, the organic molecules according to the invention have a structure of Formula IIIh:

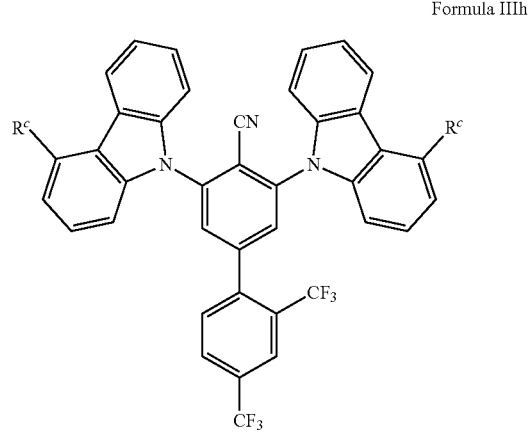

Formula IIIh wherein the abovementioned definitions apply.

In one embodiment, the organic molecules according to the invention have a structure of Formula IV:

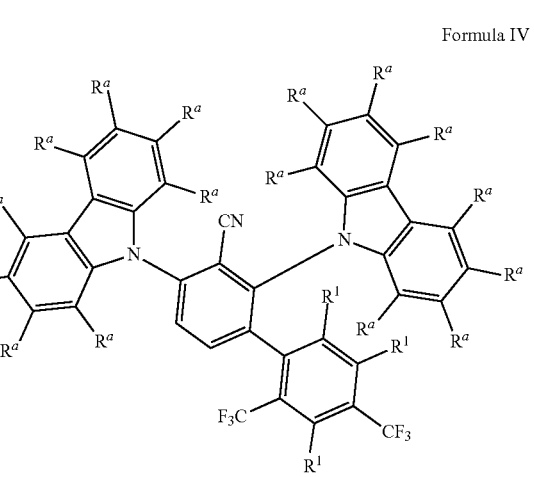

Formula IV wherein the abovementioned definitions apply.

In a further embodiment, the organic molecules according to the invention have a structure of Formula IVa:

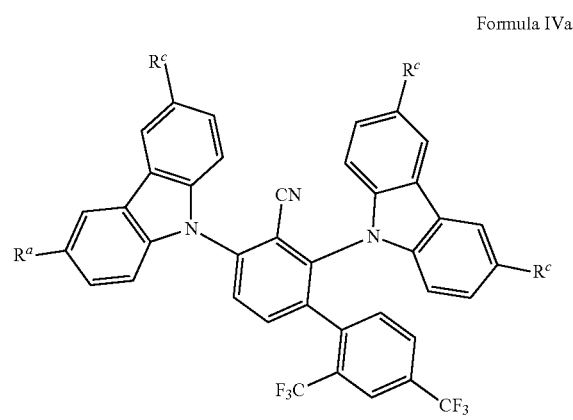

Formula IVa wherein the abovementioned definitions apply.

In a further embodiment, the organic molecules according to the invention have a structure of Formula IVb:

Formula IVb

In a further embodiment, the organic molecules according to the invention have a structure of Formula IVe:

Formula IVe

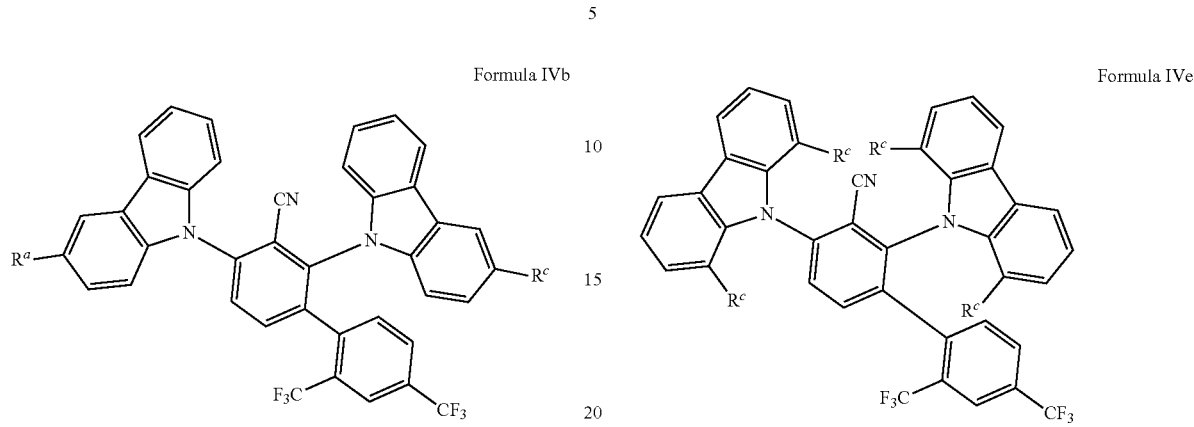

wherein the abovementioned definitions apply.

In a further embodiment, the organic molecules according to the invention have a structure of Formula IVc wherein the abovementioned definitions apply.

In a further embodiment, the organic molecules according to the invention have a structure of Formula IVf:

Formula IVc

Formula IVf

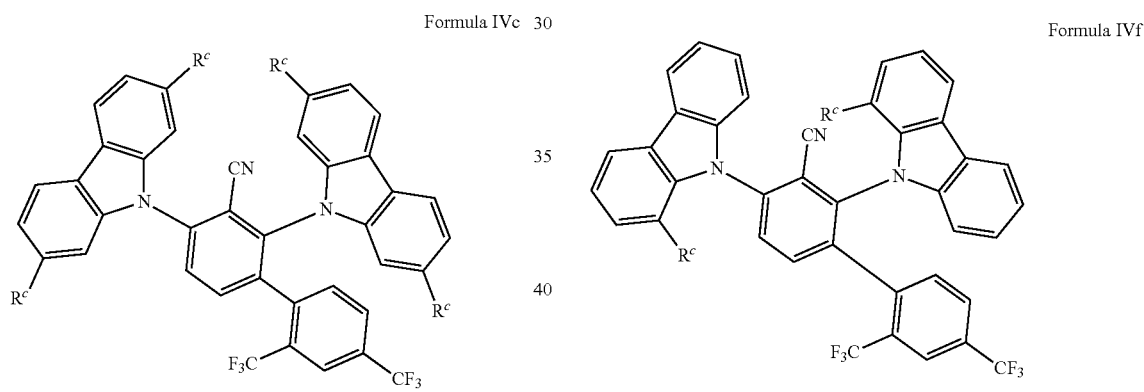

wherein the abovementioned definitions apply.

In a further embodiment, the organic molecules according to the invention have a structure of Formula IVd:

wherein the abovementioned definitions apply.

In a further embodiment, the organic molecules according to the invention have a structure of Formula IVg:

Formula IVd

Formula IVg

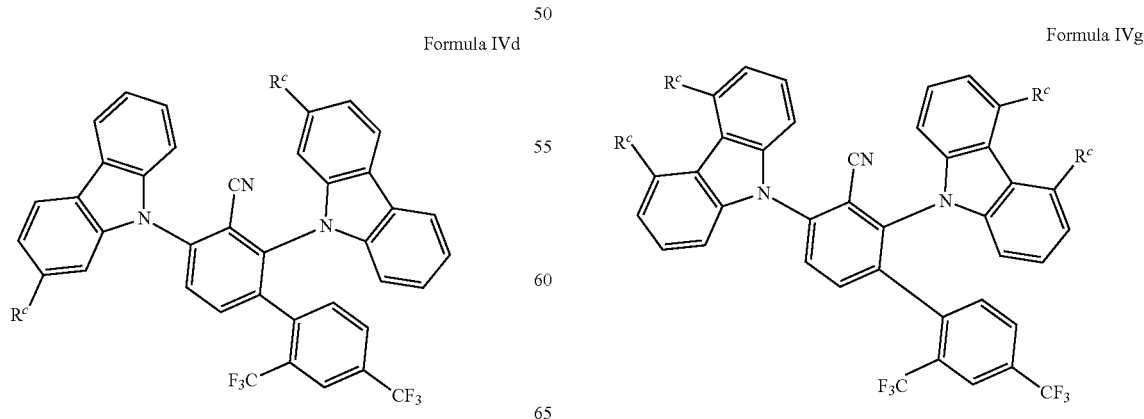

wherein the abovementioned definitions apply.

wherein the abovementioned definitions apply.

In a further embodiment, the organic molecules according to the invention have a structure of Formula IVh

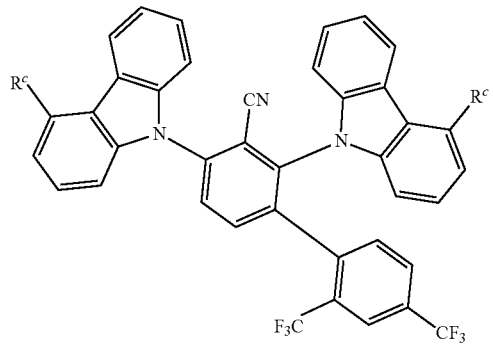

Formula IVh wherein the abovementioned definitions apply.

In one embodiment, the organic molecules according to the invention have a structure of Formula V:

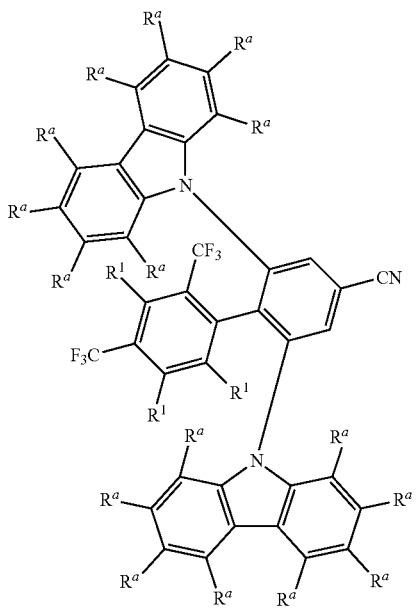

Formula V wherein the abovementioned definitions apply.

In a further embodiment, the organic molecules according to the invention have a structure of Formula Va:

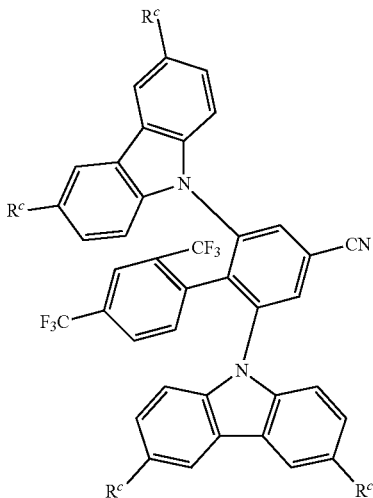

Formula Va wherein the abovementioned definitions apply.

In a further embodiment, the organic molecules according to the invention have a structure of Formula Vb:

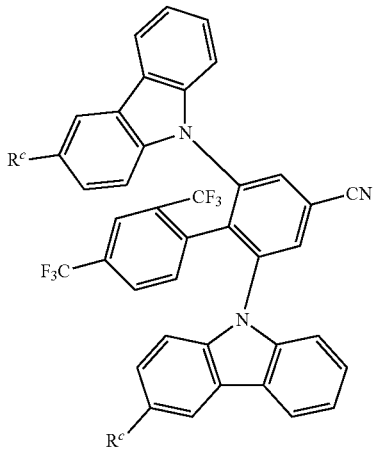

Formula Vb wherein the abovementioned definitions apply.

In a further embodiment, the organic molecules according to the invention have a structure of Formula Vc

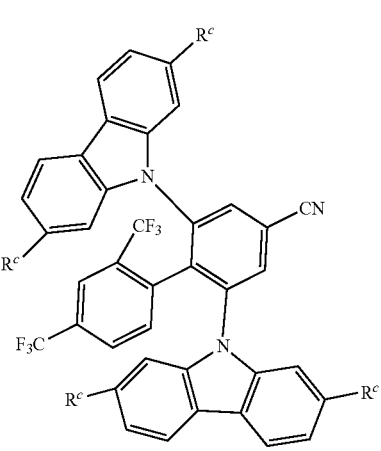

Formula Vc wherein the abovementioned definitions apply.

In a further embodiment, the organic molecules according to the invention have a structure of Formula Vd:

Formula Vd

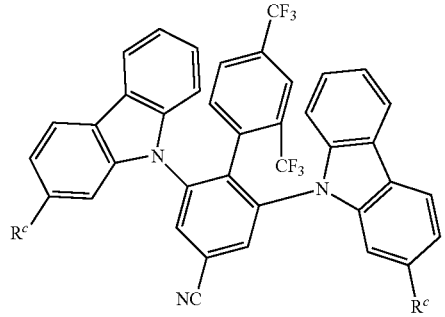

wherein the abovementioned definitions apply.

In a further embodiment, the organic molecules according to the invention have a structure of Formula Ve:

Formula Ve

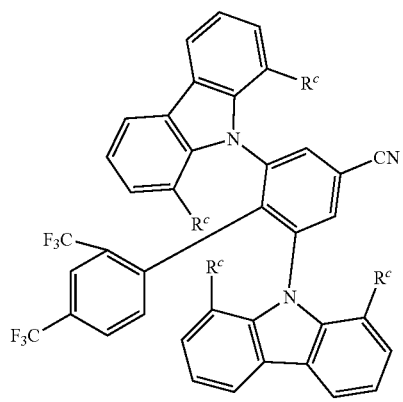

wherein the abovementioned definitions apply.

In a further embodiment, the organic molecules according to the invention have a structure of Formula Vf Formula Vf

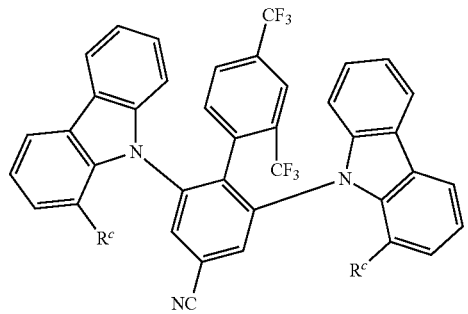

wherein the abovementioned definitions apply.

In a further embodiment, the organic molecules according to the invention have a structure of Formula Vg:

Formula Vg

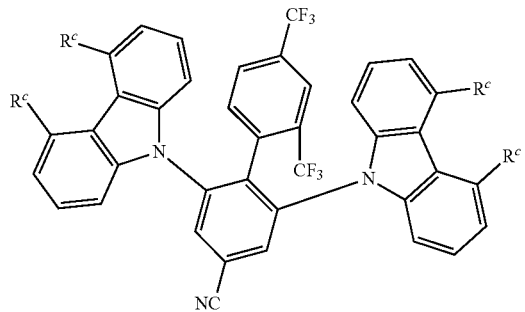

wherein the abovementioned definitions apply.

In a further embodiment, the organic molecules according to the invention have a structure of Formula Vh:

Formula Vh

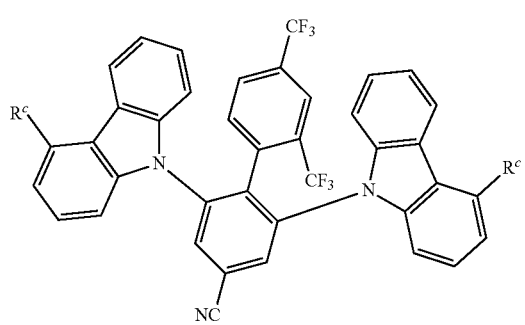

wherein the abovementioned definitions apply.

In one embodiment, the organic molecules according to the invention have a structure of Formula VI:

Formula VI

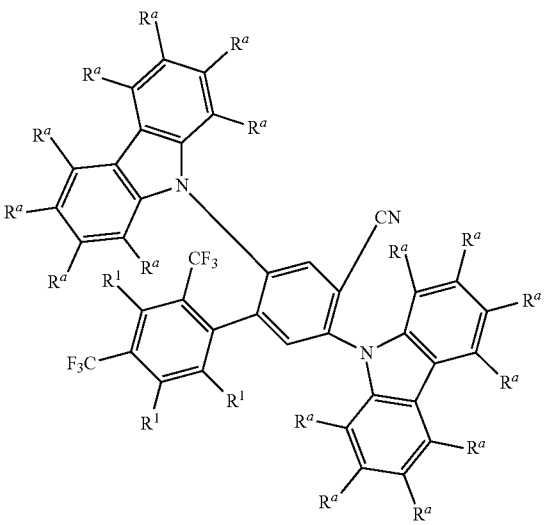

wherein the abovementioned definitions apply.

In a further embodiment, the organic molecules according to the invention have a structure of Formula VIa:

Formula VIa

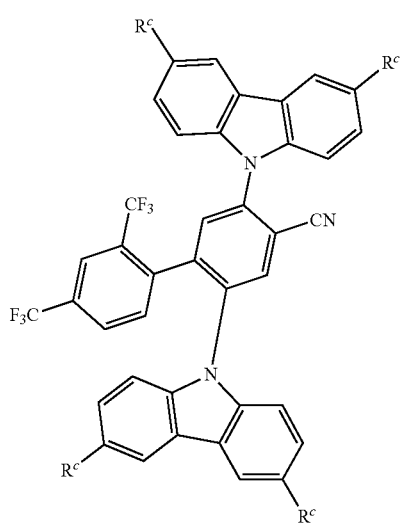

wherein the abovementioned definitions apply.

In a further embodiment, the organic molecules according to the invention have a structure of Formula VIb:

Formula VIb

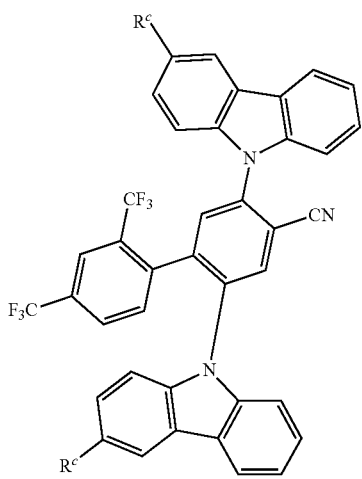

wherein the abovementioned definitions apply.

In a further embodiment, the organic molecules according to the invention have a structure of Formula VIc:

Formula VIc

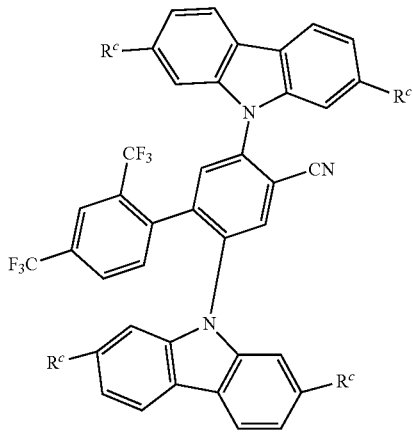

wherein the abovementioned definitions apply.

In a further embodiment, the organic molecules according to the invention have a structure of Formula VId:

Formula VId

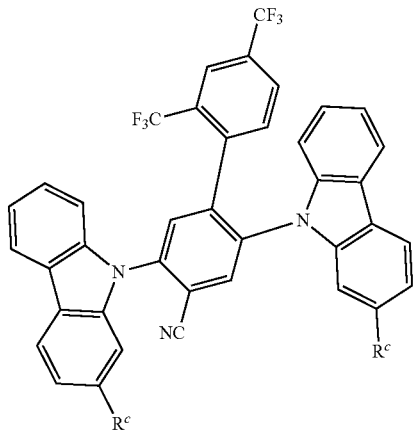

wherein the abovementioned definitions apply.

In a further embodiment, the organic molecules according to the invention have a structure of Formula VIe:

Formula VIe

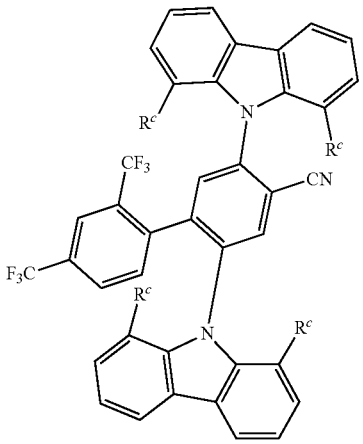

wherein the abovementioned definitions apply.

In a further embodiment, the organic molecules according to the invention have a structure of Formula VIf:

Formula VIf

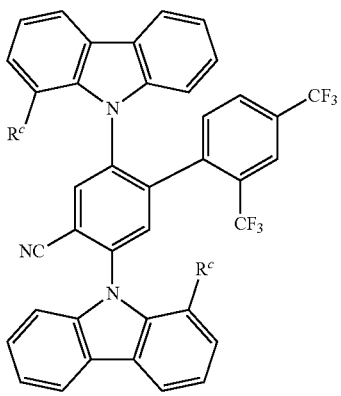

wherein the abovementioned definitions apply.

In a further embodiment, the organic molecules according to the invention have a structure of Formula VIg:

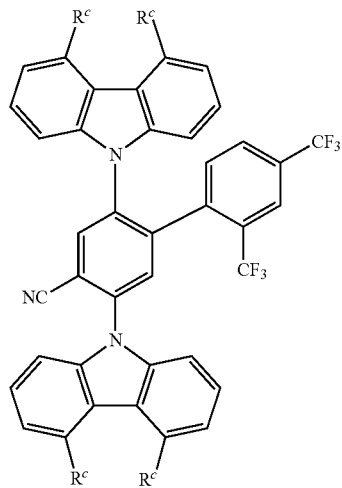

Formula VIg wherein the abovementioned definitions apply.

In a further embodiment, the organic molecules according to the invention have a structure of Formula VIh:

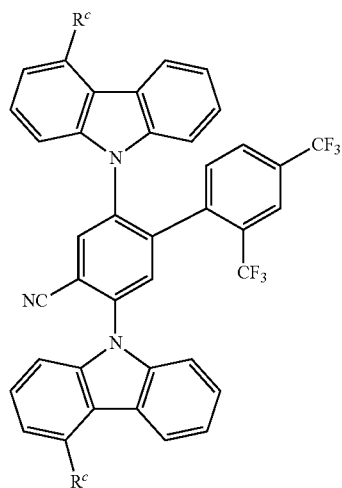

Formula VIh wherein the abovementioned definitions apply.

In one embodiment, the organic molecules according to the invention have a structure of Formula VII:

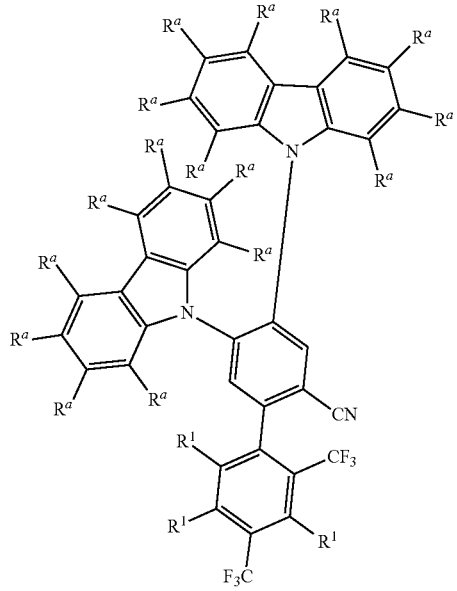

Formula VII wherein the abovementioned definitions apply.

In a further embodiment, the organic molecules according to the invention have a structure of Formula VIIa:

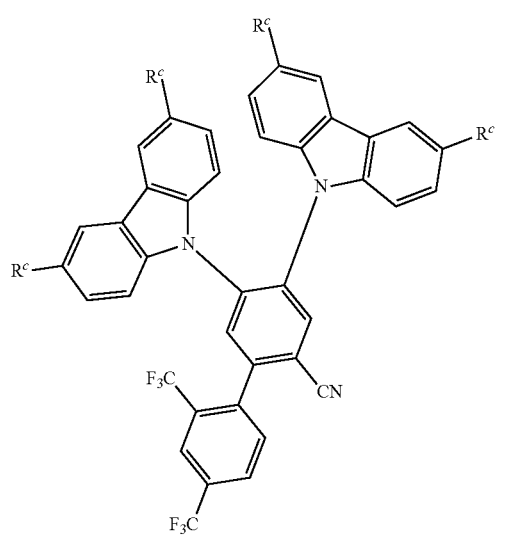

Formula VIIa wherein the abovementioned definitions apply.

In a further embodiment, the organic molecules according to the invention have a structure of Formula VIIb

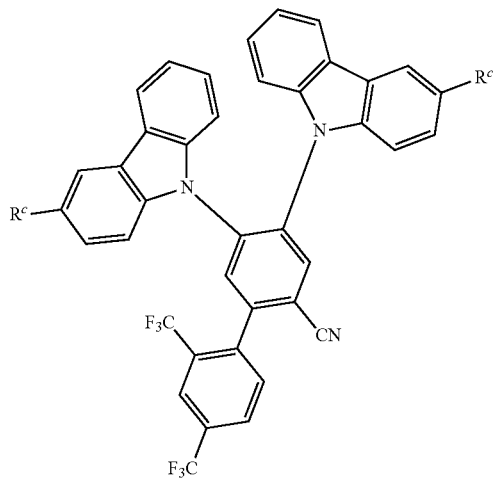

Formula VIIb wherein the abovementioned definitions apply.

In a further embodiment, the organic molecules according to the invention have a structure of Formula VIIc:

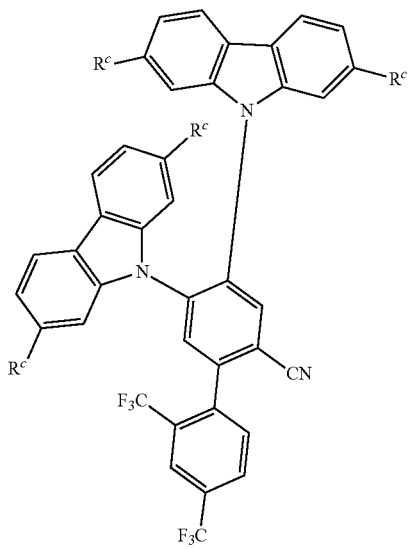

Formula VIIc wherein the abovementioned definitions apply.

In a further embodiment, the organic molecules according to the invention have a structure of Formula VIId:

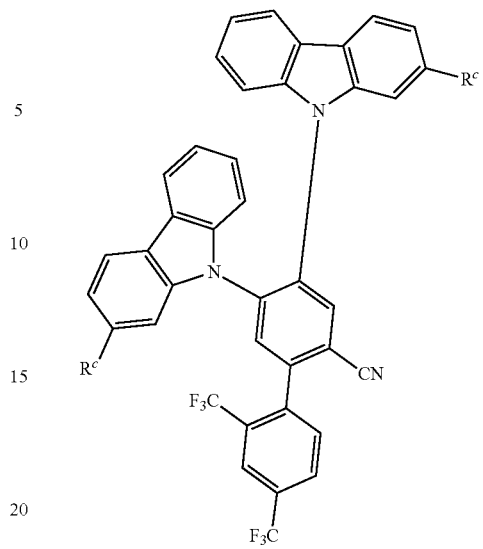

Formula VIId wherein the abovementioned definitions apply.

In a further embodiment, the organic molecules according to the invention have a structure of Formula VIIe:

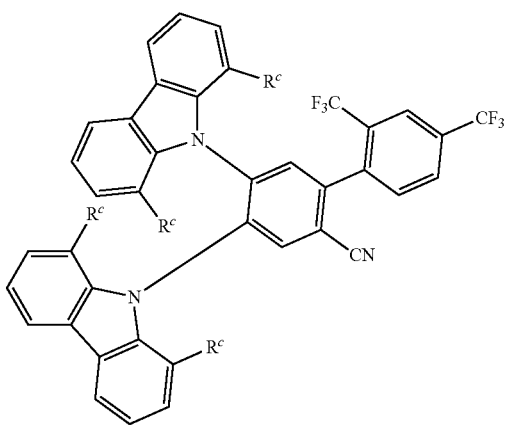

Formula VIIe wherein the abovementioned definitions apply.

In a further embodiment, the organic molecules according to the invention have a structure of Formula VIIf:

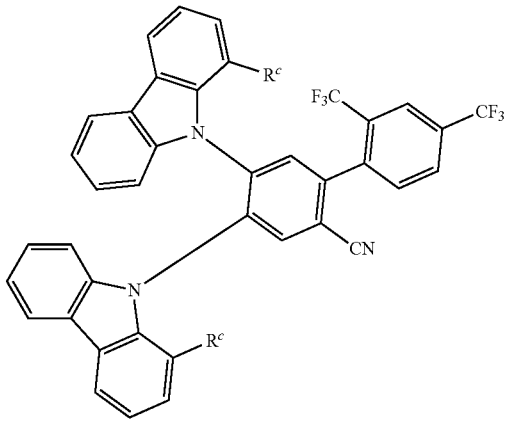

Formula VIIf wherein the abovementioned definitions apply.

In a further embodiment, the organic molecules according to the invention have a structure of Formula VIIg:

Formula VIIg
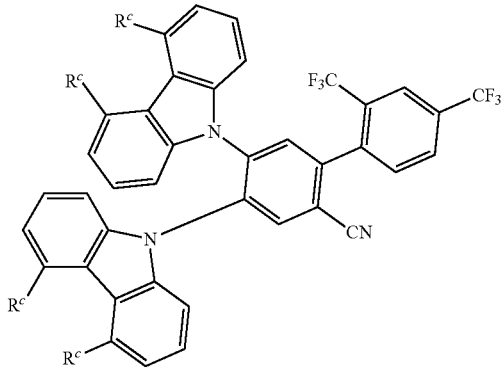

wherein the abovementioned definitions apply.

In a further embodiment, the organic molecules according to the invention have a structure of Formula VIIh:

Formula VIIh
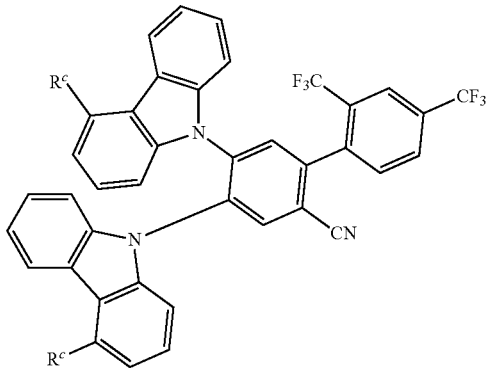

wherein the abovementioned definitions apply.

In one embodiment, the organic molecules according to the invention have a structure of Formula VIII:

Formula VIII
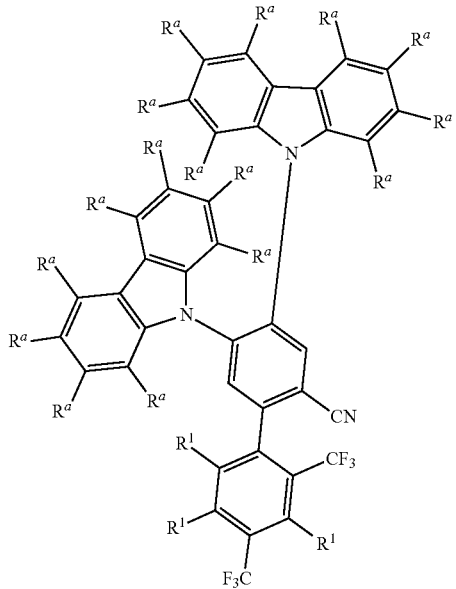

wherein the abovementioned definitions apply.

In one embodiment, in each occurrence $R^c$ is independently selected from the group consisting of Me, $^i$Pr, $^t$Bu, Ph, which can in each case be substituted with one or more radicals selected from Me, $^i$Pr, $^t$Bu, CN, $CF_3$ or Ph, and carbazolyl, which can in each case be substituted with one or more radicals selected from Me, $^i$Pr, $^t$Bu, or Ph.

In the context of this invention, an aryl group contains 6 to 60 aromatic ring atoms; a heteroaryl group contains 5 to 60 aromatic ring atoms, at least one of which represents a heteroatom. The heteroatoms are, in particular, N, O and/or S. In the event that other definitions, which differ from the stated definitions, for example with respect to the number of aromatic ring atoms or the contained heteroatoms, are specified in the description of specific embodiments of the invention, then these definitions apply.

An aryl group or heteroaryl group is understood to be a simple aromatic ring, i.e. benzene, or a simple heteroaromatic ring, for example pyridine, pyrimidine or thiophene, or a heteroaromatic polycyclic compound, for example phenanthrene, quinoline or carbazole. In the context of the present application, a condensed (annelated) aromatic or heteroaromatic polycyclic compound consists of two or more simple aromatic or heteroaromatic rings which are condensed with one another.

An aryl or heteroaryl group, which can be respectively substituted with the abovementioned radicals and which can be linked to the aromatic or heteroaromatic group via any desired positions, are in particular understood to be groups which are derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, isoquinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, napthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of said groups.

A cyclic alkyl, alkoxy or thioalkoxy group is understood here to be a monocyclic, a bicyclic or a polycyclic group.

Within the scope of the present invention, a $C_1$ to $C_{40}$ alkyl group, in which individual H atoms or $CH_2$ groups can also be substituted with the groups mentioned above, are understood to be, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, trifluoromethyl, pentafluorethyl, 2,2,2-trifluorethyl, 1,1-dimethyl-n-hex-1-yl-, 1,1-dimethyl-n-hept-1-yl-, 1,1-dimethyl-n-oct-1-yl-, 1,1-dimethyl-n-dec-1-yl-, 1,1-dimethyl-n-dodec-1-yl-, 1,1-dimethyl-n-tetradec-1-yl-, 1,1-dimethyl-n-hexadec-1-yl-, 1,1-dimethyl-n-octadec-1-yl-, 1,1-diethyln-hex-1-yl-, 1,1-diethyl-n-hept-1-yl-, 1,1-diethyl-n-oct-1-yl-, 1,1-diethyl-n-dec-1-yl-, 1,1-diethyl-n-dodec-1-yl-, 1,1-diethyl-n-tetradec-1-yl-, 1,1-diethyln-n-hexadec-1-yl-, 1,1-diethyl-n-octadec-1-yl-, 1-(n-propyl)-cyclohex-1-yl-, 1-(n-butyl)-cyclohex-1-yl-, 1-(n-hexyl)-cyclohex-1-yl-, 1-(n-octyl)-cyclohex-1-yl- and 1-(n-decyl)-cyclohex-1-yl. An alkenyl group is understood to be ethenyl, propenyl, butenyl, pentenyl, cyclopentenyl, hexenyl, cyclohexenyl, heptenyl, cycloheptenyl, octenyl, cyclooctenyl or cyclooctadienyl, for example. An alkinyl group is understood to be ethinyl, propinyl, butinyl, pentinyl, hexinyl, heptinyl or octinyl, for example. A $C_1$ to $C_{40}$ alkoxy group is understood to be methoxy, trifluoromethoxy, ethoxy, n-propoxy, i-propoxy, n-butoxy, i-butoxy, s-butoxy, t-butoxy or 2-methylbutoxy, for example.

One embodiment of the invention relates to organic molecules, which have an $\Delta E(S_1-T_1)$ value between the lowest excited singlet ($S_1$) state and the triplet ($T_1$) state below it that is no higher than 5000 cm$^{-1}$, in particular no higher than 3000 cm$^{-1}$, or no higher than 1500 cm$^{-1}$ or 1000 cm$^{-1}$ and/or an emission lifetime of at most 150 µs, in particular at most 100 µs, at most 50 µs, or at most 10 µs and/or a main emission band having a full width at half maximum of less than 0.55 eV, in particular less than 0.50 eV, less than 0.48 eV, or less than 0.45 eV.

The organic molecules in particular display an emission maximum between 420 and 500 nm, between 430 and 480 nm, in particular between 450 and 470 nm.

The molecules in particular have a "blue material index" (BMI), the quotient of the PLQY (in %) and their $CIE_y$ color coordinate of the light emitted by the molecule according to the invention, that is greater than 150, in particular greater than 200, greater than 250 or greater than 300.

In a further aspect, the invention relates to a method for producing an organic molecule according to the invention of the type described here (with a possible subsequent reaction), wherein a 2,4-bis(trifluoromethyl)-phenylboronic acid $R^1$-substituted in 3,5,6-position or a corresponding 2,4-bis (trifluoromethyl)-phenylboronate $R^2$-substituted in 3,5,6-position is used as the educt.

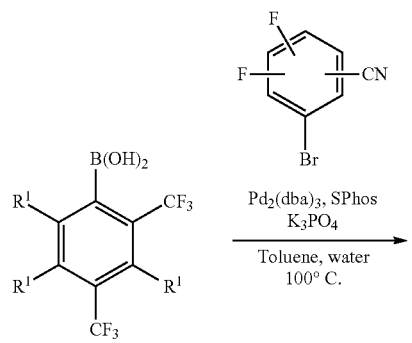

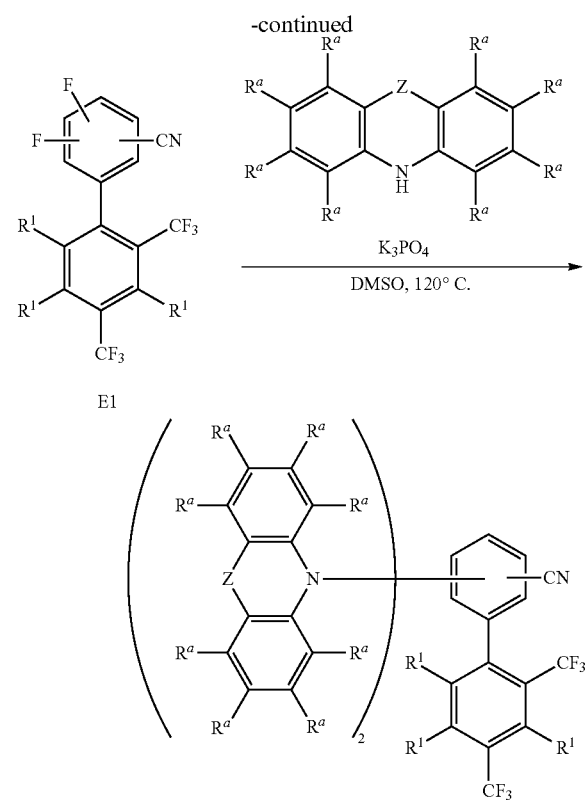

In the above schematic diagram, in one embodiment, the chemical group CN is replaced by $CF_3$.

In one embodiment, a 2,4-bis (trifluoromethyl) phenylboronic acid $R^1$-substituted in 3,5,6-position or a corresponding 2,4-bis (trifluoromethyl)-phenylboronate $R^1$-substituted in 3,5,6-position is reacted as starting material with a bromine-difluorobenzonitrile in a palladium-catalyzed cross-coupling reaction. According to the invention, 4-bromo-2,6-difluorobenzonitrile, 4-bromo-2,5-difluorobenzonitrile, 4-bromo-3,5-difluorobenzonitrile, 3-bromo-2,6-difluorobenzonitrile, 3-bromo-5,6-difluorobenzonitrile and 2-bromo-4,5-difluorobenzonitrile can be used here for example. The product is obtained by deprotonation of the corresponding amine and subsequent nucleophilic substitution of the two fluorine groups. To do this, a nitrogen heterocyclic compound is reacted with an educt E1 in the context of a nucleophilic aromatic substitution. Typical conditions include the use of a base, such as potassium phosphate tribasic or sodium hydride, in an aprotic polar solvent, such as dimethyl sulfoxide (DMSO) or N,N-dimethyl formamide (DMF).

In a further aspect, the invention relates to the use of the organic molecules as luminescent emitters or as host material in an organic optoelectronic device, in particular wherein the organic optoelectronic device is selected from the group consisting of:

organic light-emitting diodes (OLEDs), light-emitting electrochemical cells,

OLED sensors, in particular in gas and vapor sensors which are not hermetically shielded to the outside, organic diodes, organic solar cells, organic transistors, organic field-effect transistors,
organic lasers and
down-conversion elements.

In a further aspect, the invention relates to a composition having or consisting of:
(a) at least one organic molecule according to the invention, in particular as an emitter and/or host, and
(b) at least one, i.e. one or more emitter and/or host materials, that is or are different from the organic molecule according to the invention, and
(c) optionally one or more dyes and/or one or more organic solvents.

In one embodiment, the composition according to the invention consists of an organic molecule according to the invention and one or more host materials. In particular, the host material or materials possess triplet ($T_1$) and singlet ($S_1$) energy levels, which are energetically higher than the triplet ($T_1$) and singlet ($S_1$) energy levels of the organic molecule according to the invention. In one embodiment, in addition to the organic molecule according to the invention, the composition has an electron-dominant and a hole-dominant host material. The highest occupied orbital (HOMO) and the lowest unoccupied orbital (LUMO) of the hole-dominant host material are, in particular, energetically higher than that of the electron-dominant host material. The HOMO of the hole-dominant host material is energetically below the HOMO of the organic molecule according to the invention, while the LUMO of the electron-dominant host material is energetically above the LUMO of the organic molecule according to the invention. In order to avoid exciplex formation between emitter and host material or host materials, the materials should be selected such that the energy distances between the respective orbitals are small. The distance between the LUMO of the electron-dominant host material and the LUMO of the organic molecule according to the invention is, in particular, less than 0.5 eV, preferably less than 0.3 eV, even more preferably less than 0.2 eV. The distance between the HOMO of the hole-dominant host material and the HOMO of the organic molecule according to the invention is in particular less than 0.5 eV, preferably less than 0.3 eV, even more preferably less than 0.2 eV.

In a further aspect, the invention relates to an organic optoelectronic device which has an organic molecule according to the invention or a composition according to the invention. The organic optoelectronic device is, in particular, formed as a device selected from the group consisting of organic light-emitting diode (OLED); light-emitting electrochemical cell; OLED sensor, in particular gas and vapor sensors which are not hermetically shielded to the outside; organic diode; organic solar cell; organic transistor; organic field-effect transistor; organic laser and down-conversion element.

An organic optoelectronic device having
a substrate,
an anode and
a cathode, wherein the anode or the cathode are disposed on the substrate, and
at least one light-emitting layer, which is disposed between the anode and the cathode and which has an organic molecule according to the invention, represents a further embodiment of the invention.

In one embodiment, the optoelectronic device is an OLED. A typical OLED, for example, has the following layer structure:
1. Substrate (supporting material)
2. Anode
3. Hole injection layer (HIL)
4. Hole transport layer (HTL)
5. Electron blocking layer (EBL)
6. Emitting layer (EML)
7. Hole blocking layer (HBL)
8. Electron transport layer (ETL)
9. Electron injection layer (EIL)
10. Cathode.

The presence of specific layers is merely optional. Several of these layers can also coincide. Specific layers can also be present more than once in the component.

According to one embodiment, at least one electrode of the organic component is designed to be translucent. In this case, "translucent" describes a layer that is transmissive to visible light. The translucent layer can be clearly translucent, i.e. transparent, or at least partially light-absorbing and/or partially light-diffusing, so that the translucent layer can, for example, also be diffusely or milkily translucent. A layer referred to here as translucent is, in particular, designed to be as transparent as possible, so that, in particular, the absorption of light is as low as possible.

According to a further embodiment, the organic component, in particular an OLED, has an inverted structure. The inverted structure is characterized in that the cathode is located on the substrate and the other layers are disposed in a correspondingly inverted manner:
1. Substrate (supporting material)
2. Cathode
3. Electron injection layer (EIL)
4. Electron transport layer (ETL)
5. Hole blocking layer (HBL)
6. Emission layer or emitting layer (EML)
7. Electron blocking layer (EBL)
8. Hole transport layer (HTL)
9. Hole injection layer (HIL)
10. Anode The presence of specific layers is merely optional. Several of these layers can also coincide. Specific layers can also be present more than once in the component.

In one embodiment, in the inverted OLED, the anode layer of the typical structure e.g. an ITO layer (indium tin oxide), is connected as the cathode.

According to a further embodiment, the organic component, in particular an OLED, has a stacked structure. In this case, the individual OLEDs are arranged one above the other and not next to one another as usual. The production of mixed light can be made possible with the aid of a stacked structure. This structure can be used to produce white light, for example. To produce said white light, the entire visible spectrum is typically imaged by combining the emitted light of blue, green and red emitters. Furthermore, with practically the same efficiency and identical luminance, significantly longer lifetimes can be achieved in comparison to conventional OLEDs. A so-called charge generation layer (CGL) between two OLEDs is optionally used for the stacked structure. Said layer consists of an n-doped and a p-doped layer, wherein the n-doped layer is typically disposed closer to the anode.

In one embodiment—a so-called tandem OLED—two or more emission layers occur between the anode and the cathode. In one embodiment, three emission layers are arranged one above the other, wherein one emission layer emits red light, one emission layer emits green light and one emission layer emits blue light, and additional charge generation, blocking or transport layers are optionally disposed between the individual emission layers. In a further embodiment, the respective emission layers are disposed directly adjacent to one another. In another embodiment, one respective charge generation layer is situated between the emission layers. Emission layers that are directly adjacent to one another and emission layers that are separated by charge generation layers can furthermore be combined in an OLED.

An encapsulation arrangement can furthermore be disposed above the electrodes and the organic layers as well. The encapsulation arrangement can, for example, be designed in the form of a glass cover or in the form of a thin-film encapsulation arrangement.

The supporting material of the optoelectronic device can, for example, be glass, quartz, plastic, metal, a silicon wafer or any other suitable solid or flexible, optionally transparent material. The supporting material can, for example, have one or more materials in the form of a layer, a film, a plate or a laminate.

Transparent conductive metal oxides such as, for example, ITO (indium tin oxide), zinc oxide, tin oxide, cadmium oxide, titanium oxide, indium oxide or aluminum zinc oxide (AZO), $Zn_2SnO_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides, for example, can be used as the anode of the optoelectronic device.

PEDOT:PSS (poly-3,4-ethylenedioxythiophene:polystyrene sulfonic acid), PEDOT (poly-3,4-ethylenedioxythiophene), m-MTDATA (4,4',4"-tris[phenyl(m-tolyl)amino]triphenylamine), Spiro-TAD (2,2',7,7'-tetrakis(N,N-diphenylamino)-9,9-spirobifluorene), DNTPD (4,4'-bis[N-[4-{N,N-bis(3-methyl-phenyl)amino}phenyl]-N-phenylamino]biphenyl), NPB (N,N'-bis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzene), MeO-TPD (N,N,N',N'-tetrakis(4-methoxyphenyl)benzene), HAT-CN (1,4,5,8,9,11-hexaazatriphenylene-hexacarbonitrile) or Spiro-NPD (N,N'-diphenyl-N,N'-bis-(1-naphthyl)-9,9'-spirobifluorene-2,7-diamine), for example, are suitable materials for an HIL. The layer thickness is 10-80 nm, for example. Small molecules (e.g. copper phthalocyanine (CuPc e.g. 10 nm thick)) or metal oxides, such as $MoO_3$, $V_2O_5$, can also be used.

Tertiary amines, carbazole derivatives, polyethylenedioxythiophene doped with polystyrene sulfonic acid, polyaniline poly-TPD (poly(4-butylphenyl-diphenyl-amine)) doped with camphorsulfonic acid, [alpha]-NPD (poly(4-butylphenyl-diphenyl-amine)), TAPC (4,4'-cyclohexylidene-bis[N,N-bis(4-methylphenyl)benzenamine]), TCTA (tris(4-carbazoyl-9-ylphenyl)amine), 2-TNATA (4,4',4"-tris[2-naphthyl(phenyl)amino]triphenylamine), Spiro-TAD, DNTPD, NPB, NPNPB, MeO-TPD, HAT-CN or TrisPcz (9,9'-diphenyl-6-(9-phenyl-9H-carbazole-3-yl)-9H,9'H-3,3'-bicarbazole) can be used as materials for an HTL. The layer thickness is 10 nm to 100 nm, for example.

The HTL can have a p-doped layer which has an inorganic or organic dopant in an organic hole transporting matrix. Transition metal oxides such as vanadium oxide, molybdenum oxide or tungsten oxide, for example, can be used as the inorganic dopant. Tetrafluorotetracyanoquinodimethane (F4-TCNQ), copper pentafluorobenzoate (Cu(I)pFBz) or transition metal complexes can, for example, be used as the organic dopants. The layer thickness is 10 nm to 100 nm, for example.

MCP (1,3-bis(carbazole-9-yl)benzene), TCTA, 2-TNATA, mCBP (3,3-Di(9H-carbazole-9-yl)biphenyl), tris-Pcz (9,9'-diphenyl-6-(9-phenyl-9H-carbazole-3-yl)-9H,9'H-3,3'-bicarbazole), CzSi (9-(4-tert-butylphenyl)-3,6-bis(triphenylsilyl)-9H-carbazole) or DCB (N,N'-dicarbazolyl-1,4-dimethylbenzene) can, for example, be used as the materials of an electron blocking layer. The layer thickness is 10 nm to 50 nm, for example.

The emitter layer EML or emission layer consists of or contains emitter material or a mixture having at least two emitter materials and optionally one or more host materials. Suitable host materials are, for example, mCP, TCTA, 2-TNATA, mCBP, CBP (4,4'-Bis-(N-carbazolyl)-biphenyl), Sif87 (dibenzo[b,d]thiophene-2-yltriphenylsilane), Sif88 (dibenzo[b,d]thiophene-2-yl)diphenylsilane), 9-[3-(dibenzofuran-2-yl)phenyl]-9H-carbazole, 9-[3-(dibenzofuran-2-yl)phenyl]-9H-carbazole, 9-[3-(dibenzothiophene-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) TST (2,4,6-tris(9,9'-spirobifluorene-2-yl)-1,3,5-triazine) and/or DPEPO (Bis[2-((oxo)diphenylphosphino)phenyl]ether). In one embodiment, the EML contains 50-80 wt %, preferably 60-75 wt % of a host material selected from the group consisting of CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophene-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole; 10-45 wt %, preferably 15-30 wt % T2T and 5-40 wt %, preferably 10-30 wt. %, of an organic molecule according to the invention as the emitter. The common matrix materials, such as CBP, are suitable for emitter material emitting in the green or in the red range or for a mixture having at least two emitter materials. UHG matrix materials (ultra-high energy gap materials) (see, for example, M. E. Thompson et al, Chem. Mater. 2004, 16, 4743) or other so-called wide-gap matrix materials can be used for emitter material emitting in the blue range or a mixture having at least two emitter materials. The layer thickness is 10 nm to 250 nm, for example.

The hole blocking layer HBL can, for example, have BCP (2,9-dimethyl-4,7-diphenyl-1,10-phenanthroline=bathocuproine), bis-(2-methyl-8-hydroxyquinolinato)-(4-phenylphenolato)-aluminum(III) (BAlq), Nbphen (2,9-bis(naphthalene-2-yl)-4,7-diphenyl-1,10-phenanthroline), Alq3 (aluminum-tris(8-hydroxyquinoline)), T2T, TSPO1 (diphenyl-4-triphenylsilyl-phenylphosphine oxide) or TCB/TCP (1,3,5-tris(N-carbazolyl)benzene/1,3,5-tris(carbazole)-9-yl)benzene). The layer thickness is 10 nm to 50 nm, for example.

The electron transport layer ETL can, for example, have materials on the basis of $AlQ_3$, TSPO1, Nbphen, BPyTP2 (2,7-di(2,2'-bipyridine-5-yl)triphenyl)), Sif87, Sif88, BmPyPhB (1,3-bis[3,5-di(pyridine-3-yl)phenyl]benzene) or BTB (4,4'-bis-[2-(4,6-diphenyl-1,3,5-triazinyl)]-1,1'-biphenyl). The layer thickness is 10 nm to 200 nm, for example.

CsF, LiF, 8-hydroxyquinolinolatolithium (Liq), $Li_2O$, $BaF_2$, MgO or NaF can be used as materials for a thin electron injection layer EIL.

Metals or alloys, for example Al, Al>AlF, Ag, Pt, Au, Mg, Ag:Mg, can be used as materials of the cathode layer. Typical layer thicknesses are 100 nm to 200 nm. In particular, one or more metals are used, which are stable when exposed to air and/or which are self-passivating, for example by forming a thin protective oxide layer.

Aluminum oxide, vanadium oxide, zinc oxide, zirconium oxide, titanium oxide, hafnium oxide, lanthanum oxide, tantalum oxide, for example, are suitable materials for encapsulation.

In one embodiment of the organic optoelectronic device according to the invention, the organic molecule according to the invention is used as the emission material in a light-emitting layer EML, wherein it is used either as a pure layer or in combination with one or more host materials.

One embodiment of the invention relates to organic optoelectronic devices which have an external quantum efficiency (EQE) at 1000 cd/m² greater than 5%, in particular greater than 8%, in particular greater than 10%, or greater than 13%, or greater than 16% and in particular greater than 20% and/or an emission maximum at a wavelength between 420 nm and 500 nm, in particular between 430 nm and 490 nm, or between 440 nm and 480 nm, and in particular between 450 nm and 470 nm and/or an LT80 value at 500 cd/m² greater than 30 h, in particular greater than 70 h, or greater than 100 h, or greater than 150 h and in particular greater than 200 h.

In another embodiment, the mass fraction of the organic molecule according to the invention of the light-emitting layer EML in a light-emitting layer in devices emitting optical light, in particular in OLEDs, is between 1% and 80%. In one embodiment of the organic optoelectronic device according to the invention, the light-emitting layer is disposed on a substrate, wherein an anode and a cathode are preferably disposed on the substrate and the light-emitting layer is disposed between the anode and the cathode.

In one embodiment, the light-emitting layer can have only one organic molecule according to the invention in 100% concentration, wherein the anode and the cathode are disposed on the substrate, and the light-emitting layer is disposed between the anode and the cathode.

In one embodiment of the organic optoelectronic device according to the invention, a hole- and electron-injecting layer is disposed between the anode and the cathode, and a hole- and electron-transporting layer is disposed between the hole- and electron-injecting layer, and the light-emitting layer is disposed between the hole- and electron-transporting layer.

In another embodiment of the invention, the organic optoelectronic device has: a substrate, an anode, a cathode and at least one respective hole- and electron-injecting layer, and at least one respective hole- and electron-transporting layer, and at least one light-emitting layer, which has the organic molecule according to the invention and one or more host materials, the triplet (T₁) and singlet (S₁) energy levels of which are energetically higher than the triplet (T₁) and singlet (S₁) energy levels of the organic molecule, wherein the anode and the cathode are disposed on the substrate, and the hole- and electron-injecting layer is disposed between the anode and the cathode, and the hole- and electron-transporting layer is disposed between the hole- and electron-injecting layer, and the light-emitting layer is disposed between the hole- and electron-transporting layer.

In a further aspect, the invention relates to a method for producing an optoelectronic component. To do this, an organic molecule according to the invention is used.

In one embodiment, the production method comprises the processing of the organic molecule according to the invention by means of a vacuum evaporation method or from a solution.

The invention also relates to a method for producing an optoelectronic device according to the invention, in which at least one layer of the optoelectronic device
  is coated using a sublimation process,
  is coated using an OVPD (organic vapor phase deposition) process,
  is coated using a carrier-gas sublimation, and/or
  is produced from solution or using a pressure process.

Known methods are used for the production of the optoelectronic device according to the invention. The layers are generally disposed individually onto a suitable substrate in successive deposition method steps. The common methods, such as thermal evaporation, chemical vapor deposition (CVD), physical vapor deposition (PVD) can be used for the vapor deposition. For active matrix OLED (AMOLED) displays, deposition takes place onto an AMOLED backplane as the substrate.

Layers can alternatively be deposited from solutions or dispersions in suitable solvents. Spin coating, dip coating and jet pressure methods are examples of suitable coating methods. According to the invention, the individual layers can be produced via the same as well as via respective different coating methods.

EXAMPLES

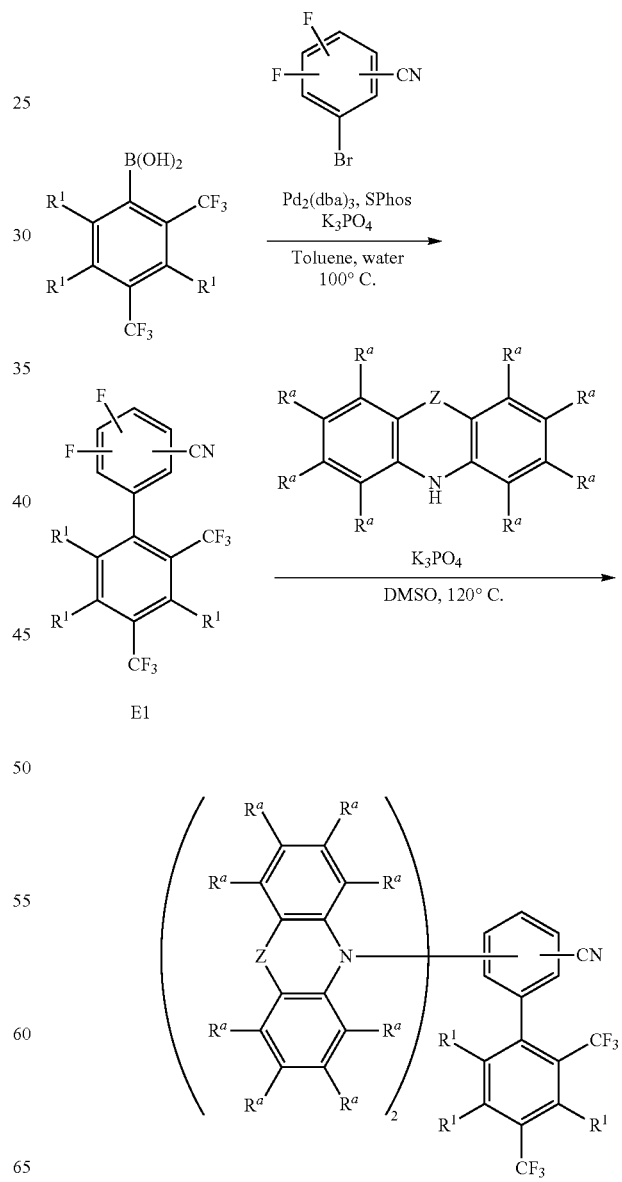

General Synthesis Specification AAV1:

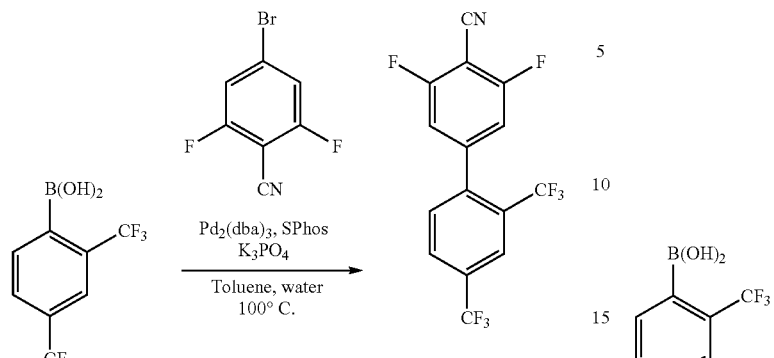

2,4-bis(trifluoromethyl)-phenyl boronic acid (1.50 equivalent), 4-bromo-2,6-difluorobenzonitrile (1.00 equivalent), $Pd_2(dba)_3$ (0.02 equivalent), 2-dicyclohexylphosphino-2',6'-dimethoxybiphenyl)SPhos( )0.08 equivalent (and tribasic potassium phosphate) 2.50 equivalent (toluene a in nitrogen under stirred are/mixture water) ratio 20:1 (at 100° C. for 16 hours. The reaction mixture is then added to saturated sodium chloride solution and extracted two times with dichloromethane. The combined organic phases are washed with saturated sodium chloride solution, dried over $MgSO_4$, and the solvent is removed. The product is filtered through a little silica gel and then recrystallized. The product is obtained as a solid.

According to the invention, a corresponding boronic acid ester can be used instead of a boronic acid.

General Synthesis Specification AAV2:

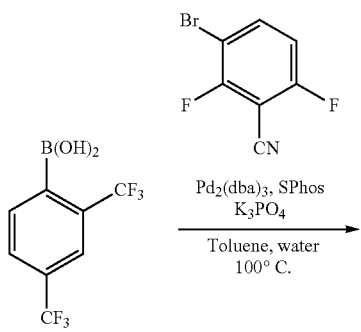

The synthesis of Z2 is analogous to AAV1, wherein 2,4-bis (trifluoromethyl) phenyl boronic acid is reacted with 3-bromo-2,6-difluorobenzonitrile.

General Synthesis Specification AAV3:

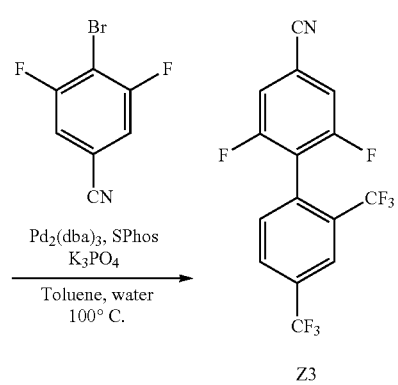

The synthesis of Z3 is analogous to AAV1, wherein 2,4-bis (trifluoromethyl) phenyl boronic acid is reacted with 4-bromo-3,5-difluorobenzonitrile.

General Synthesis Specification AAV4:

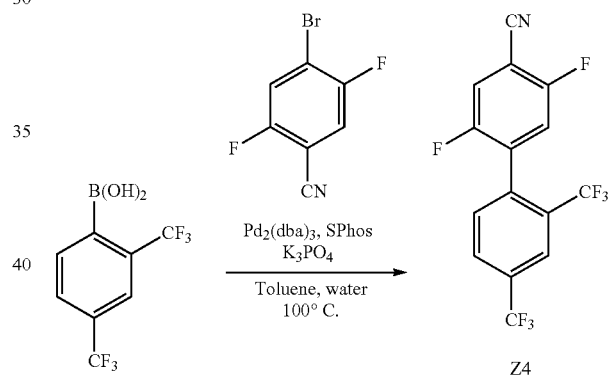

The synthesis of Z4 is analogous to AAV1, wherein 2,4-bis (trifluoromethyl) phenyl boronic acid is reacted with 4-bromo-2,5-difluorobenzonitrile.

General Synthesis Specification AAV5:

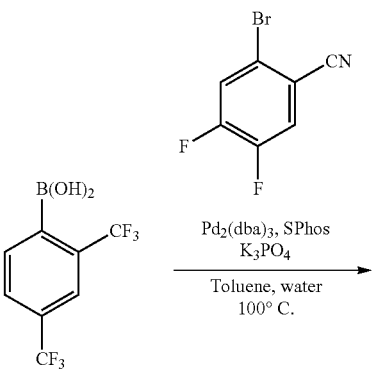

-continued
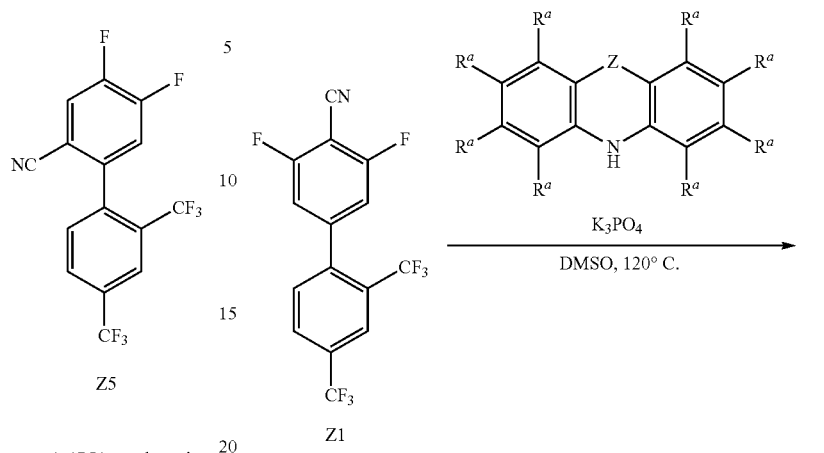
Z5
The synthesis of Z5 is analogous to AAV1, wherein 2,4-bis (trifluoromethyl) phenylboronic acid is reacted with 2-bromo-4,5-difluorobenzonitrile.
General Synthesis Specification AAV6:
Z6
The synthesis of Z6 is analogous to AAV1, wherein 2,4-bis (trifluoromethyl) phenylboronic acid is reacted with 3-bromo-5,6-difluorobenzonitrile.
General Synthesis Specification AAV7:
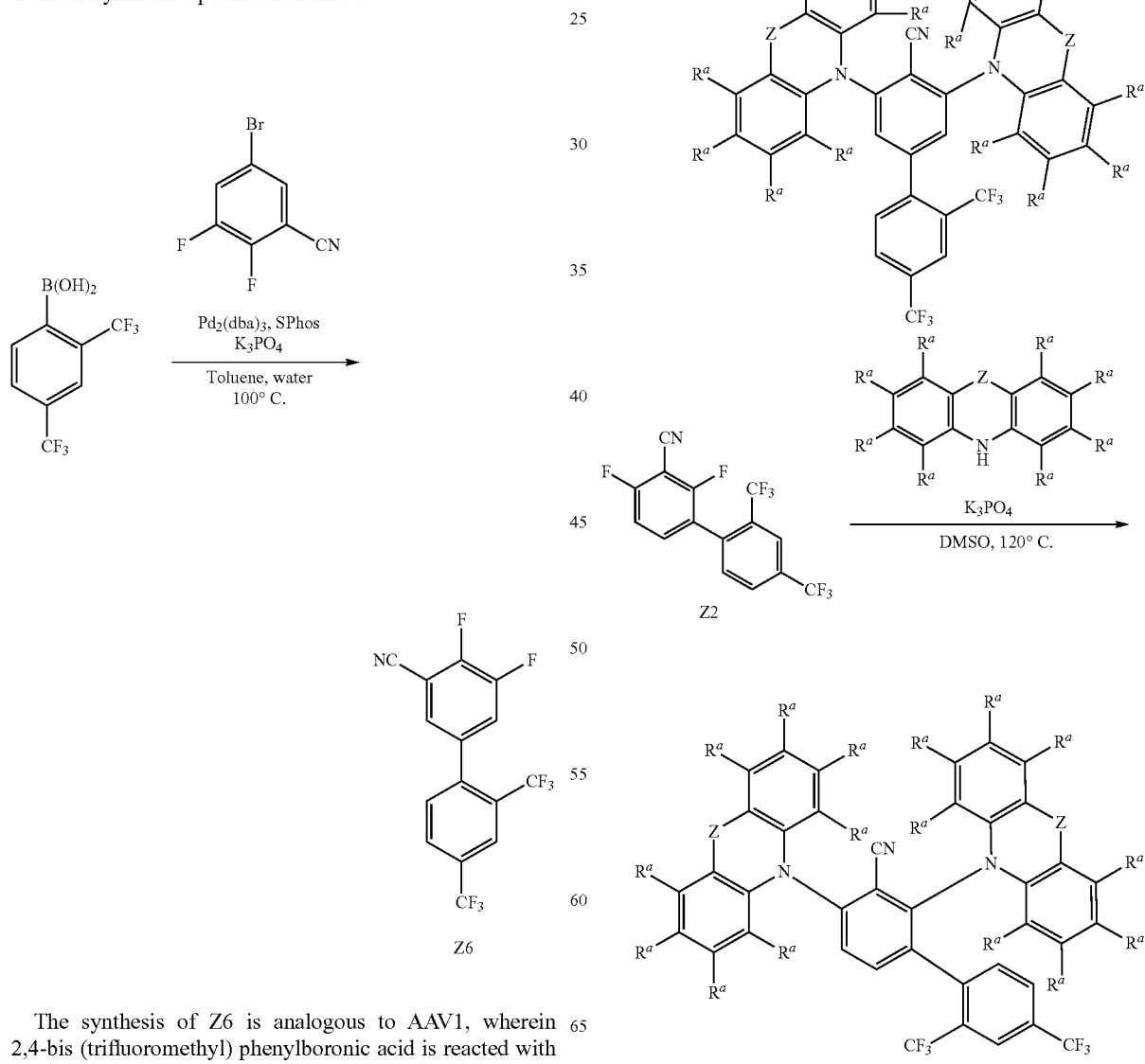

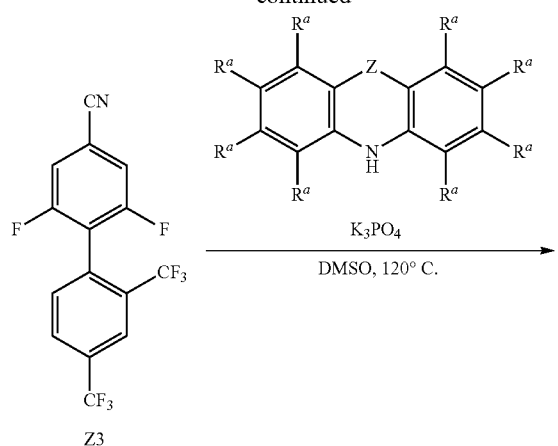
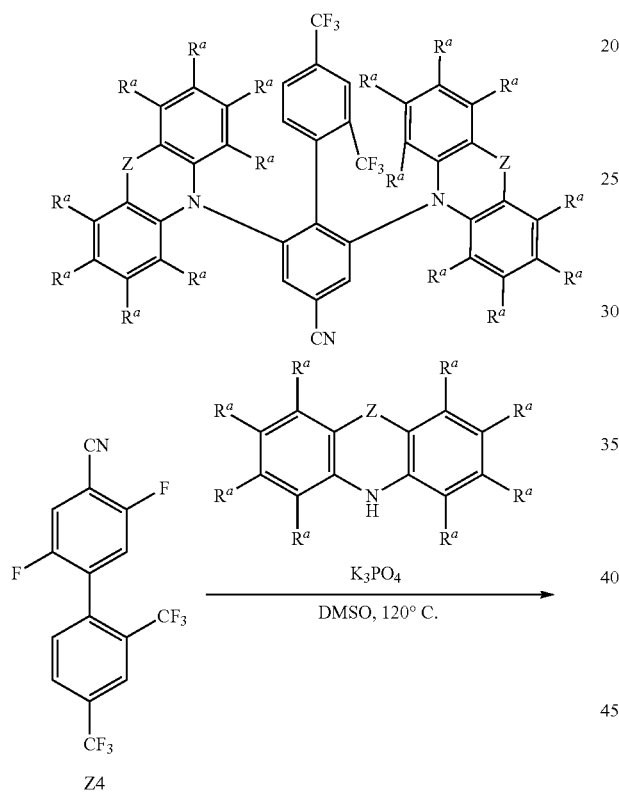
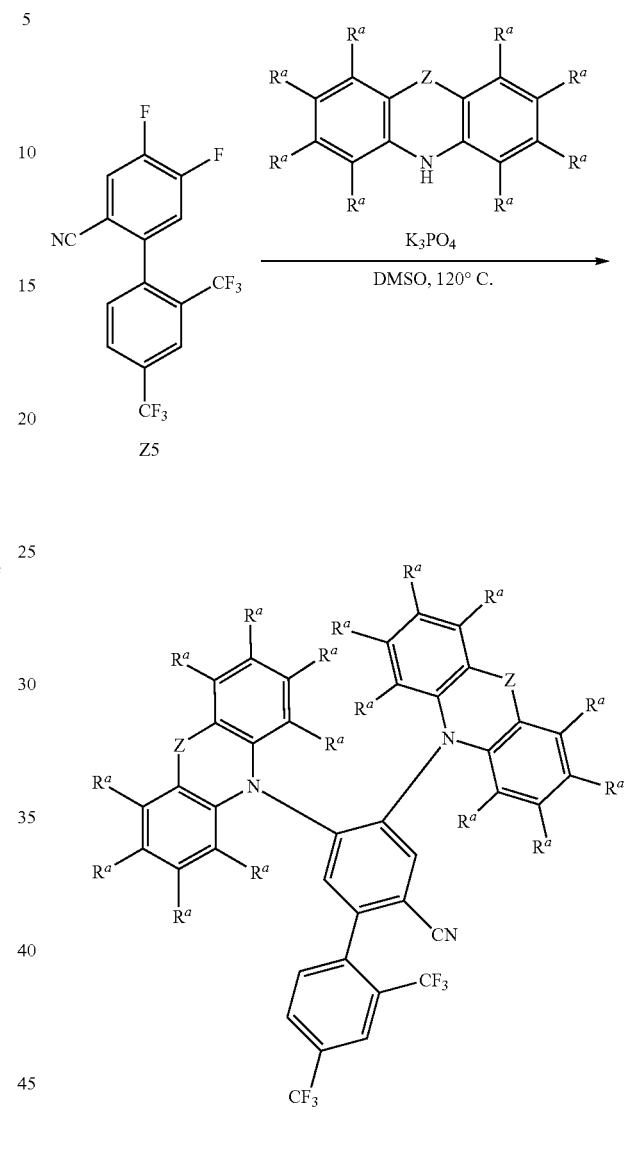
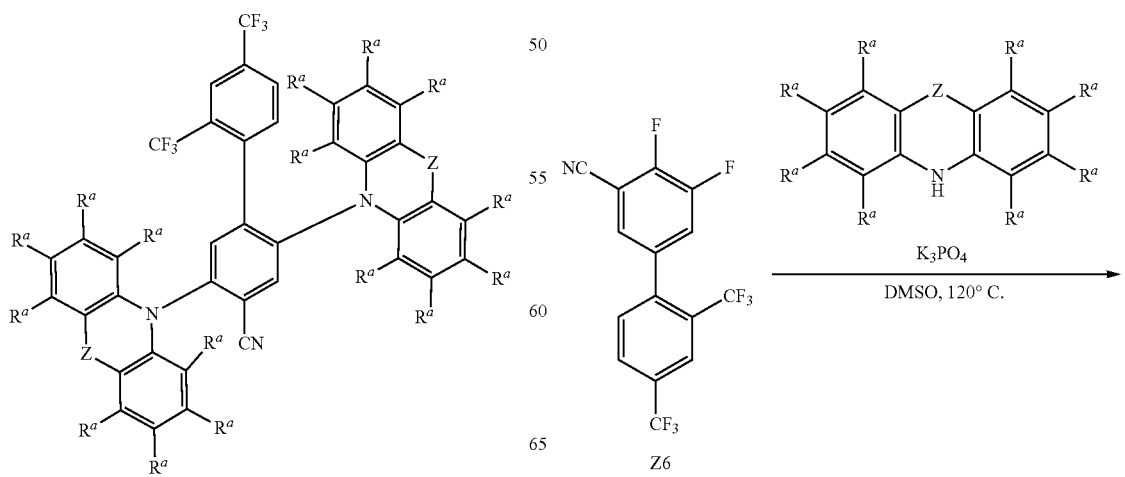

-continued

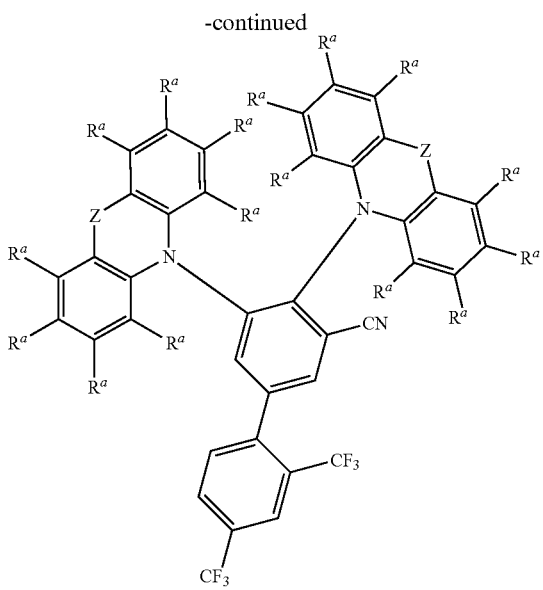

Z1, Z2, Z3, Z4, Z5 or Z6 (respectively 1.00 equivalent), the corresponding donor molecule D-H (2.00 equivalent) and potassium phosphate tribasic (4.00 equivalent) are suspended in DMSO under nitrogen and stirred at 110° C. (16 h). The reaction mixture is then added to saturated sodium chloride solution and extracted three times with dichloromethane. The combined organic phases are washed twice with saturated sodium chloride solution, dried over magnesium sulfate, and the solvent is subsequently removed. Lastly, the raw product was purified by recrystallization out of toluene or by means of flash chromatography. The product is obtained as a solid.

D-H in particular corresponds to a 3,6-substituted carbazole (e.g. 3,6-dimethylcarbazole, 3,6-diphenylcarbazole, 3,6-di-tert-butylcarbazole), a 2,7-substituted carbazole (e.g. 2,7-dimethylcarbazole, 2,7-diphenylcarbazole, 2,7-di-tert-butylcarbazole), an 1,8-substituted carbazole (e.g. 1,8-dimethylcarbazole, 1,8-diphenylcarbazole, 1,8-di-tert-butylcarbazole), a 1-substituted carbazole (e.g. 1-methylcarbazole, 1-phenylcarbazole, 1-tert-butylcarbazole), a 2-substituted carbazole (e.g. 2-methylcarbazole, 2-phenylcarbazole, 2-tert-butylcarbazole) or a 3-substituted carbazole (e.g. 3-methylcarbazole, 3-phenylcarbazole, 3-tert-butylcarbazole). In particular, a halocarbazole, in particular 3-bromocarbazole or 3,6-dibromocarbazole, can be used as DH, which in a subsequent reaction for example in a corresponding boronic acid, for example (carbazol-3-yl) boronic acid, or in a corresponding boronic acid ester, for example (carbazole 3-yl) boronic acid ester is reacted, for example, by reaction with bis (pinacol) boronic acid ester (CAS No. 73183-34-3). In a subsequent reaction, one or more radicals $R^a$, which is used as halogenated eductR$^a$-Hal, preferably $R^a$—Cl and $R^a$—Br, is introduced via a coupling reaction in place of the boronic acid group or the boronic acid ester group. Alternatively, one or more radicals $R^a$ can be introduced by reaction of the previously introduced halocarbazole with boronic acids of the radical $R^a$ ($R^a$—B(OH)$_2$) or corresponding boronic acid esters are introduced.

Photophysical Measurements
Pretreatment of Optical Glasses

All glasses (cuvettes and substrates made of quartz glass, diameter: 1 cm) were cleaned after every use: washed three times in each case with dichloromethane, acetone, ethanol, demineralized water, placed in 5% Hellmanex solution for 24 h, thoroughly rinsed with demineralized water. The optical glasses were dried by blowing nitrogen over them.
Sample Preparation, Film: Spin Coating
Device: Spin150, SPS Euro.

The sample concentration was equivalent to 10 mg/ml, prepared in toluene or chlorobenzene. Program: 1) 3 s at 400 rpm; 2) 20 s at 1000 rpm at 1000 rpm/s. 3) 10 s at 4000 rpm at 1000 rpm/s. After coating, the films were dried on a LHG precision heating plate for 1 min at 70° C. in air.
Photoluminescence Spectroscopy and TCSPC Steady-state emission spectroscopy was carried out using a fluorescence spectrometer of the Horiba Scientific company, Model Fluoromax-4, equipped with a 150 W xenon arc lamp, excitation and emission monochromators and a Hamamatsu R928 photomultiplier tube, as well as a "Time-Correlated Single Photon Counting" (TCSPC) option. The emission and excitation spectra were corrected by means of standard correction curves.

The emission decay times were likewise measured on this system, using the TCSPC method with the FM-2013 accessories and a TCSPC hub of the Horiba Yvon Jobin company.
Excitation sources:

NanoLED 370 (wavelength: 371 nm, pulse duration: 1.1 ns)

NanoLED 290 (wavelength: 294 nm, pulse duration: <1 ns)

SpectraLED 310 (wavelength: 314 nm)

SpectraLED 355 (wavelength: 355 nm).

The analysis (exponential fitting) was performed using the DataStation software package and the DAS6 analysis software. The fit was specified with the aid of the Chi-square method $$c^2 = \sum_{k=1}^{i} \frac{(e_i - o_i)^2}{e_i}$$

with $e_i$: Variable predicted by the fit and $o_i$: measured variable.
Quantum Efficiency Determination The measurement of the photoluminescence quantum yield (PLQY) was carried out by means of an Absolute PL Quantum Yield Measurement C9920-03G system of the company Hamamatsu Photonics. Said system consists of a 150 W xenon gas discharge lamp, automatically adjustable Czerny-Turner monochromators (250-950 nm) and an Ulbricht sphere with a high reflectance Spectralon coating (a Teflon derivative), which is connected via a fiber optic cable to a PMA-12 multichannel detector with a BT (back-thinned)-CCD chip having 1024×122 pixels (size 24×24 µm). The analysis of the quantum efficiency and the CIE coordinates was carried out using the software U6039-05 Version 3.6.0. The emission maximum is measured in nm, the quantum yield Φ is measured in % and the CIE color coordinates are stated as x, y values.

The photoluminescence quantum yield was determined according to the following protocol:
1) Implementation of quality assurance measures: Anthracene in ethanol at a known concentration serves as the reference material.
2) Determination of the excitation wavelength: The absorption maximum of the organic molecule was first determined and excited with said wavelength.

3) Implementation of the sample measurement:

The absolute quantum yield of degassed solutions and films was determined under a nitrogen atmosphere.

The calculation was performed within the system according to the following equation:

$$\Phi_{PL} = \frac{n_{photon}, \text{emitted}}{n_{photon}, \text{absorbed}} = \frac{\int \frac{\lambda}{hc}[Int_{emitted}^{sample}(\lambda) - Int_{absorbed}^{sample}(\lambda)]d\lambda}{\int \frac{\lambda}{hc}[Int_{emitted}^{reference}(\lambda) - Int_{absorbed}^{reference}(\lambda)]d\lambda}$$

with the photon number $n_{photon}$ and the intensity Int.

Production and Characterization of Organic Electroluminescence Devices from the Gas Phase With the organic molecules according to the invention, OLED devices can be produced by means of vacuum sublimation techniques. If a layer contains multiple components, the ratio of said components is stated in percent by weight.

These not yet optimized OLEDs can be characterized in the usual manner. To do this, the electroluminescence spectra, the external quantum efficiency (measured in %) as a function of the brightness and calculated from the light detected by the photodiode, and the current are recorded. The lifetime of the OLEDs can be determined from the time profile of the electroluminescence spectra. The indicated LT50 value corresponds to the time at which the luminance has fallen to 50% of the starting value. The LT70 value analogously corresponds to the time at which the luminance has fallen to 70% of the starting value.

The indicated values are obtained from the average of the various pixels of an OLED. The spectra depicted in each case show a measurement series of a pixel.

HPLC-MS:

HPLC-MS spectroscopy was measured using an HPLC system of the company Agilent (1100 series) with a connected MS detector (Thermo LTQ XL). An Agilent Eclipse Plus C18 column with a particle size of 3.5 μm, a length of 150 mm and an inner diameter of 4.6 mm was used for the HPLC. This was carried out without a precolumn and at room temperature using the solvents acetonitrile, water and tetrahydrofuran in the following concentrations:

| Solvent A: | $H_2O$ (90%) | MeCN (10%) |
|---|---|---|
| Solvent B: | $H_2O$ (10%) | MeCN (90%) |
| Solvent C: | THF (100%) | |

An injection volume of 15 μL and a concentration of 10 μg/ml were used with the following gradient:

| Flow [ml/min] | Time [min] | A [%] | B [%] | C [%] | Pressure [Bar] |
|---|---|---|---|---|---|
| 0.3 | 0 | 80 | 20 | — | 115 |
| 0.3 | 5 | 80 | 20 | — | 115 |
| 0.3 | 14 | 0 | 90 | 10 | 65 |
| 0.3 | 25 | 0 | 90 | 10 | 65 |
| 0.3 | 26 | 80 | 20 | — | 115 |
| 0.3 | 33 | 80 | 20 | — | 115 |

The sample is ionized by means of APCI (Atmospheric Pressure Chemical Ionization).

Example 1

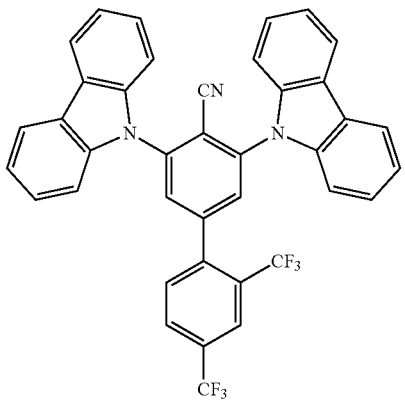 [SMILES: N#Cc1c(-n2c3ccccc3c3ccccc32)cc(-c2ccc(C(F)(F)F)cc2C(F)(F)F)cc1-n1c2ccccc2c2ccccc21]

Example 1 was produced in accordance with AAV1 (Yield 54%) and AAV7 (Yield 38%).

MS (HPLC-MS), m/z (retention time): 645, (6.80 min)

FIG. 1 shows the emission spectrum of Example 1 (10% in PMMA). The emission maximum is at 448 nm. The photoluminescence quantum yield (PLQY) is 85% and the full width at half maximum is 0.46 eV. The emission lifetime is 74 μs.

Example 2

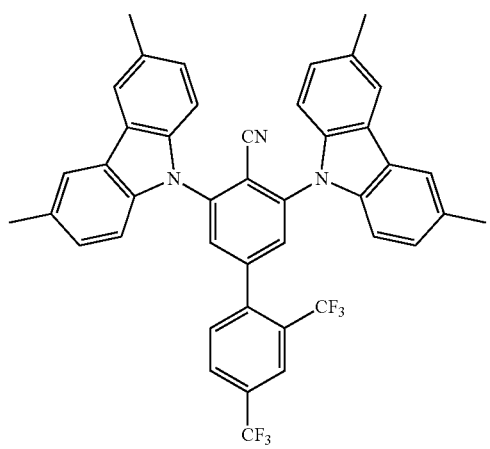

Example 2 was produced in accordance with AAV1 (Yield 54%) and AAV7 (Yield 79%).

MS (HPLC-MS), m/z (retention time): 702, (8.33 min)

Figure 2:
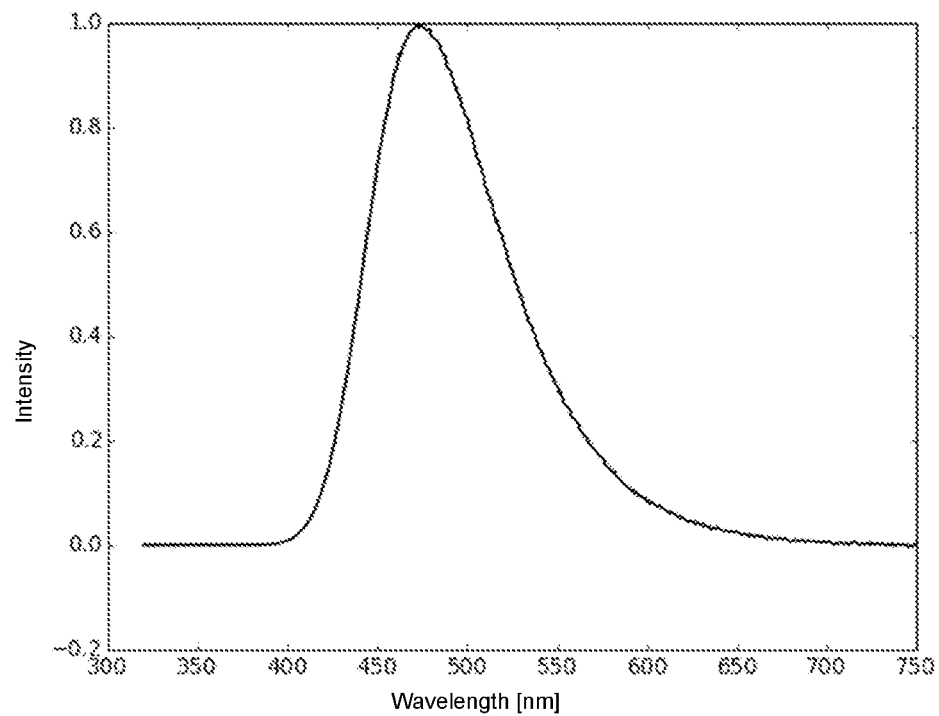
FIG. 2 is an emission spectrum of Example 2 (10% in PMMA).

FIG. 2 shows the emission spectrum of Example 2 (10% in PMMA). The emission maximum is at 474 nm. The photoluminescence quantum yield (PLQY) is 91% and the half-width is 0.46 eV. The emission lifetime is 7 μs.

Example 3

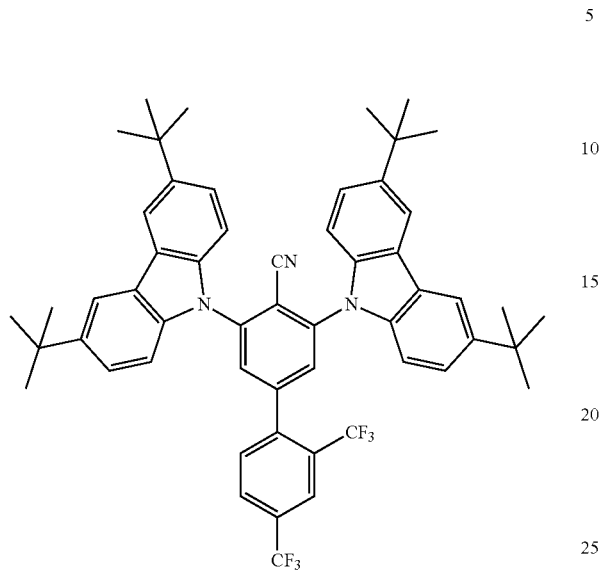

Figure 3:
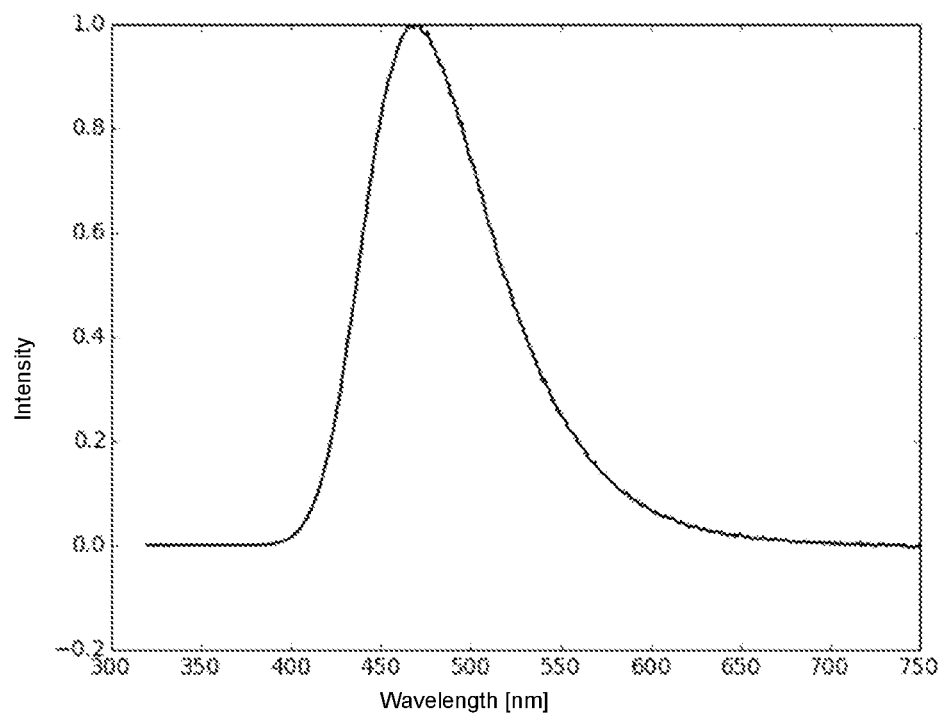
FIG. 3 is an emission spectrum of Example 3 (10% in PMMA).

Example 3 was produced in accordance with AAV1 (Yield 54%) and AAV7 (Yield 58%). FIG. 3 shows the emission spectrum of Example 3 (10% in PMMA). The emission maximum is at 469 nm. The photoluminescence quantum yield (PLQY) is 90% and the full width at half maximum is 0.46 eV. The emission lifetime is 9 μs.

Example 4

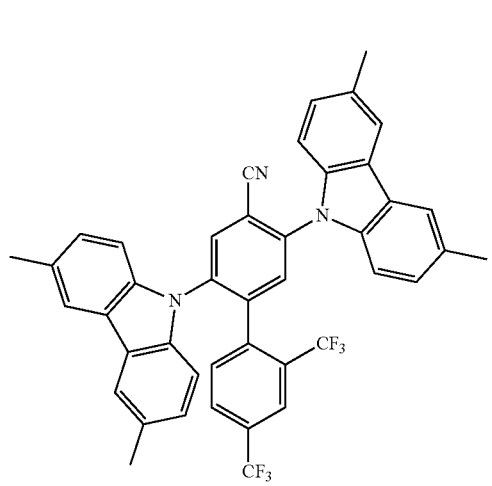

Example 4 was produced in accordance with AAV4 (Yield 25%) and AAV7.

Figure 4:
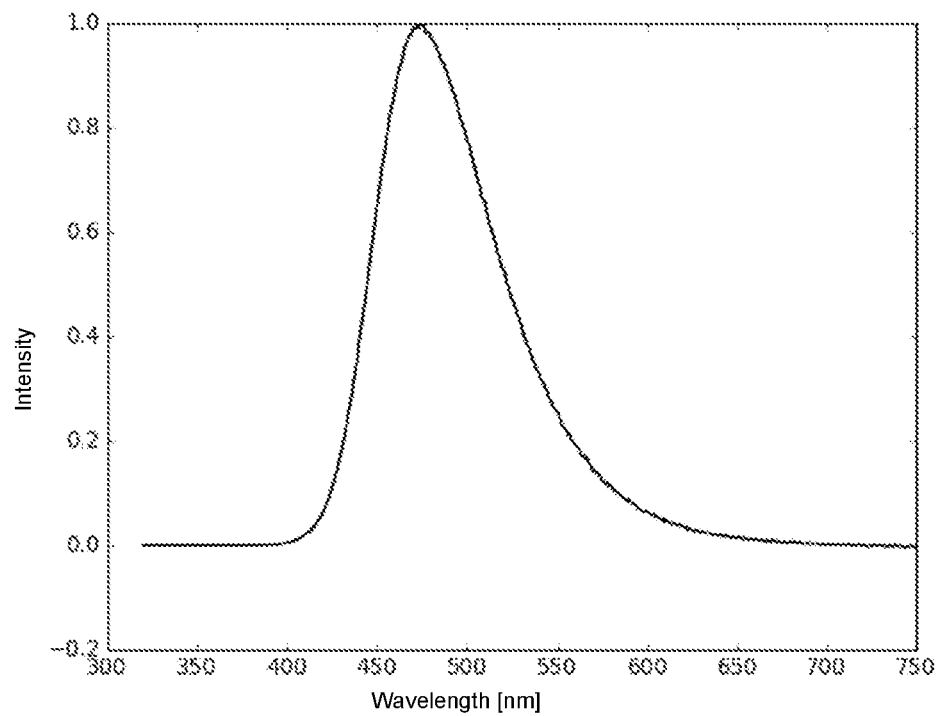
FIG. 4 is an emission spectrum of Example 4 (10% in PMMA).

FIG. 4 shows the emission spectrum of Example 4 (10% in PMMA). The emission maximum is at 475 nm. The photoluminescence quantum yield (PLQY) is 93% and the full width at half maximum is 0.42 eV.

Example 5

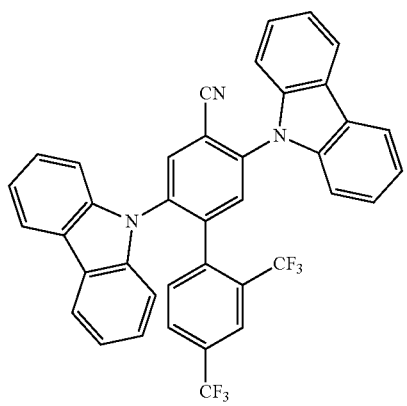 [SMILES: N#Cc1cc(-n2c3ccccc3c3ccccc32)c(-c2ccc(C(F)(F)F)cc2C(F)(F)F)cc1-n1c2ccccc2c2ccccc21]

Example 5 was produced according to AAV1 and AAV7.

Figure 5:
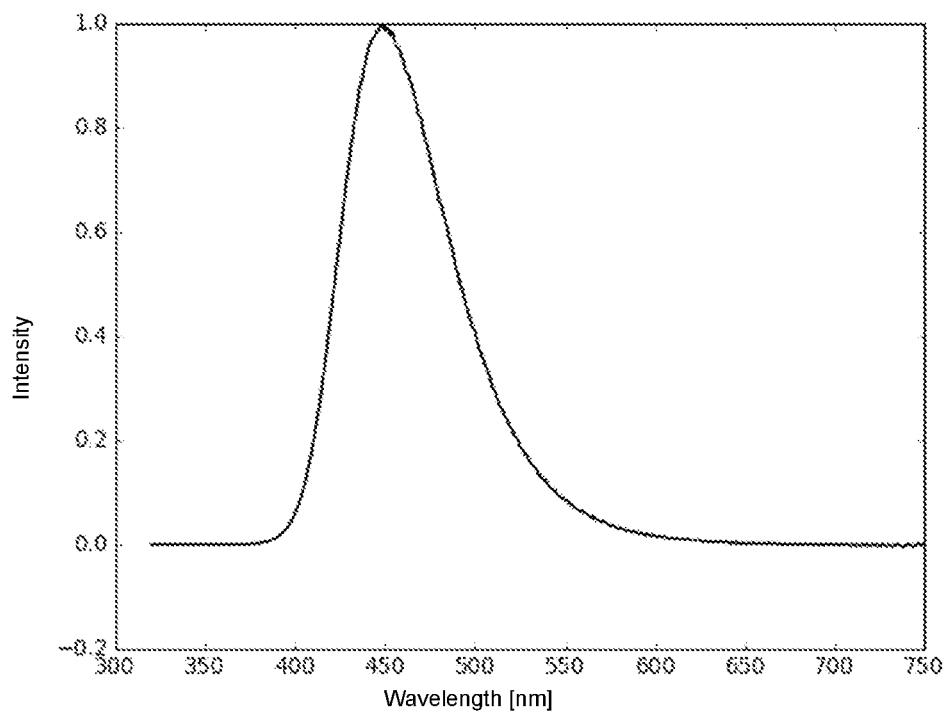
FIG. 5 is an emission spectrum of Example 5 (10% in PMMA).

FIG. 5 shows the emission spectrum of Example 5 (10% in PMMA). The emission maximum is at 449 nm. The photoluminescence quantum yield (PLQY) is 84% and the half-width is 0.42 eV.

Example 6

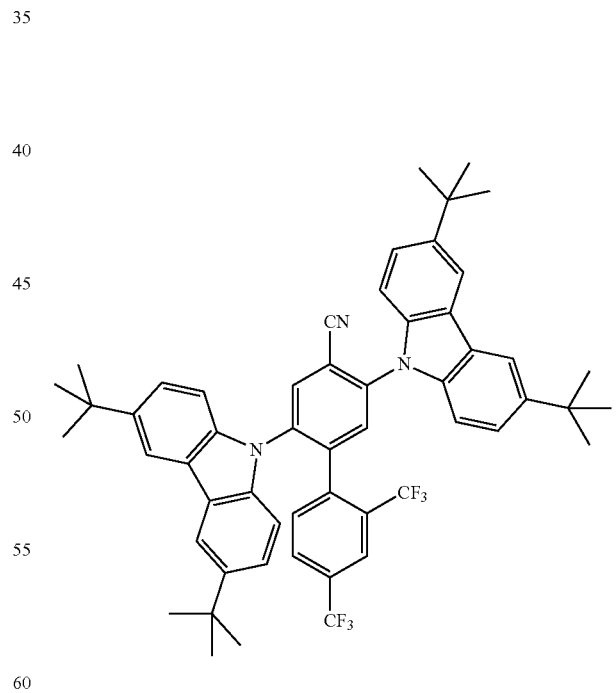

Example 6 was produced in accordance with AAV4 (Yield 63%) and AAV7.

Figure 6:
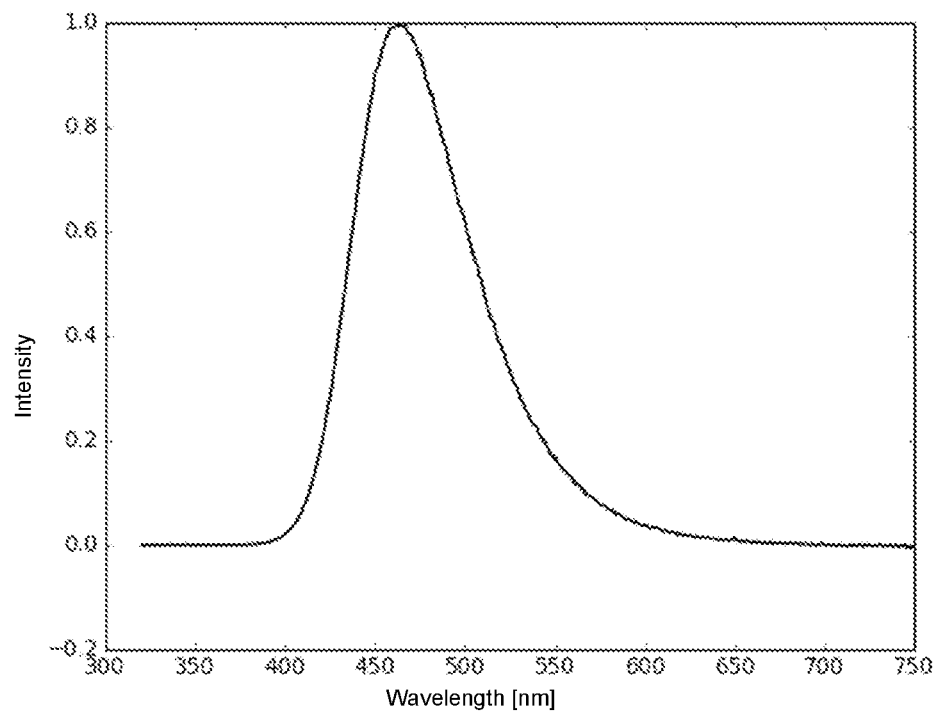
FIG. 6 is an emission spectrum of Example 6 (10% in PMMA).

FIG. 6 shows the emission spectrum of Example 6 (10% in PMMA). The emission maximum is at 463 nm. The photoluminescence quantum yield (PLQY) is 94% and the full width at half maximum is 0.46 eV.

Example 7

Example 7 was produced in accordance with AAV1 (Yield 54%) and AAV7.

Figure 7:
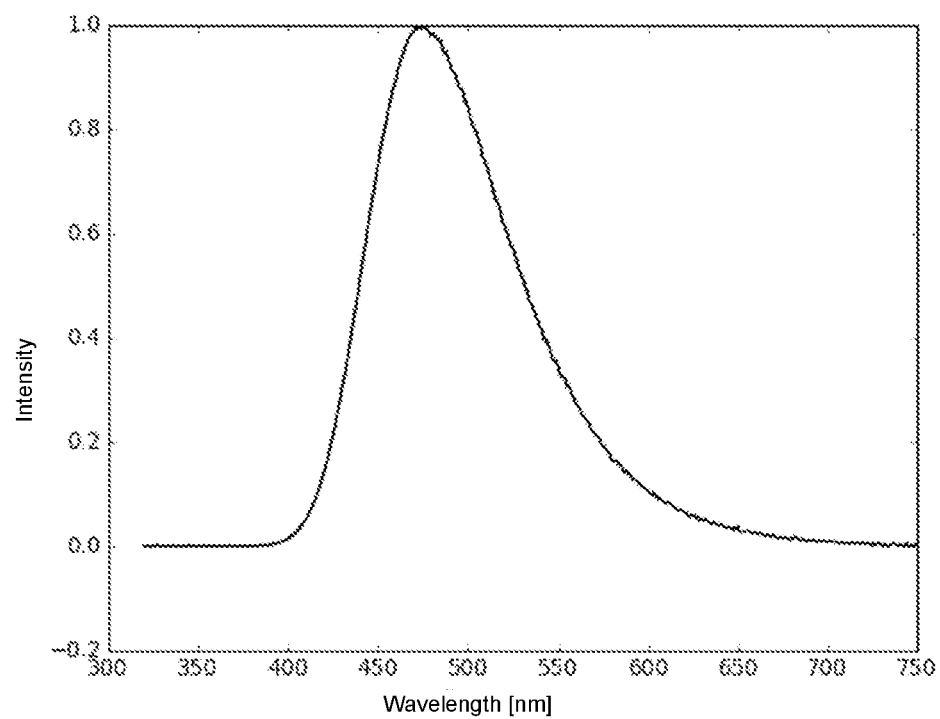
FIG. 7 is an emission spectrum of Example 7 (10% in PMMA).

FIG. 7 shows the emission spectrum of Example 7 (10% in PMMA). The emission maximum is at 475 nm. The photoluminescence quantum yield (PLQY) is 79% and the half-width is 0.49 eV. The emission lifetime is 6 μs.

Example 8

Example 8 was produced in accordance with AAV1 (Yield 54%) and AAV7.

Figure 8:
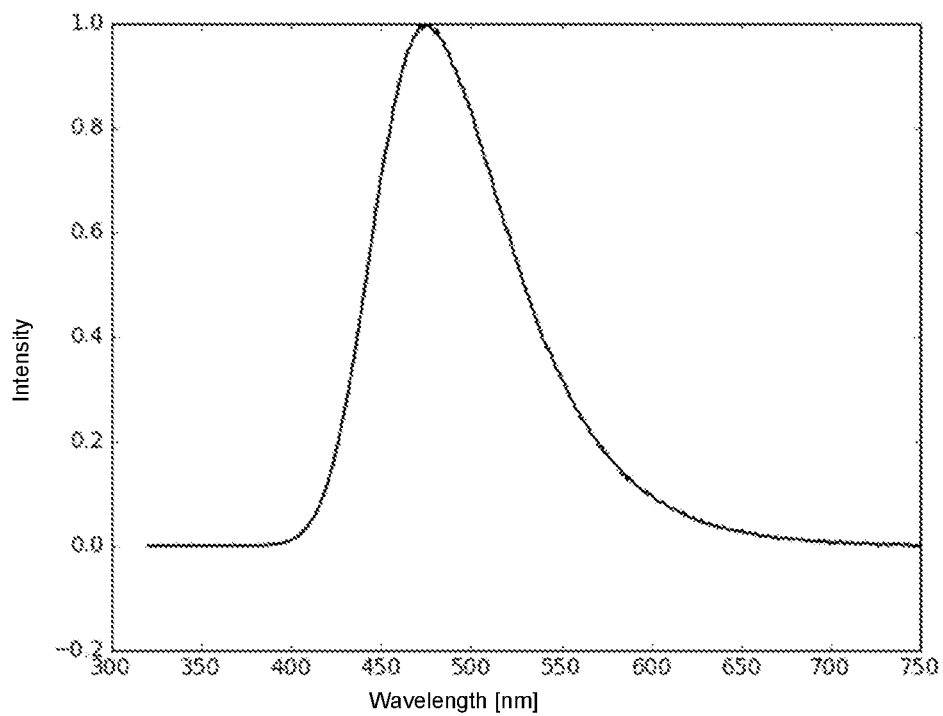
FIG. 8 is an emission spectrum of Example 8 (10% in PMMA).

FIG. 8 shows the emission spectrum of Example 8 (10% in PMMA). The emission maximum is at 472 nm. The photoluminescence quantum yield (PLQY) is 86% and the half-width is 0.47 eV.

Example 9

Example 9 was produced in accordance with AAV1 (Yield 54%) and AAV7.

Figure 9:
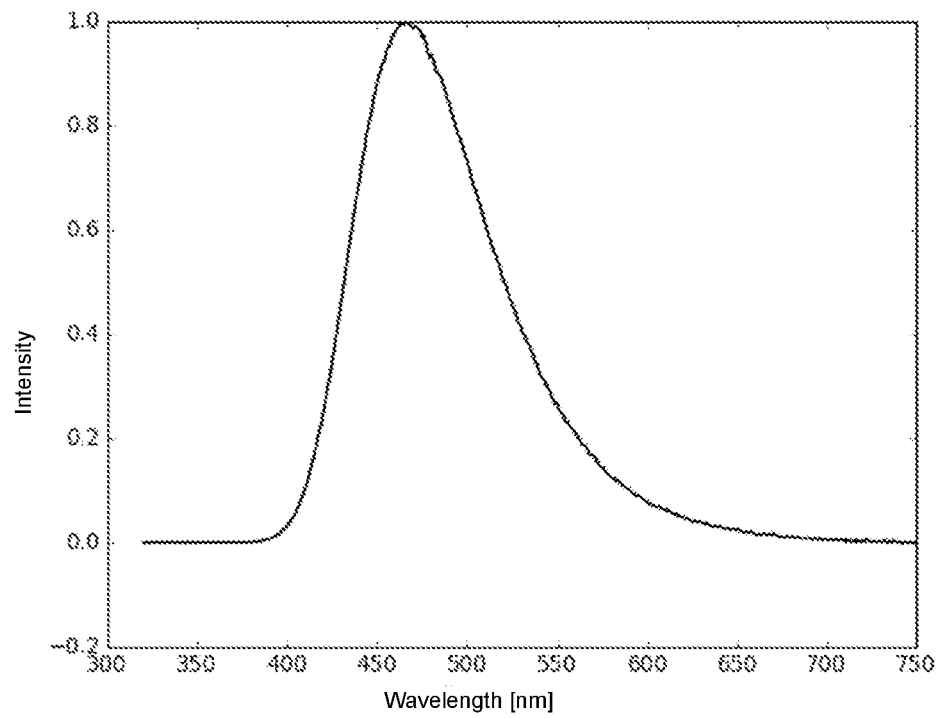
FIG. 9 is an emission spectrum of Example 9 (10% in PMMA).

FIG. 9 shows the emission spectrum of Example 9 (10% in PMMA). The emission maximum is at 466 nm. The photoluminescence quantum yield (PLQY) is 75% and the full width at half maximum is 0.50 eV.

Example 10

Example 10 was produced according to AAV1 and AAV7.

Figure 10:
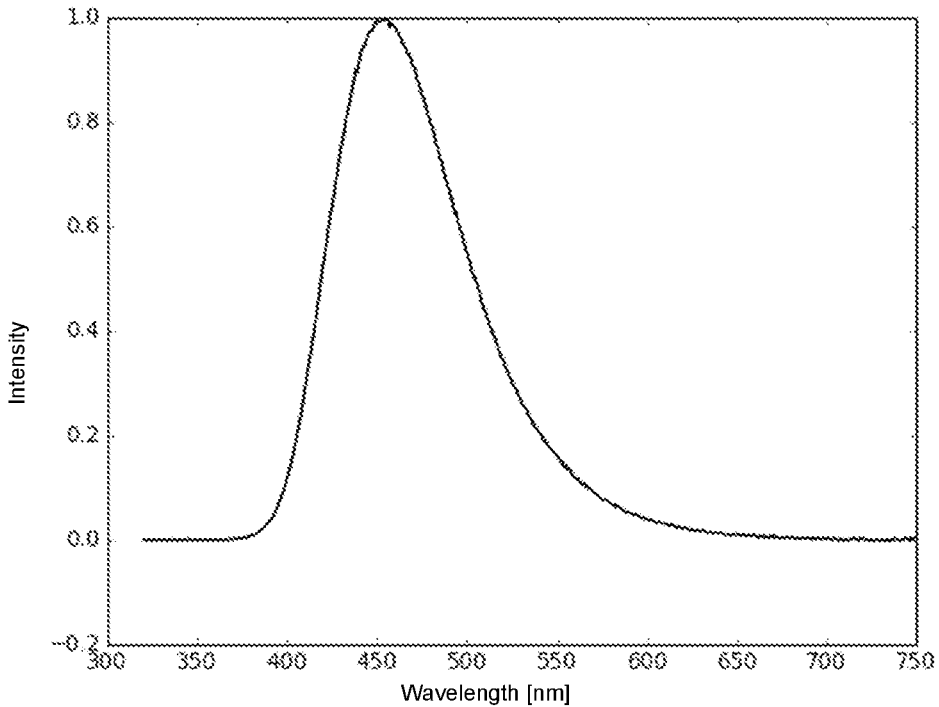
FIG. 10 is an emission spectrum of Example 10 (10% in PMMA).

FIG. 10 shows the emission spectrum of Example 10 (10% in PMMA). The emission maximum is at 454 nm. The photoluminescence quantum yield (PLQY) is 80% and the full width at half maximum is 0.50 eV.

Example 11

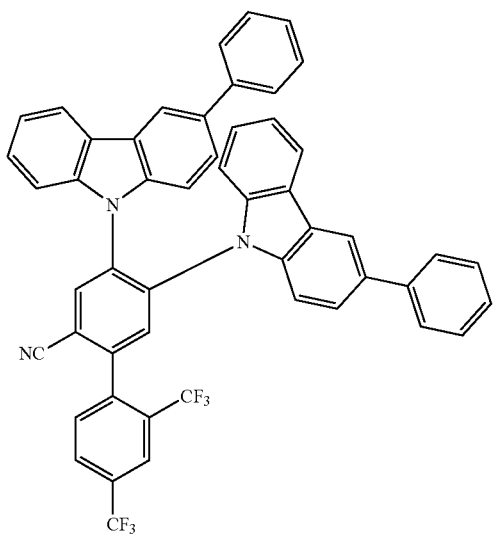 [SMILES: N#Cc1cc(-n2c3ccccc3c3cc(-c4ccccc4)ccc32)c(-n2c3ccccc3c3cc(-c4ccccc4)ccc32)cc1-c1ccc(C(F)(F)F)cc1C(F)(F)F]

Example 11 was produced according to AAV5 and AAV7.

Figure 11:
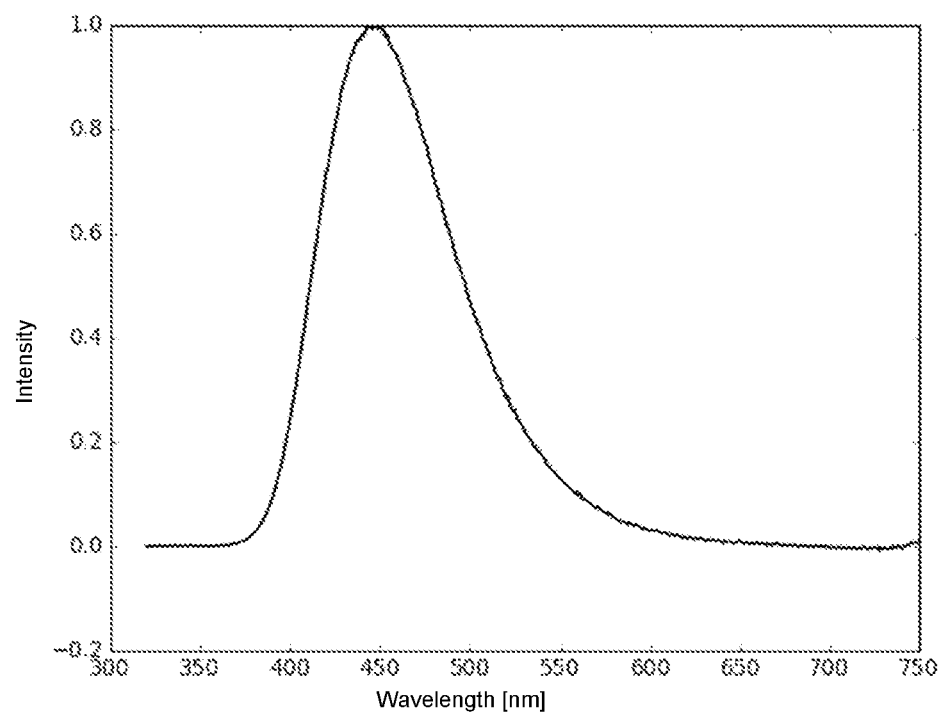
FIG. 11 is an emission spectrum of Example 11 (10% in PMMA).

FIG. 11 shows the emission spectrum of Example 11 (10% in PMMA). The emission maximum is at 448 nm. The photoluminescence quantum yield (PLQY) is 73% and the half-width is 0.52 eV.

Example 12

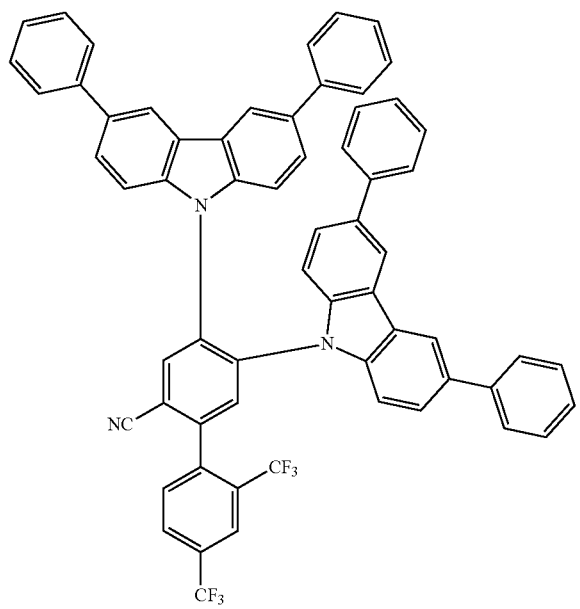 [SMILES: N#Cc1cc(-n2c3ccc(-c4ccccc4)cc3c3cc(-c4ccccc4)ccc32)c(-n2c3ccc(-c4ccccc4)cc3c3cc(-c4ccccc4)ccc32)cc1-c1ccc(C(F)(F)F)cc1C(F)(F)F]

Example 12 was produced according to AAV1 and AAV7.

Figure 12:
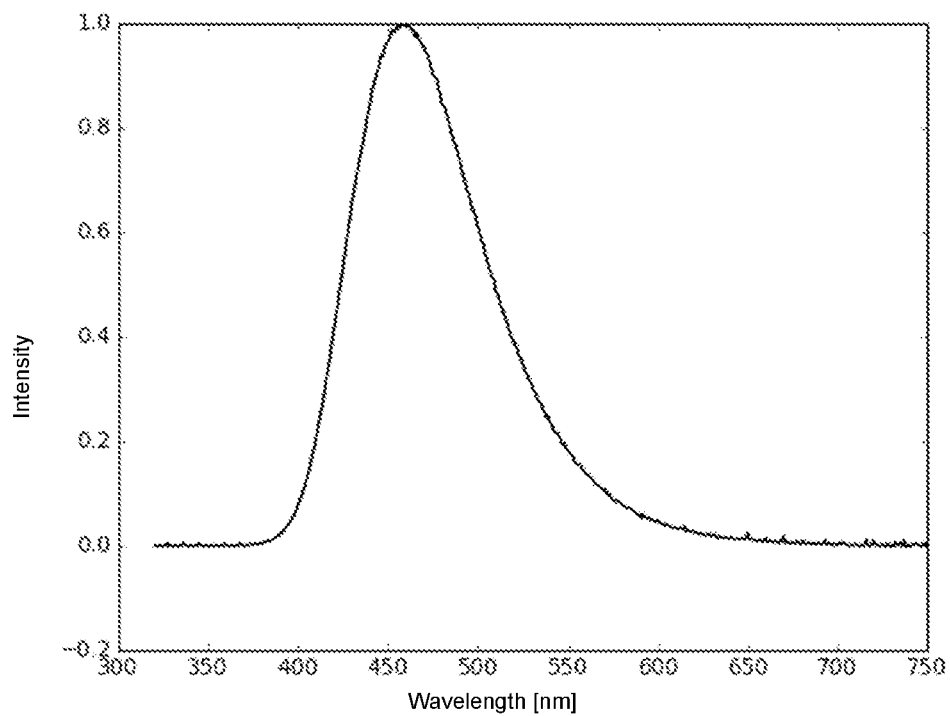
FIG. 12 is an emission spectrum of Example 12 (10% in PMMA).

FIG. 12 shows the emission spectrum of Example 12 (10% in PMMA). The emission maximum is at 457 nm. The photoluminescence quantum yield (PLQY) is 78% and the full width at half maximum is 0.49 eV.

Example 13

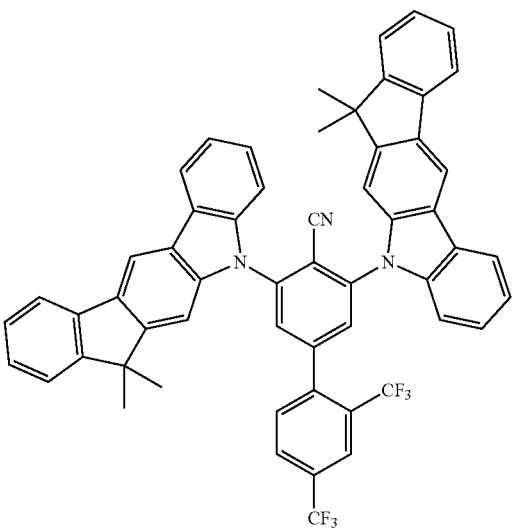 [SMILES: CC1(C)c2ccccc2-c2cc3c4ccccc4n(-c4cc(-c5ccc(C(F)(F)F)cc5C(F)(F)F)cc(-n5c6ccccc6c6cc7c(cc65)C(C)(C)c5ccccc5-7)c4C#N)c3cc21]

Example 13 was produced in accordance with AAV1 (Yield 54%) and AAV7 (Yield 59%).

Figure 13:
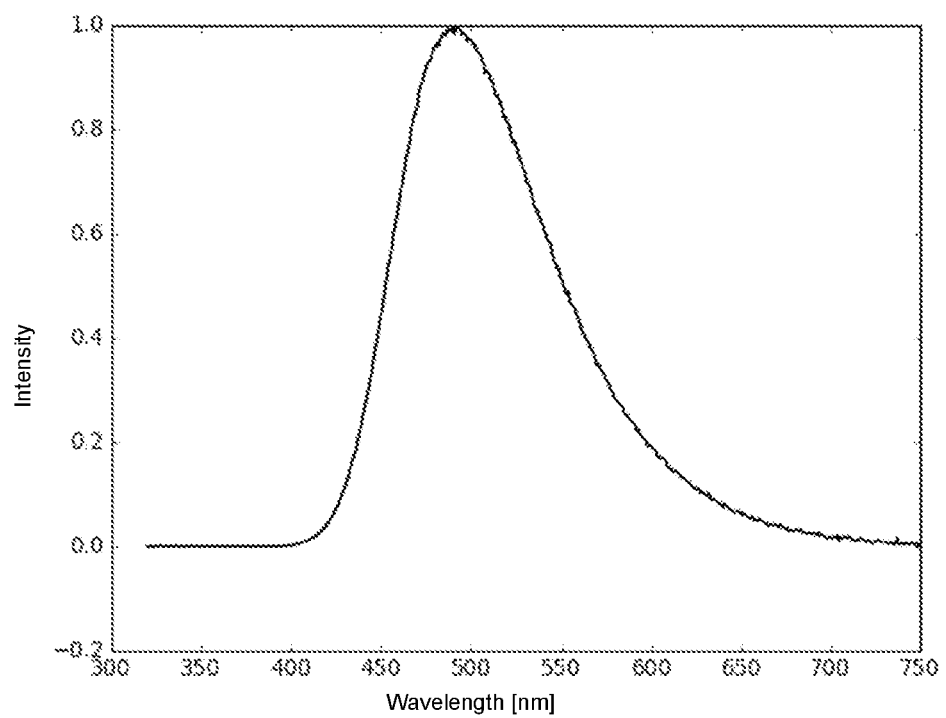
FIG. 13 is an emission spectrum of Example 13 (10% in PMMA).

FIG. 13 shows the emission spectrum of Example 13 (10% in PMMA). The emission maximum is at 492 nm. The photoluminescence quantum yield (PLQY) is 62% and the full width at half maximum is 0.49 eV. The emission lifetime is 14 µs.

Example D1

Molecule 13 was tested in the OLED component D1 with the following structure (the fraction of the molecule according to the invention and the host molecule in the emission layer in each case is indicated in percent by weight):

| Layer | Thickness | Material |
| --- | --- | --- |
| 9 | 100 nm | Al |
| 8 | 2 nm | Liq |
| 7 | 40 nm | NBPhen |
| 5 | 20 nm | 13 (20%): 9-[3,5-bis (2-dibenzofuranyl) phenyl]-9H-carbazole (80%) |
| 3 | 10 nm | TCTA |
| 2 | 80 nm | NPB |
| 1 | 130 nm | ITO |
| Substrate | | Glass |

The emission maximum is 503 nm, CIEx was 0.25 and the CIEy: 0.43 at 6V determined. The EQE at 1000 cd/m$^2$ is 9.4±0.1% and the LT80 at 500 cd/m$^2$ is 132 h.

Further Examples of Organic Molecules According to the Invention
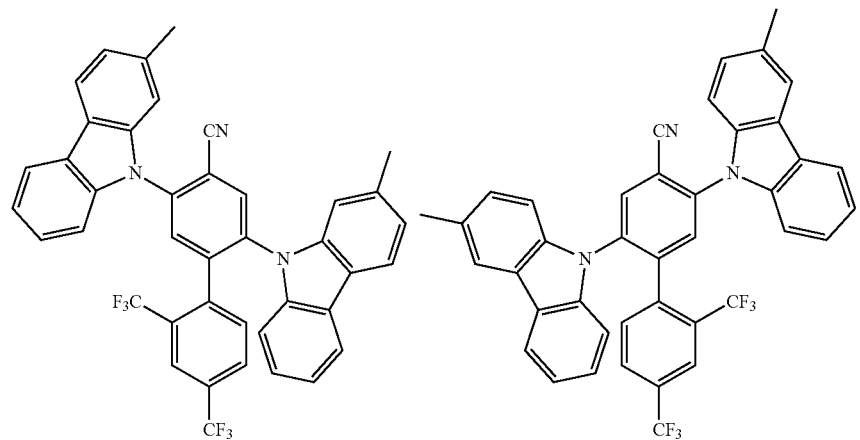
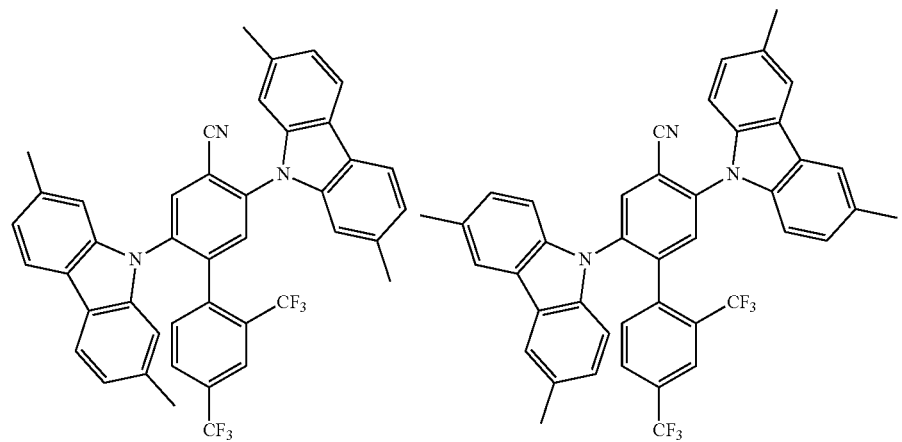
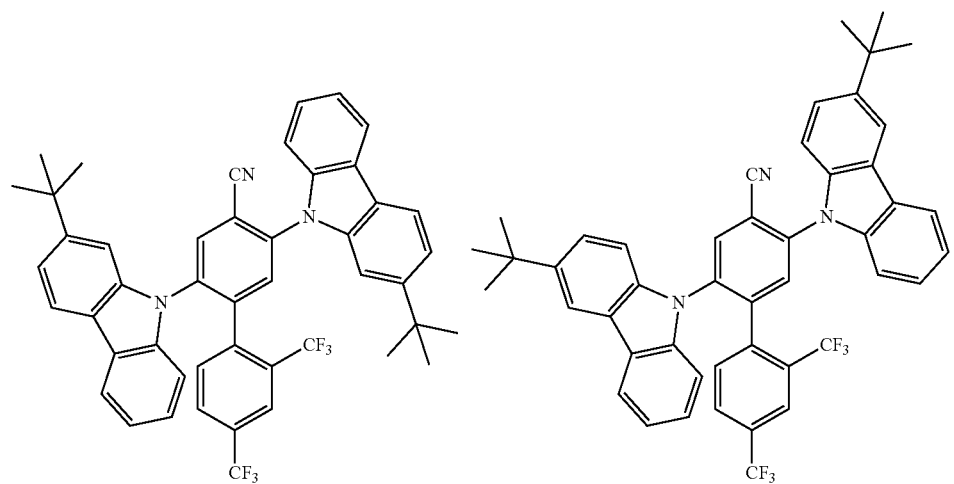

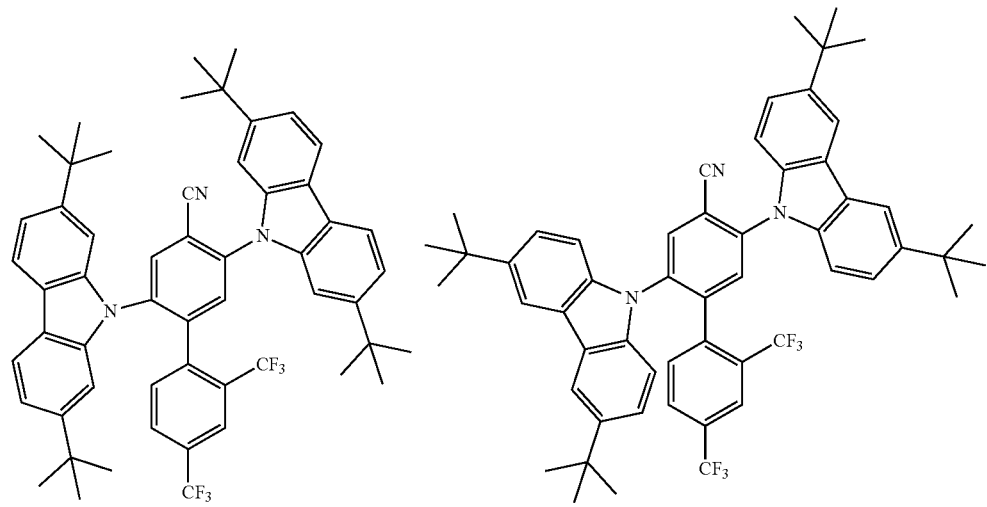
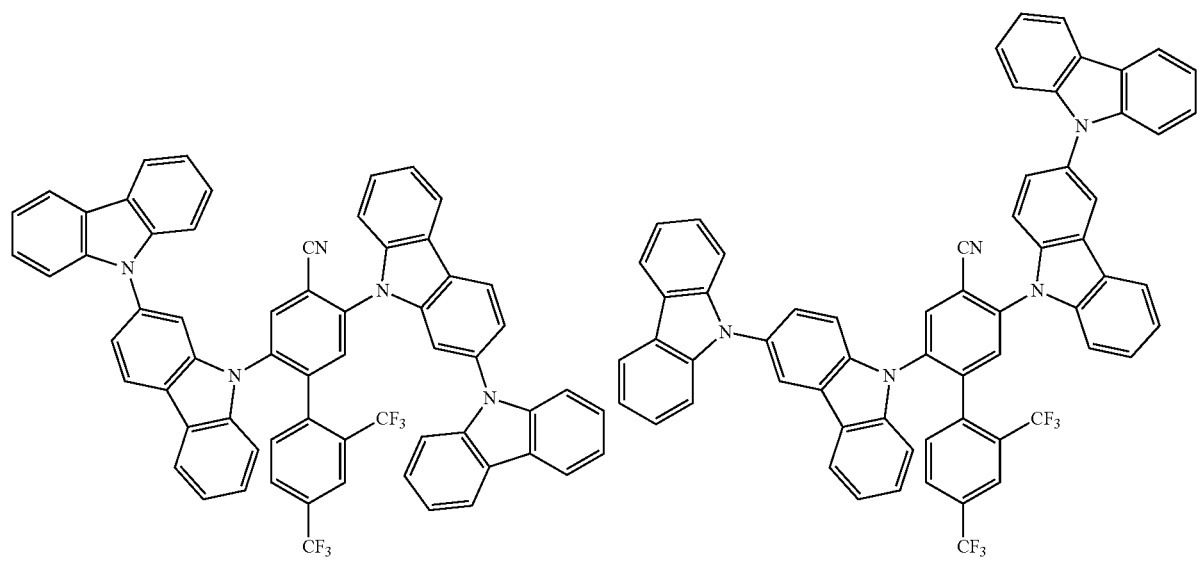

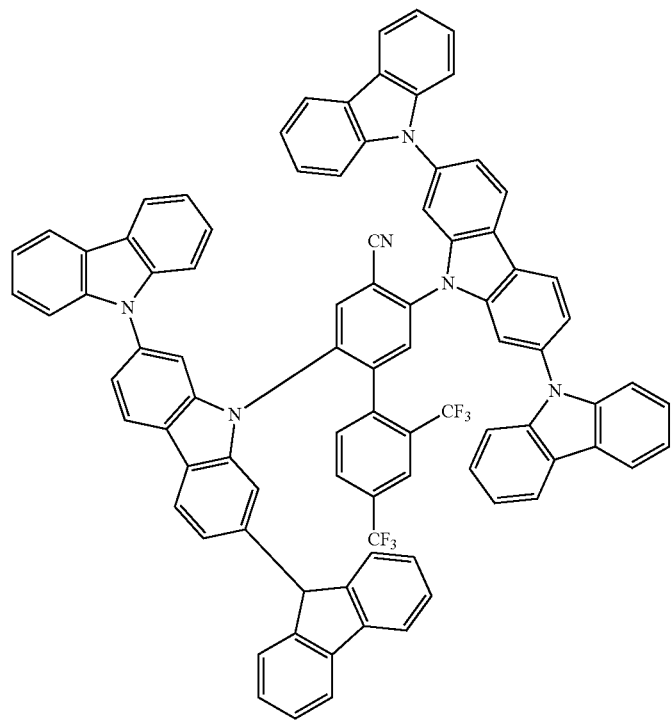
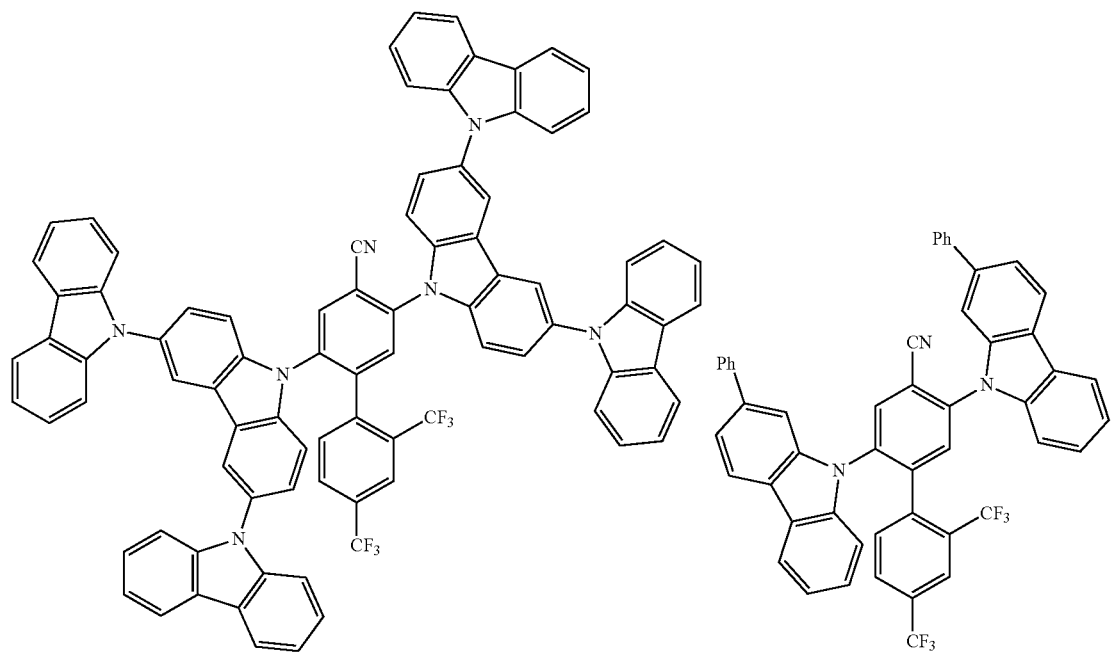

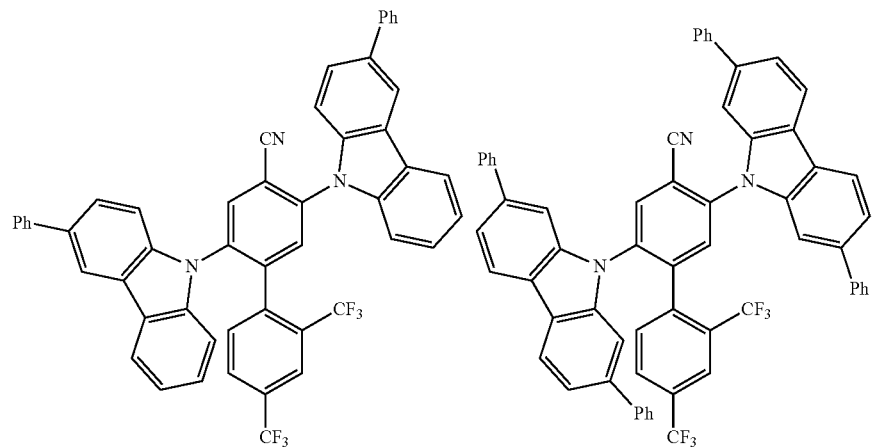
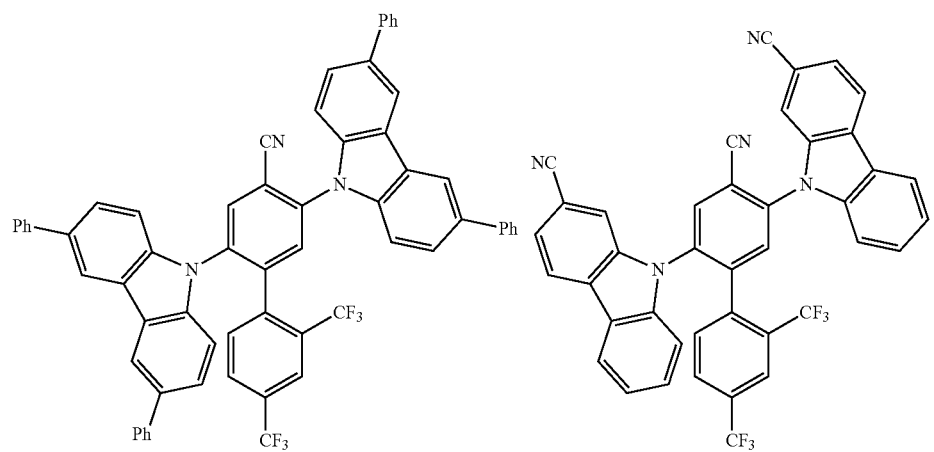
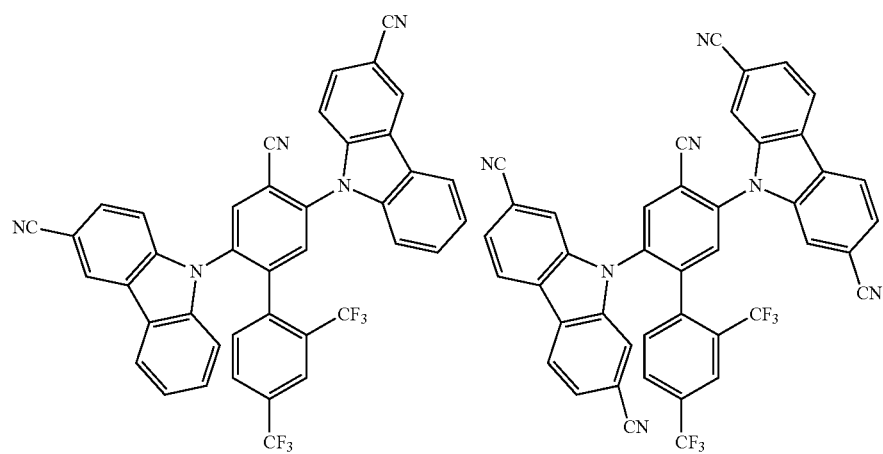

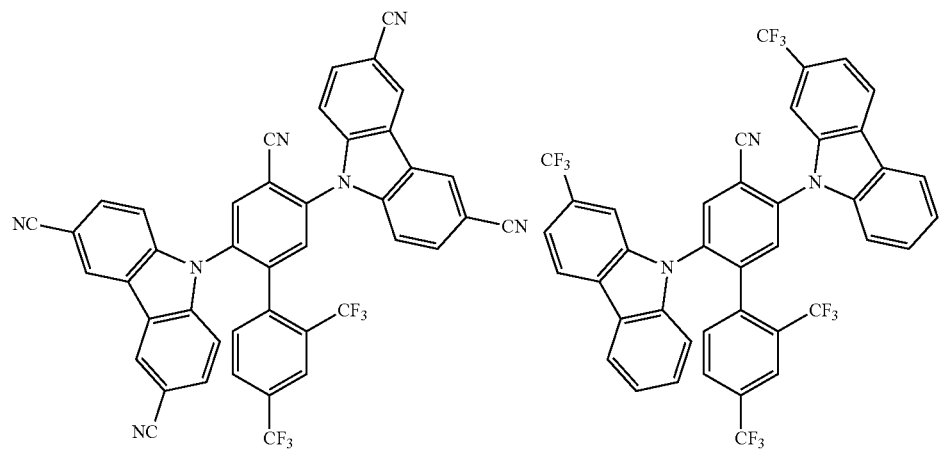
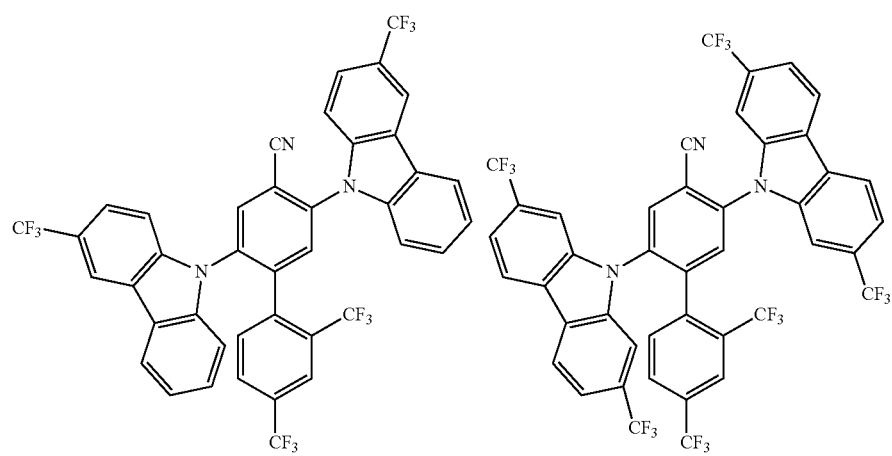
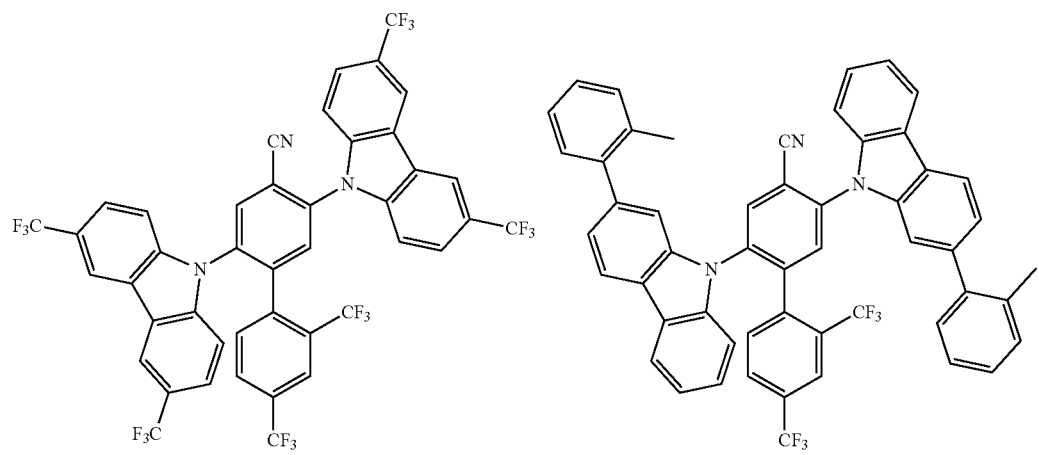

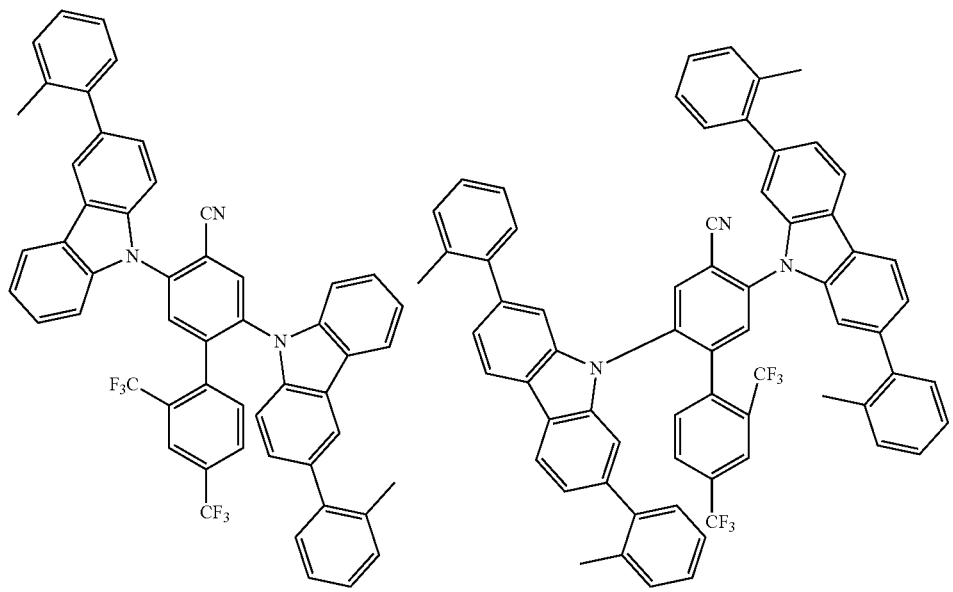
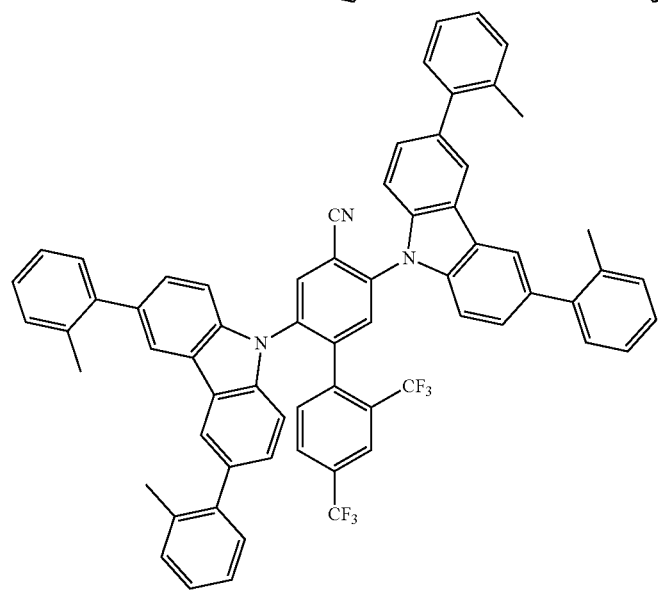
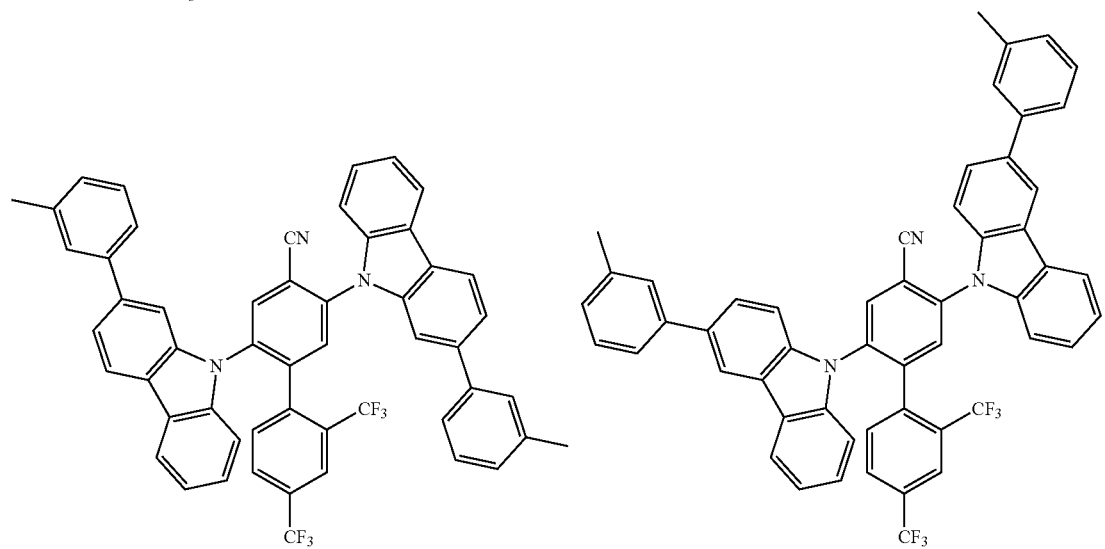

-continued
67
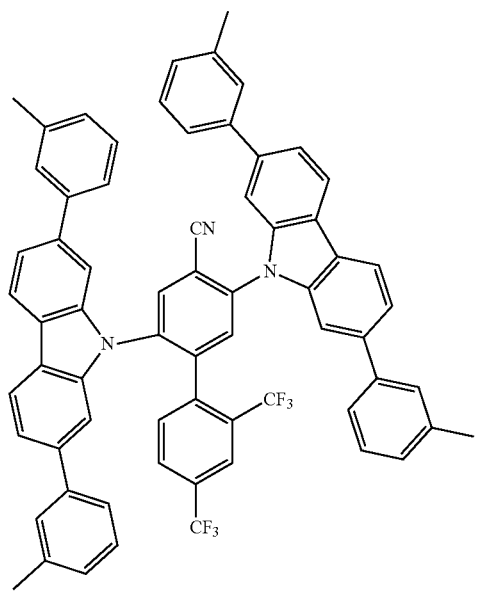
68
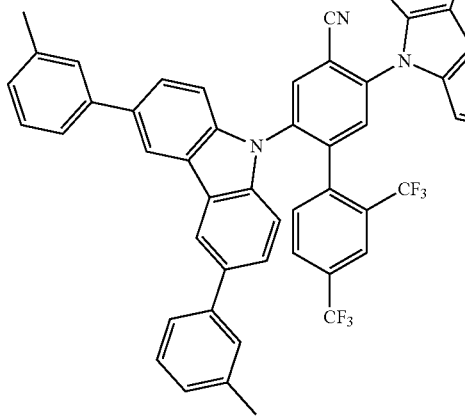
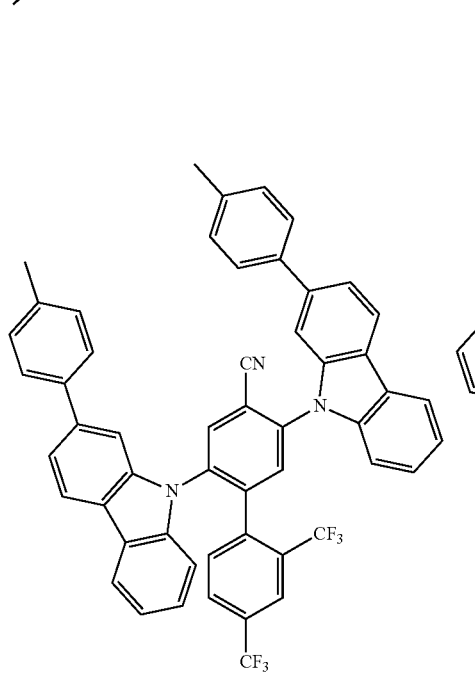
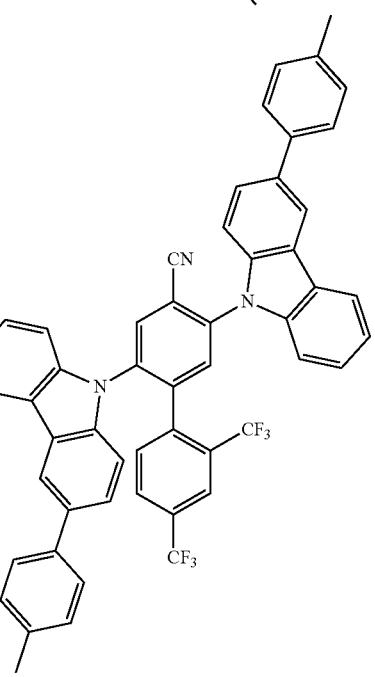
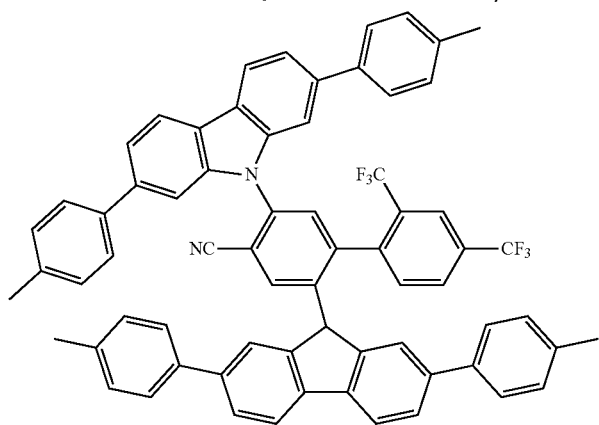

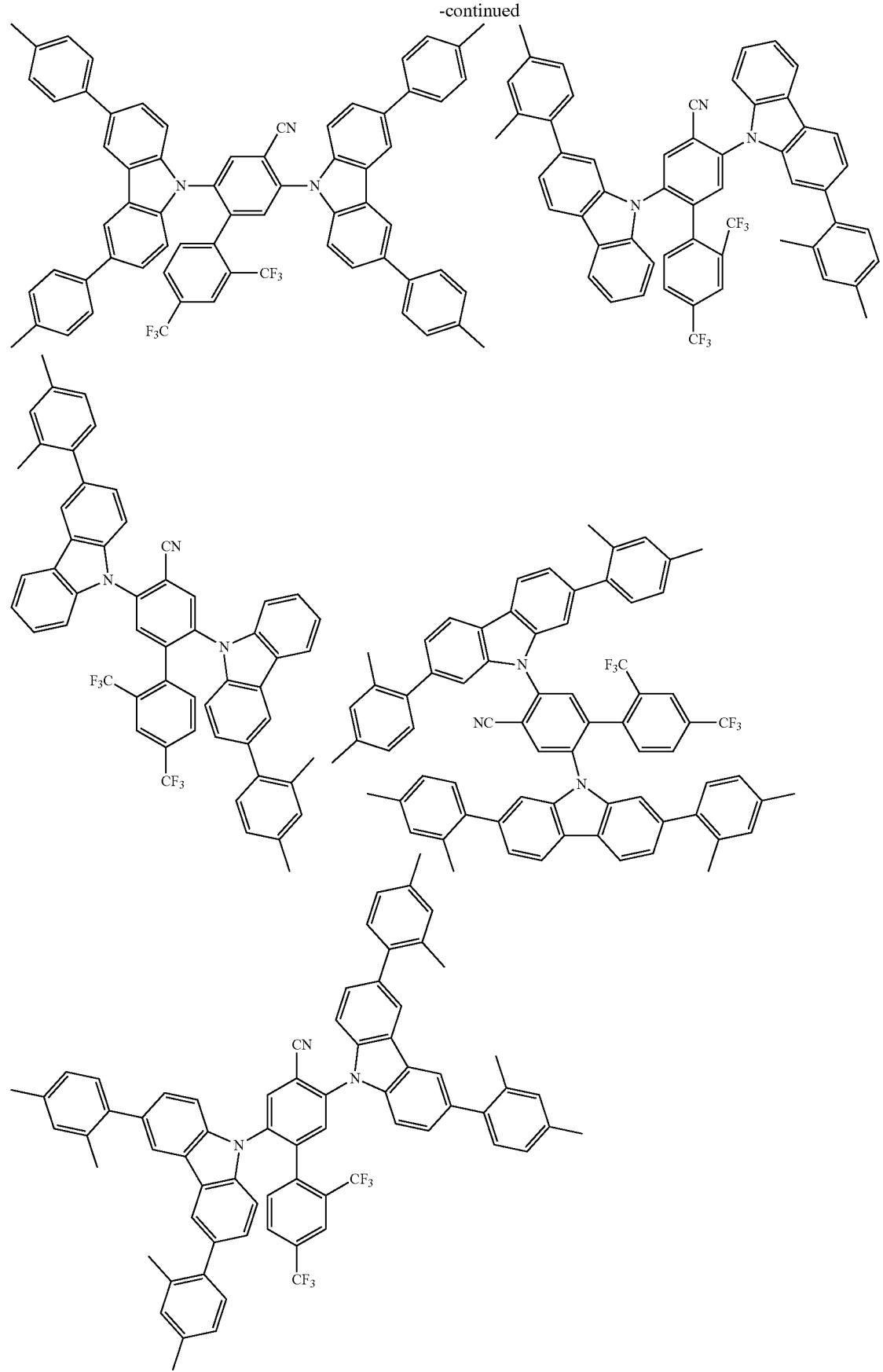

-continued
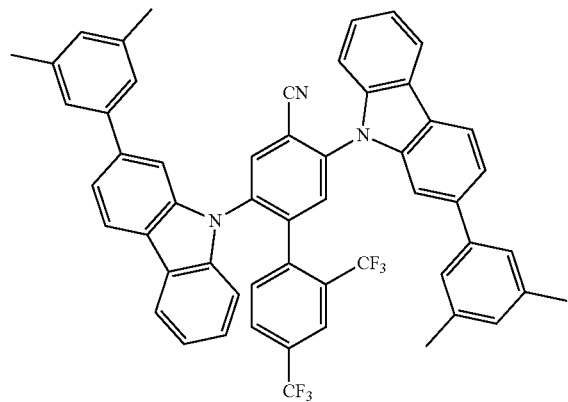
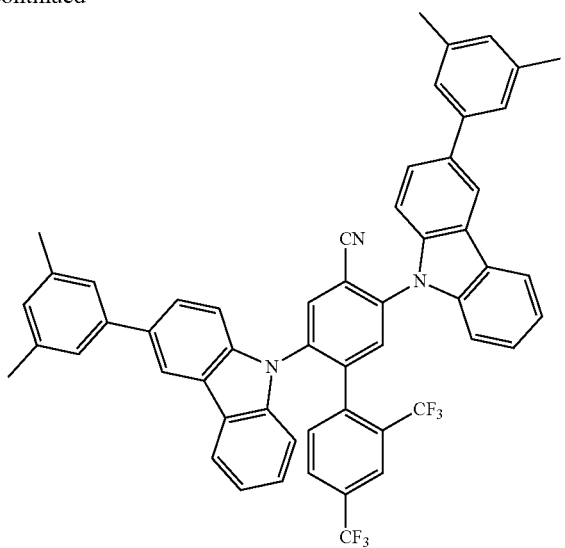
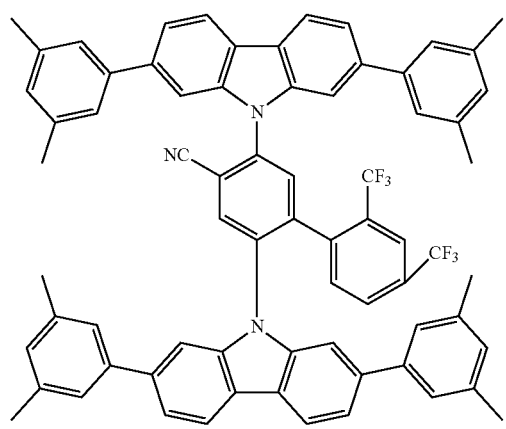
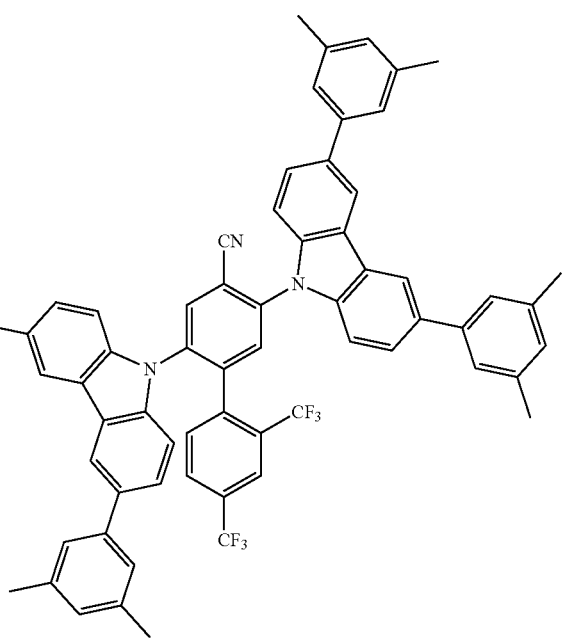
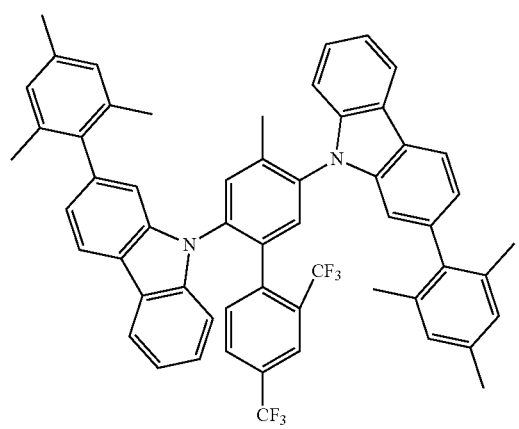
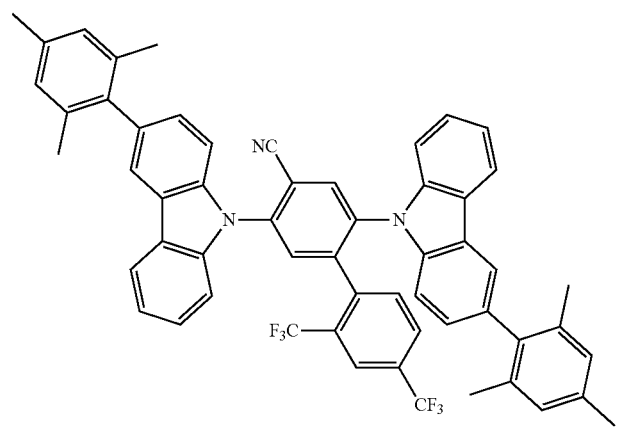

-continued
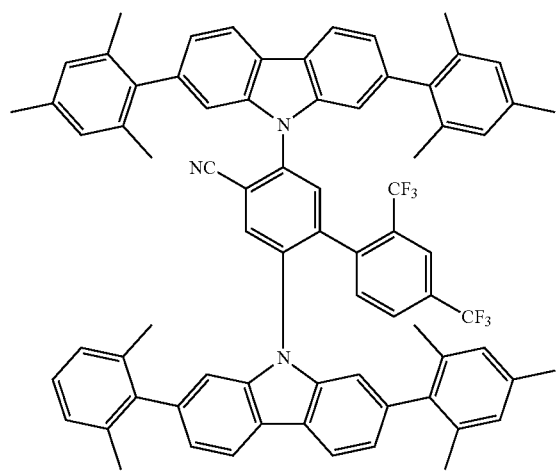
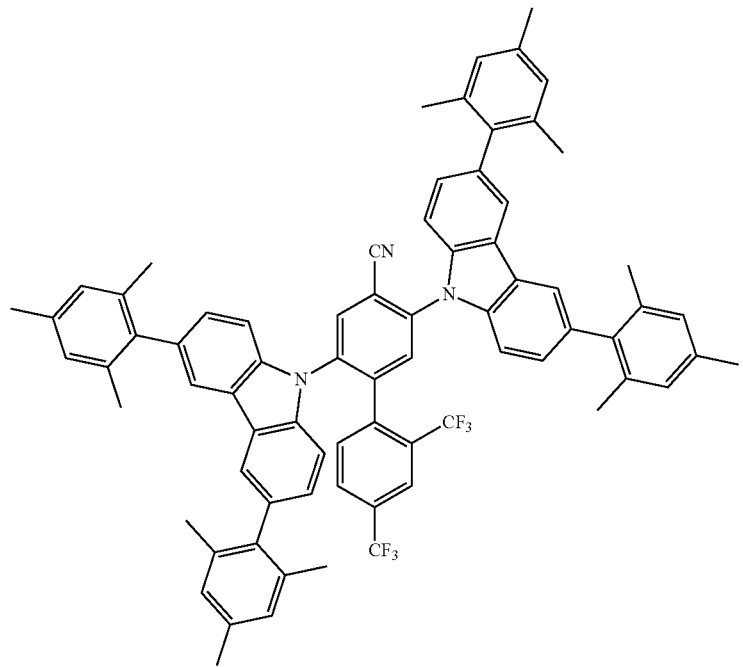
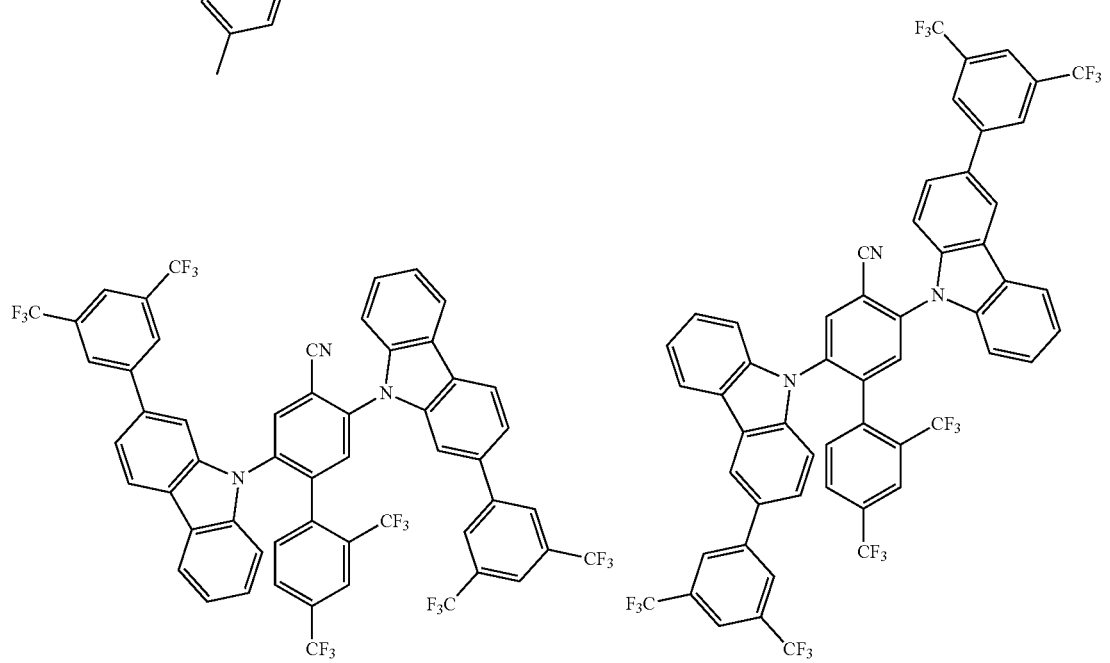

-continued
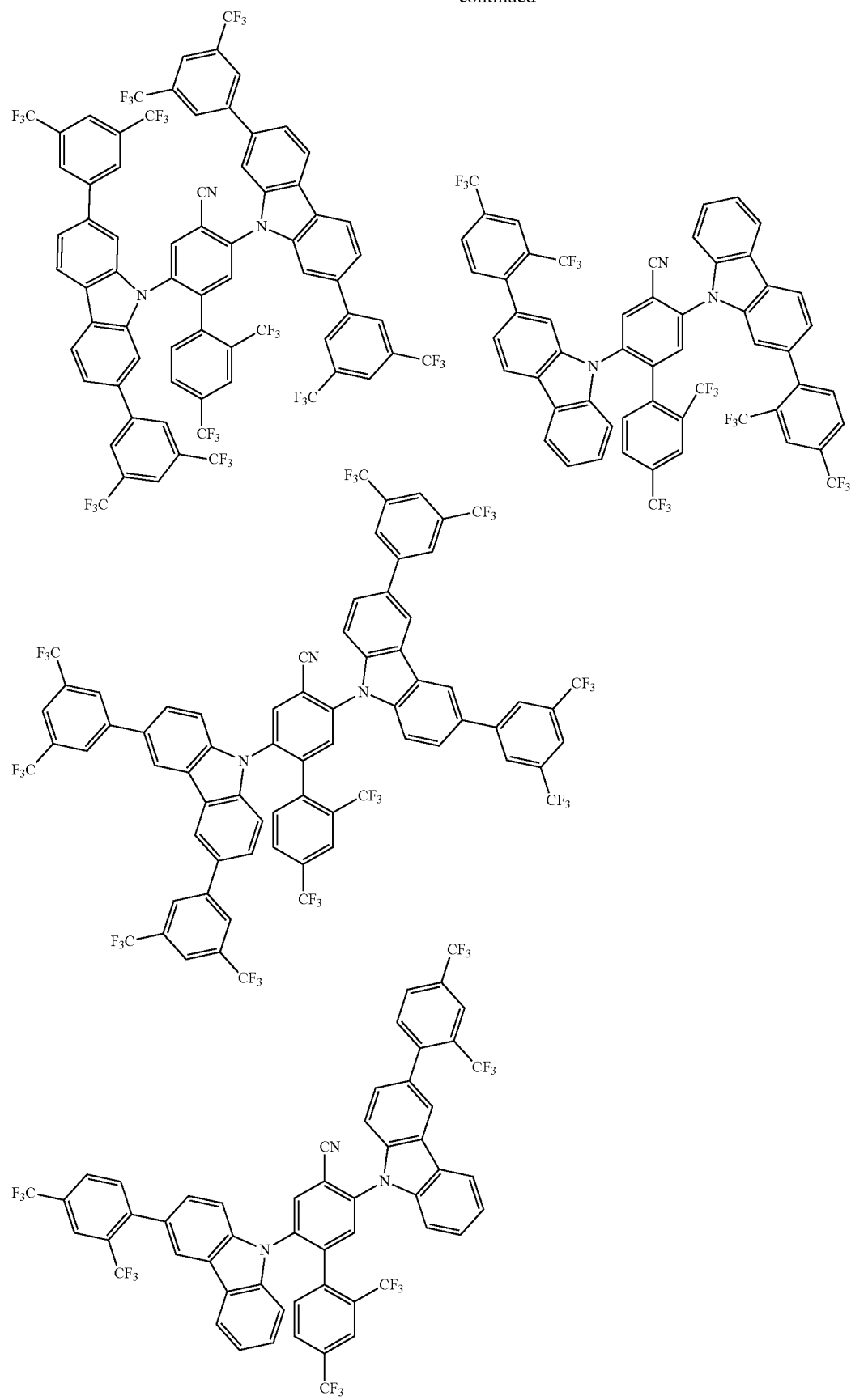

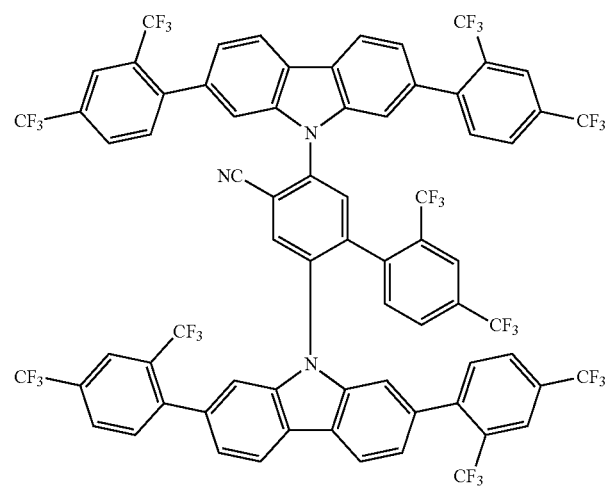
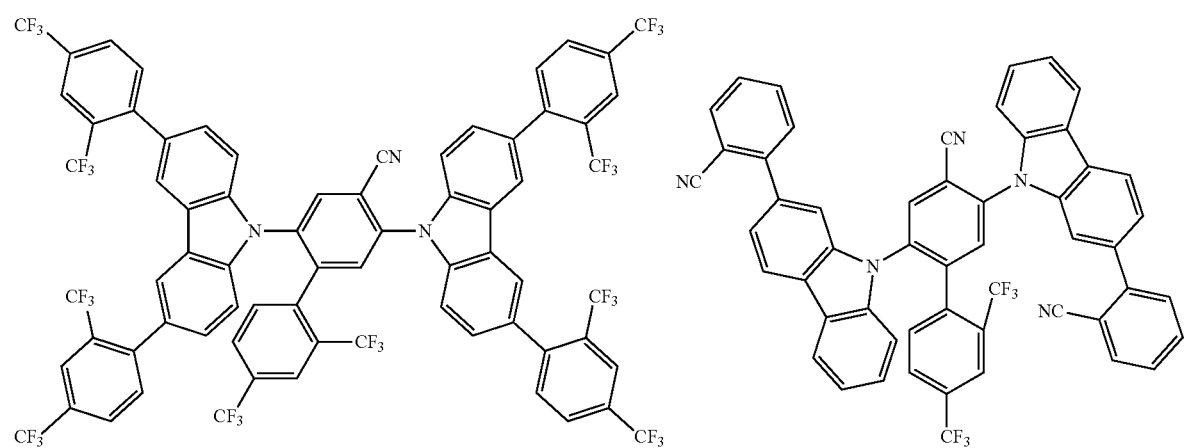
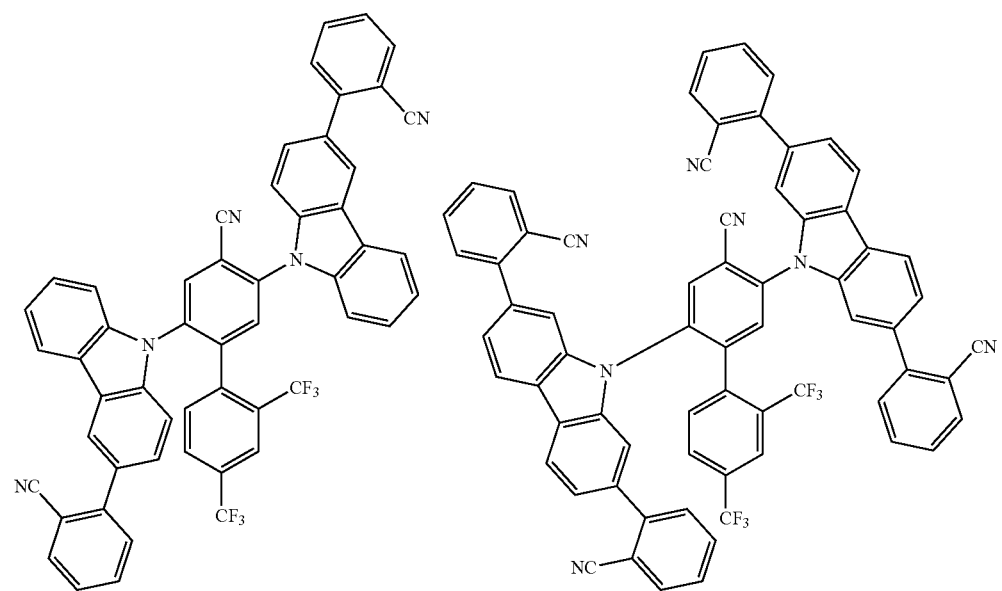

-continued
79  80
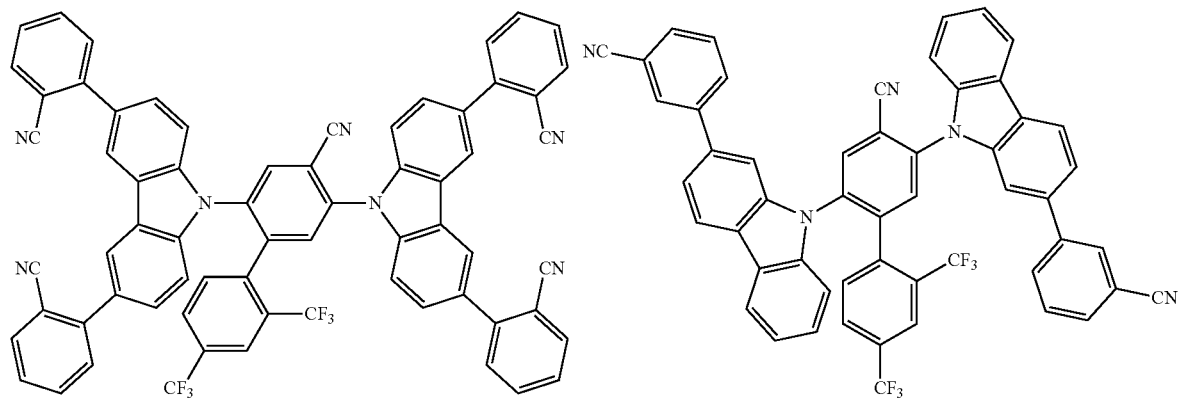
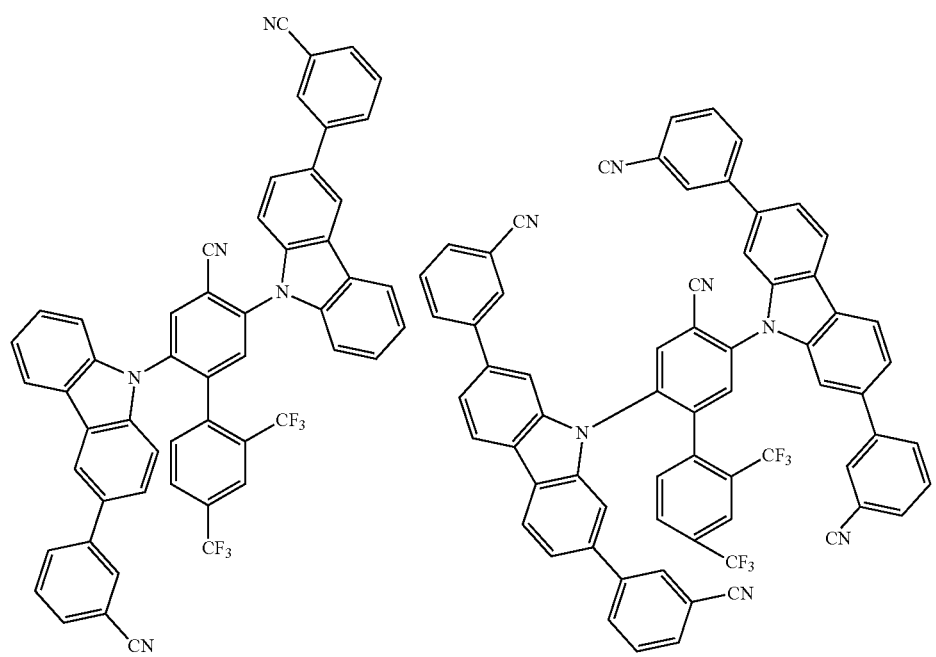
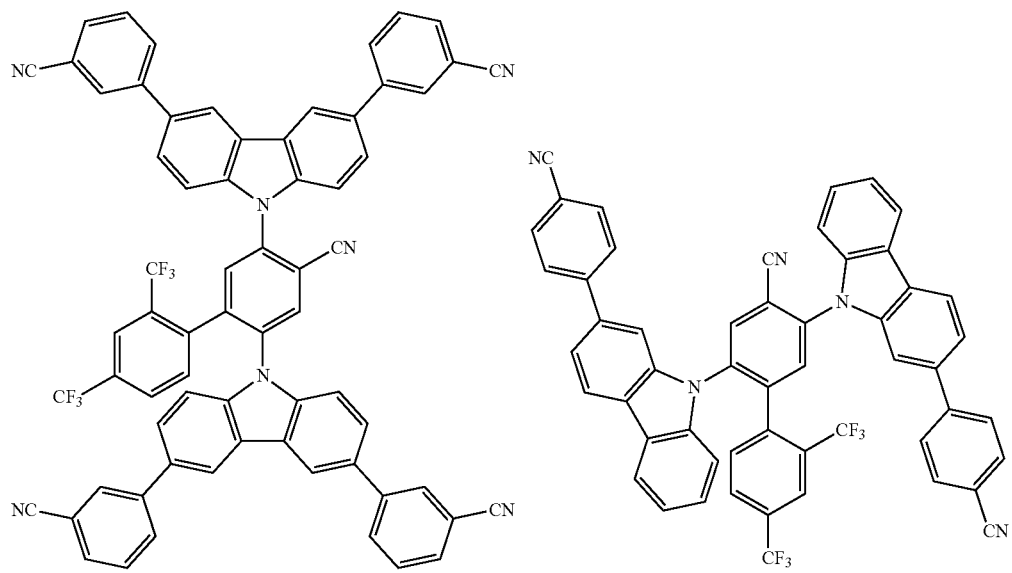

-continued
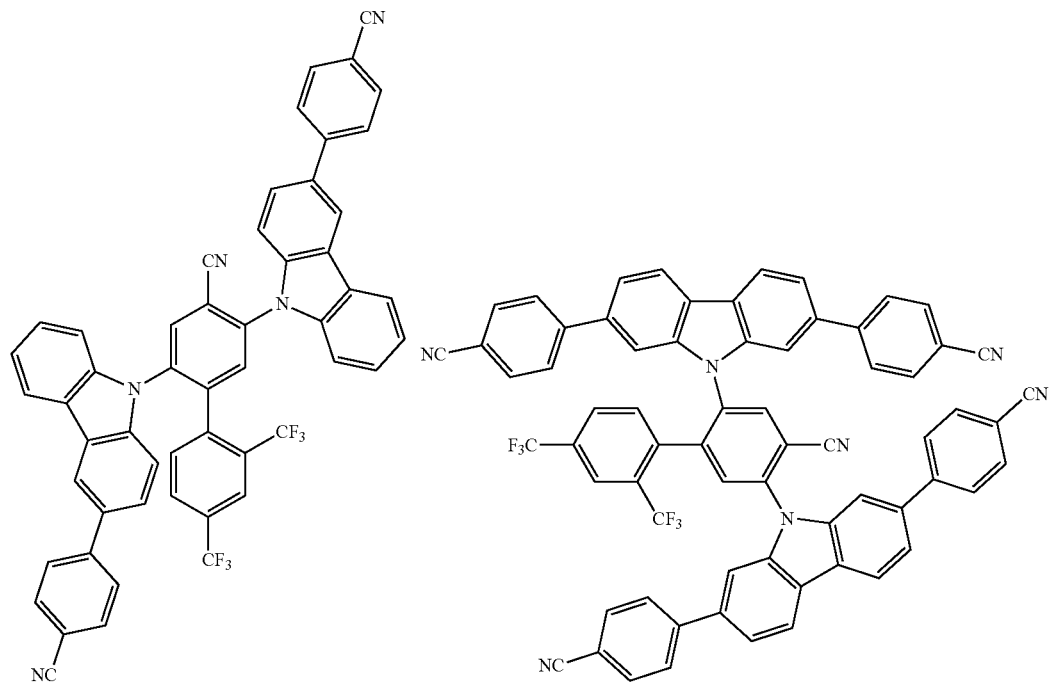
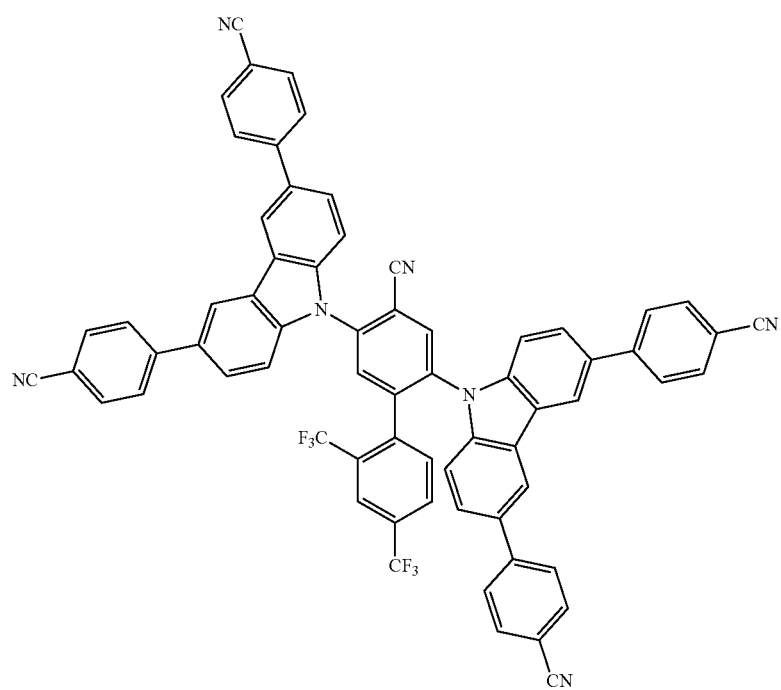

-continued
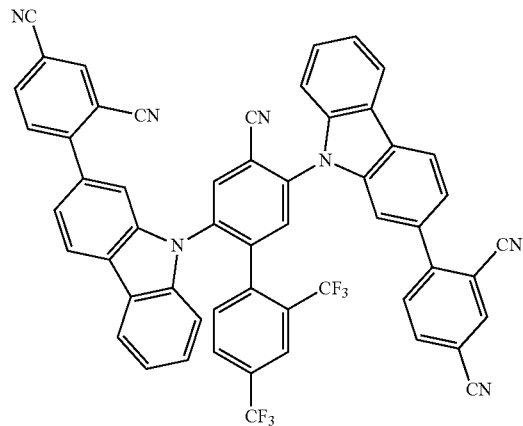
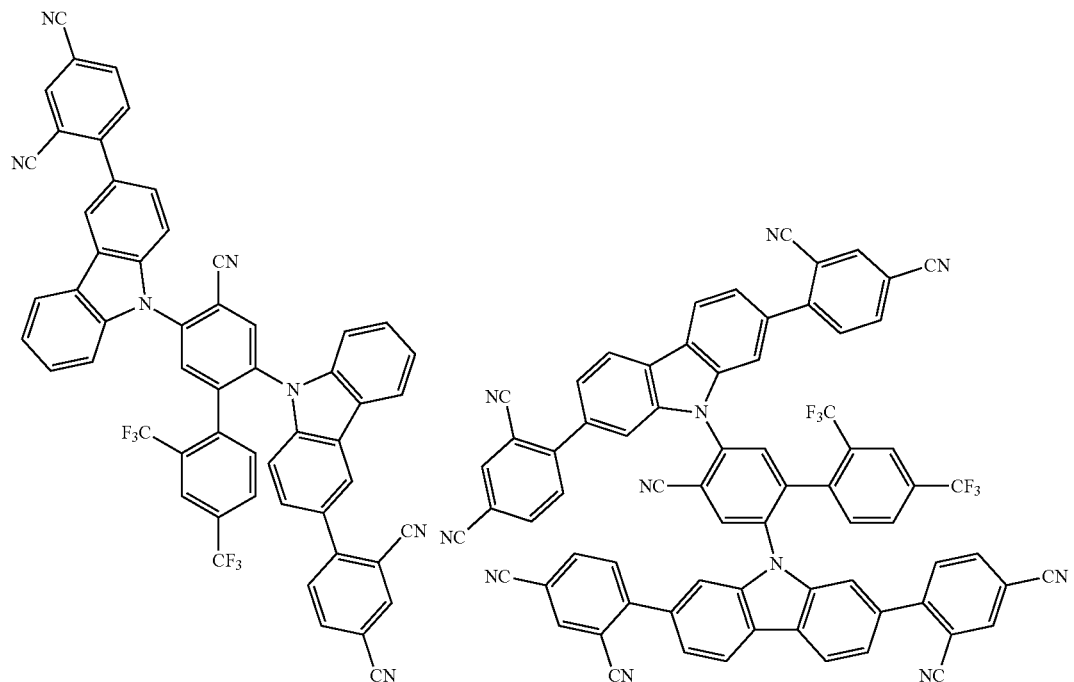
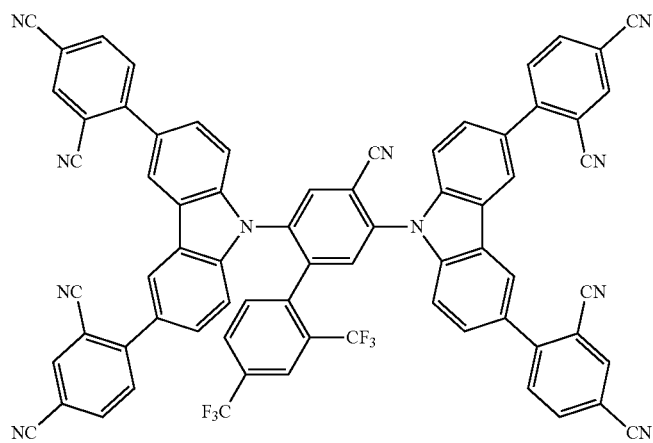

-continued
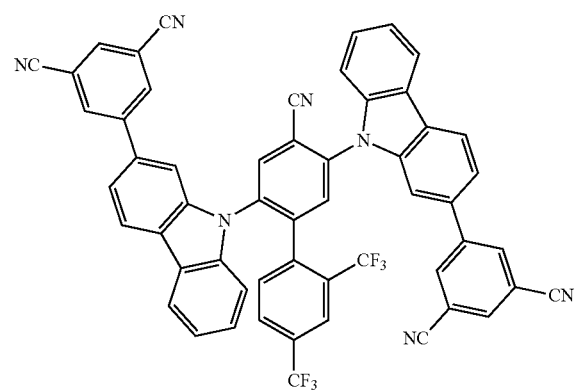
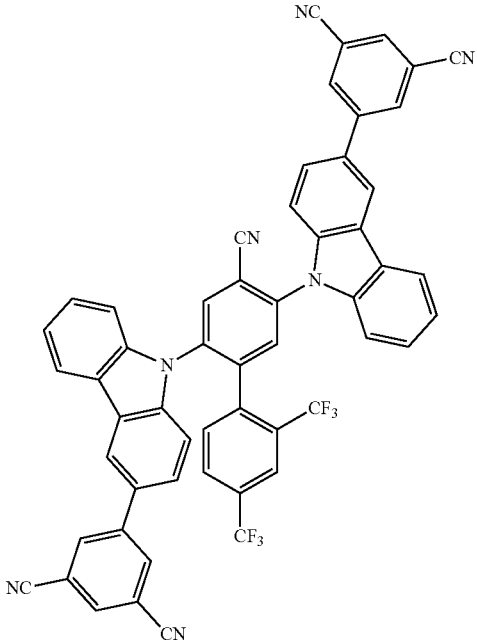
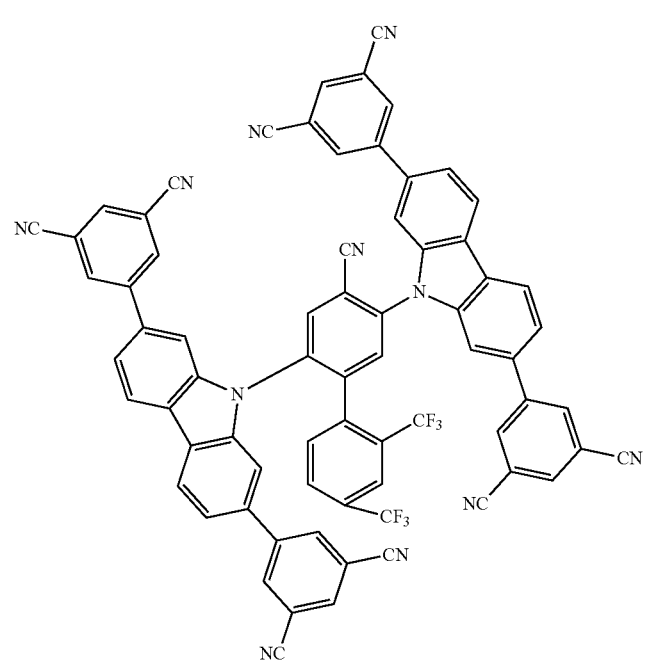
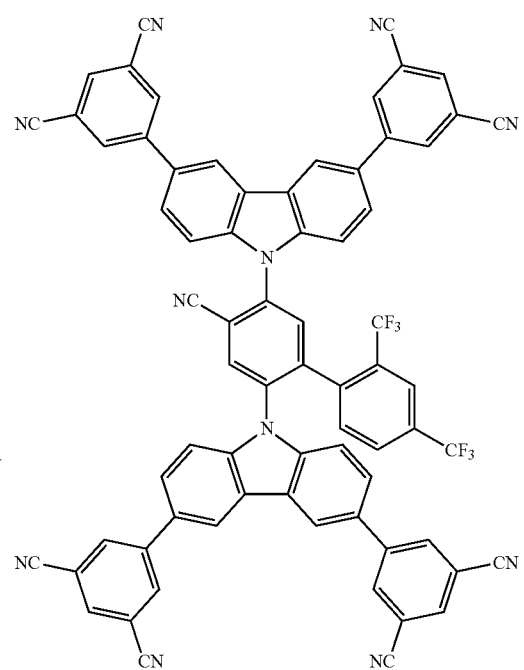

-continued
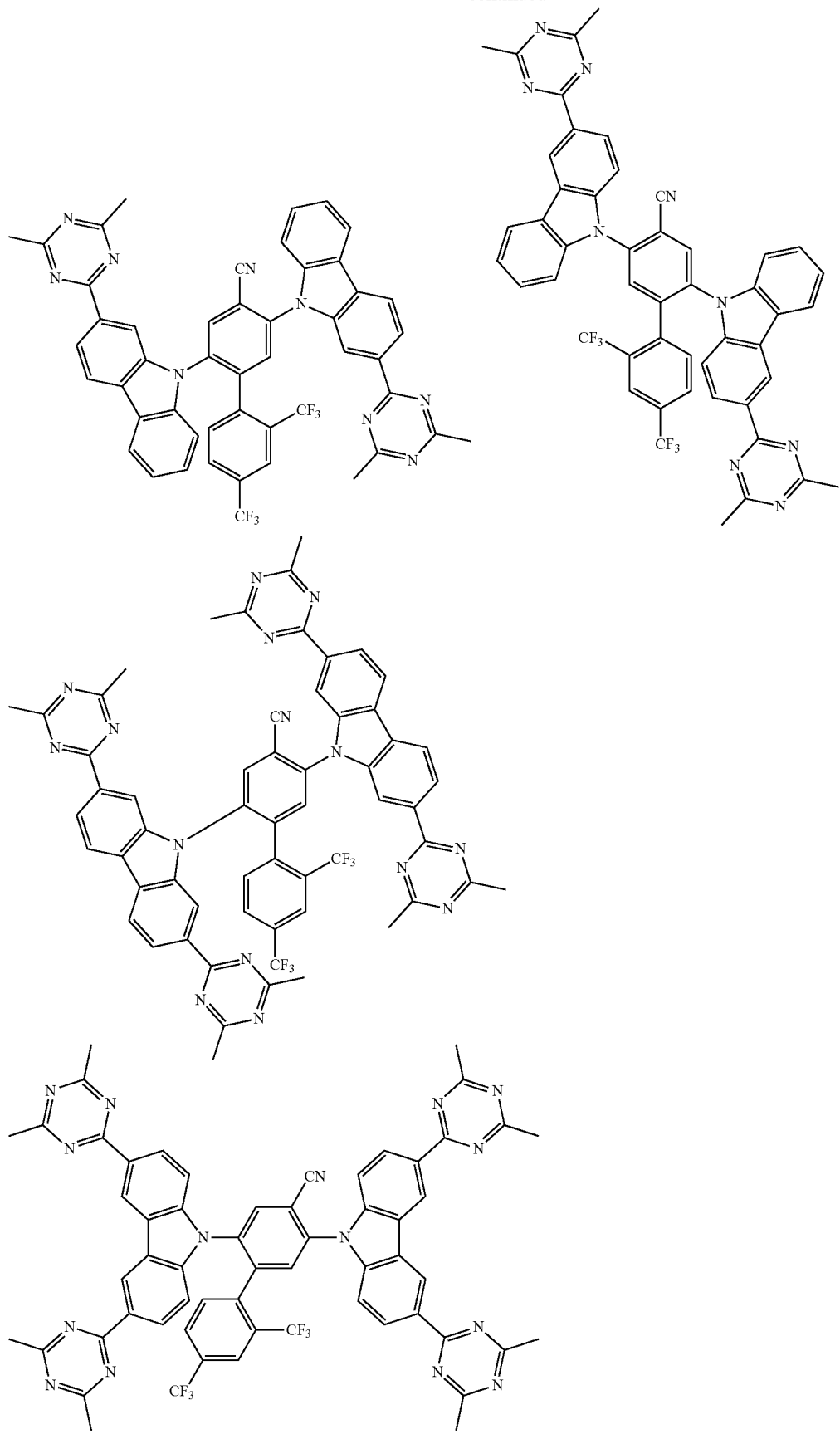

-continued
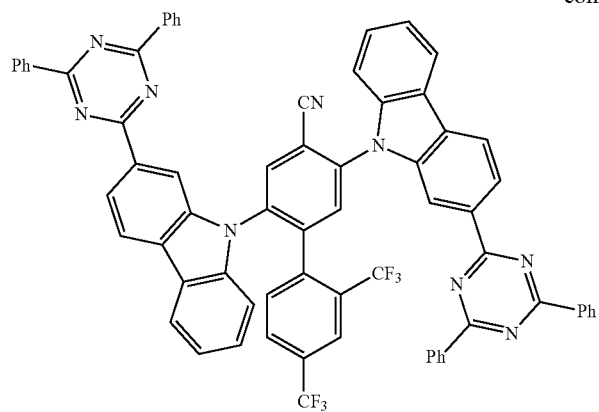
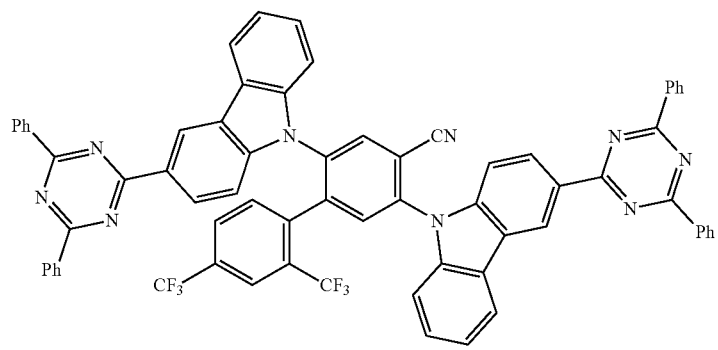
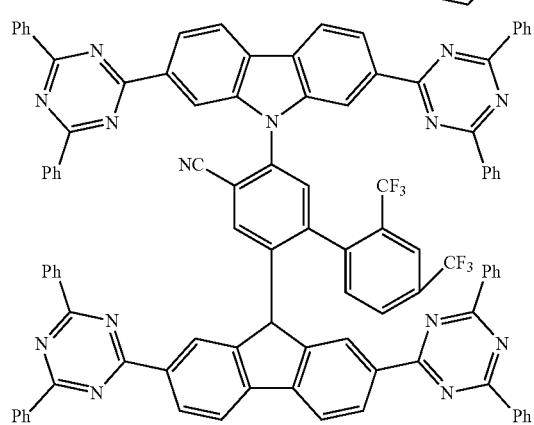
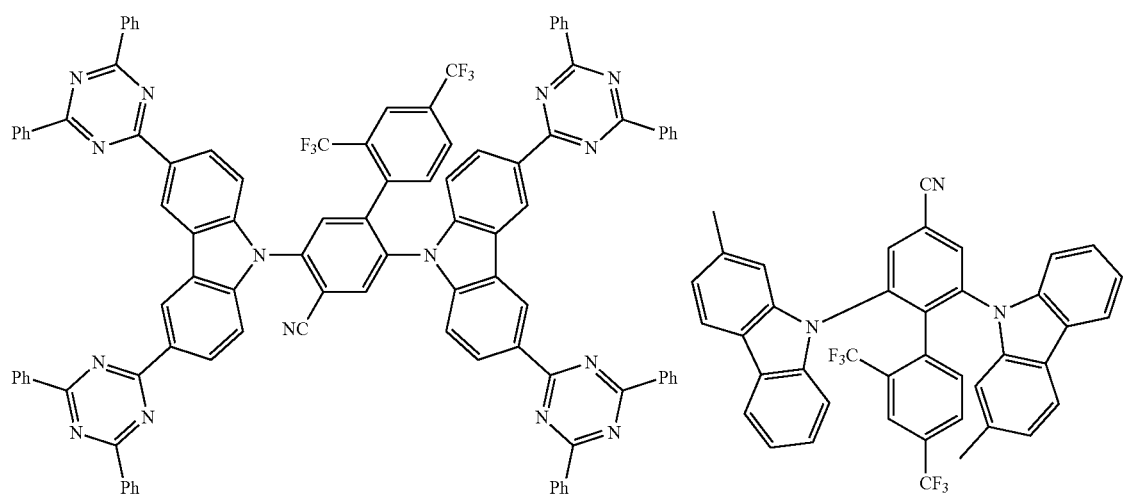

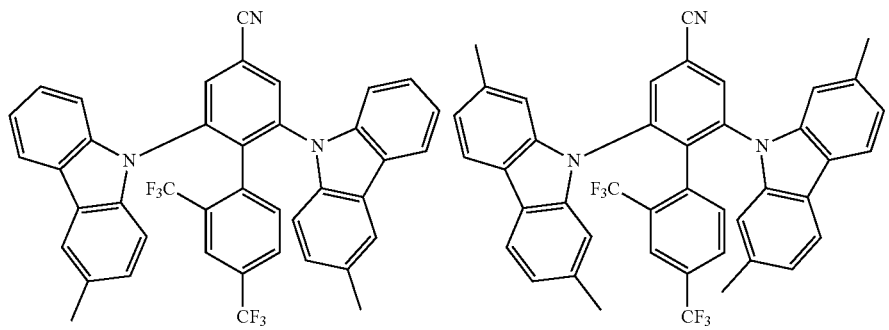
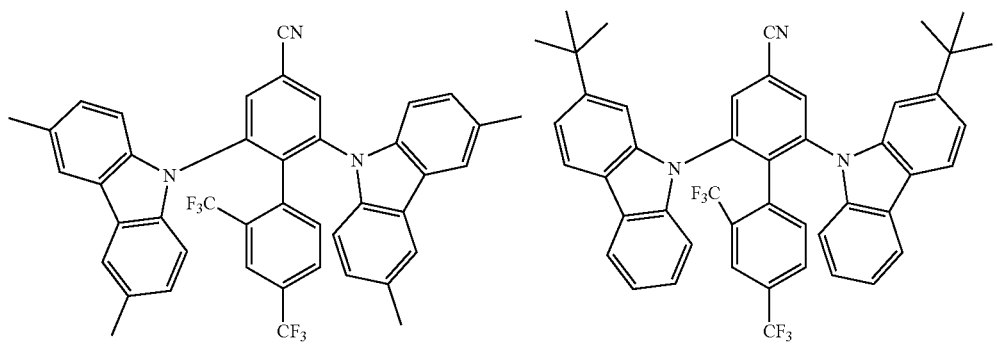
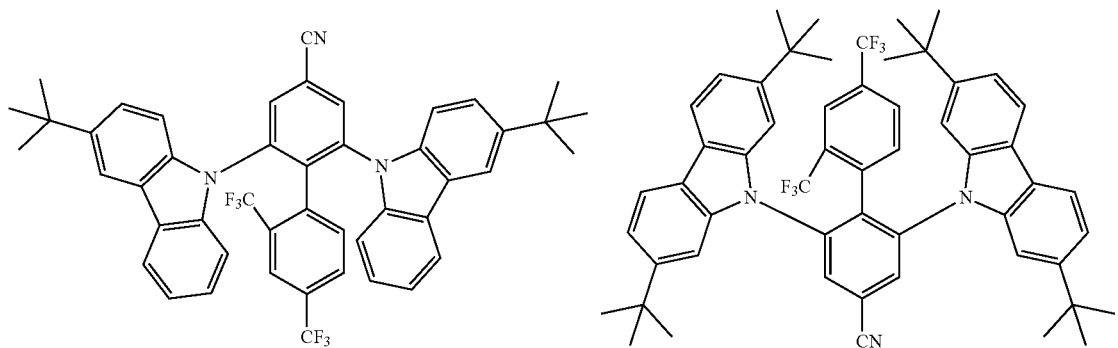
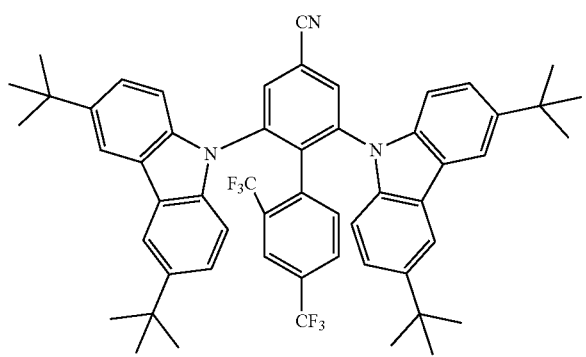

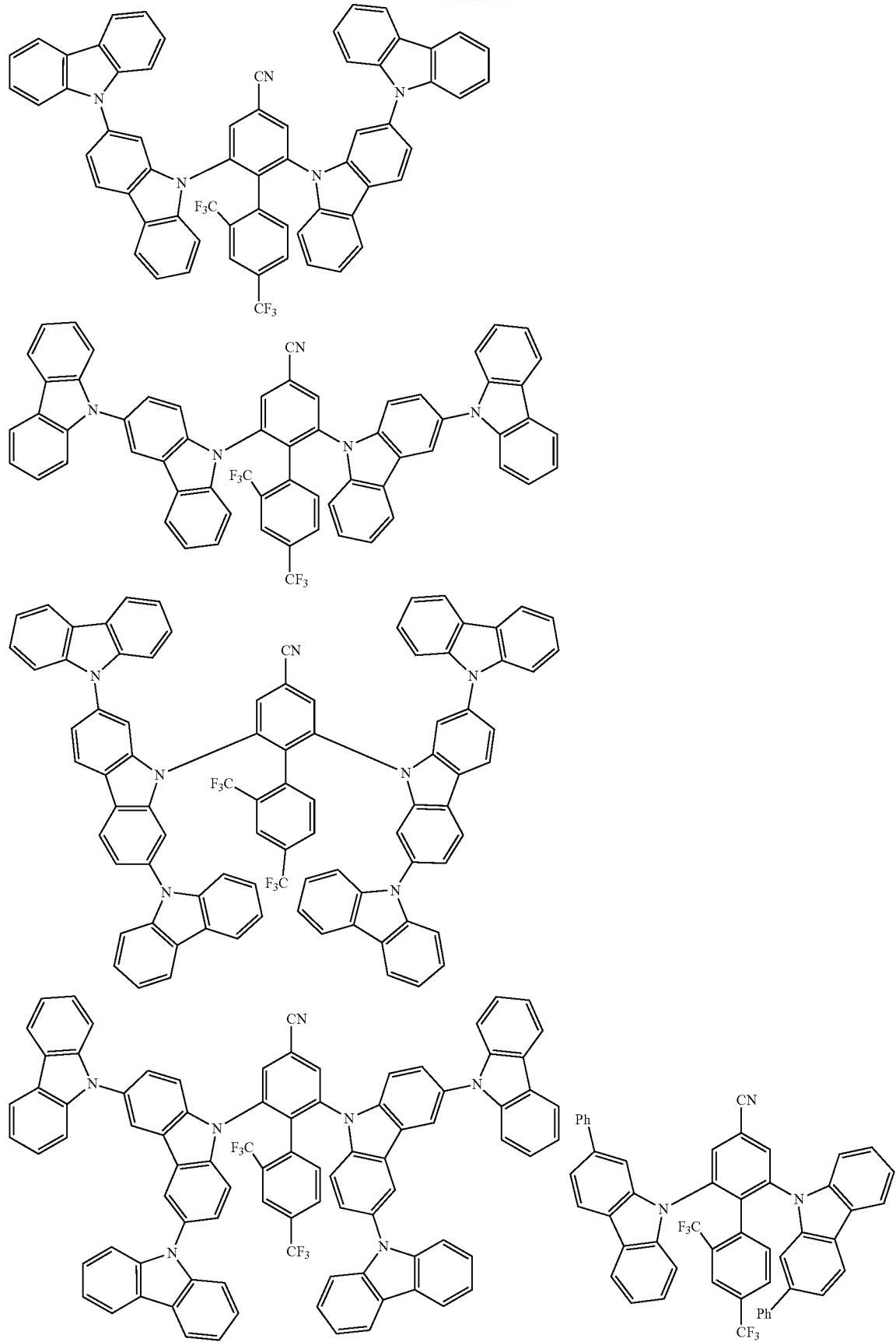

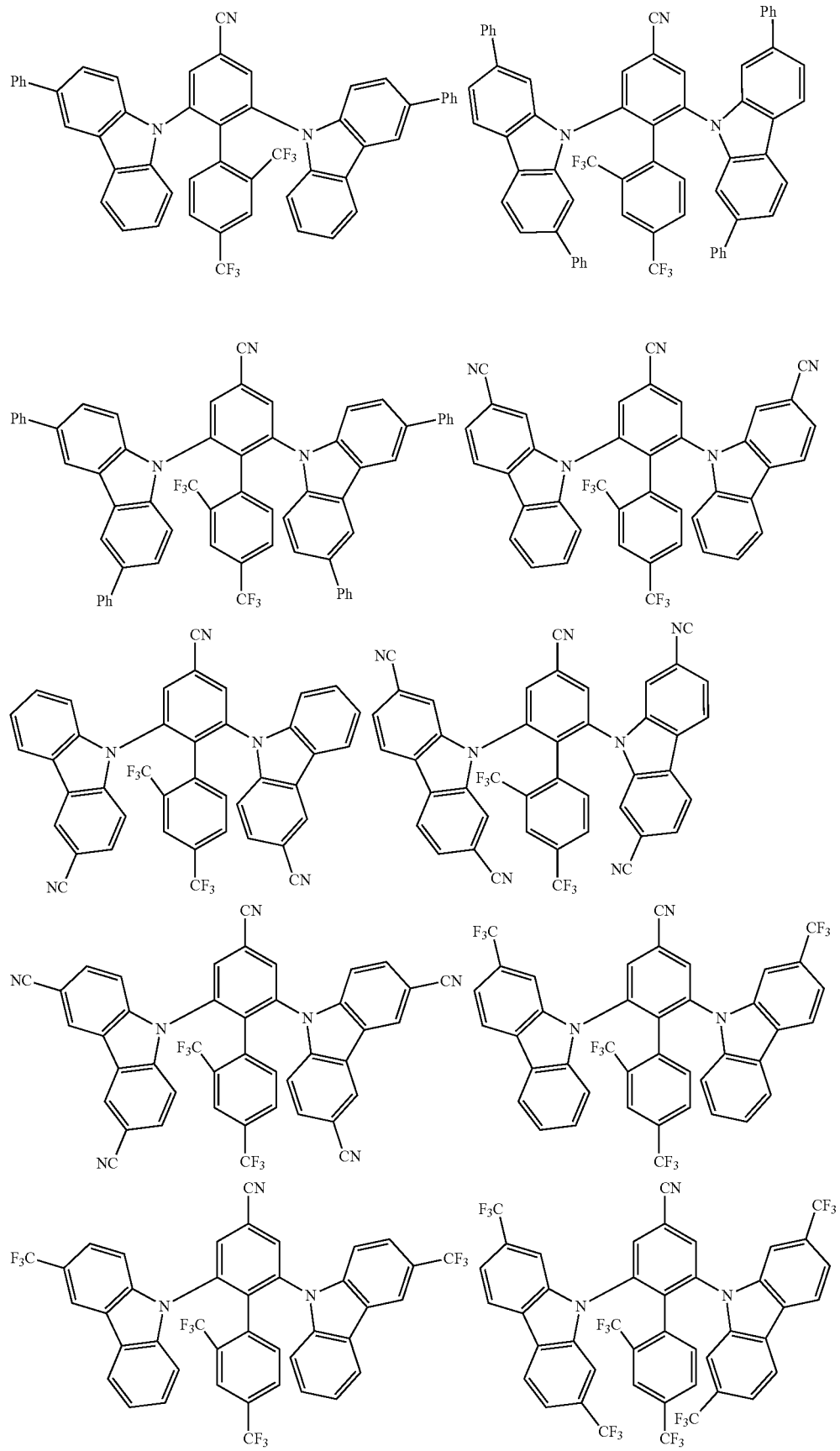

-continued
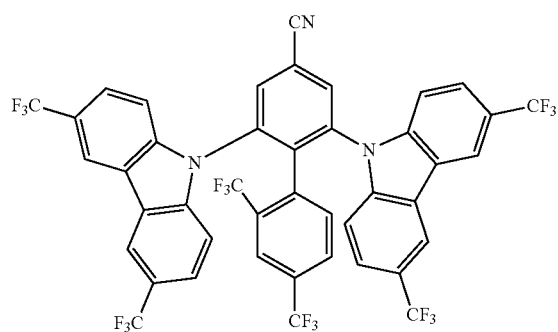
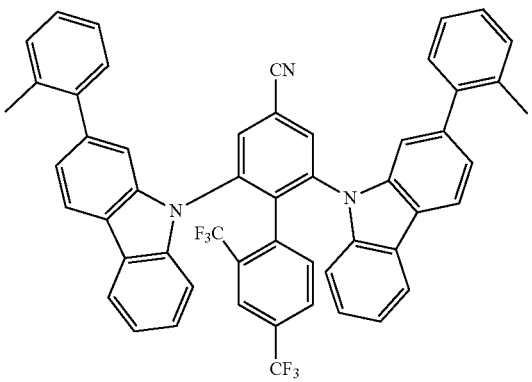
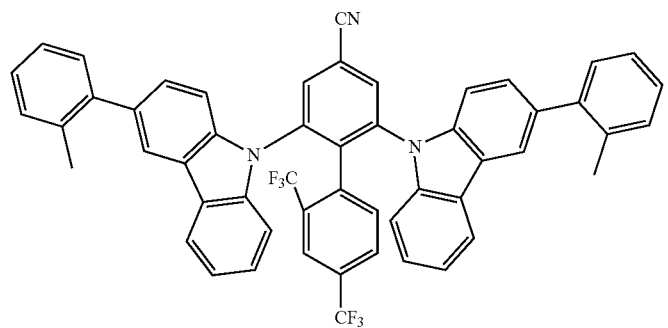
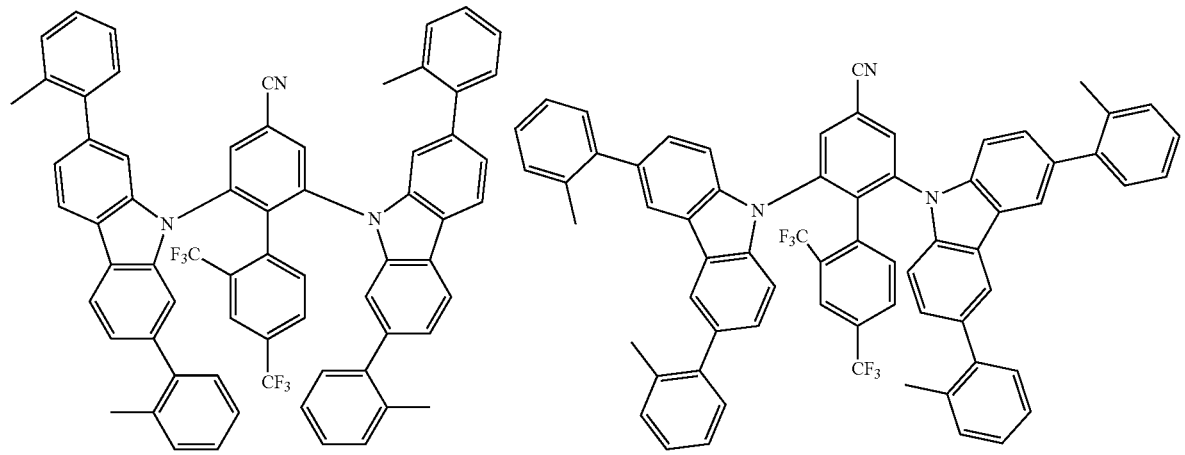
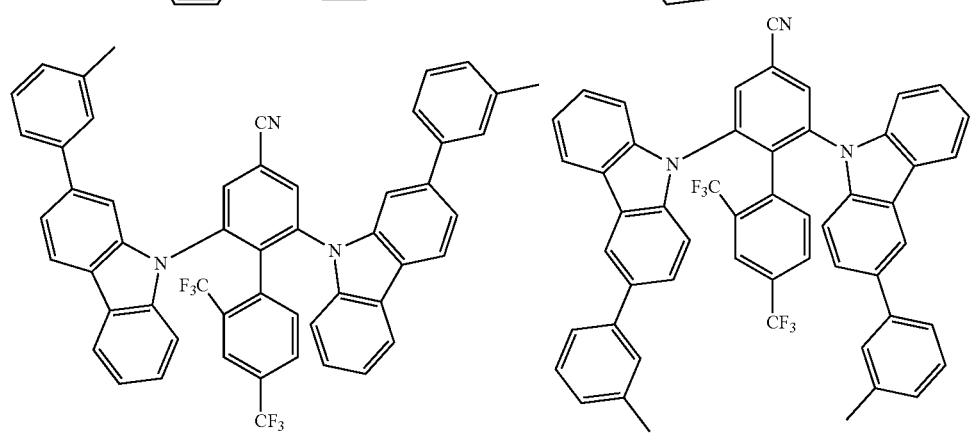

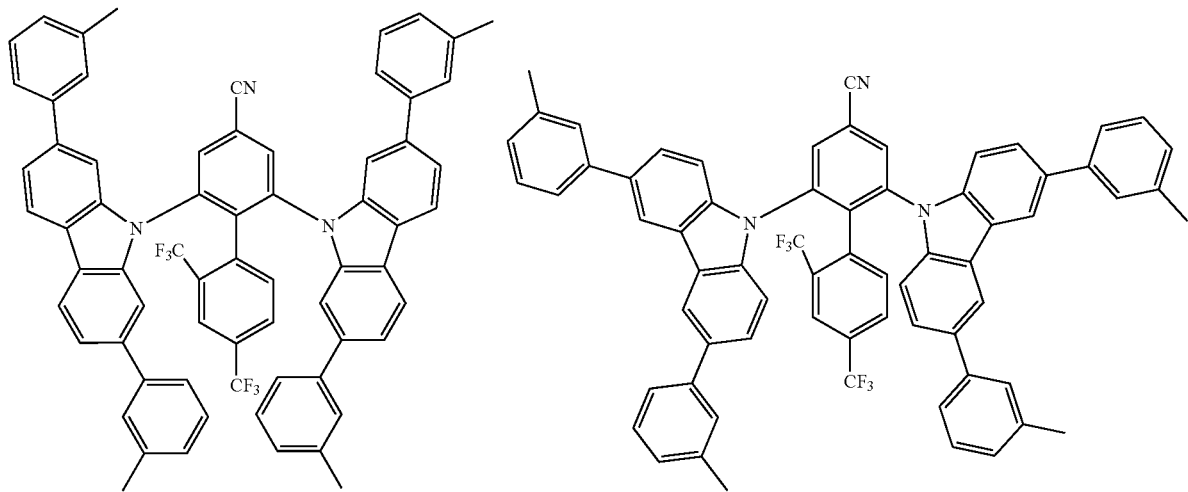
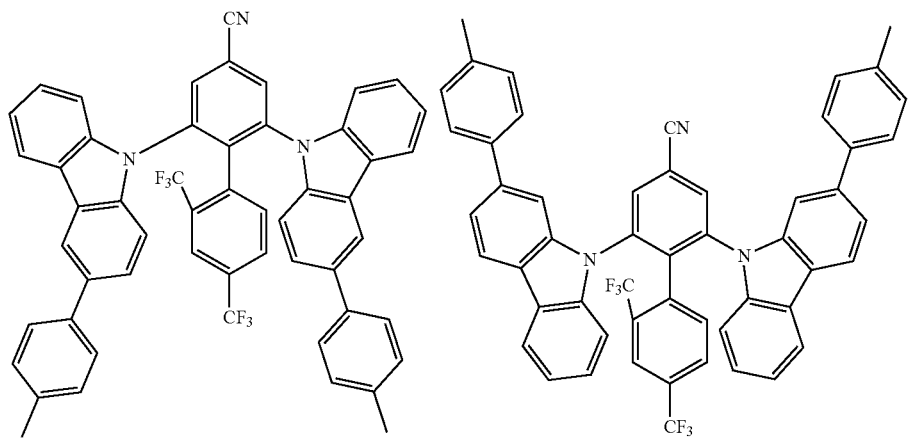
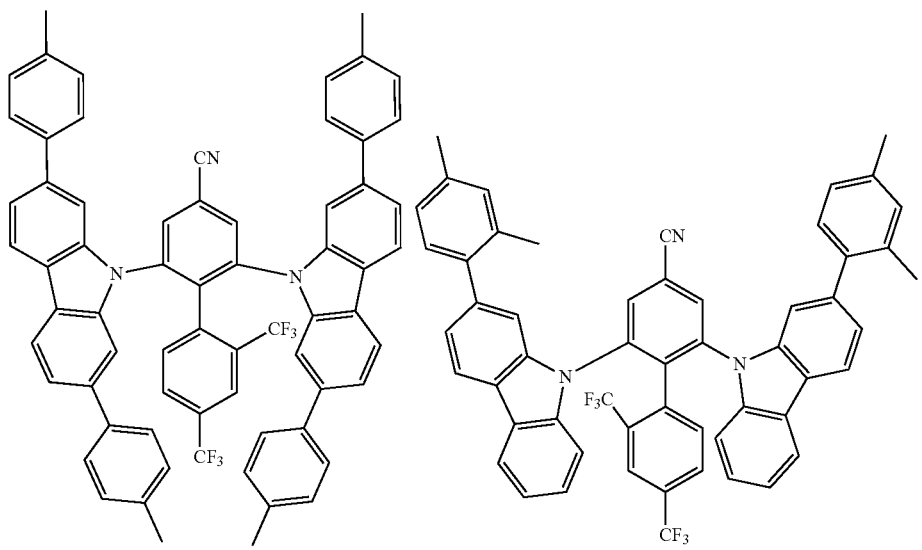

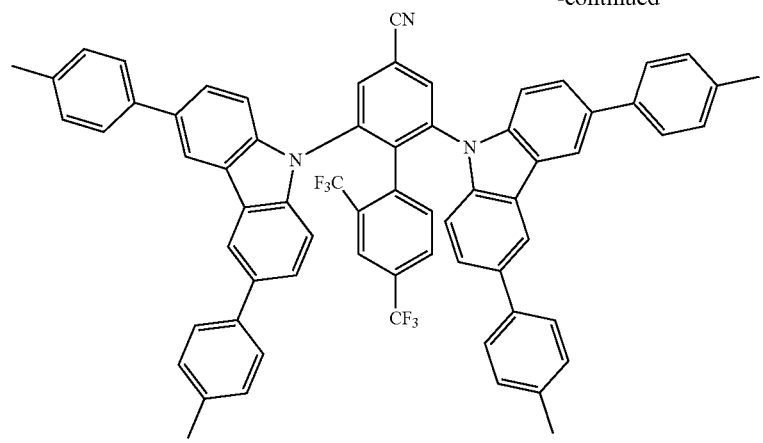
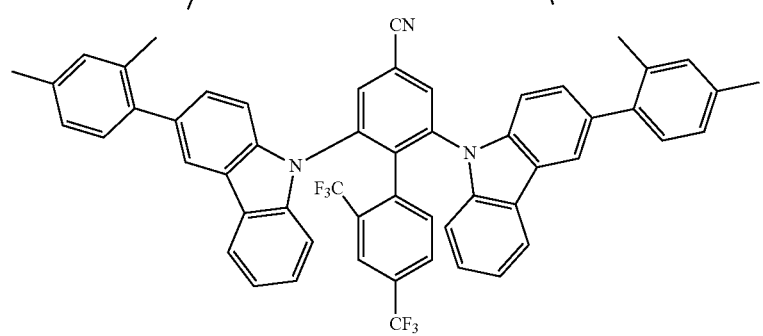
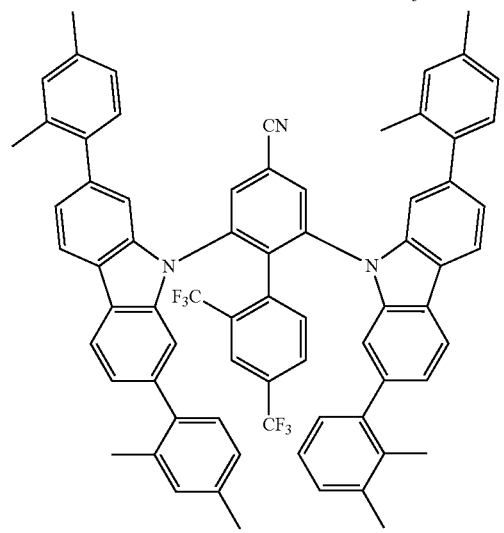
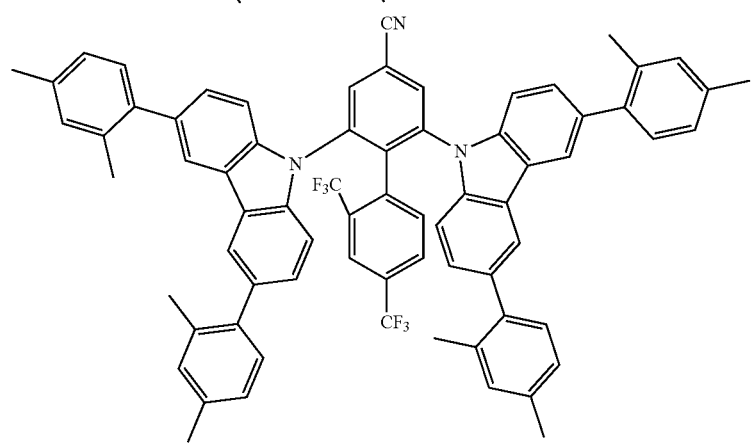

-continued
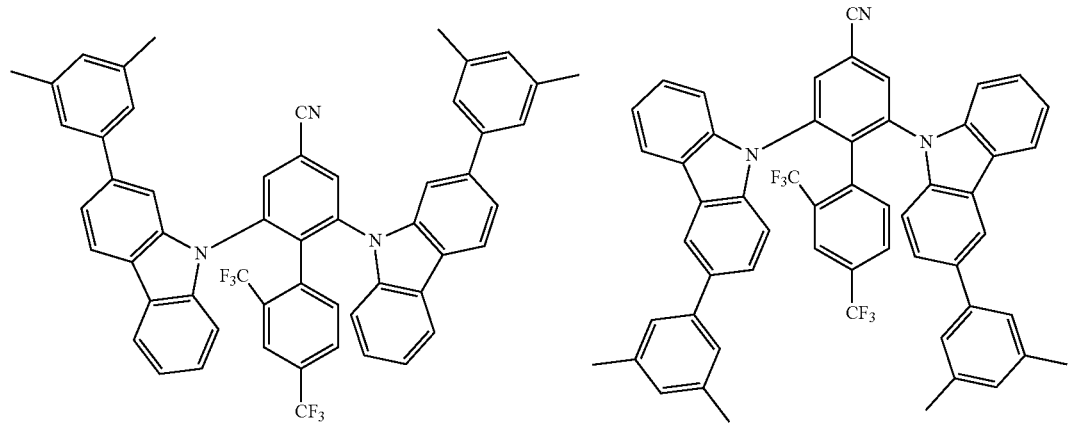
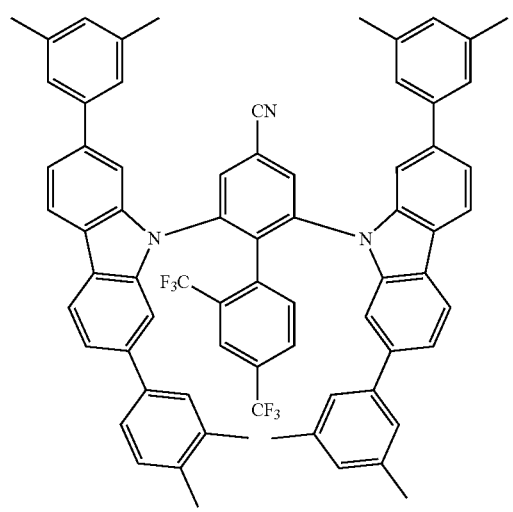
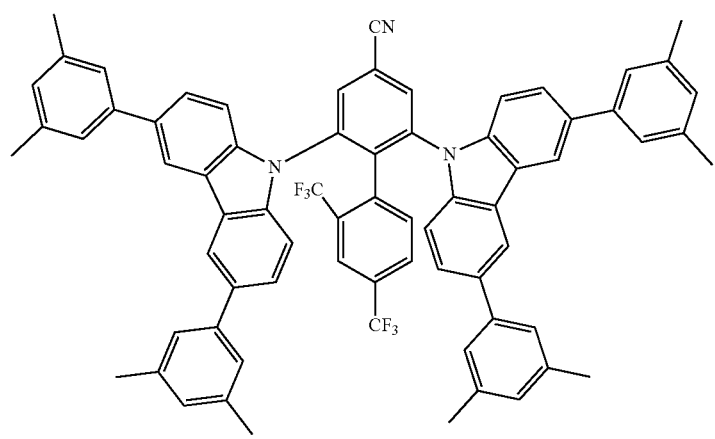

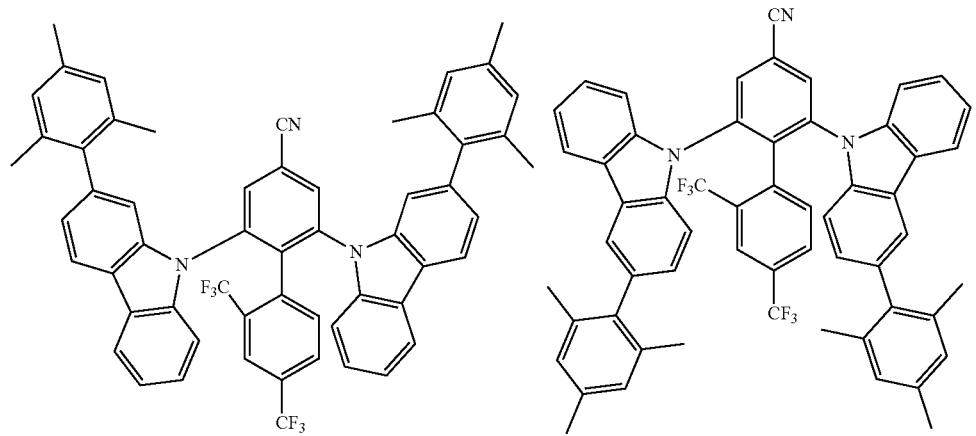
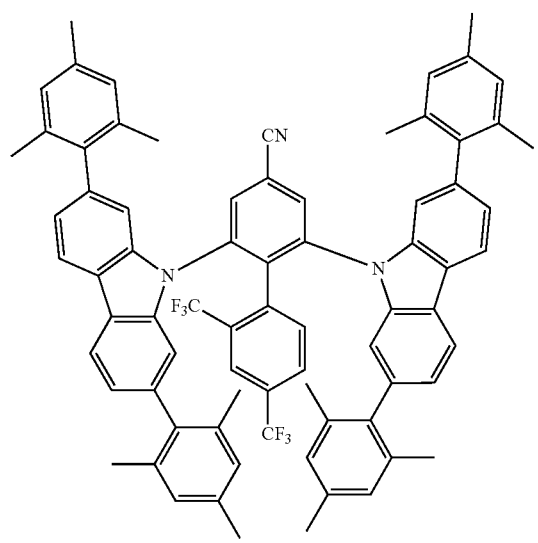
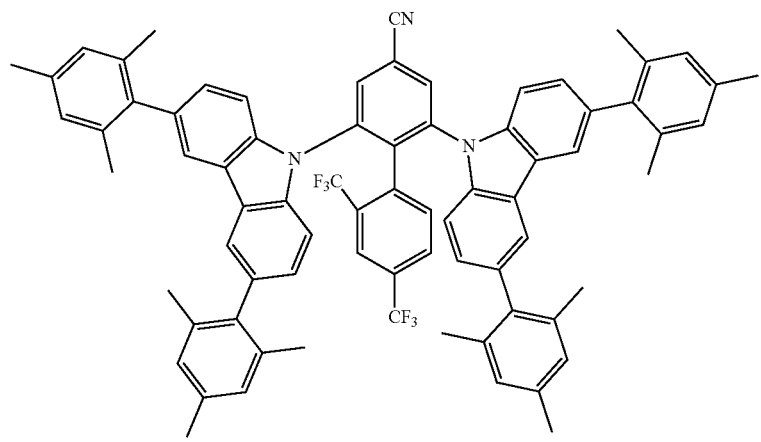

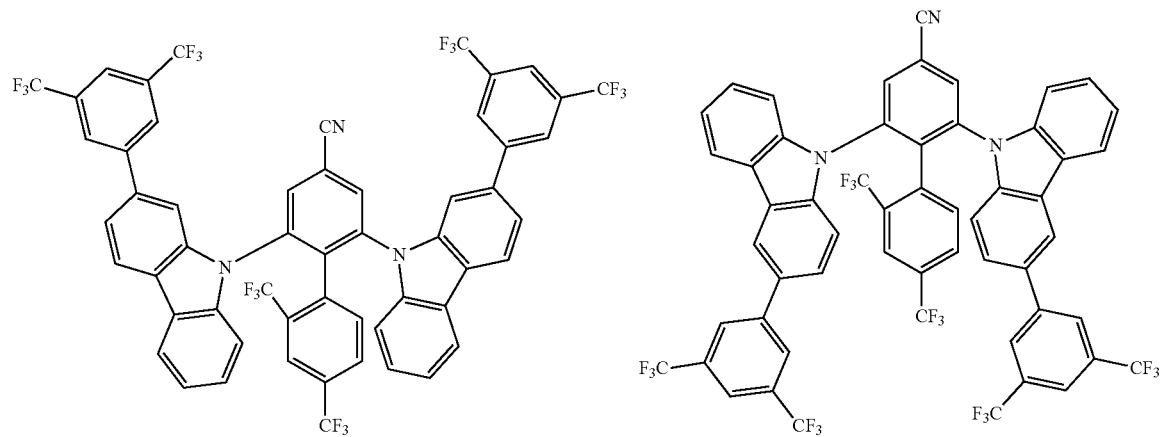
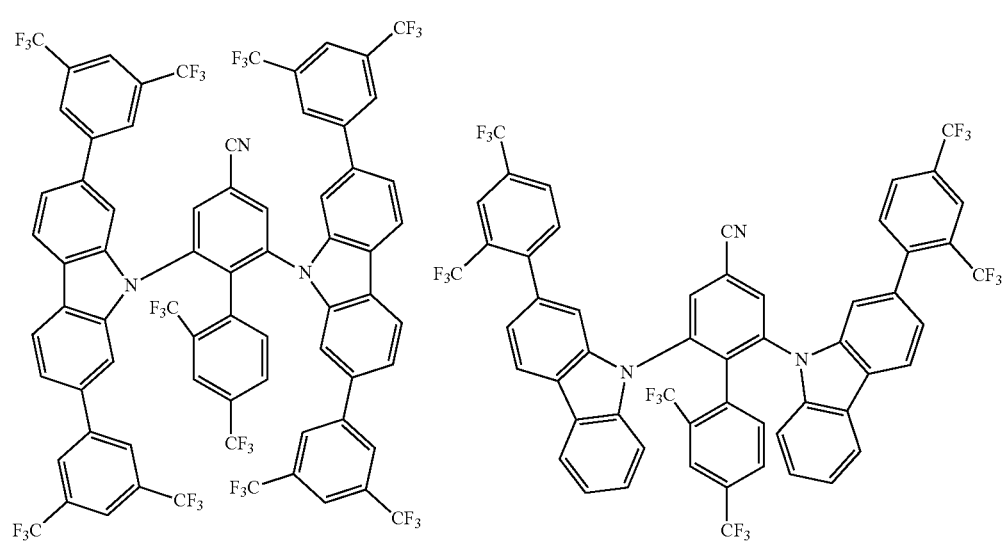
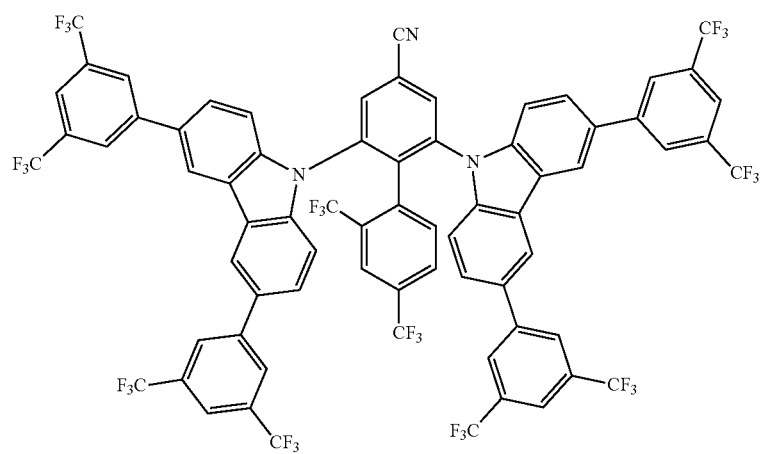

-continued
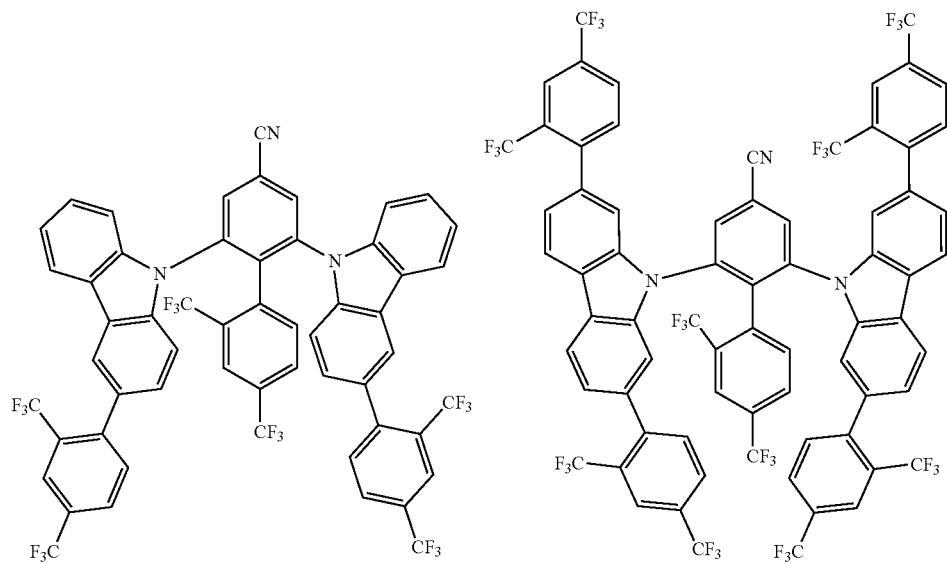
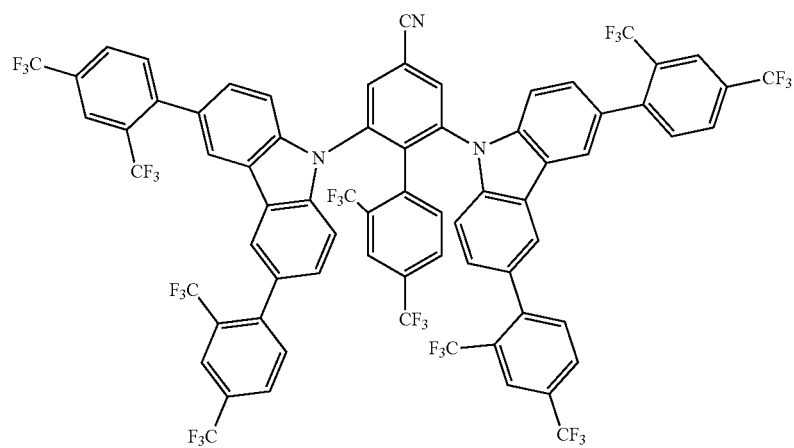
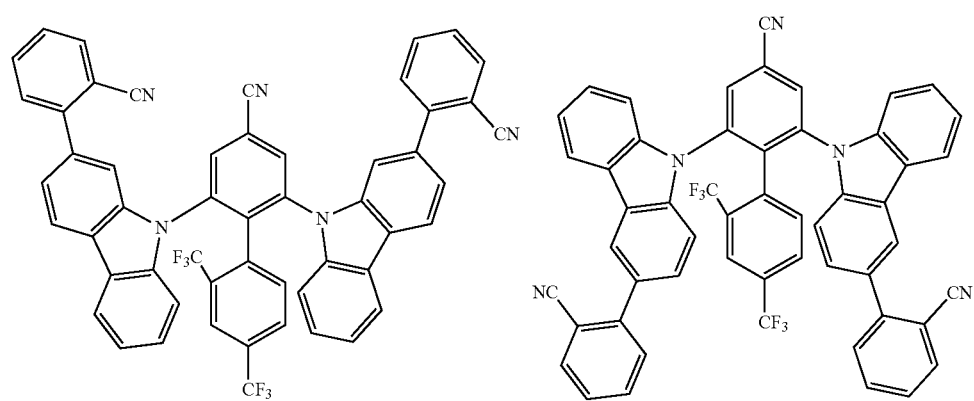

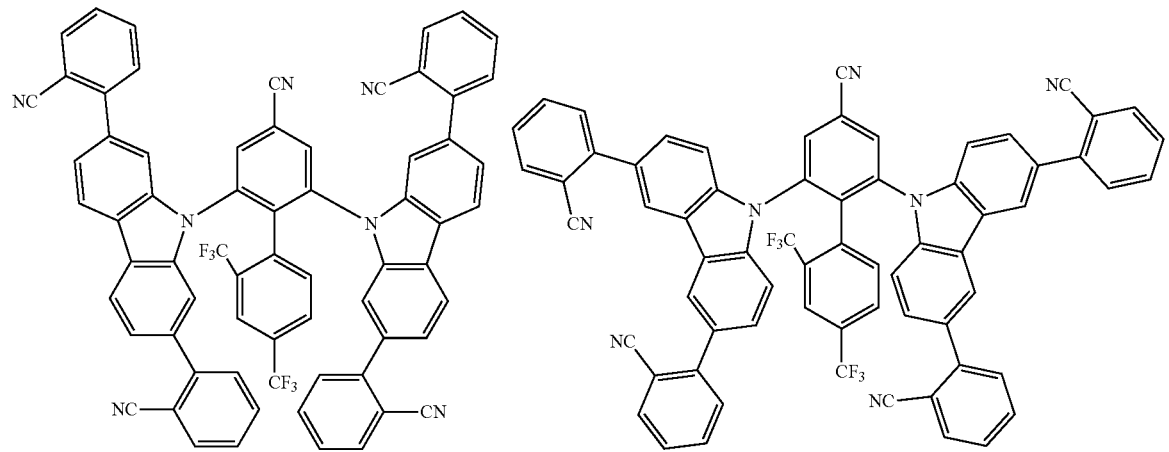
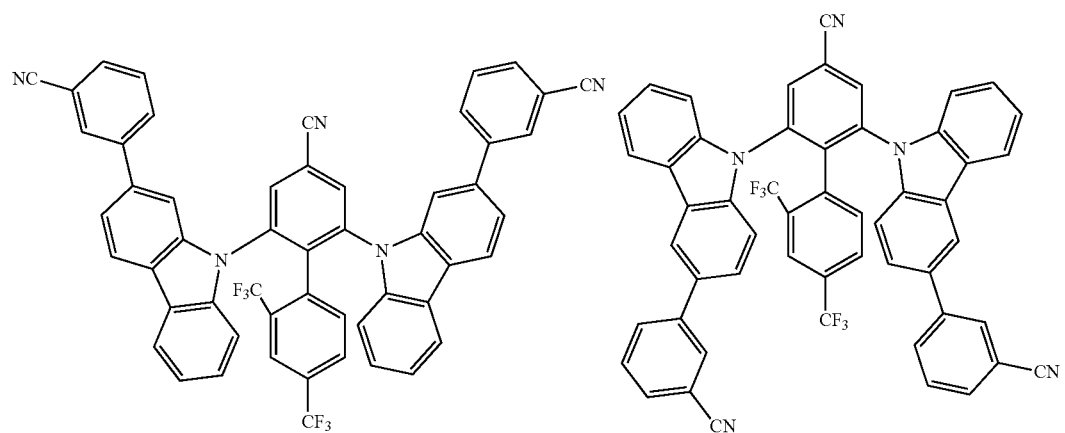
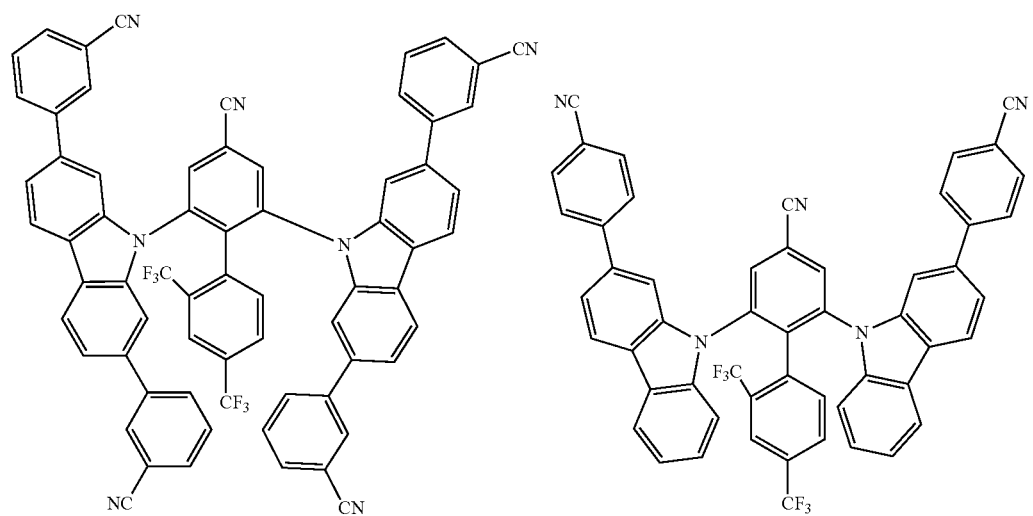

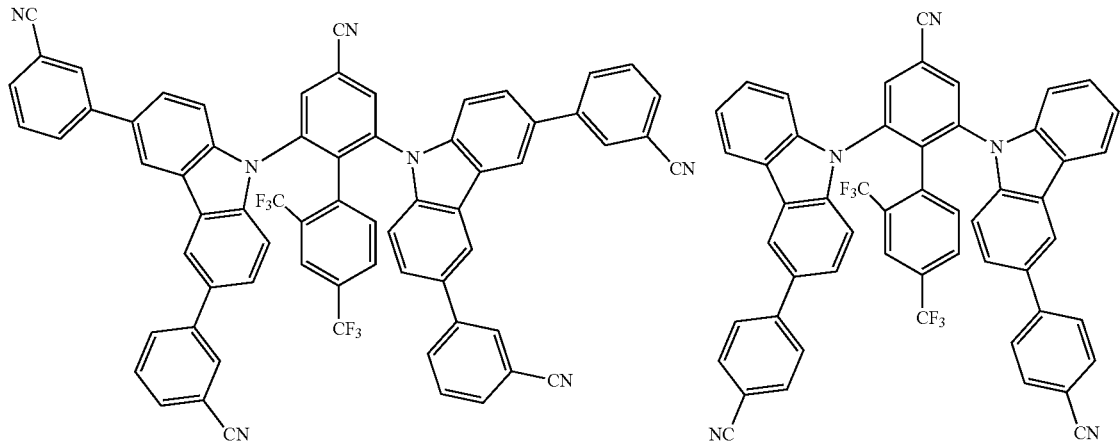
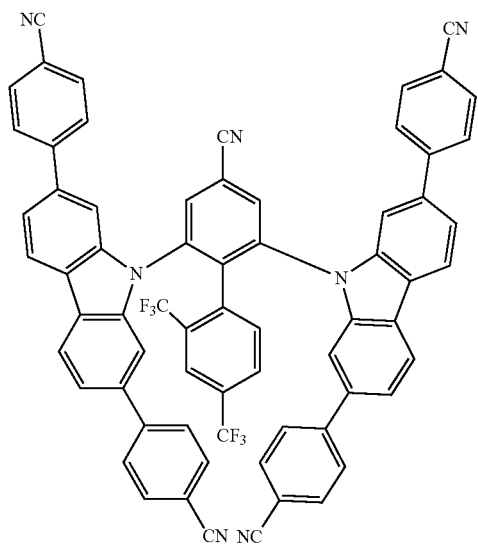
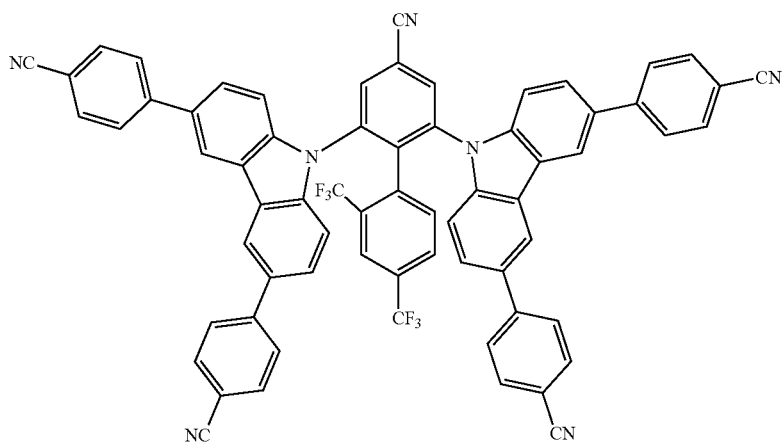

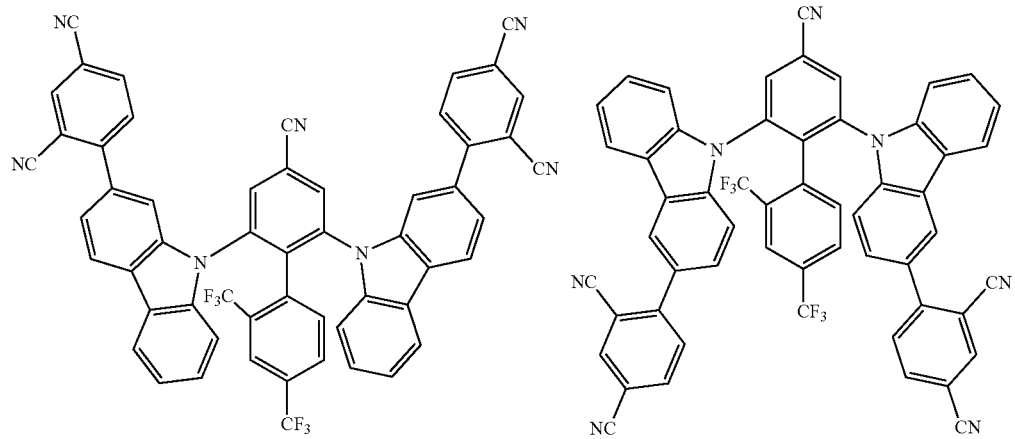
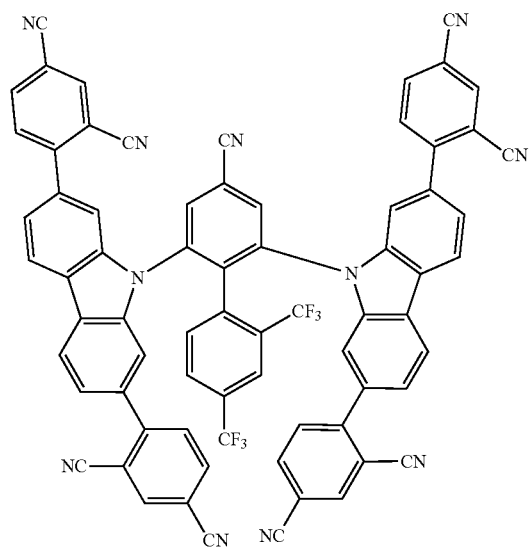
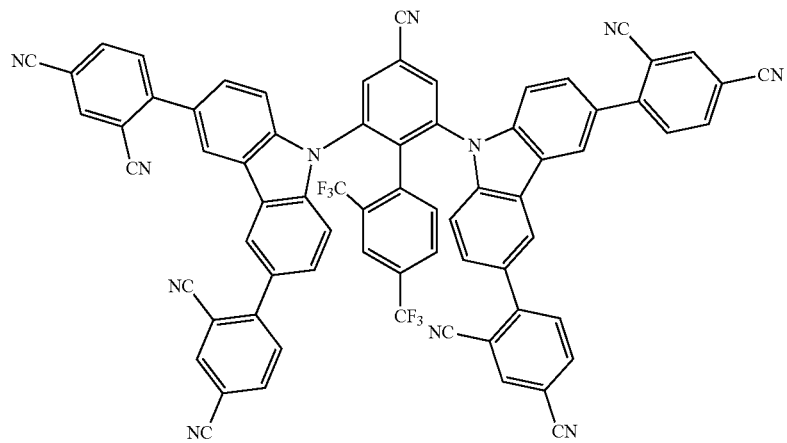

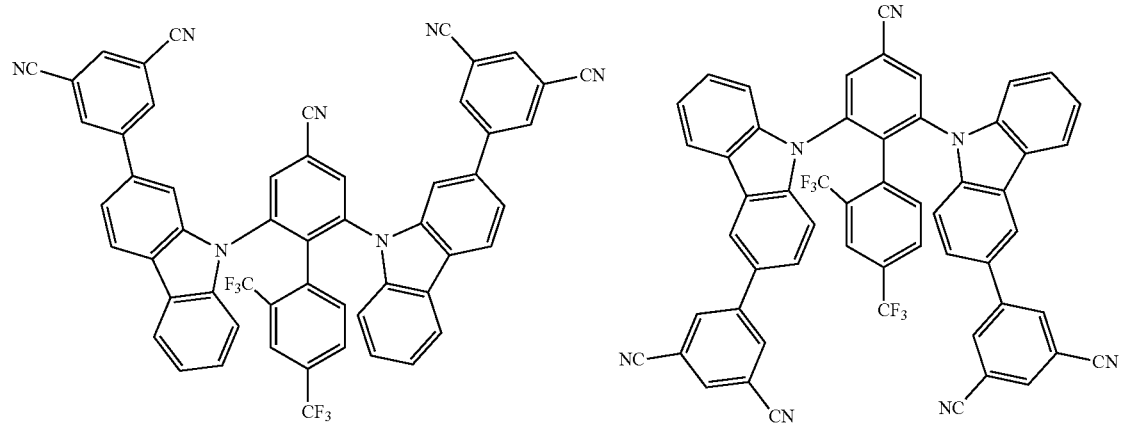
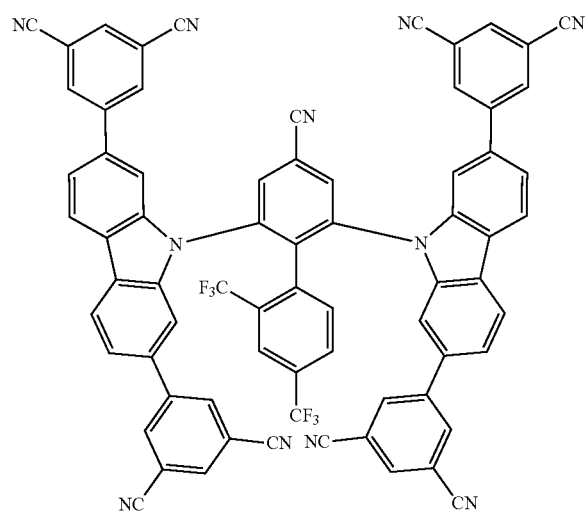
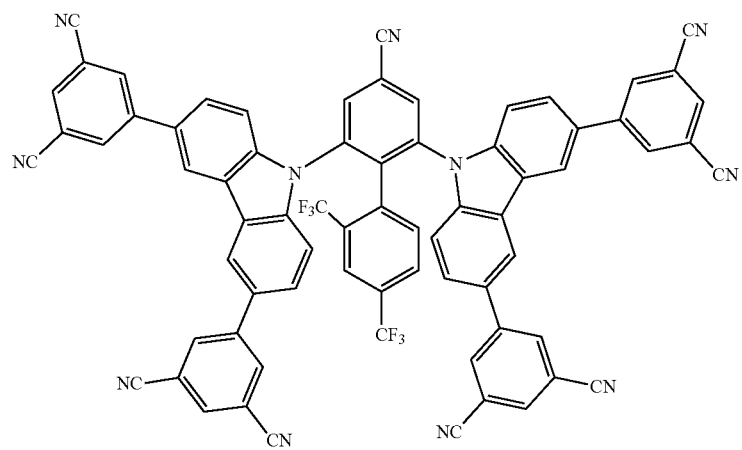

-continued
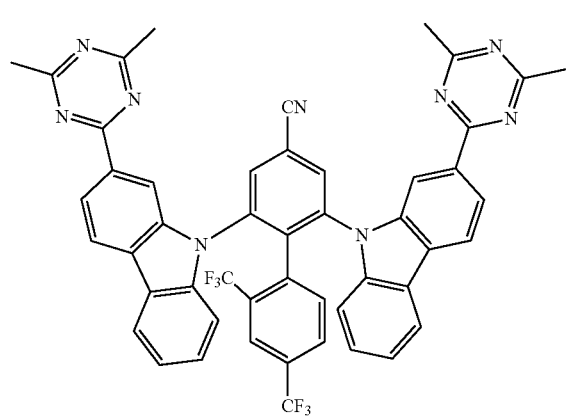
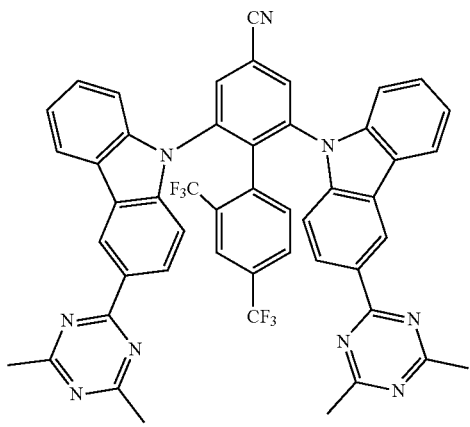
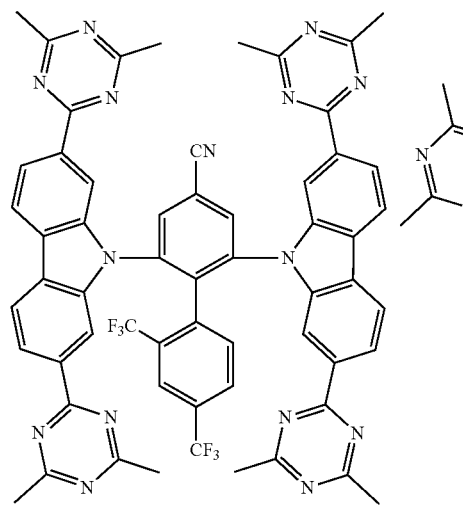
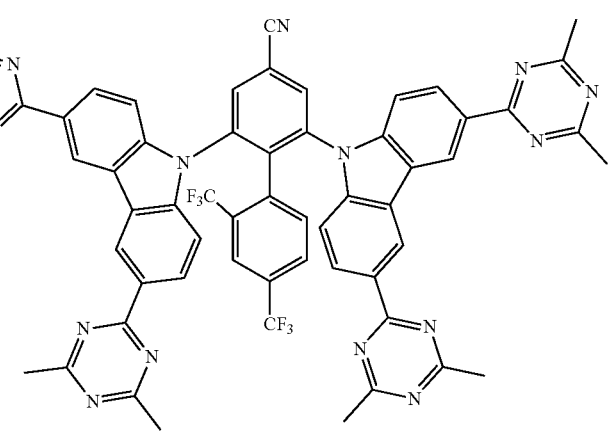
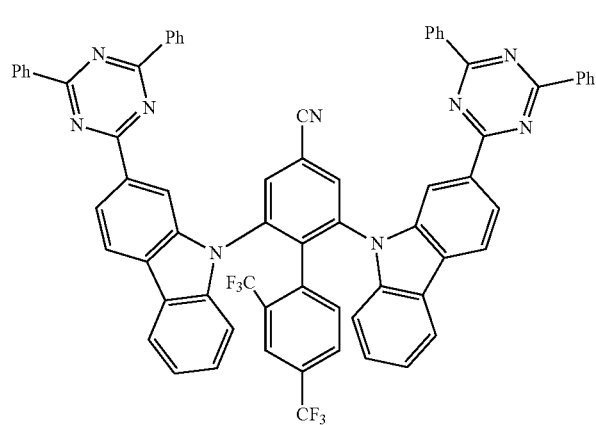
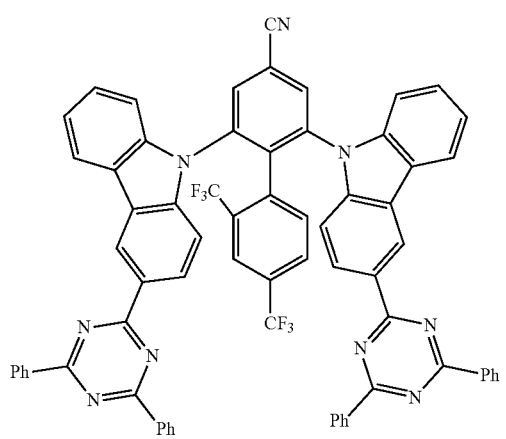

121
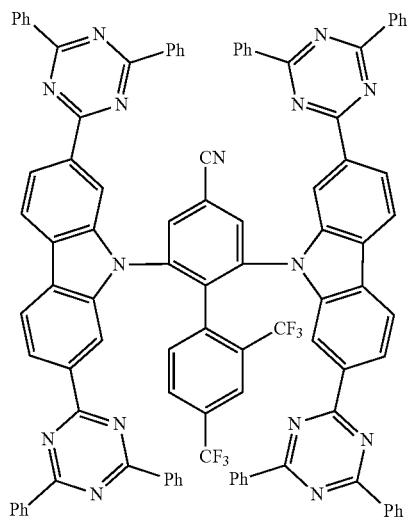
122
-continued
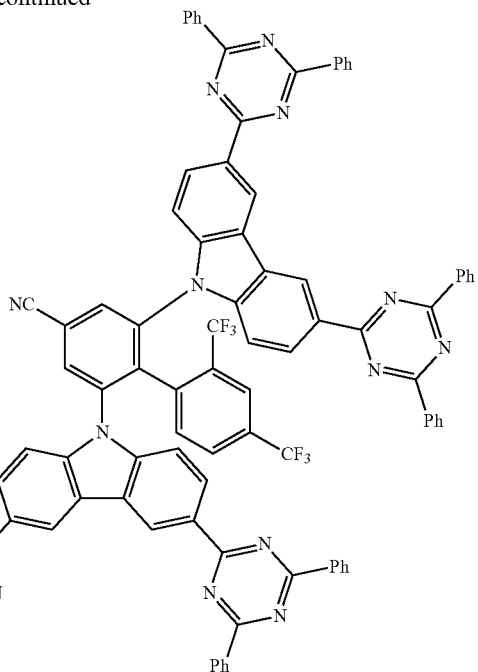
-continued
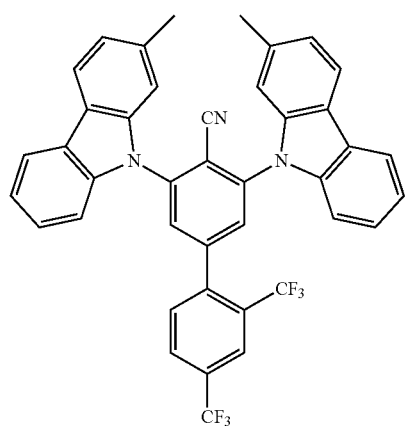
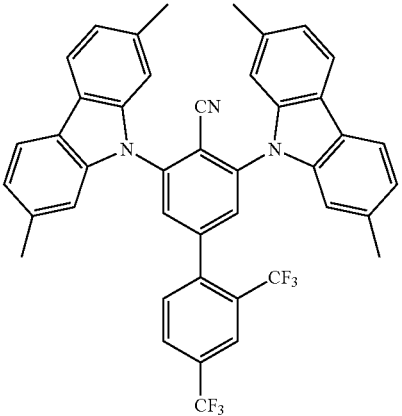
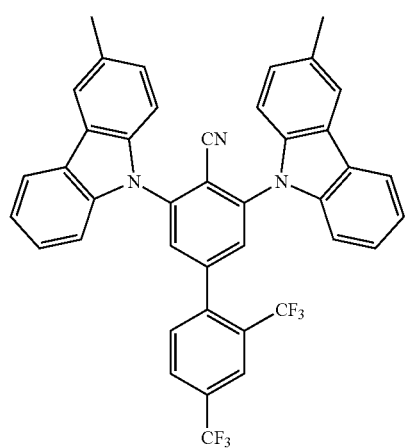
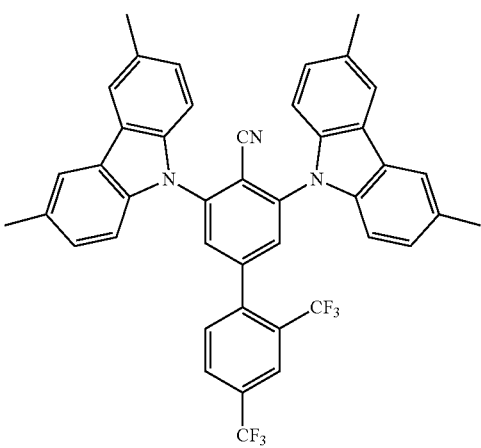

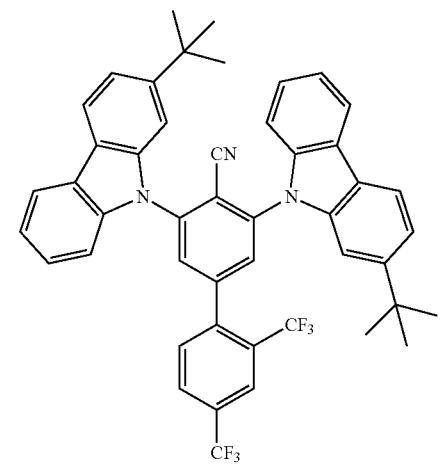
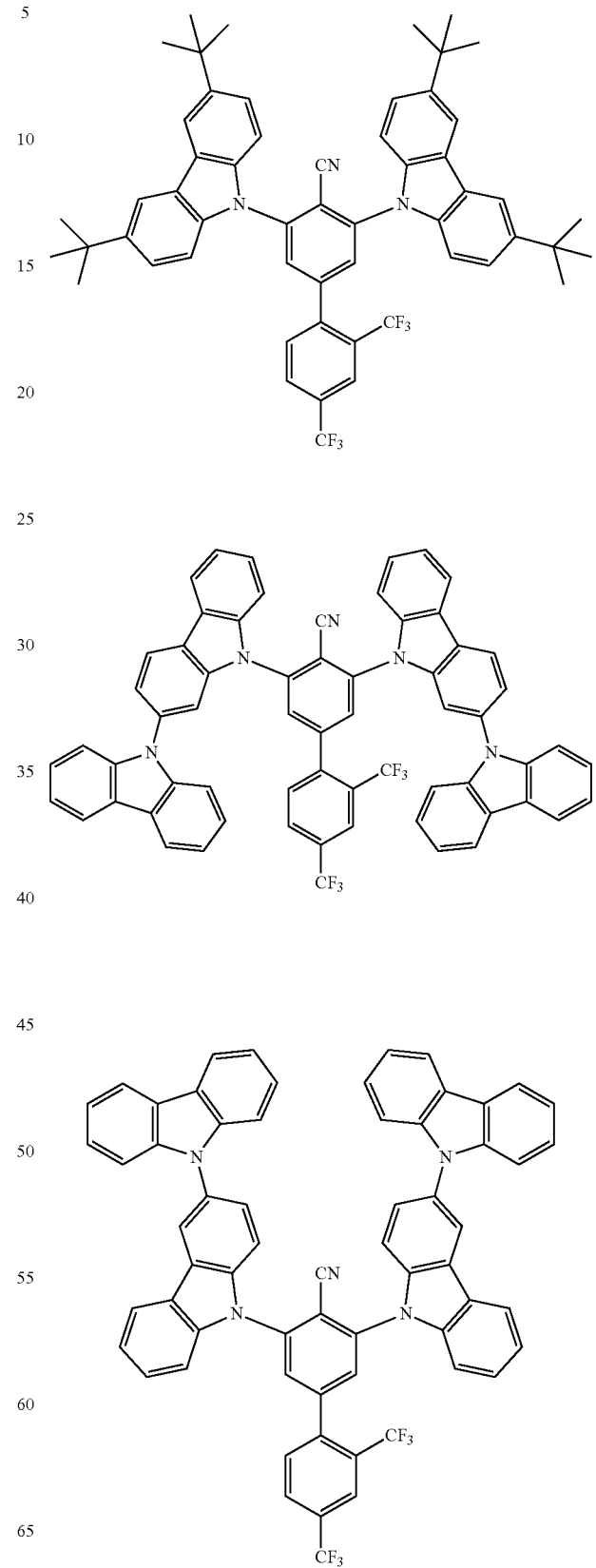

-continued
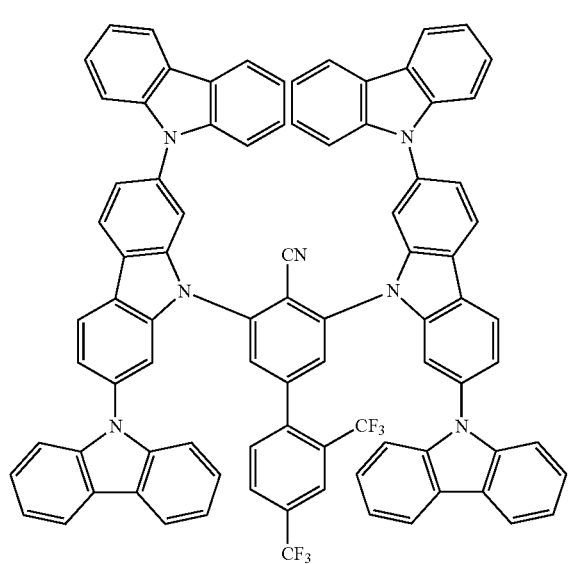
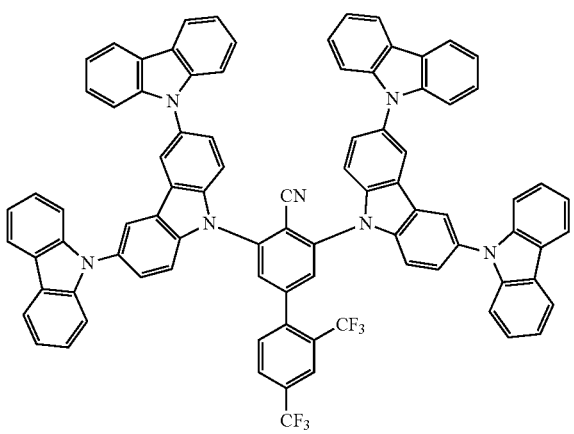
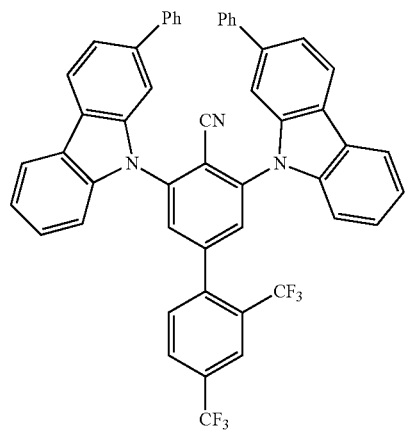
-continued
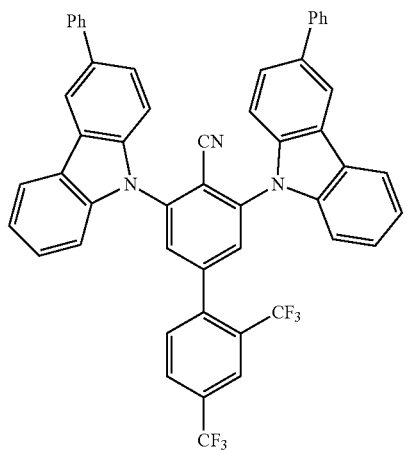
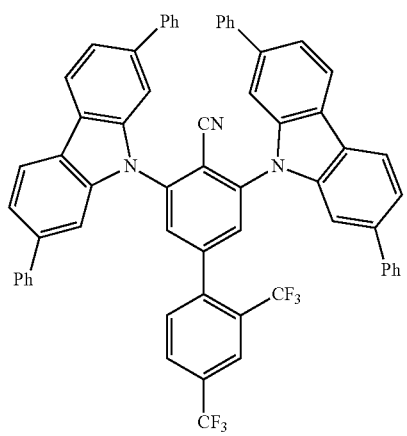
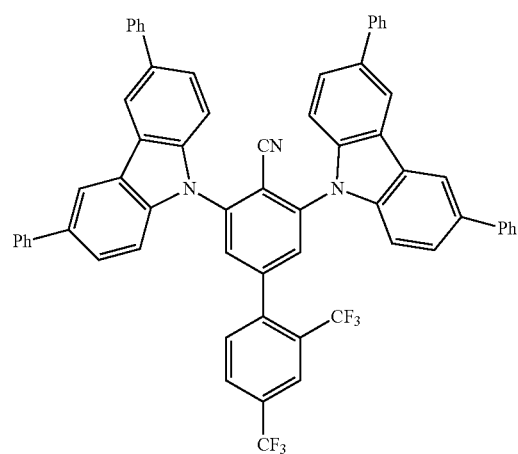

127
-continued
128
-continued
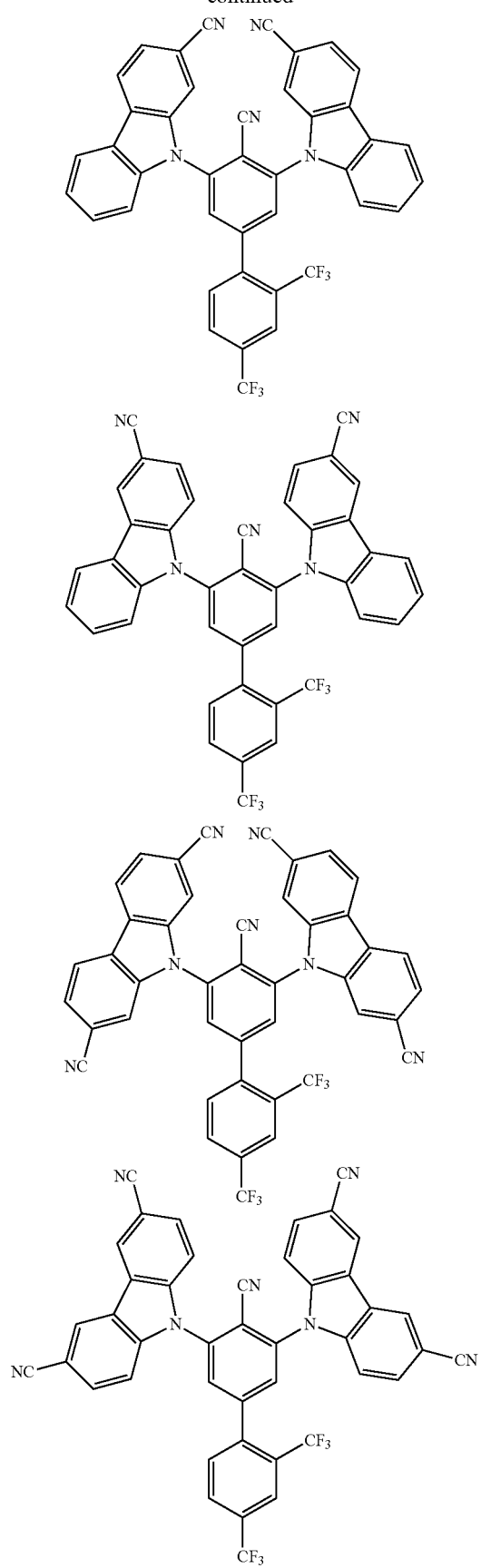
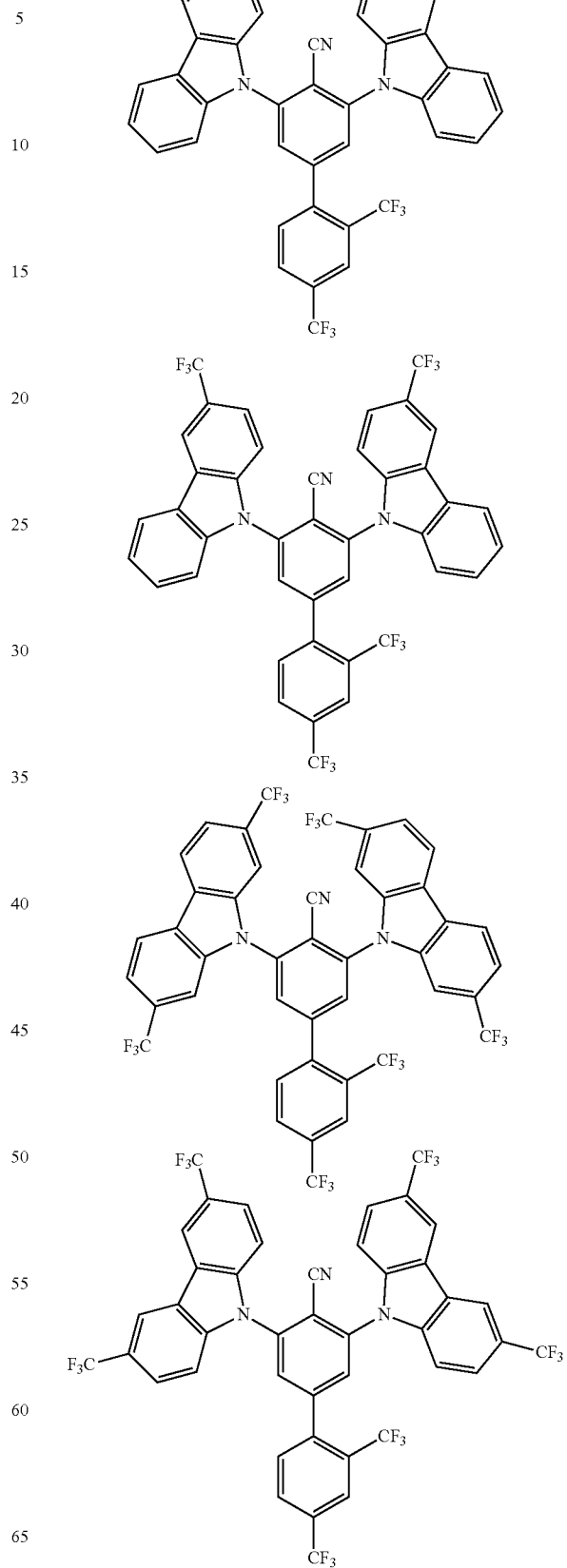

129
-continued
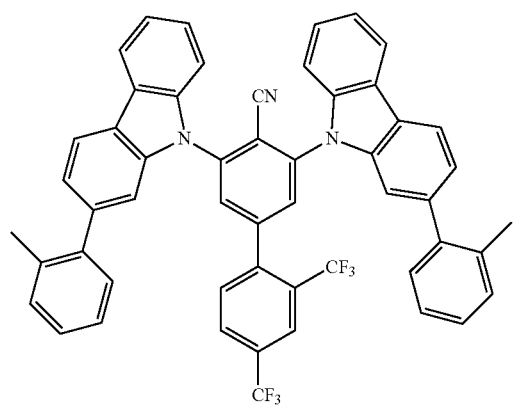
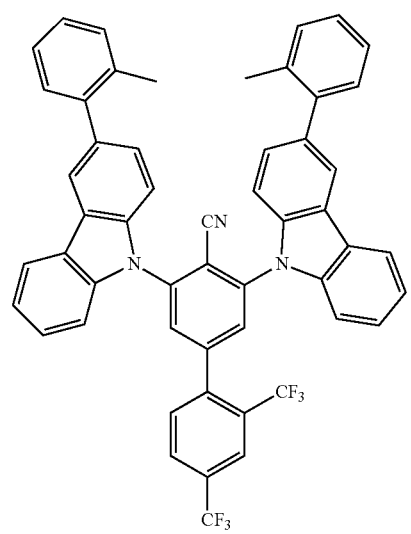
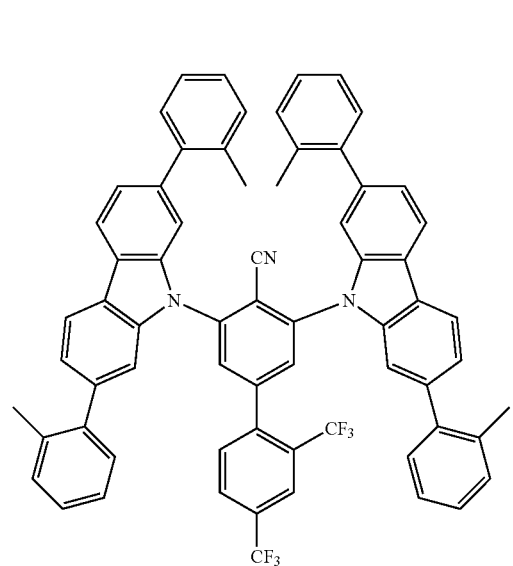
130
-continued
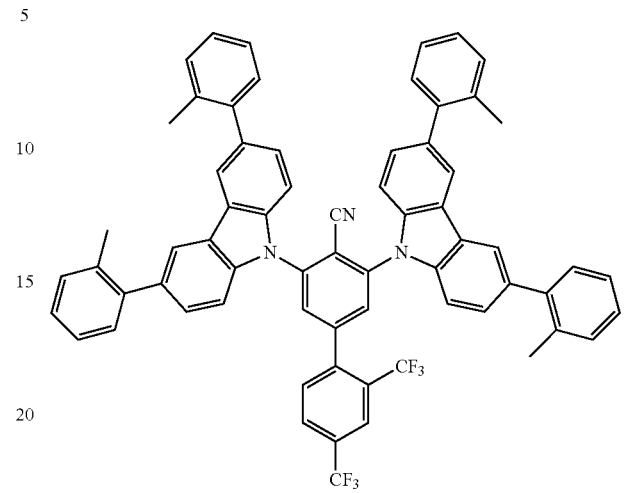
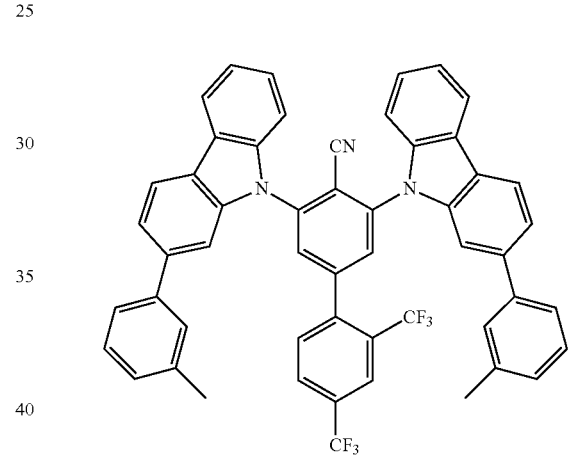
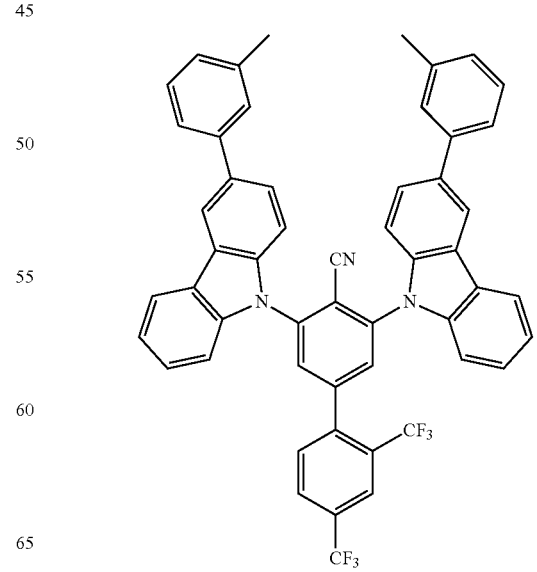

131
-continued
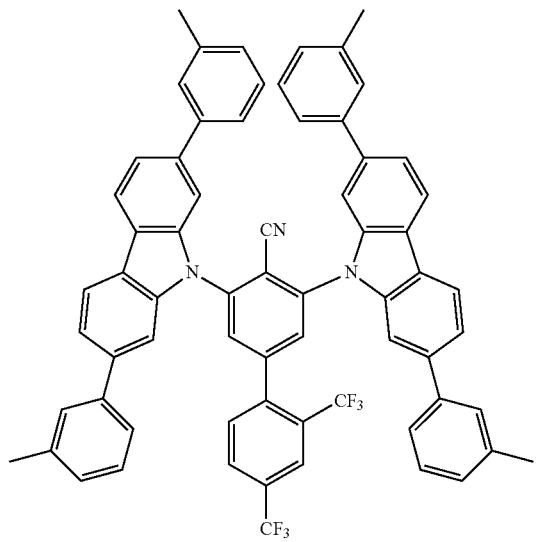
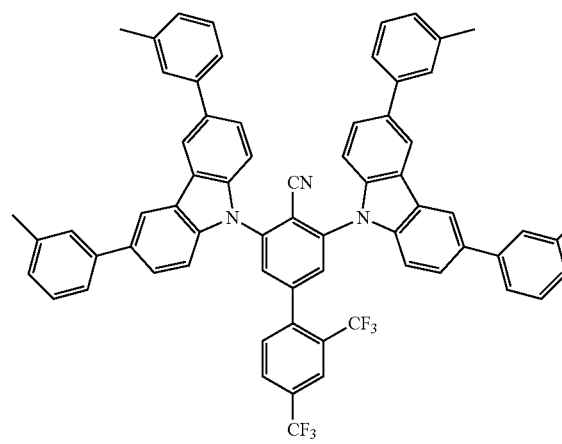
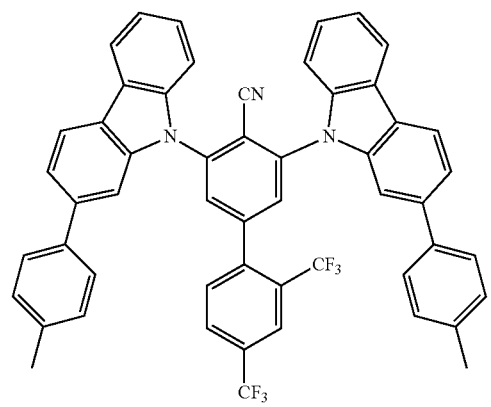
132
-continued
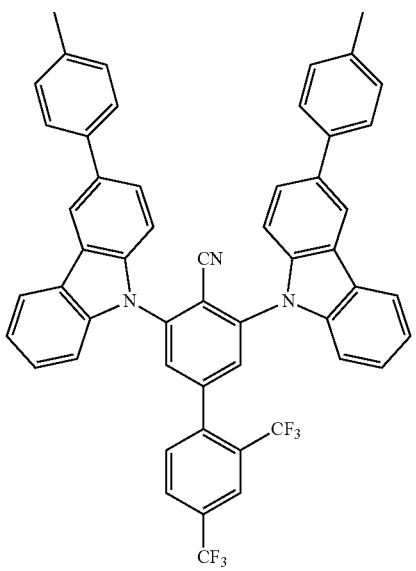
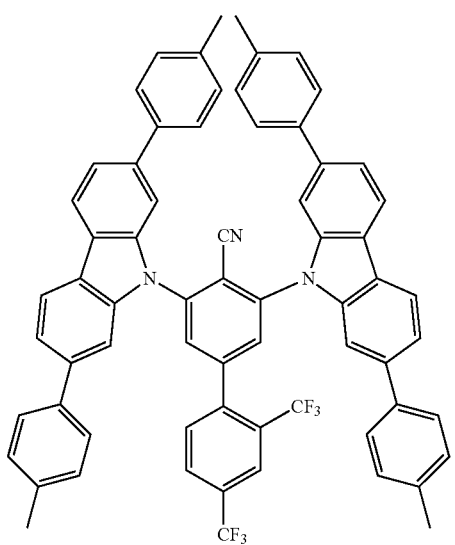
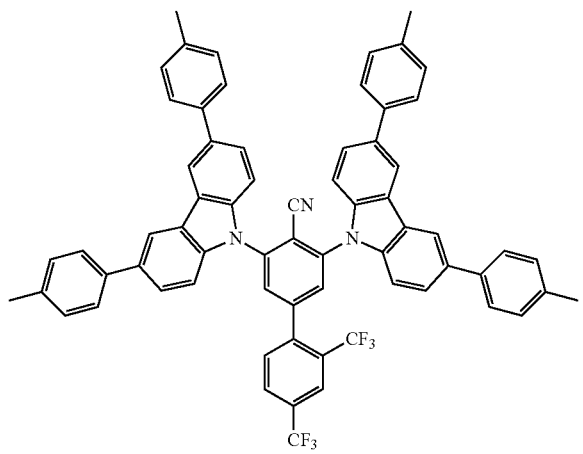

133
-continued
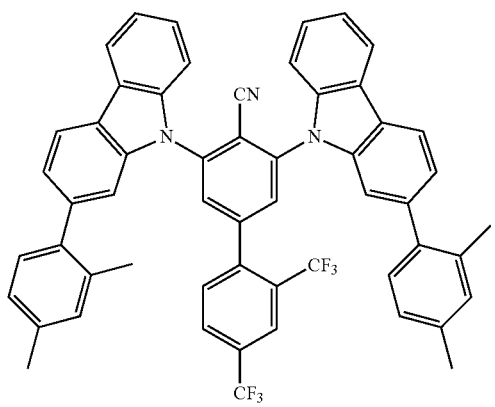
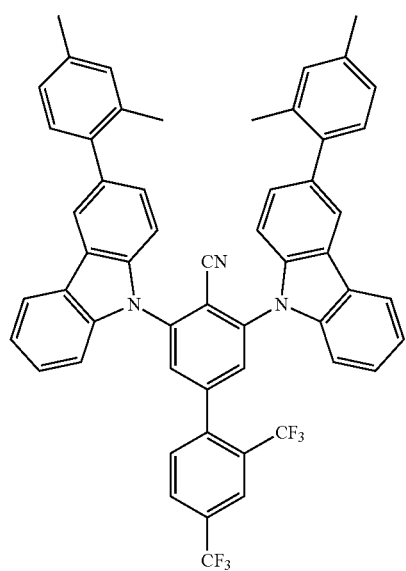
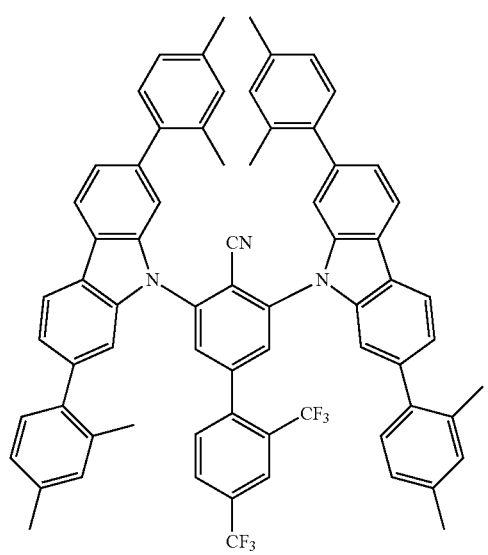
134
-continued
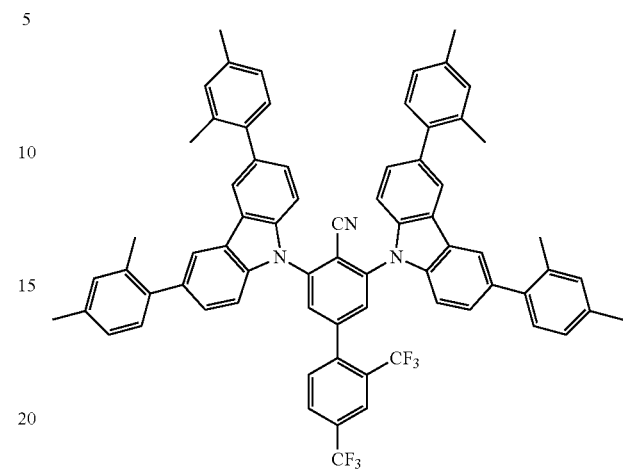
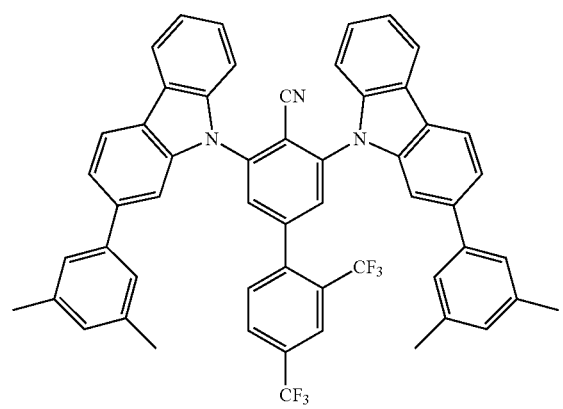

135
-continued
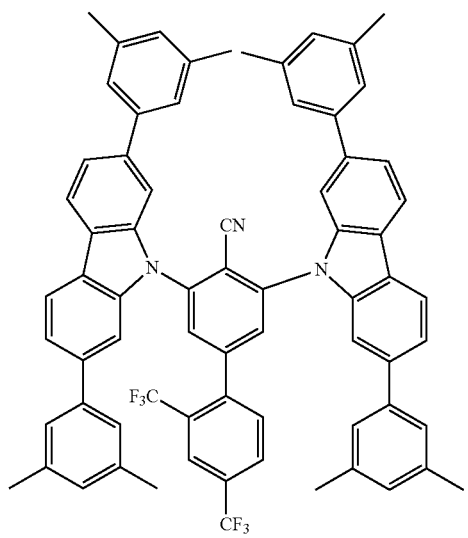
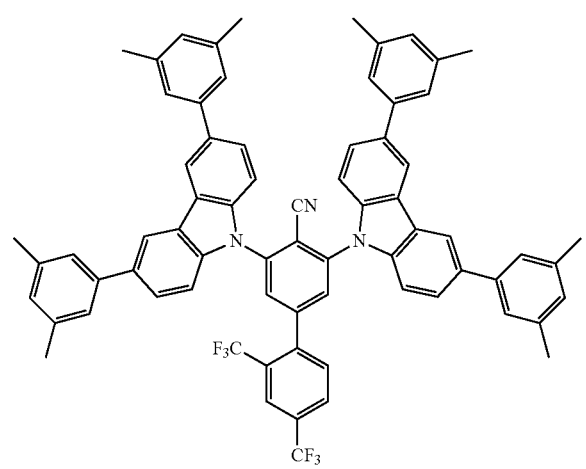
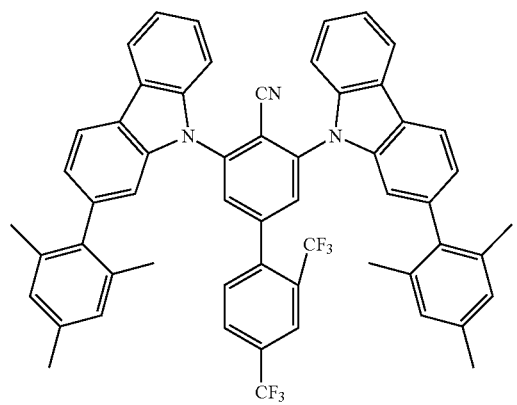
136
-continued
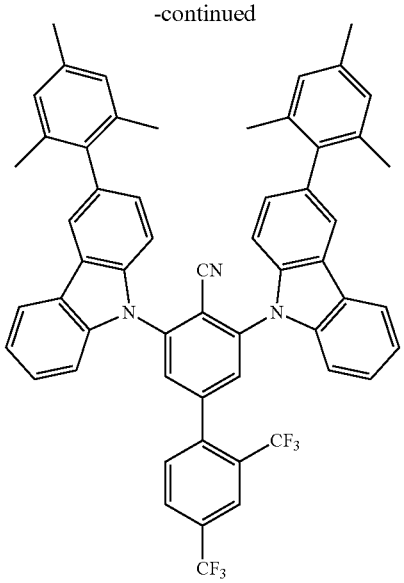
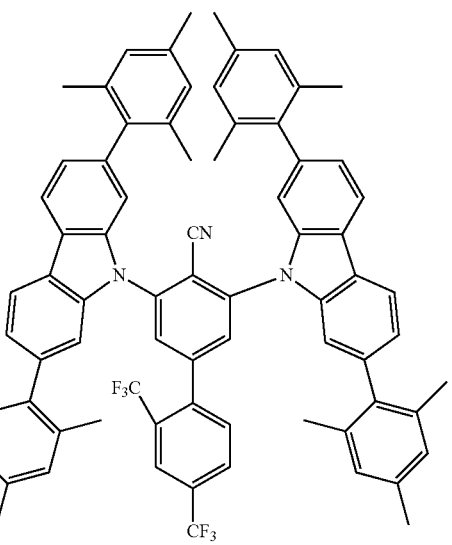
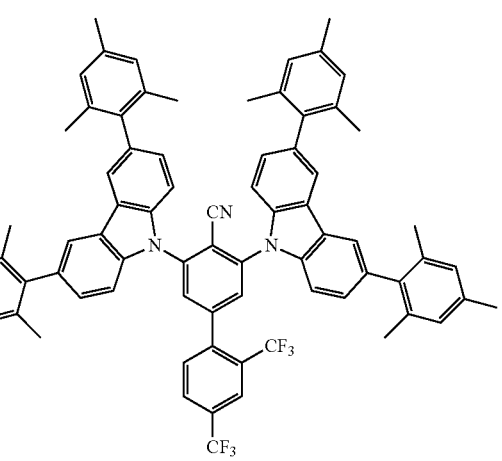

137
-continued
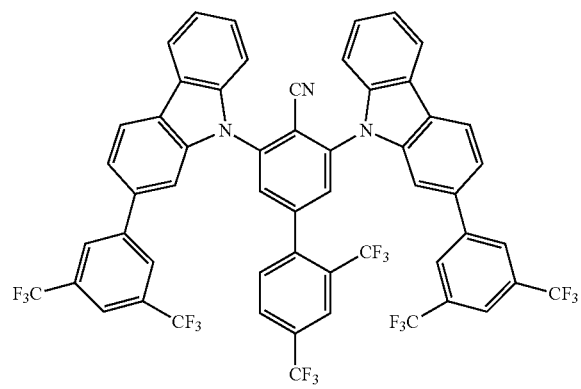
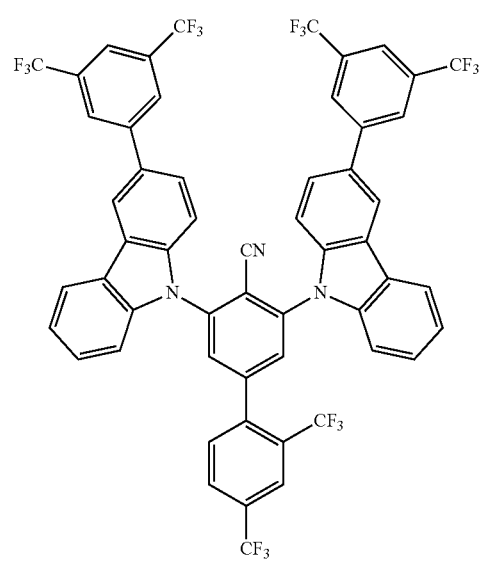
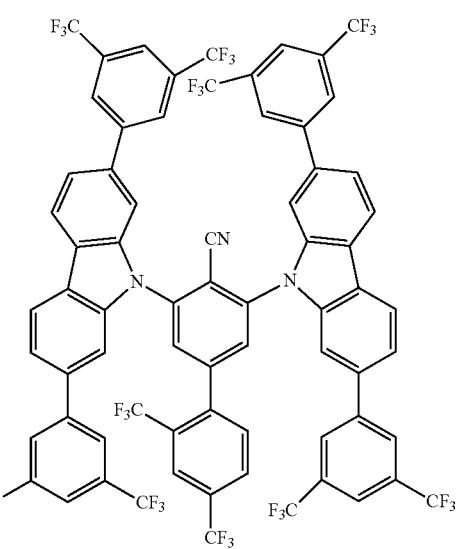
138
-continued
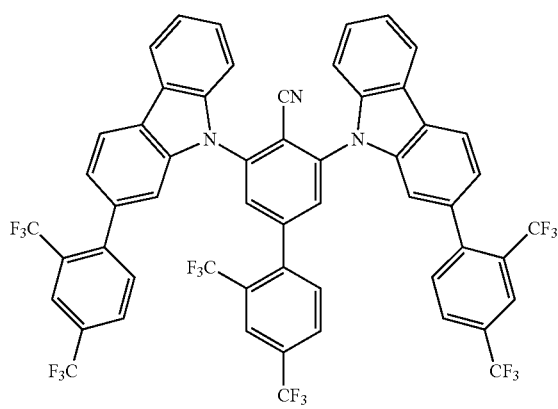
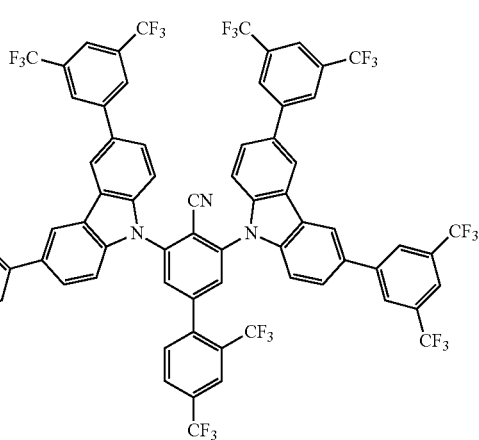
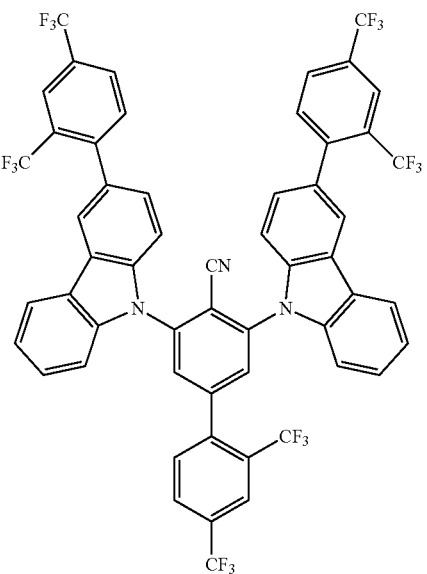

139
-continued
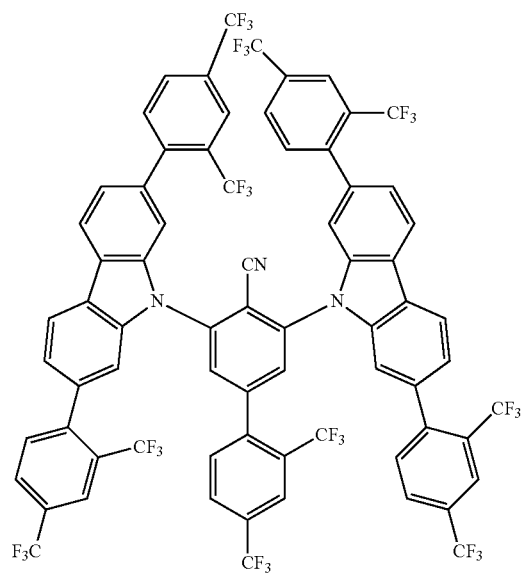
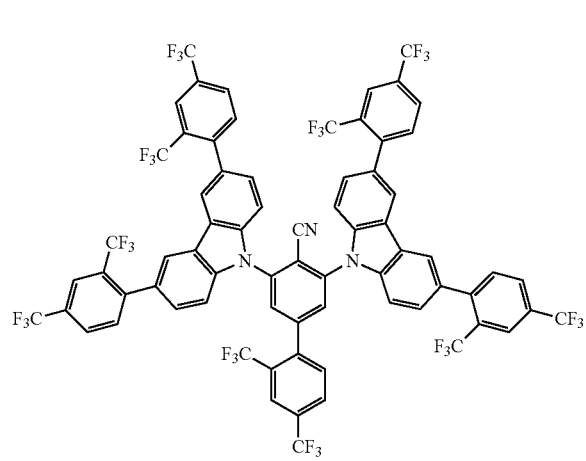
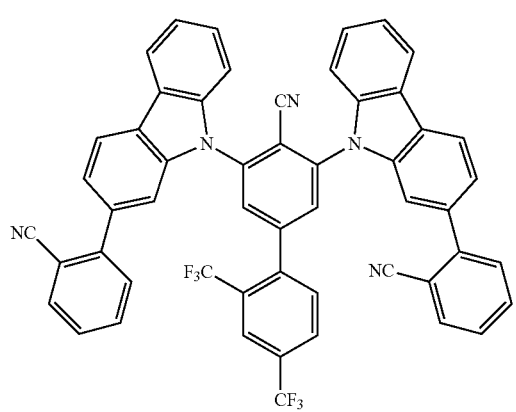
140
-continued
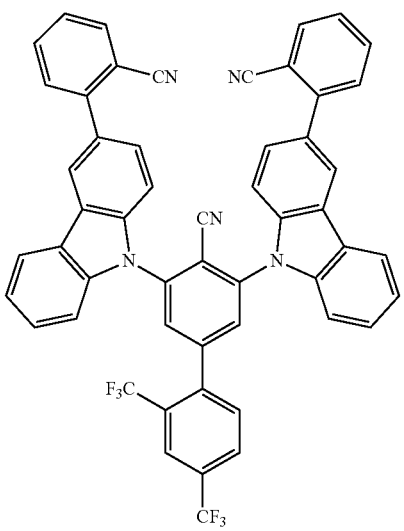
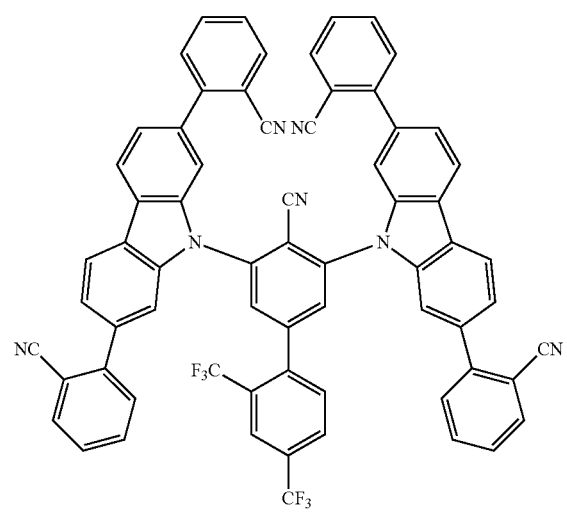
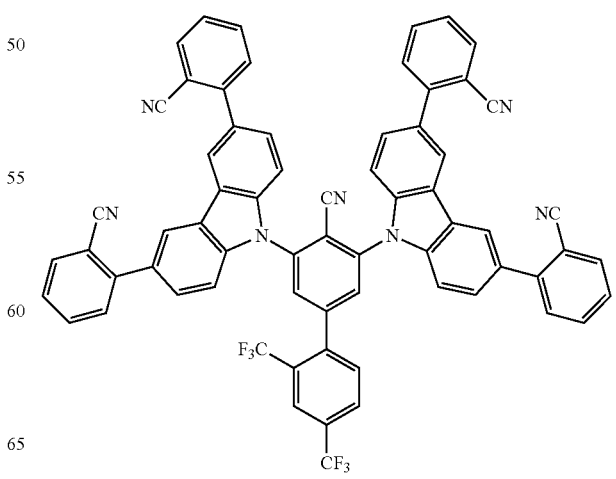

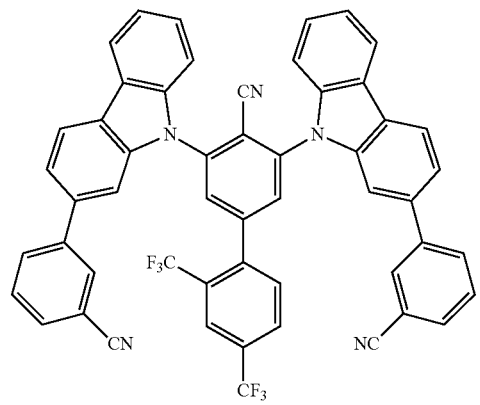
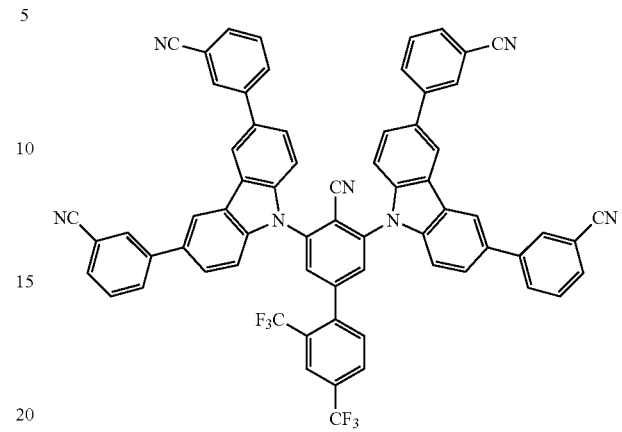
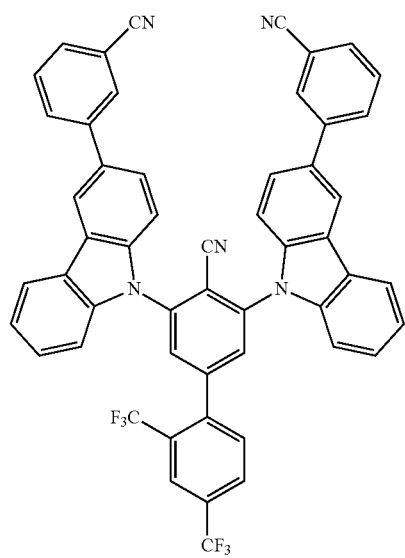
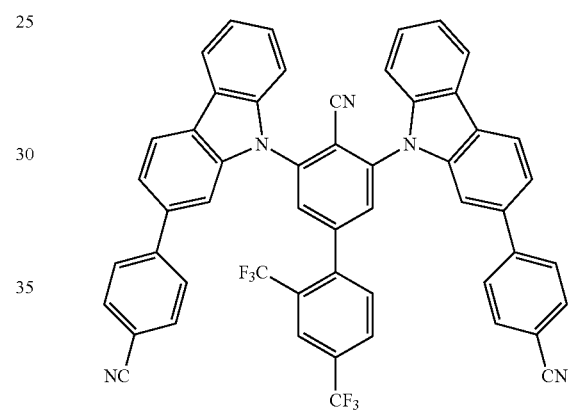
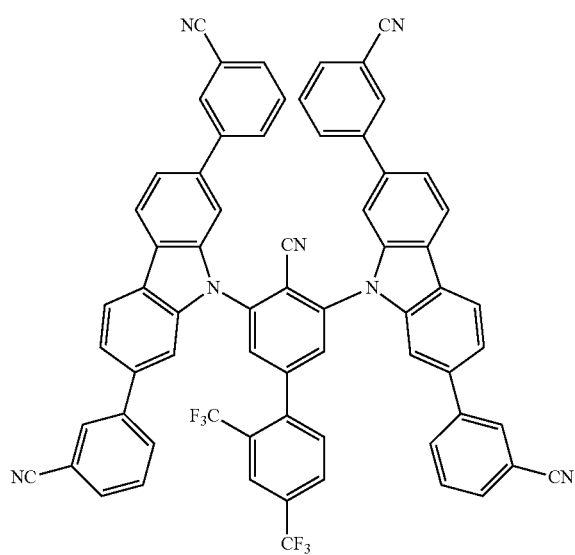
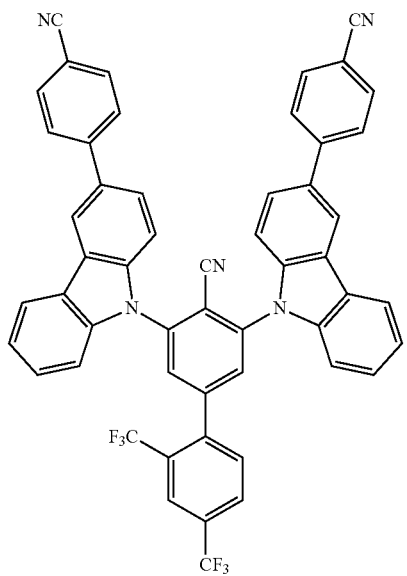

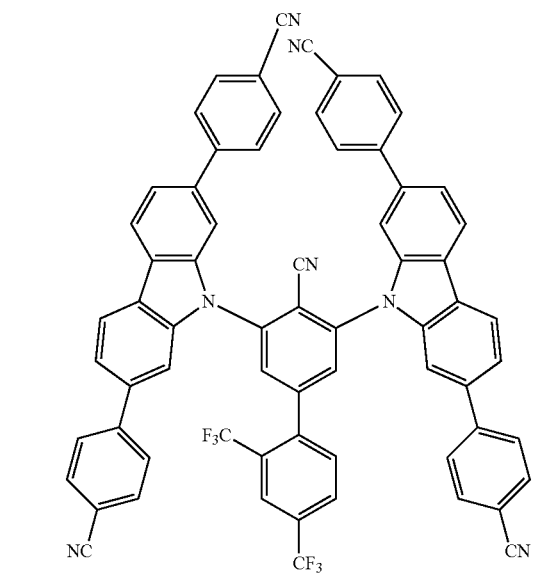
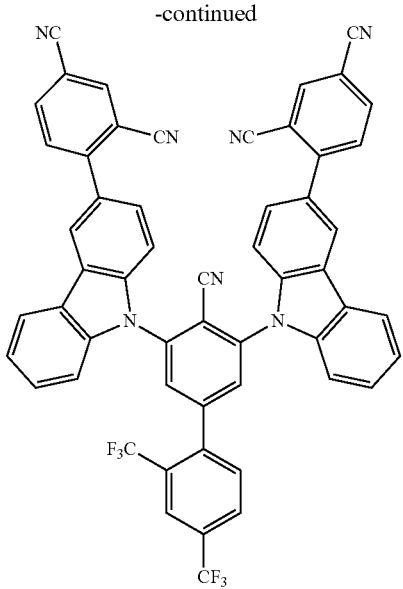
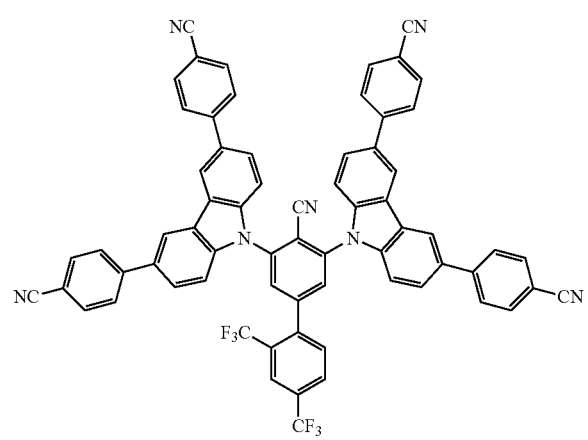
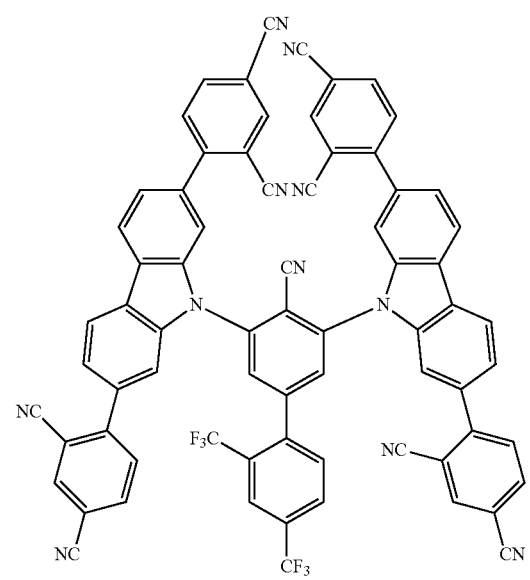
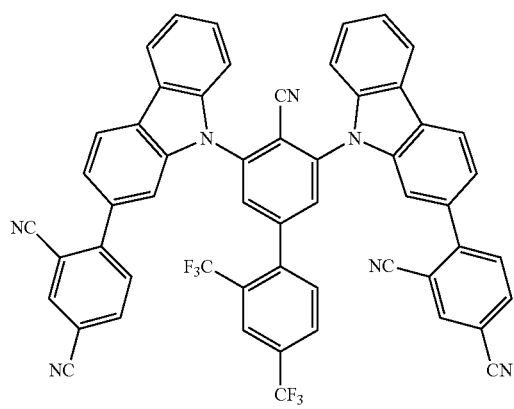
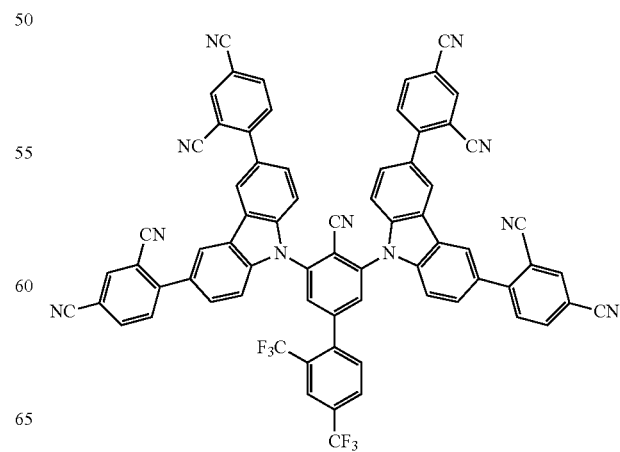

-continued
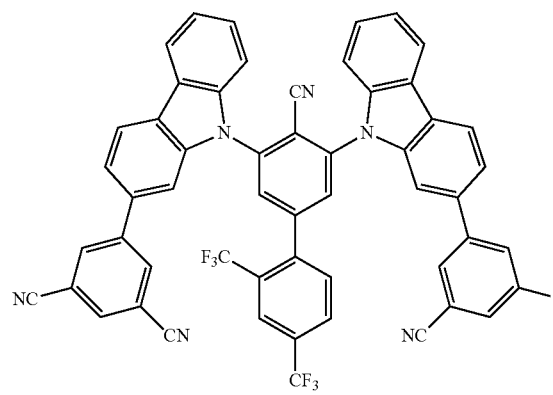
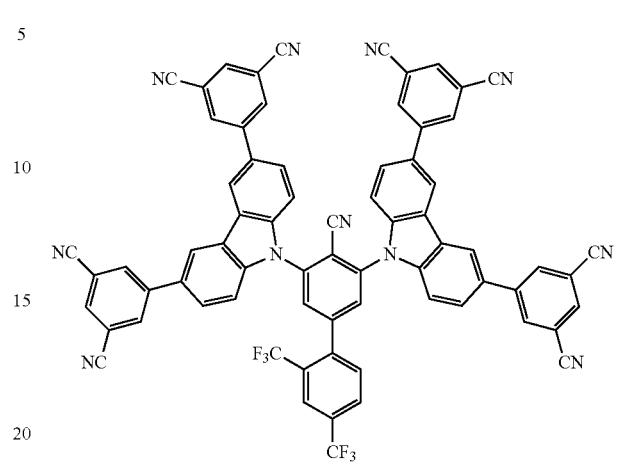
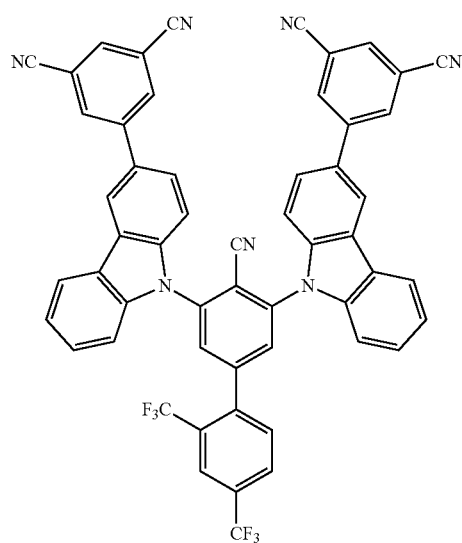
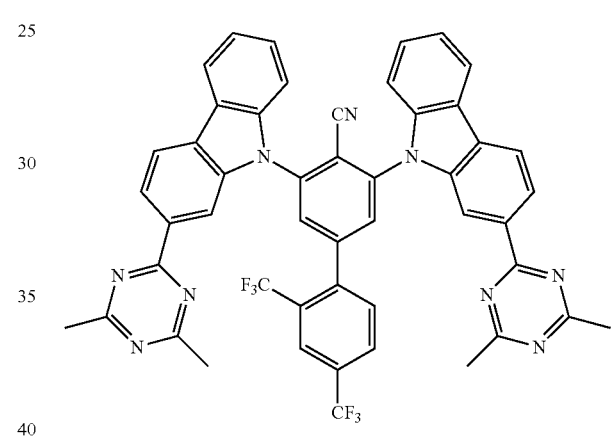
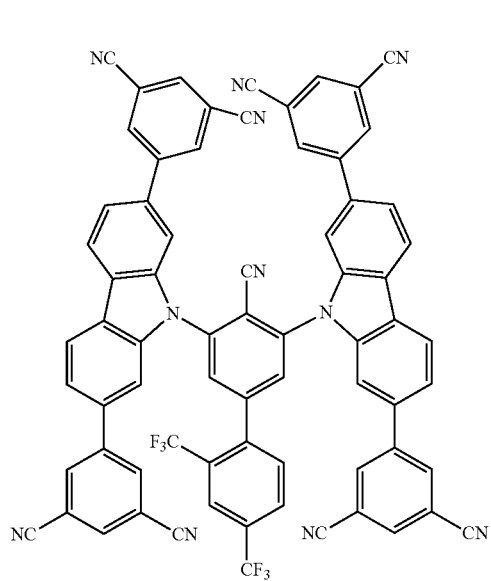
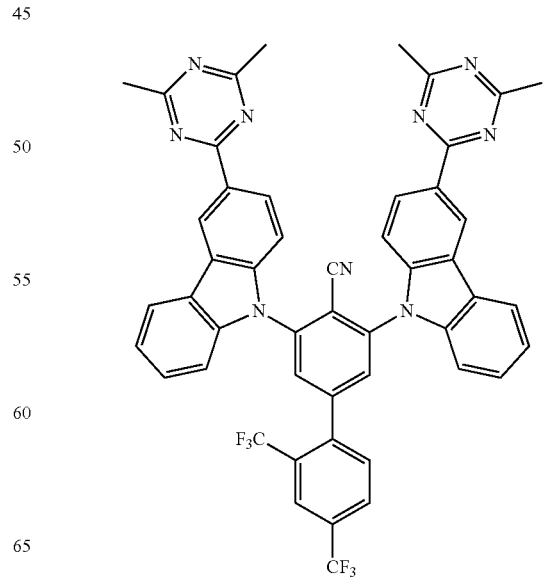

147
-continued
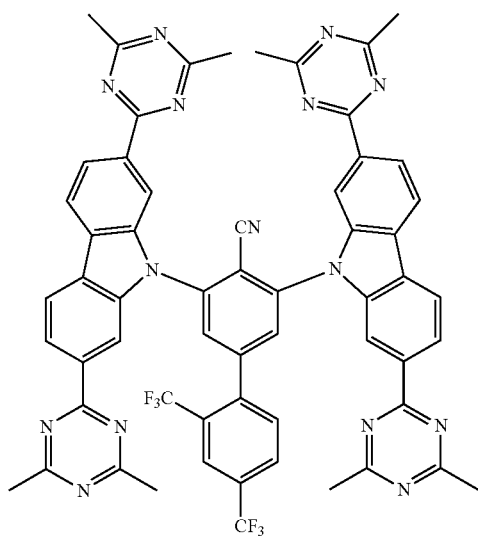
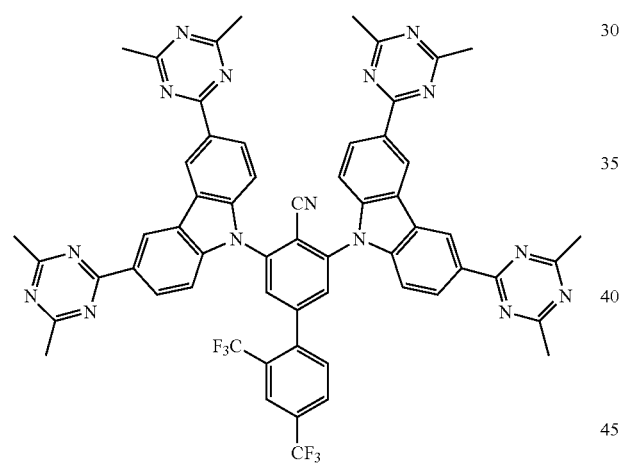
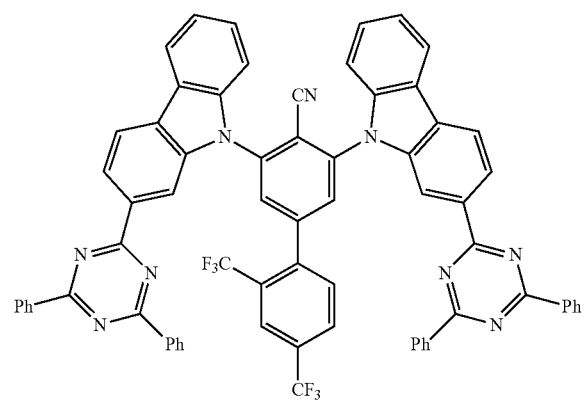
148
-continued
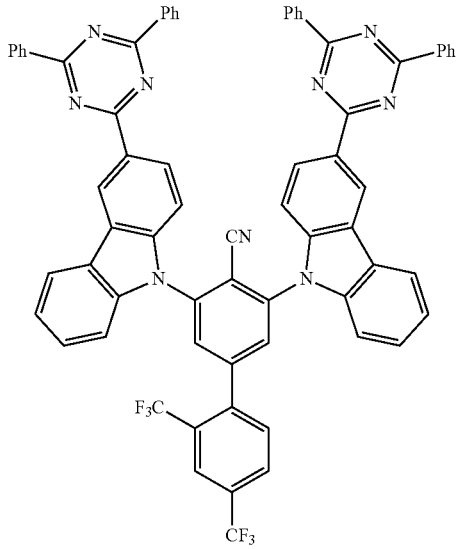
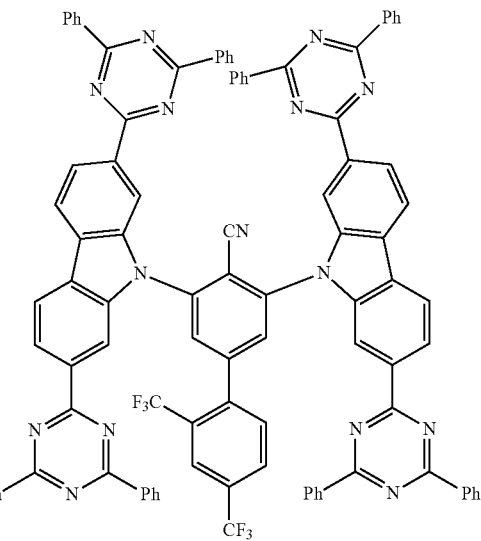
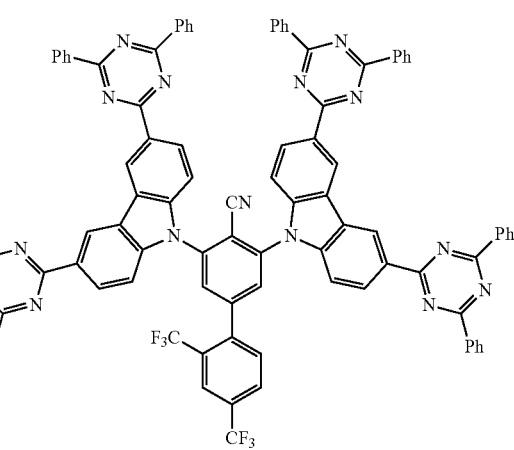

149
-continued
150
-continued
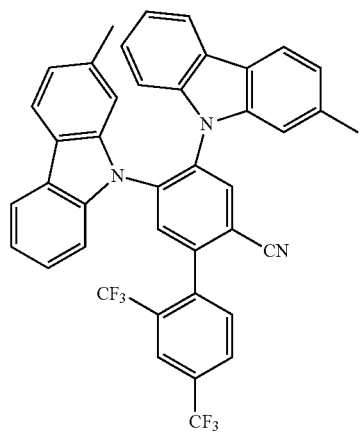
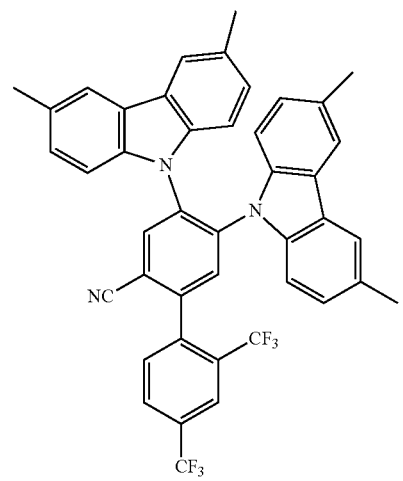
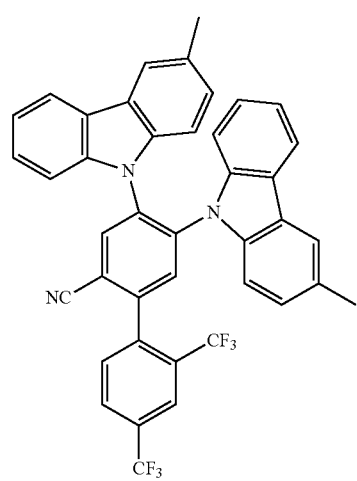
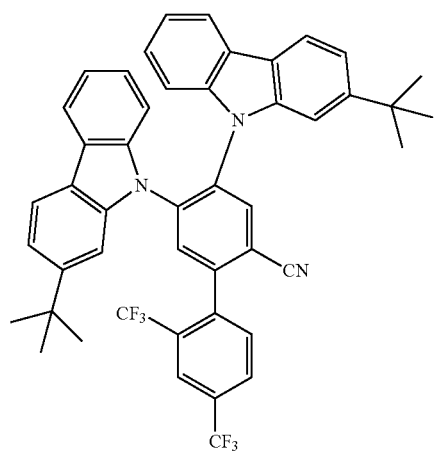
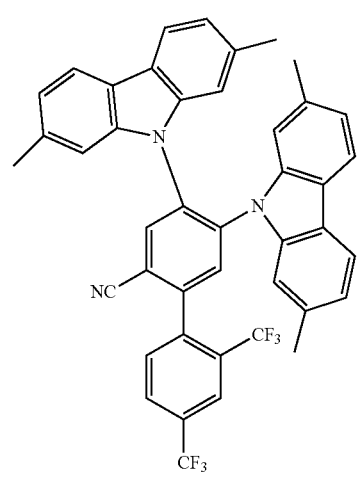
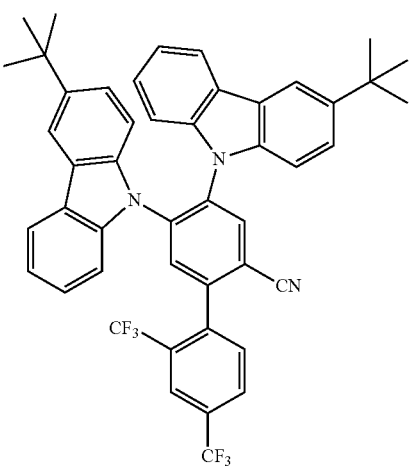

151
-continued
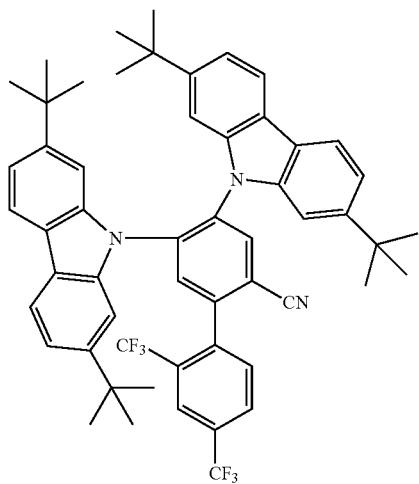
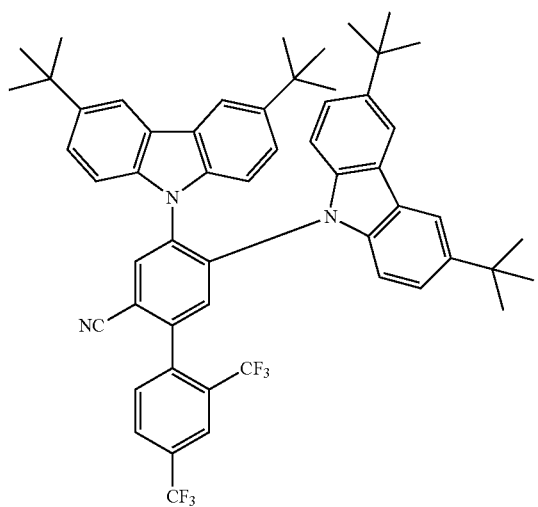
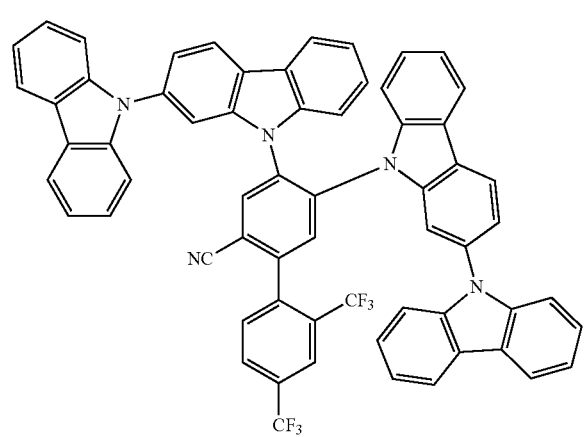
152
-continued
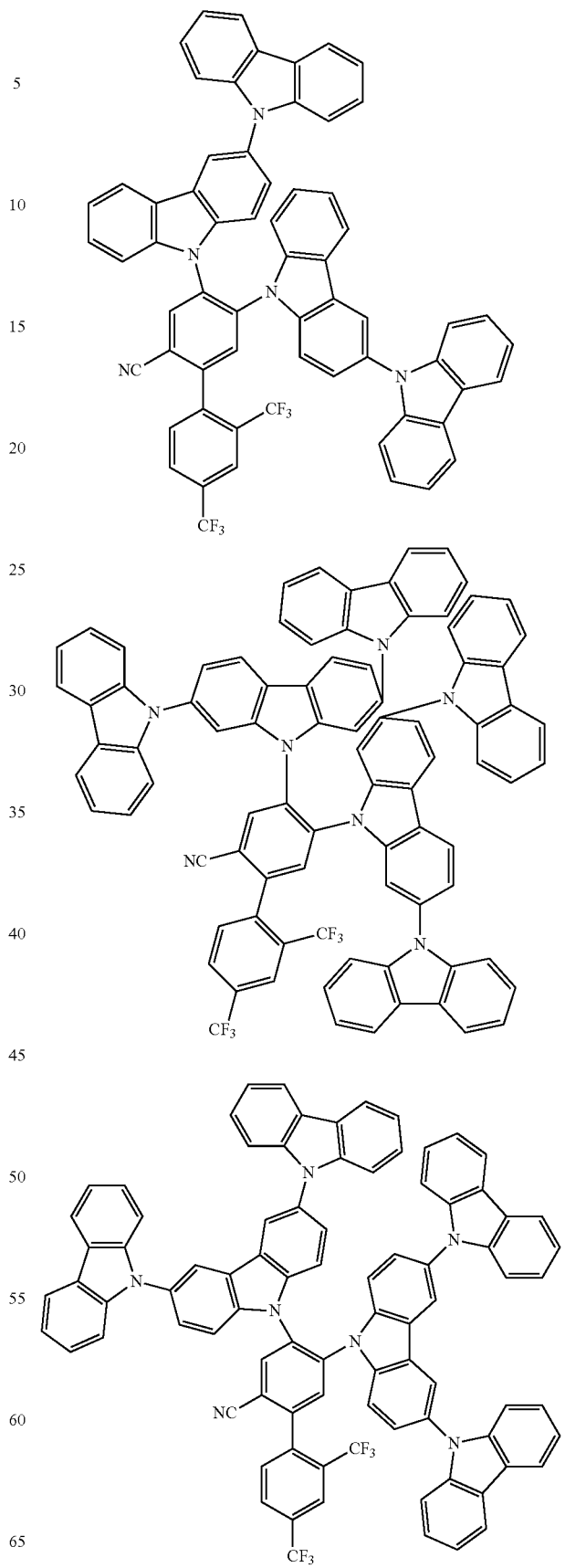

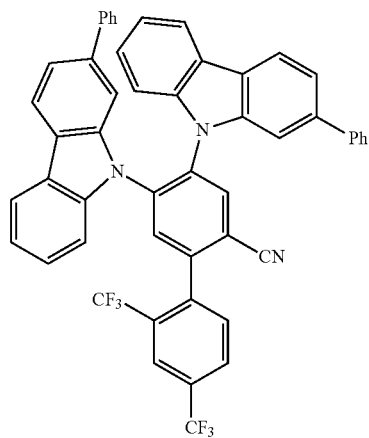
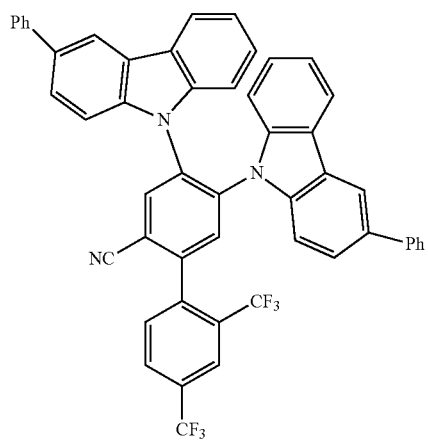
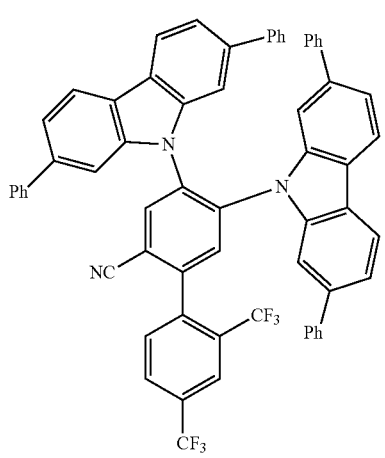
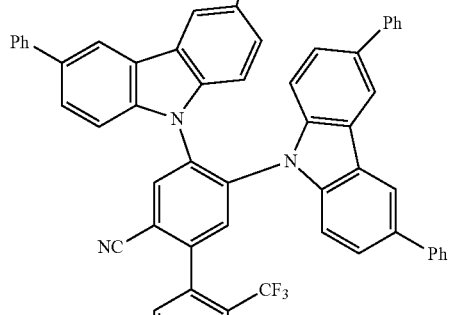
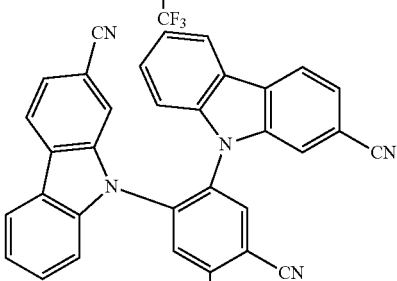
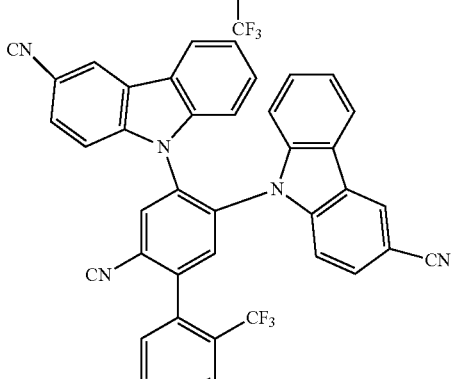
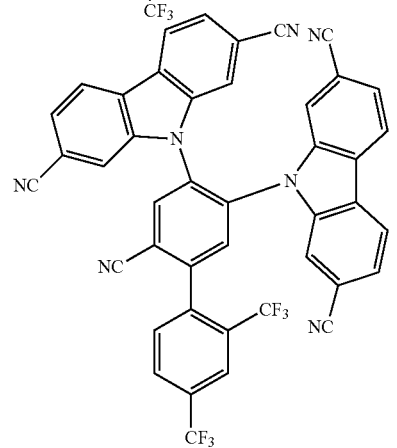

155
-continued
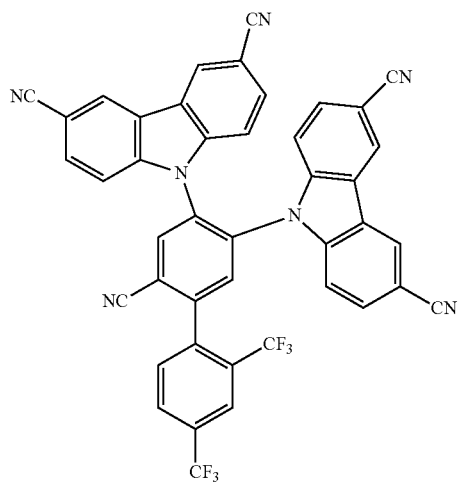
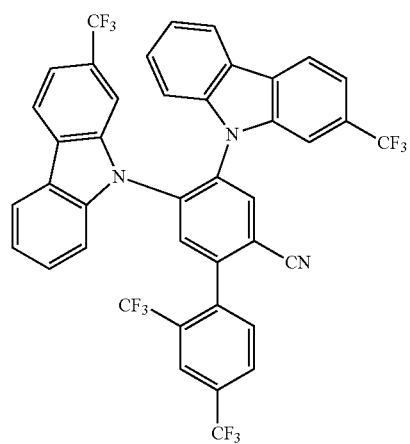
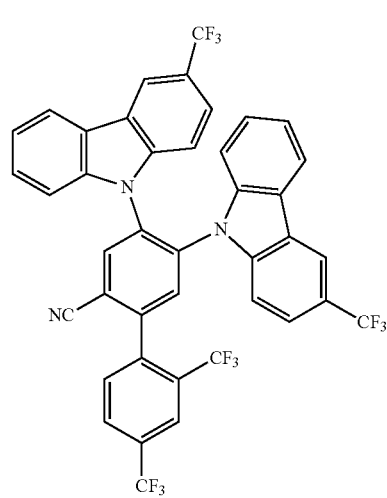
156
-continued
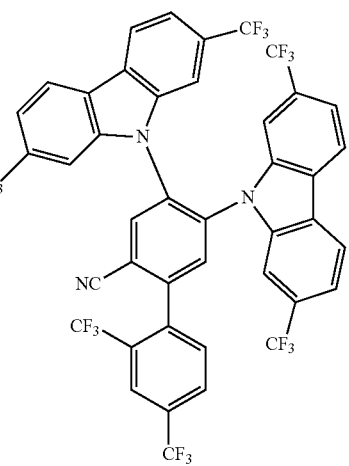
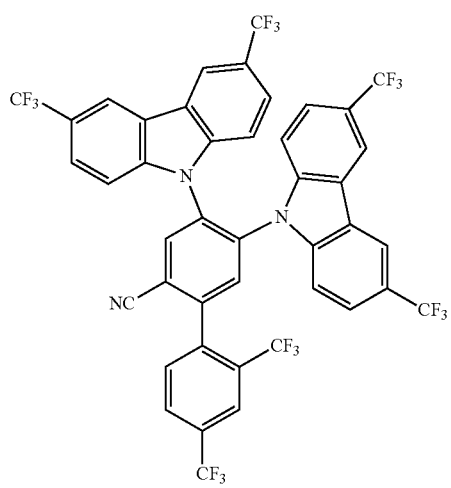
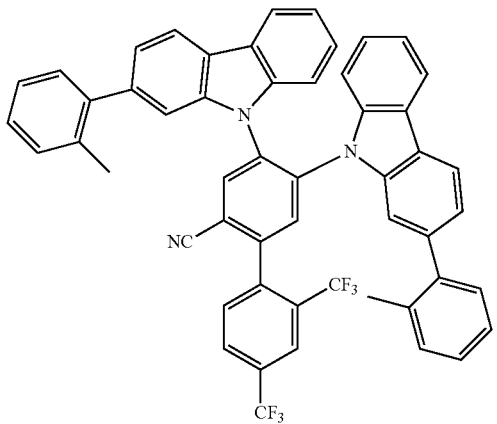

157
-continued
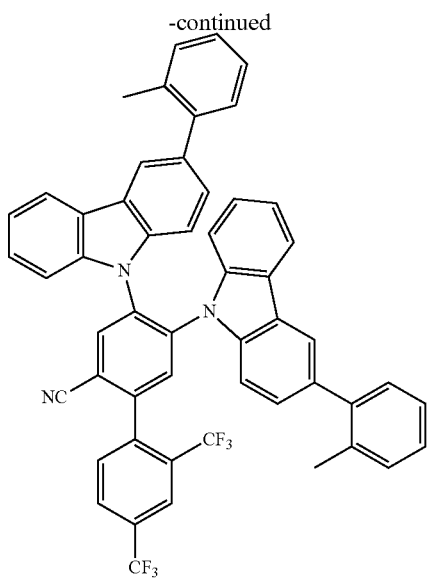
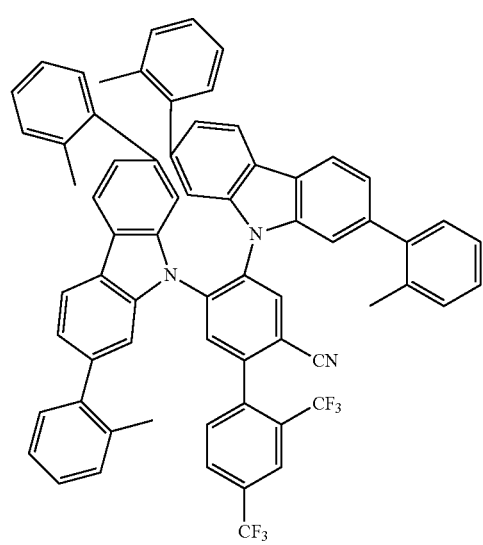
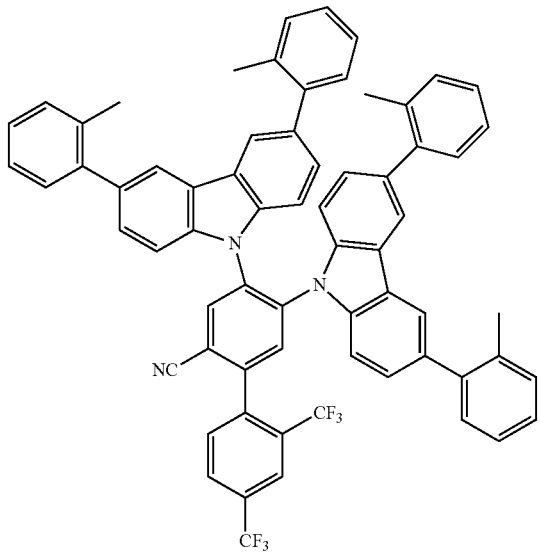
158
-continued
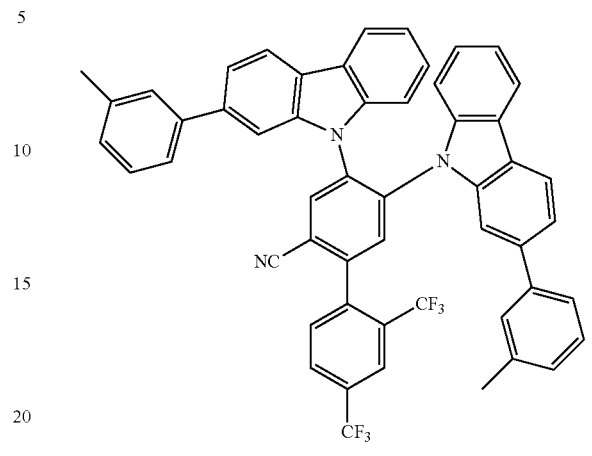
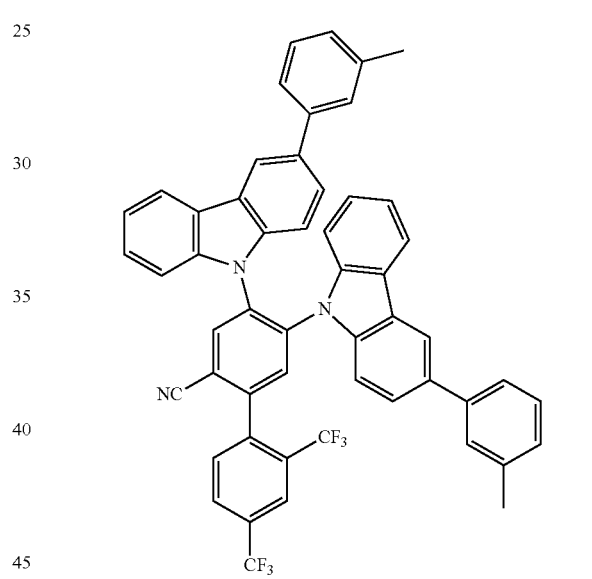
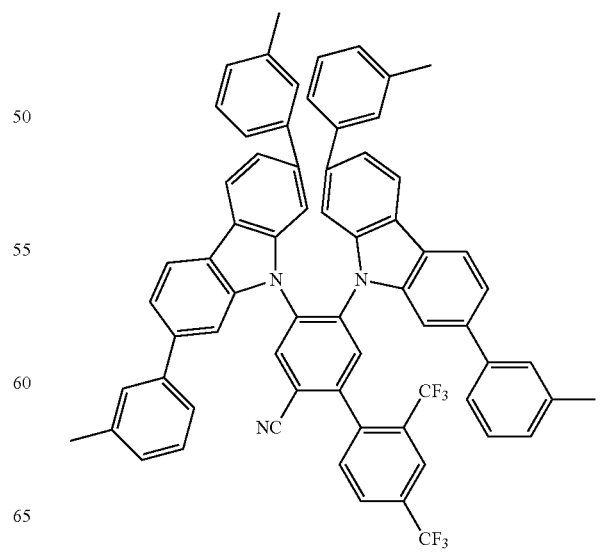

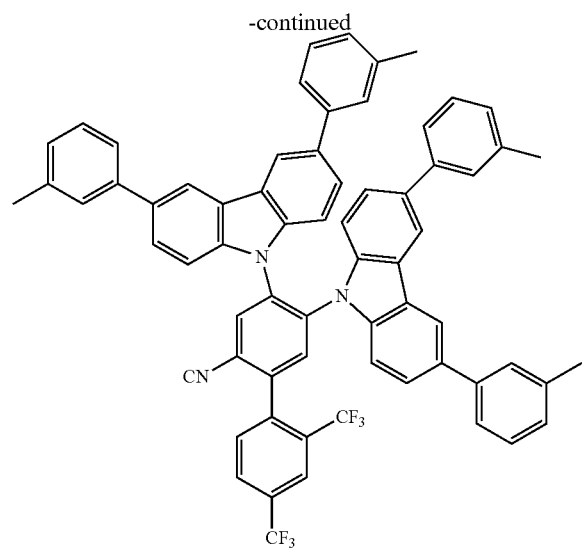
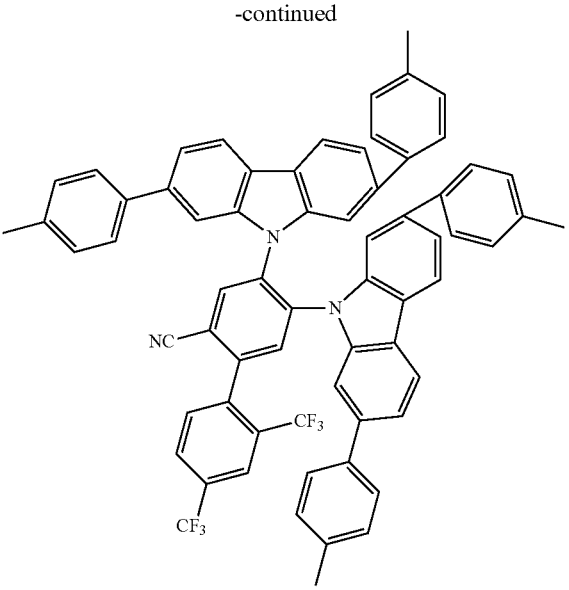

161 162
-continued -continued
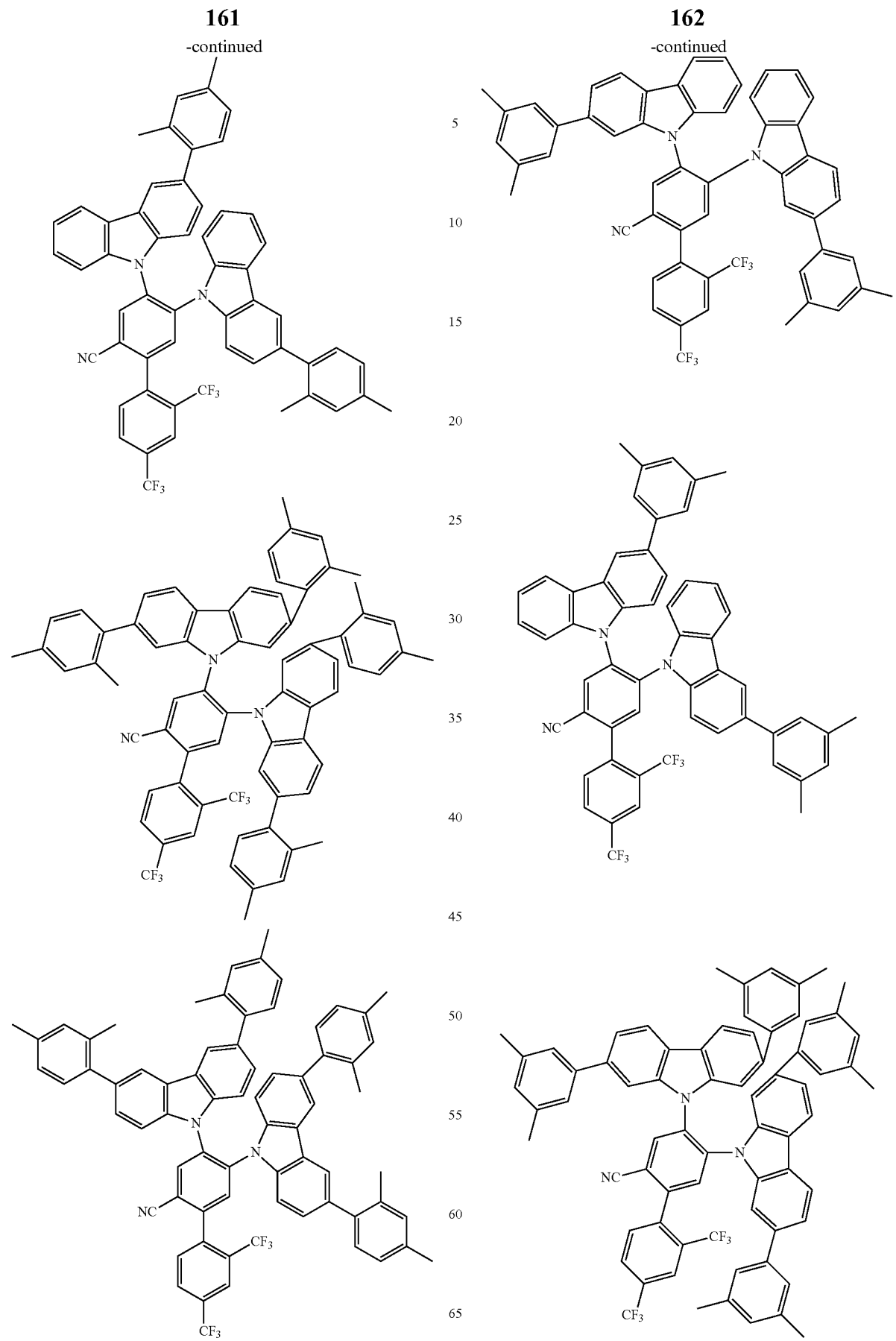

163
-continued
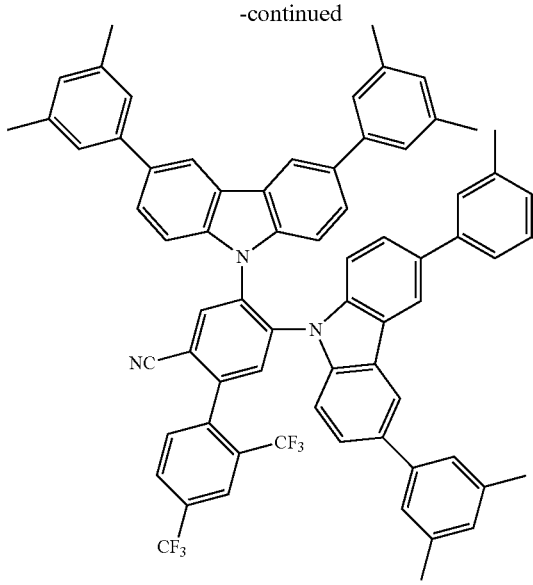
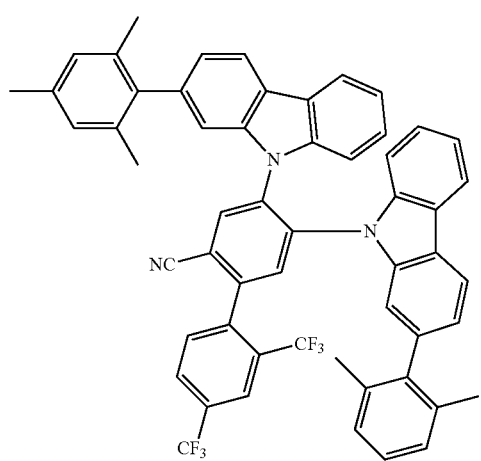
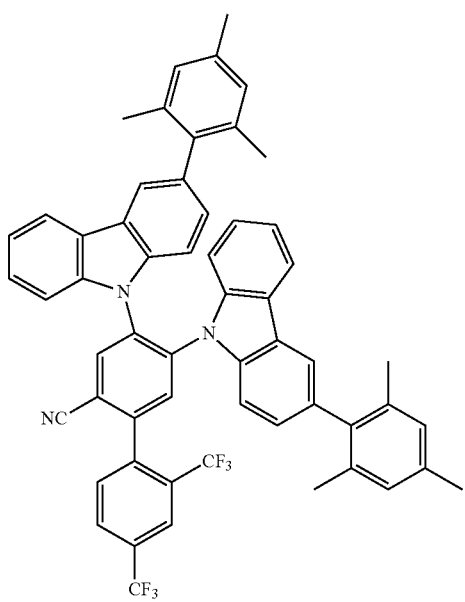
164
-continued
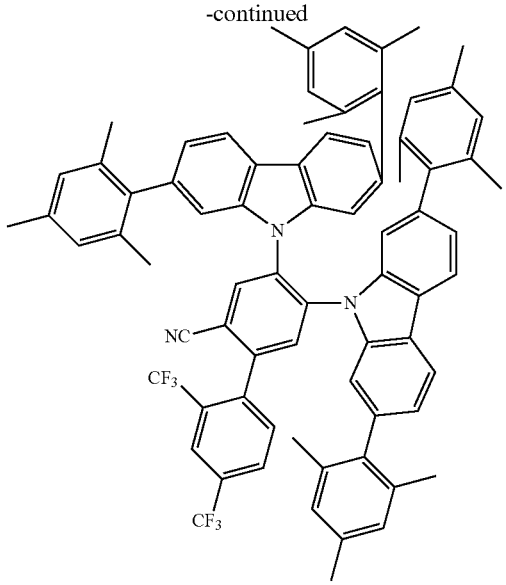
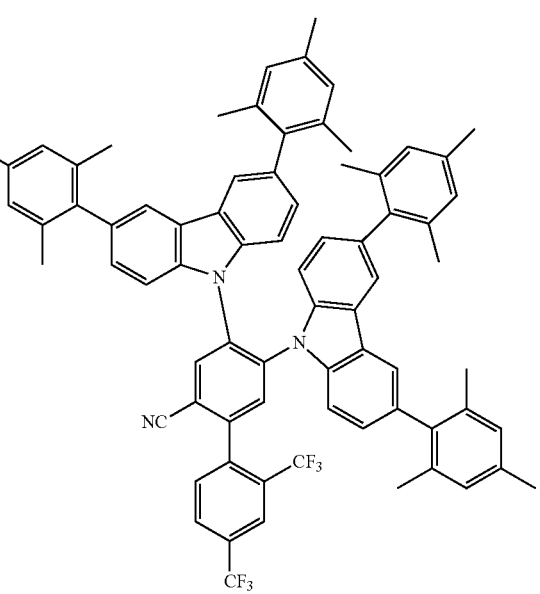
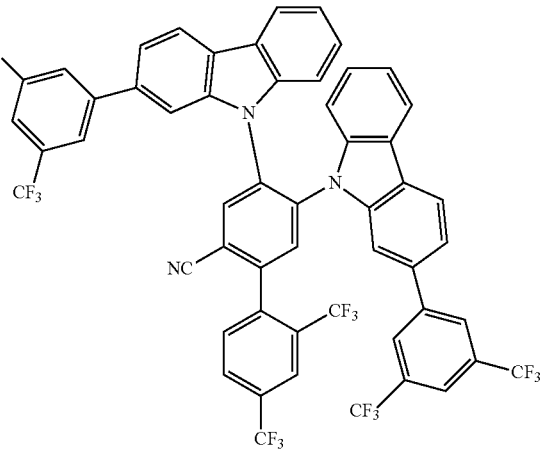

165
-continued
166
-continued
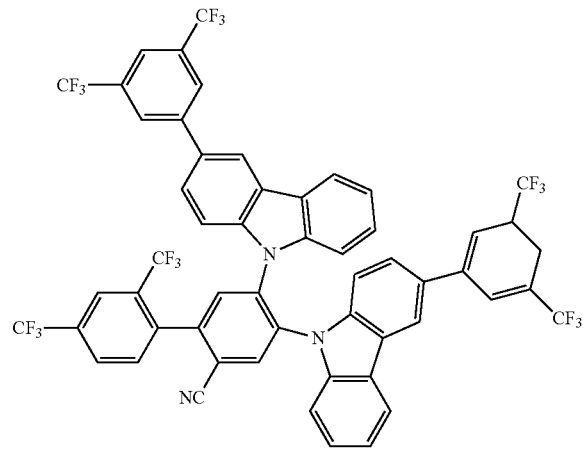
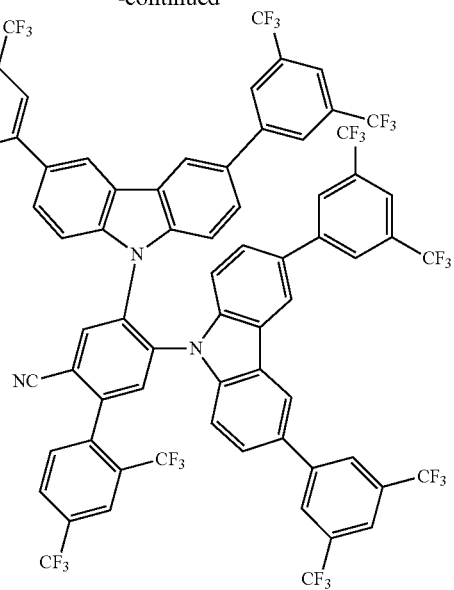
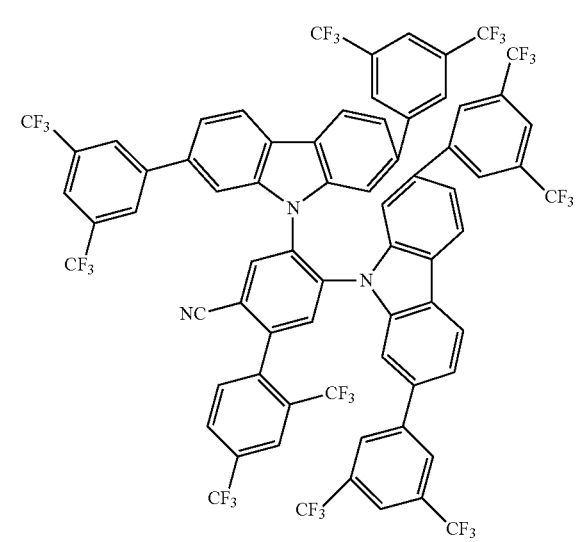
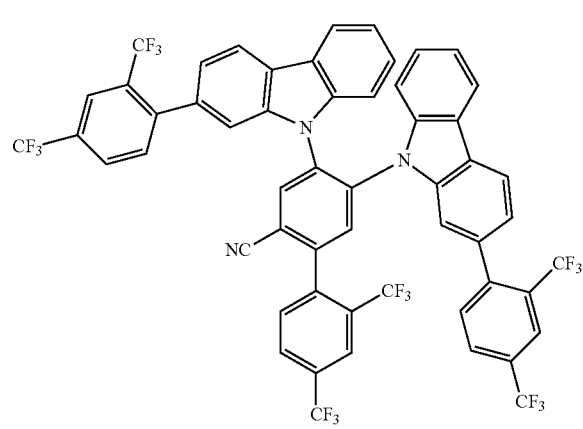
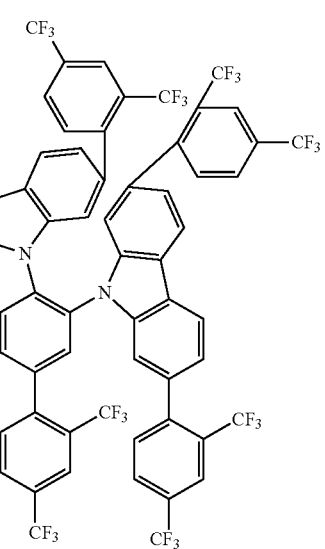

167
-continued
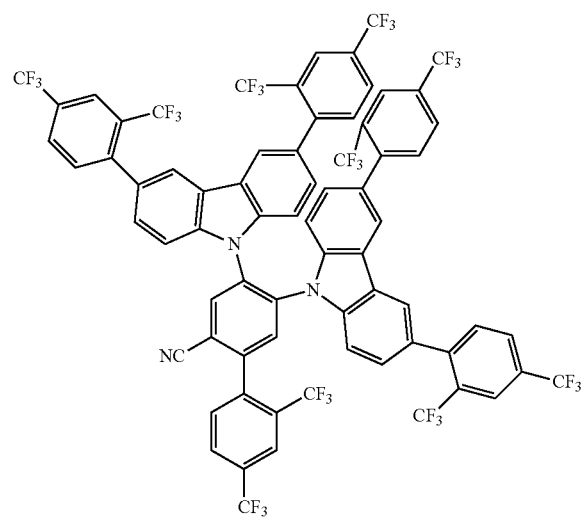
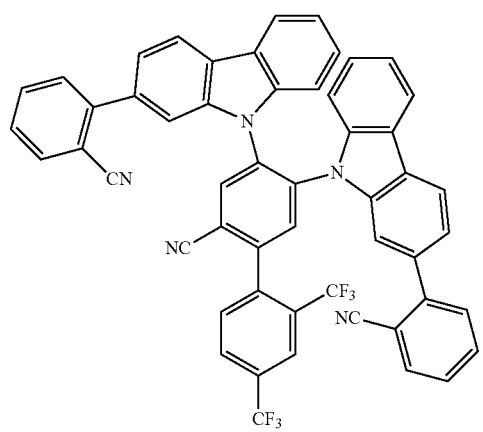
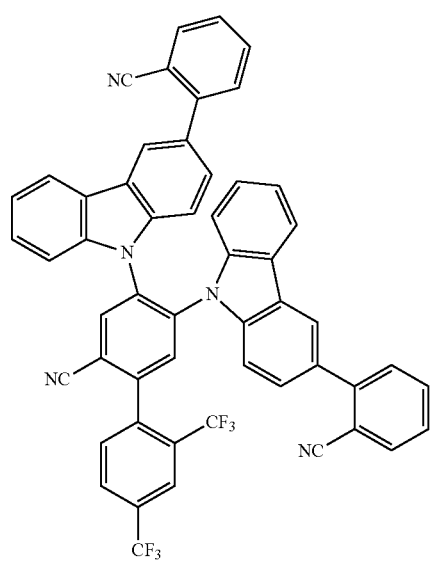
168
-continued
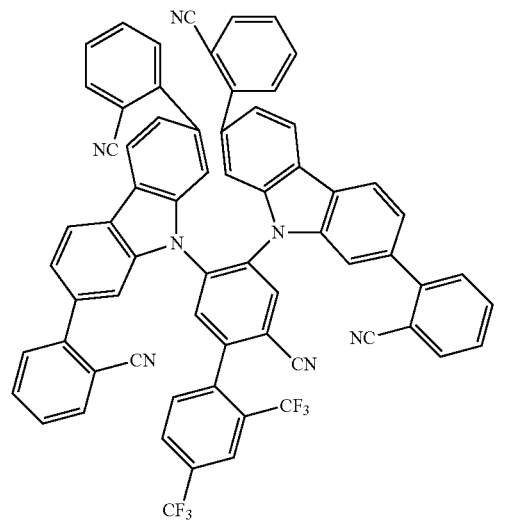
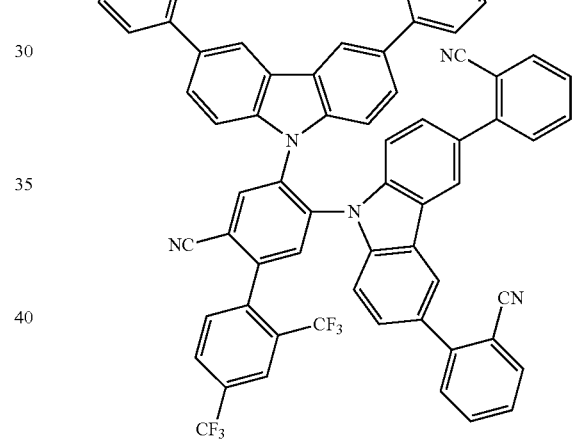
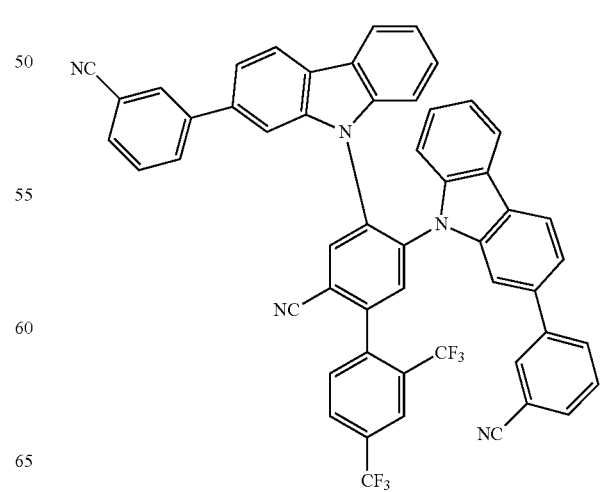

169
-continued
170
-continued
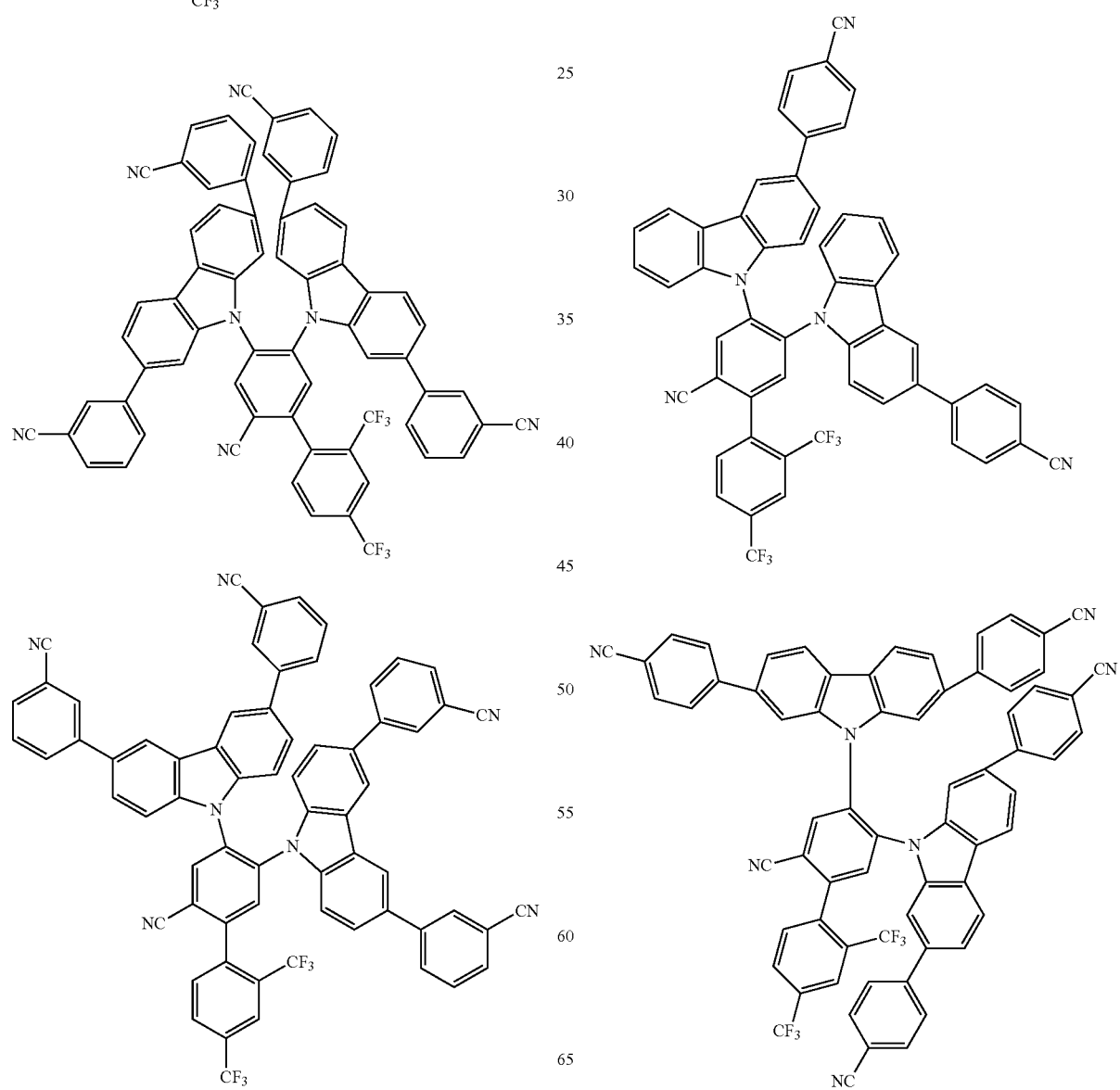

171
-continued
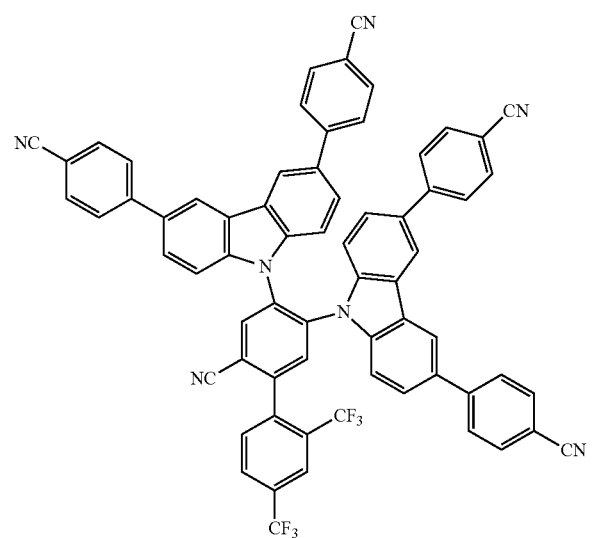
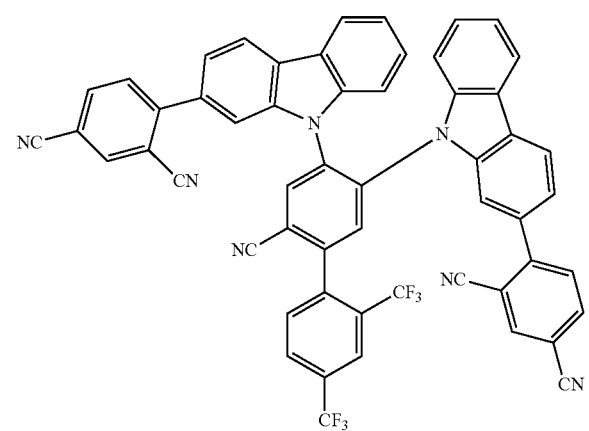
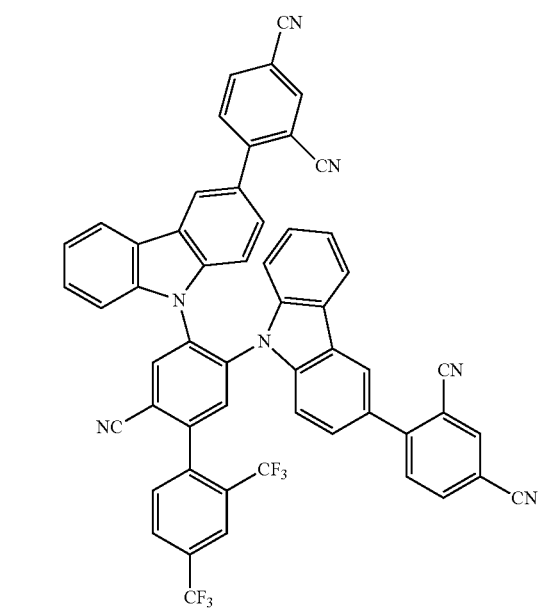
172
-continued
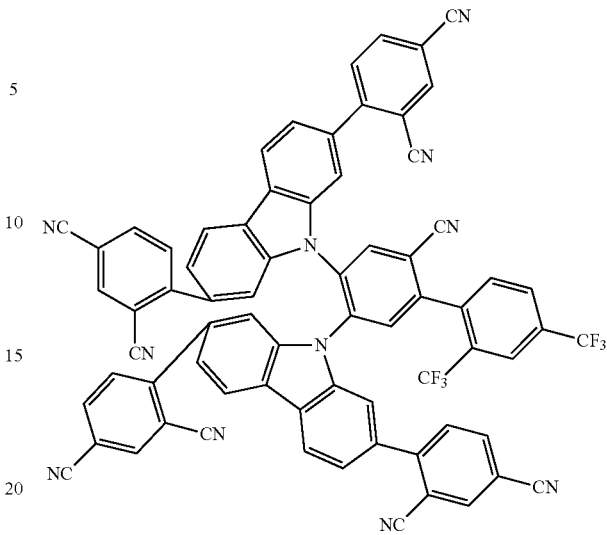
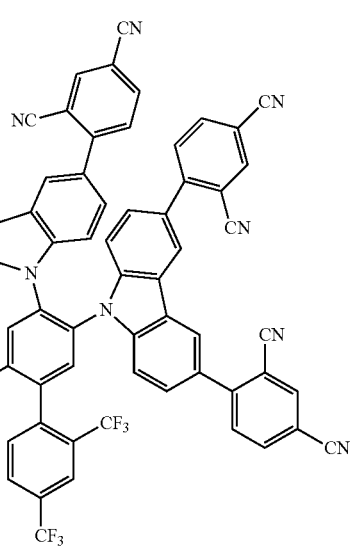
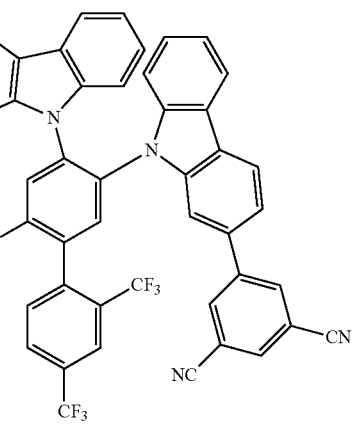

173
-continued
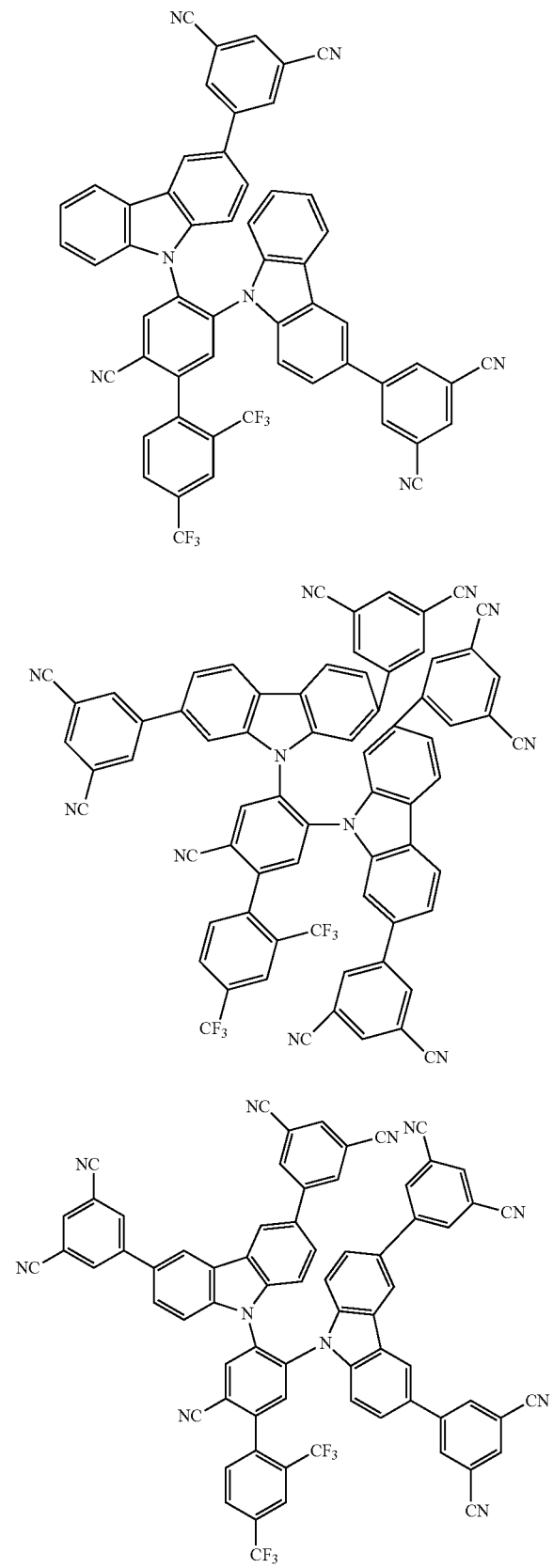
174
-continued
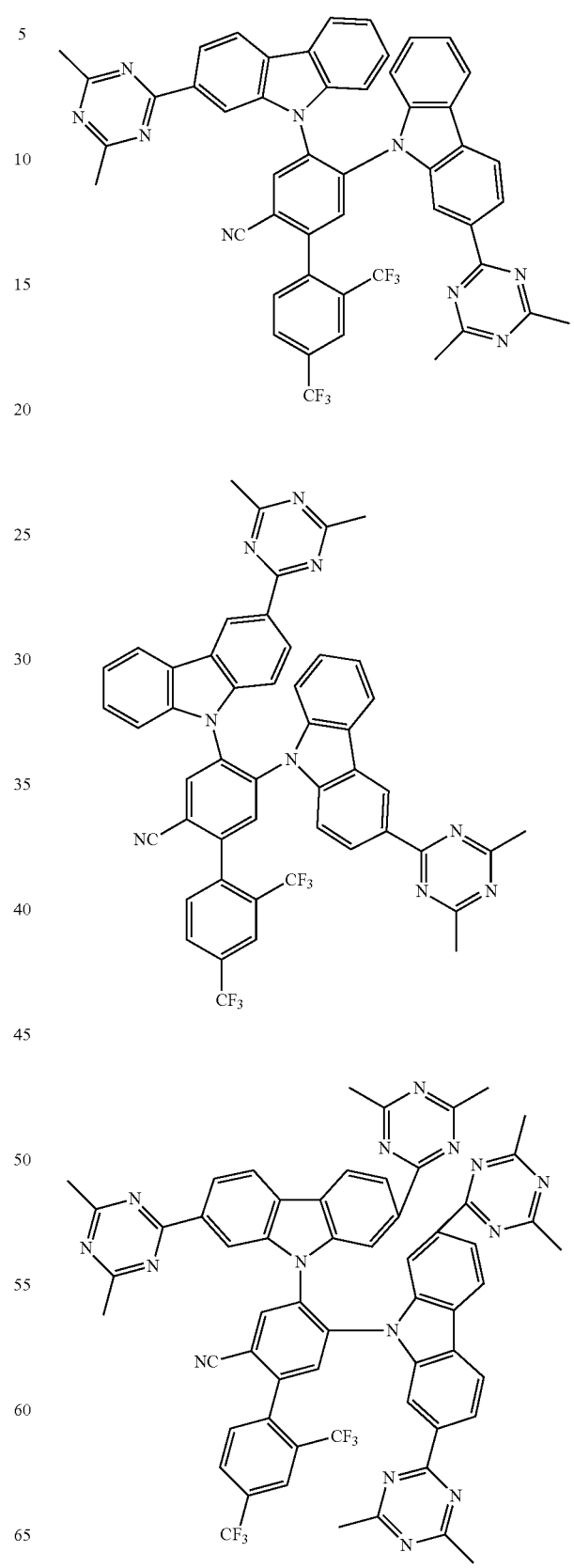

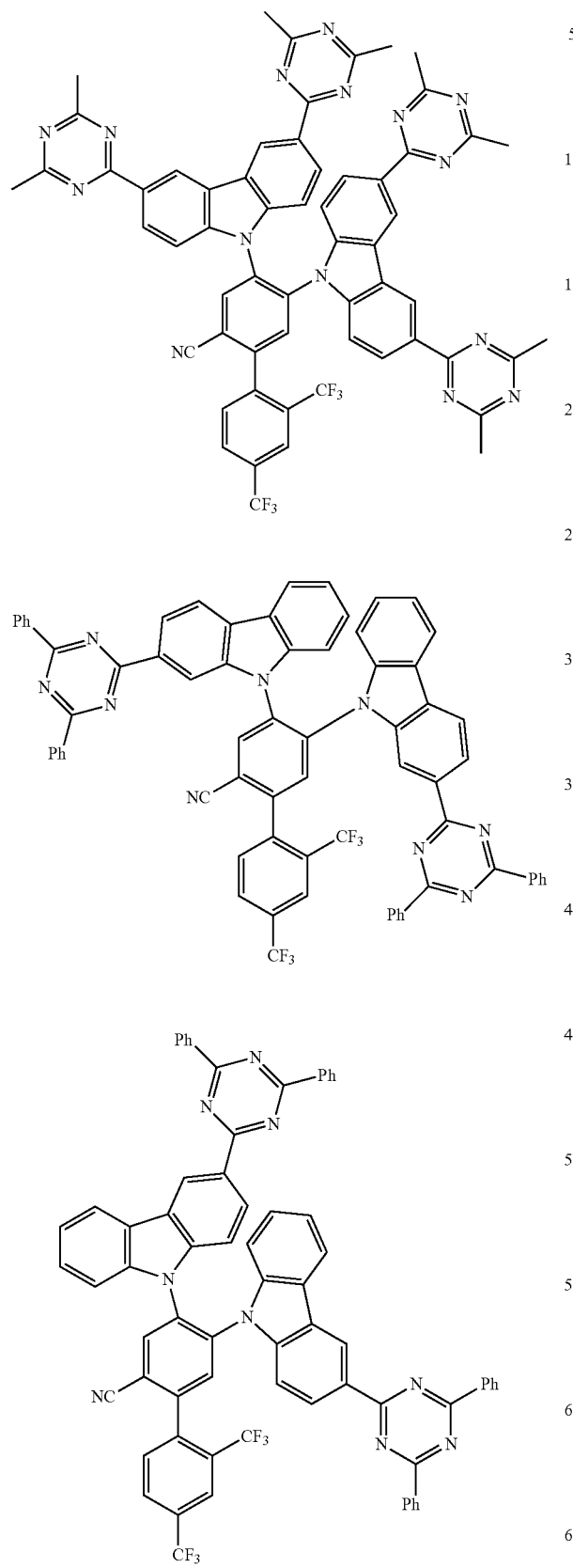
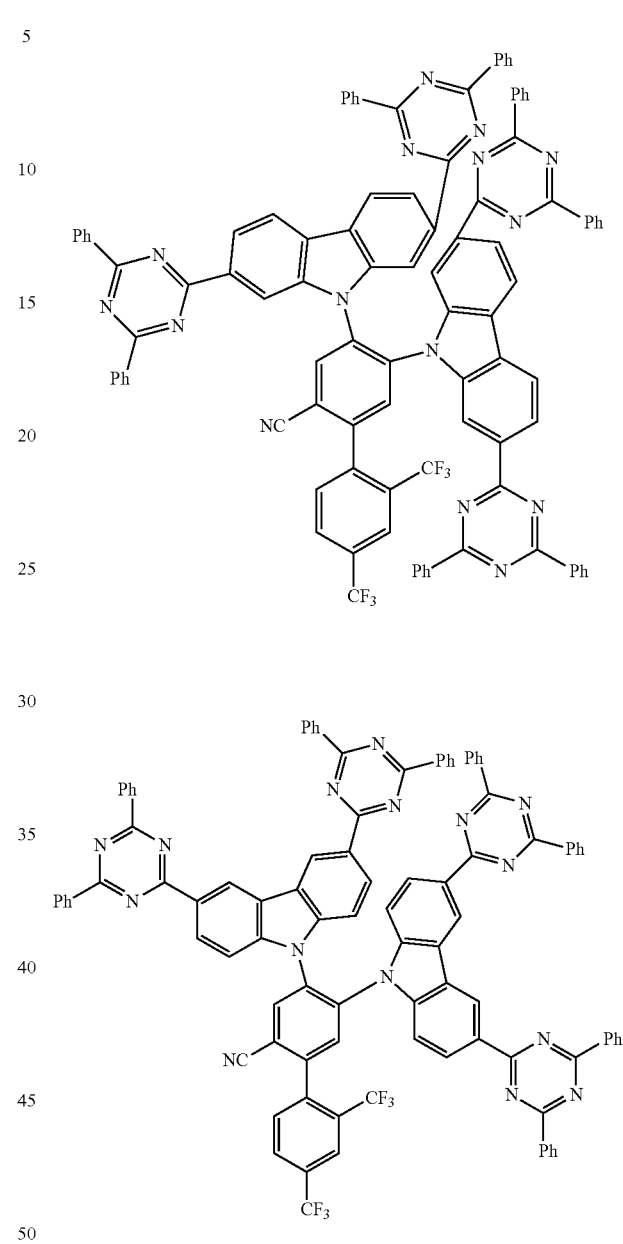

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:
1. An organic molecule comprising a compound represented by a structure of Formula Va-Vh:

Formula Va
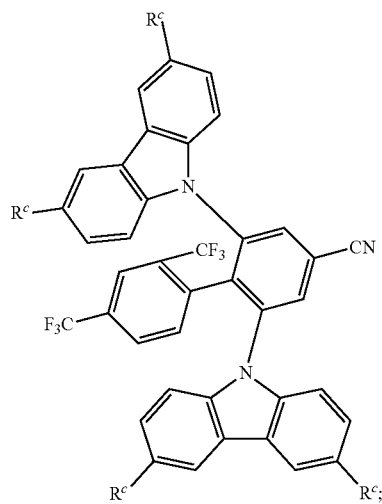
Formula Vb
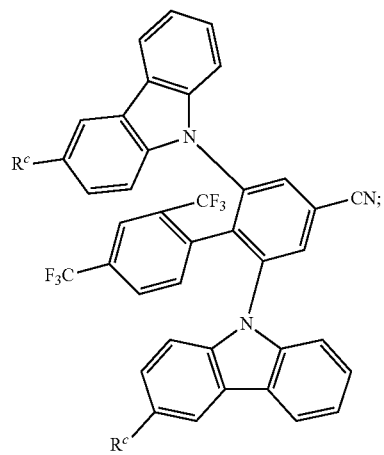
Formula Vc
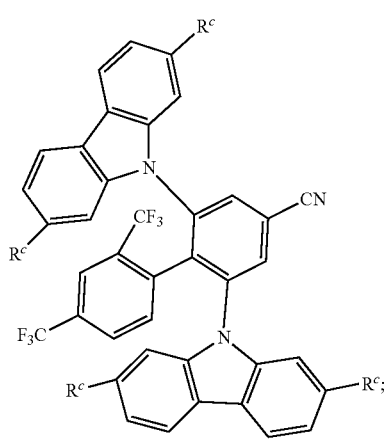
Formula Vd
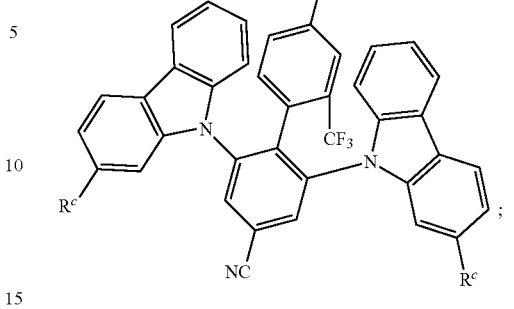
Formula Ve
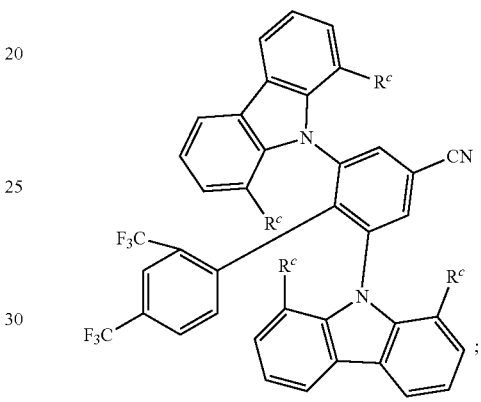
Formula Vf
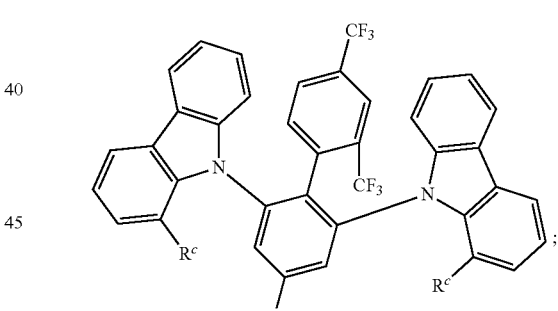
Formula Vg
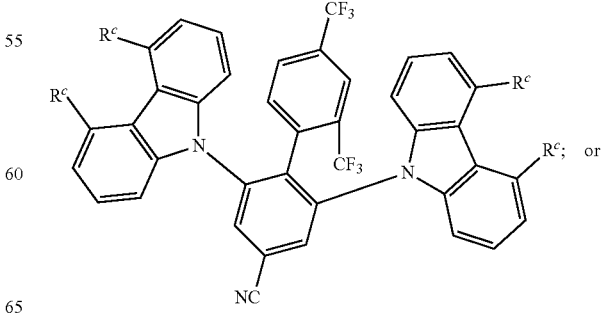
or Formula Vh

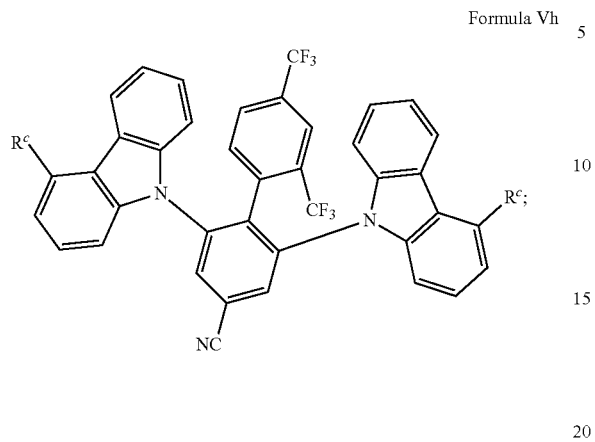

Formula VIa

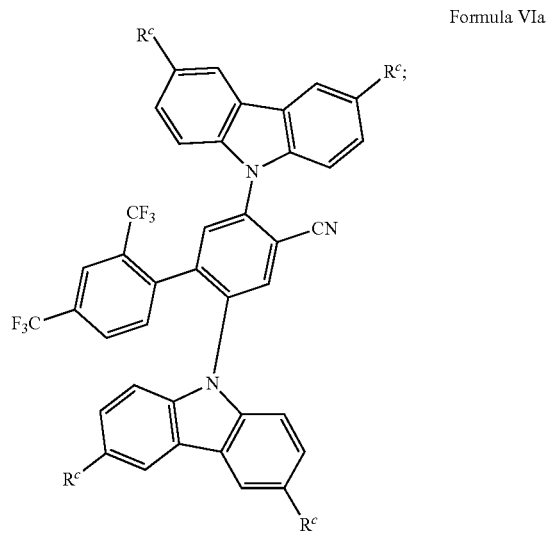

wherein
in each occurrence $R^c$ is independently selected from the group consisting of Me, $^iPr$, $^tBu$, CN, $CF_3$, Ph, which can be respectively substituted with one or more radicals selected from Me, $^iPr$, $^tBu$, CN, $CF_3$ or Ph, pyridinyl, which can be respectively substituted with one or more radicals selected from Me, $^iPr$, $^tBu$, CN, $CF_3$ or Ph, pyrimidinyl, which can be respectively substituted with one or more radicals selected from Me, $^iPr$, $^tBu$, CN, $CF_3$ or Ph, carbazolyl, which can be respectively substituted with one or more radicals selected from Me, $^iPr$, $^tBu$, CN, $CF_3$ or Ph, triazinyl, which can be respectively substituted with one or more radicals selected from Me, $^iPr$, $^tBu$, CN, $CF_3$ or Ph, and $N(Ph)_2$.

2. An optoelectronic device comprising the organic molecule according to claim 1, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

3. The optoelectronic device according to claim 2, comprising:
a substrate;
an anode;
a cathode, wherein the anode or the cathode is disposed on the substrate; and
at least one light-emitting layer disposed between the anode and the cathode and which comprises the organic molecule.

4. An optoelectronic device comprising the organic molecule according to claim 1, wherein the organic molecule is one of an emitter and an absorber in the optoelectronic device.

5. An organic molecule comprising a compound represented by a structure of Formula VIa-VIh:

Formula VIb

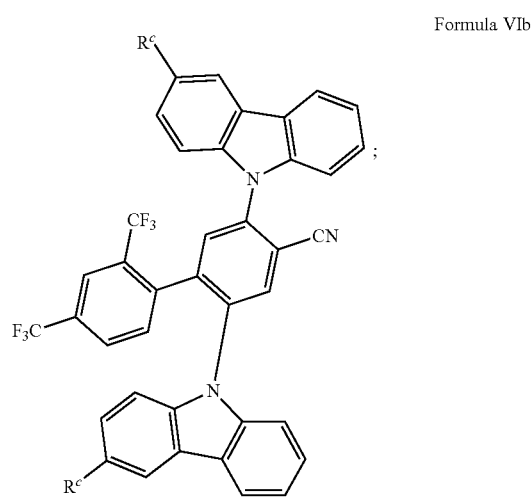

Formula VIc

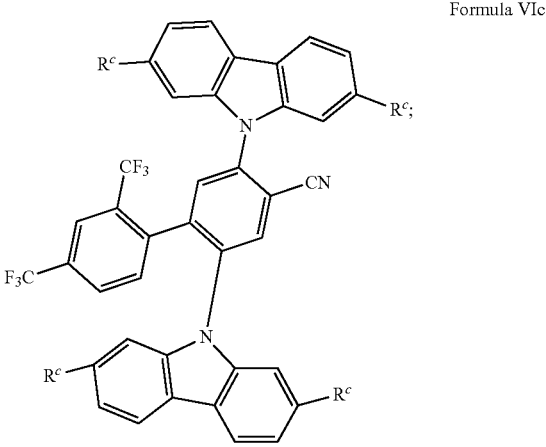

-continued

Formula VId

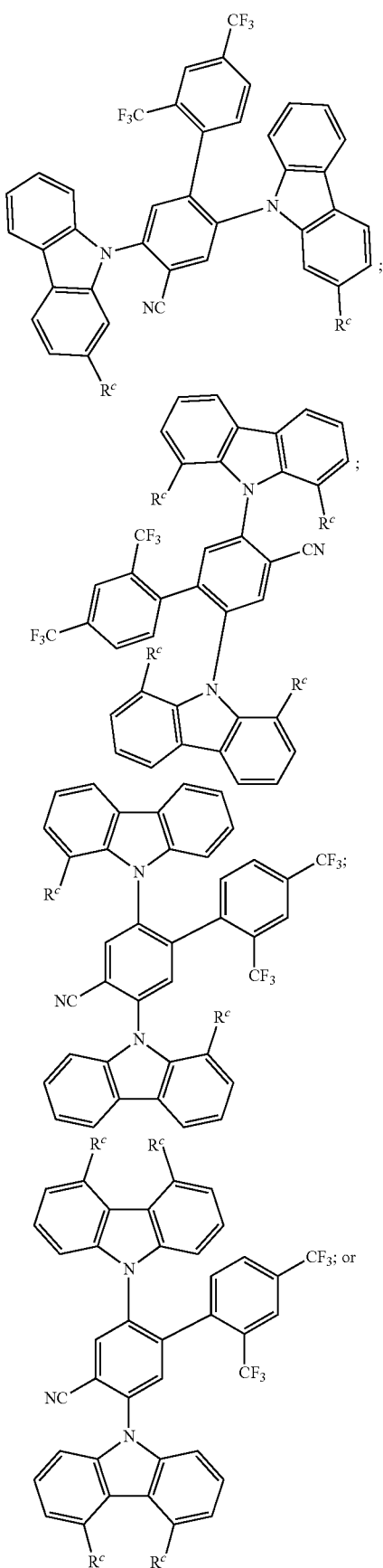

Formula VIe

Formula VIf

Formula VIg

-continued

Formula VIh

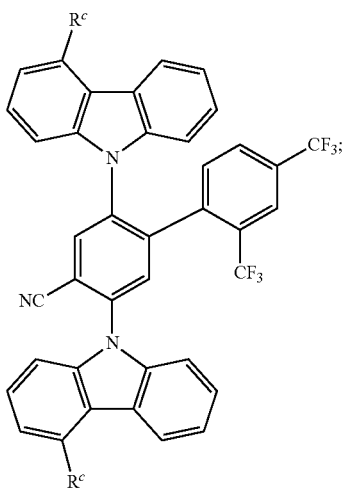

wherein
in each occurrence $R^c$ is independently selected from the group consisting of Me, $^i$Pr, $^t$Bu, CN, CF$_3$, Ph, which can be respectively substituted with one or more radicals selected from Me, $^i$Pr, $^t$Bu, CN, CF$_3$ or Ph, pyridinyl, which can be respectively substituted with one or more radicals selected from Me, $^i$Pr, $^t$Bu, CN, CF$_3$ or Ph, pyrimidinyl, which can be respectively substituted with one or more radicals selected from Me, $^i$Pr, $^t$Bu, CN, CF$_3$ or Ph, carbazolyl, which can be respectively substituted with one or more radicals selected from Me, $^i$Pr, $^t$Bu, CN, CF$_3$ or Ph, triazinyl, which can be respectively substituted with one or more radicals selected from Me, $^i$Pr, $^t$Bu, CN, CF$_3$ or Ph, and N(Ph)$_2$.

6. An optoelectronic device comprising the organic molecule according to claim 5, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

7. The optoelectronic device according to claim 6, comprising:
    a substrate;
    an anode;
    a cathode, wherein the anode or the cathode is disposed on the substrate; and
    at least one light-emitting layer disposed between the anode and the cathode and which comprises the organic molecule.

8. An optoelectronic device comprising the organic molecule according to claim 5, wherein the organic molecule is one of an emitter and an absorber in the optoelectronic device.

9. A composition comprising:
    (a) at least one organic molecule as an emitter and/or host;
    (b) one or more emitter and/or host materials different from the at least one organic molecule of component (a); and
    (c) optionally one or more dyes and/or one or more solvents;
    wherein the at least one organic molecule of component (a) comprises a compound represented by a structure of Formula IIIc-IIIh:

Formula IIIc
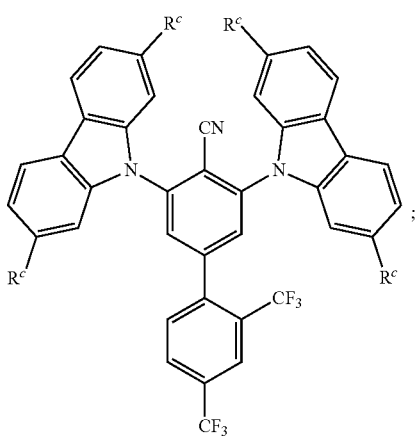

Formula IIId
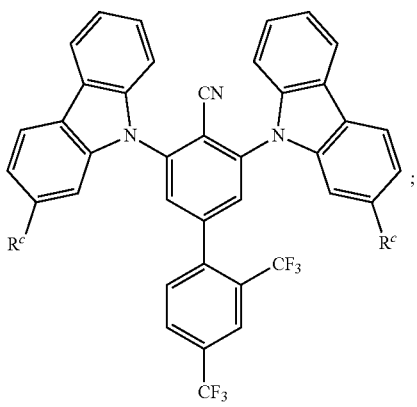

Formula IIIe
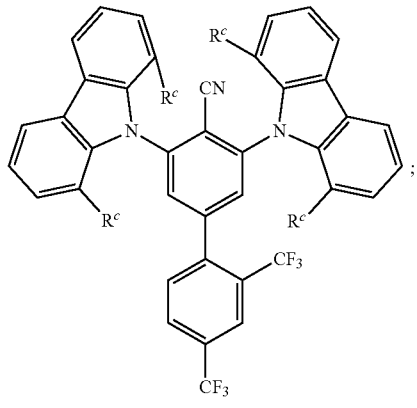

Formula IIIf
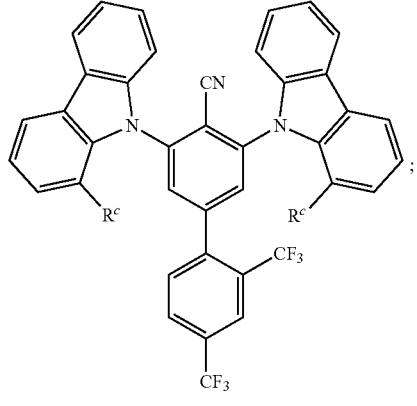

Formula IIIg
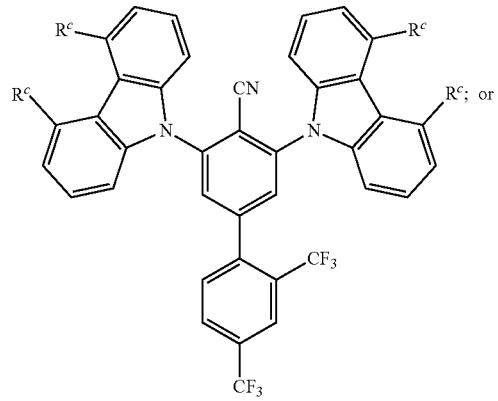

Formula IIIh
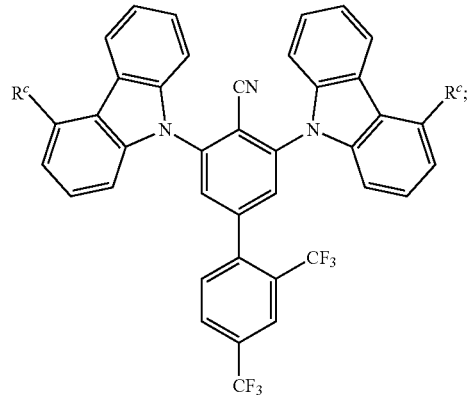

wherein
in each occurrence $R^c$ is independently selected from the group consisting of Me, $^i$Pr, $^t$Bu, CN, CF$_3$, Ph, which can be respectively substituted with one or more radicals selected from Me, $^i$Pr, $^t$Bu, CN, CF$_3$ or Ph, pyridinyl, which can be respectively substituted with one or more radicals selected from Me, $^i$Pr, $^t$Bu, CN, CF$_3$ or Ph, pyrimidinyl, which can be respectively substituted with one or more radicals selected from Me, $^i$Pr, $^t$Bu, CN, CF$_3$ or Ph, carbazolyl, which can be respectively substituted with one or more radicals selected from Me, $^i$Pr, $^t$Bu, CN, CF$_3$ or Ph, triazinyl, which can be respectively substituted with one or more radicals selected from Me, $^i$Pr, $^t$Bu, CN, CF$_3$ or Ph, and N(Ph)$_2$.

10. An optoelectronic device comprising the composition according to claim 9, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

11. A composition comprising:
(a) at least one organic molecule according to claim 1 as an emitter and/or host;
(b) one or more emitter and/or host materials different from the at least one organic molecule according to claim 1; and
(c) optionally one or more dyes and/or one or more solvents.

12. An optoelectronic device comprising the composition according to claim 11, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

13. A composition comprising:
(a) at least one organic molecule according to claim 5 as an emitter and/or host;
(b) one or more emitter and/or host materials different from the at least one organic molecule according to claim 5; and
(c) optionally one or more dyes and/or one or more solvents.

14. An optoelectronic device comprising the composition according to claim 13, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

15. An organic molecule comprising a compound represented by a structure of Formula VIIa-VIIh:

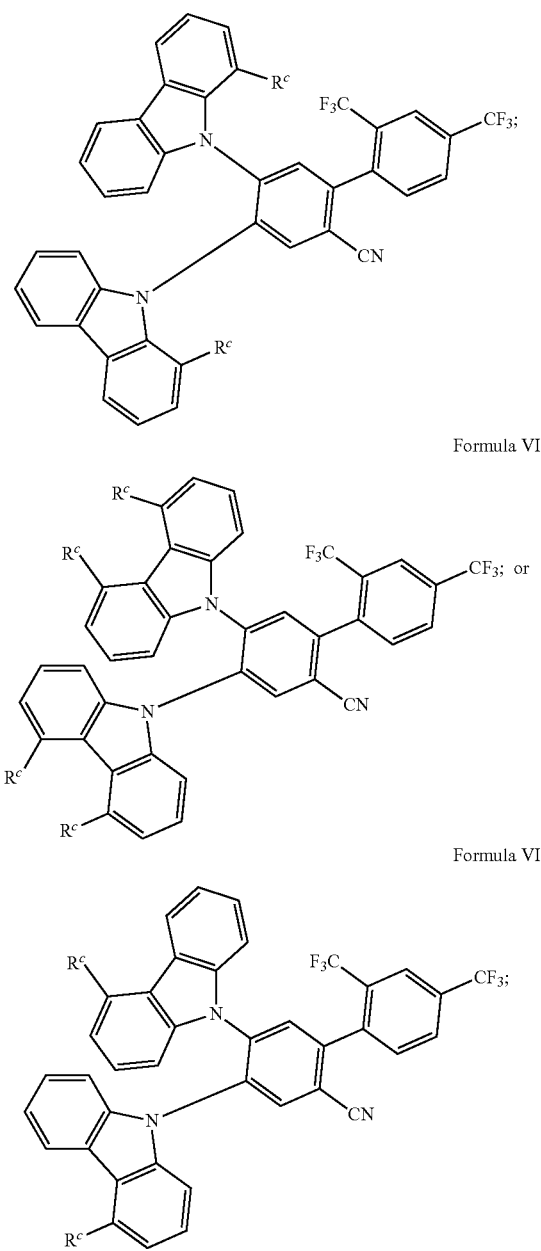

Formula VIIf

Formula VIIg

Formula VIIh wherein
in each occurrence $R^c$ is independently selected from the group consisting of Me, $^i$Pr, $^t$Bu, CN, $CF_3$, Ph, which can be respectively substituted with one or more radicals selected from Me, $^i$Pr, $^t$Bu, CN, $CF_3$ or Ph, pyridinyl, which can be respectively substituted with one or more radicals selected from Me, $^i$Pr, $^t$Bu, CN, $CF_3$ or Ph, pyrimidinyl, which can be respectively substituted with one or more radicals selected from Me, $^i$Pr, $^t$Bu, CN, $CF_3$ or Ph, carbazolyl, which can be respectively substituted with one or more radicals selected from Me, $^i$Pr, $^t$Bu, CN, $CF_3$ or Ph, triazinyl, which can be respectively substituted with one or more radicals selected from Me, $^i$Pr, $^t$Bu, CN, $CF_3$ or Ph, and $N(Ph)_2$.

16. An optoelectronic device comprising the organic molecule according to claim 15, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

17. The optoelectronic device according to claim 16, comprising:
 a substrate;
 an anode;
 a cathode, wherein the anode or the cathode is disposed on the substrate; and
 at least one light-emitting layer disposed between the anode and the cathode and which comprises the organic molecule.

18. An optoelectronic device comprising the organic molecule according to claim 15, wherein the organic molecule is one of an emitter and an absorber in the optoelectronic device.

19. A composition comprising:
 (a) at least one organic molecule according to claim 15 as an emitter and/or host;
 (b) one or more emitter and/or host materials different from the at least one organic molecule according to claim 15; and
 (c) optionally one or more dyes and/or one or more solvents.

20. An optoelectronic device comprising the composition according to claim 19, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

* * * * *